United States Patent [19]

Cram

[11] 4,001,279
[45] Jan. 4, 1977

[54] ASYMMETRIC MACROCYCLES CONTAINING OXYGEN AND BINAPHTHYL RING MEMBERS

[75] Inventor: Donald J. Cram, Los Angeles, Calif.

[73] Assignee: The Regents of the University of California, Berkeley, Calif.

[22] Filed: Mar. 5, 1974

[21] Appl. No.: 448,333

Related U.S. Application Data

[63] Continuation-in-part of Ser. No. 346,089, March 29, 1973, abandoned.

[52] U.S. Cl. .................... 260/340.3; 260/47 UP; 260/239 D; 260/239 DD; 260/247; 260/327 R; 260/346.2 M; 260/456 R; 260/468 G; 260/478; 260/515 R; 260/534 R; 260/568; 260/570.5 R; 260/575; 260/609 R; 260/611 A; 260/612 R; 260/619 R

[51] Int. Cl.$^2$ .................................. C07D 321/00

[58] Field of Search ........................... 260/340.3

[56] References Cited

UNITED STATES PATENTS 3,687,978  8/1972  Pedersen .................. 260/340.3

OTHER PUBLICATIONS

Pedersen, Journ. Amer, Chem. Soc., 89, 26, Dec. 1967.

*Primary Examiner*—Ethel G. Love
*Attorney, Agent, or Firm*—John T. Reynolds; Willard L. Cheesman

[57] ABSTRACT

Chiral, hinged and functionalized host multiheteromacrocycles of the oxygen, nitrogen and sulfur-containing type are disclosed possessing holes sized to afford selective complexation of specific guest substances and shapes to recognize chirally guest molecules by virtue of the chiral steric barrier of the 2,2'-diheteroatom-1,1'-binaphthyl grouping, the naphthyl-naphthyl dihedral angle, and the provision of ortho positioned side chain substituents (arms) bearing terminal functional groups which act as counterions or additional complexing sites, and the provision of remote position side chain substituents used to control solubility and volatility properties or to bond the multiheteromacrocycles to solid supports.

23 Claims, No Drawings

ASYMMETRIC MACROCYCLES CONTAINING OXYGEN AND BINAPHTHYL RING MEMBERS

The invention described herein was made in the performance of work under research grants from the U.S. Public Health Service and the National Science Foundation.

CROSS REFERENCE TO RELATED APPLICATIONS

This is a continuation-in-part of application Ser. No. 346,089, filed Mar. 29, 1973, now abandoned.

BACKGROUND OF THE INVENTION

Macrocycles, and particularly macrocyclic polyethers are known compounds and have been referred to in the literature as "crown" compounds in reference to the crown-like appearance of the polyalkoxy cyclic chain in the molecular structural model. Such compounds are disclosed in U.S. Pat. Nos. 3,562,295, 3,686,225, and 3,687,978.

These prior art crown compounds are characterized as composed of alkyleneoxy chains, particularly ethyleneoxy chains, or ethyleneoxy chains upon which is fused a phenylene or cyclohexylene radical in one or more positions, examples being 2,3,11,12-dibenzo-1,4,7,10,13,16-hexoxacyclooctadeca-2,11-diene and 2,5,8,15,18,21-hexoxatricyclo-[20.4.0$^{9,14}$]hexacosane disclosed in the U.S. Pat. No. 3,687,978. These prior compounds are known to form complexes with a wide variety of ionic metal compounds, and they have been suggested as useful agents in carrying normally insoluble reagent substances into solution in non-hydroxylic media.

Such crown compounds have been described extensively in the literature, for example:
J. Am. Chem. Soc. 89 2495–6
J. Am. Chem. Soc. 89 7017–36
J. Am. Chem. Soc. 92 386–91
J. Am. Chem. Soc. 92 391–94
J. Org. Chem. 36 254–57
Angew. Chem. Int. Ed. 11 16–25
Fed. Proc. 27 1305–08
Endeavor 30 142–6
J. Am. Chem. Soc. 92 4321–30
J. Am. Chem. Soc. 93 2231–35
J. Am. Chem. Soc. 93 2235–43

In the article, Angew. Chem. Int. Ed. 11 16–25, there is disclosed a system of nomenclature whereby such crown compounds can be referred to with greater simplicity of language than is required by the formal systems of nomenclature for organic compounds.

Although the compounds of this invention contain ethyleneoxy units, they do not possess the necessary overall structural features of crowns. Crown compounds possess high symmetry elements, and none of their atoms are rigidly held far from the best plane of the oxygen atoms. The macrocycles described here are all asymmetric, and contain rigid planes of atoms held perpendicular to the best plane of the macrocycle, and which extend above and below that plane. Crown compounds contain patterns of

units, and in some cases

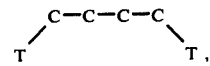

units. The macrocycles described here contain at least one

each pair of carbon atoms being incorporated in an aromatic ring. In these formulas T stands for O, S or NH or NTs. Although some of the macrocycles described here possess some of the properties of crown compounds, many of the properties of the presently described macrocycles are unique, and are not shared by crown compounds.

Prior macrocycles noted above also include those which contain sulfur in the cycle in place of oxygen, and a number have been described in J. Org. Chem. 36 254–57 wherein sulfur atoms replace one to four oxygen atoms in crown-5, crown-6, and crown-7 compounds.

In the prior compounds, macrocycles containing up to 4 fused rings have been described, each ring being either a benzene or a cyclohexyl ring.

In the later patent specifically referred to above, such macrocycles containing additional nuclear substituents on the aromatic rings are described.

The prior macrocycles are all characterized by high molecular symmetry, and have an ability to complex other substances such as metal cations, depending upon the size of the hole of the crown and the diameter of the cation. All rings fused to the crowns are situated on the periphery of the macrocycle by involvements of 1,2-linkages, or at most, 1,3-linkages. Such fused rings involve a pair of vicinal carbon atoms including broadly such rings as phenylene, naphthylene, phenylanthrylene, anthrylene, cyclohexylene, and the like.

The prior art compounds, particularly those involving peripherally fused rings, are prepared by utilizing a vicinal dihydric phenol such as catechol which is caused to react with a dihalide containing ether oxygen atoms. By selecting the appropriate dihalide and adjusting reaction conditions, the macrocycles can be formed relatively simply. More complex crowns can be formed using the vicinal dihydric phenol in which one hydroxyl group has been blocked to achieve partial reaction with the dihalide; followed by unblocking and further reaction with dihalide.

SUMMARY OF THE INVENTION

This invention relates to multiheteromacrocycles of the following formulas:

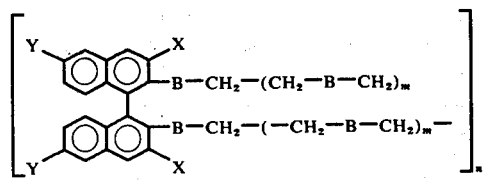

I    n = 1 to 3 each *m* taken separately = 0 to 5, the sum being at least 1,

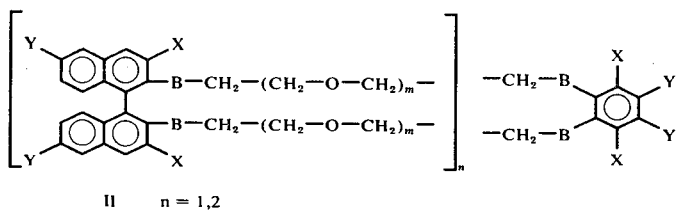

II  n = 1,2 each *m* taken separately = 0 to 5, the sum being at least 1, wherein B = —O—; —S—;

X = $(CH_2)_vR$, where $v$ = 1 to 3 and R = H, $CH_3$, $CO_2H$, $SO_3H$, $PO(OH)_2$, $NH_2$, $N(CH_3)_2$, $N(CH_2CH_2)_2O$, OH, $OCH_3$, or $NHCOCH_3$; and $CH_2OH$; $CH_2Cl$; $CH_2OCH_2CO_2H$; $CH_2OCH_2CO_2CH_3$; $CH_2OCH_2CH_2PO(OH)_2$; $CH_2OCH_2CH_2SO_3H$; $CH_2SCH_2CO_2H$; $CH_2CH_2CO_2H$; $CH_2SCH_2CH_2CO_2H$.

Y = H, Br, $NH_2$, $CO_2H$, $SO_3H$, $CH=CH_2$, $CH_2OH$, $CH_3CO$, $CH_2Cl$, $CH_2OCH_2CO_2H$, $CH_2SCH_2CO_2H$, $CH_2CO_2H$, $Si(CH_3)_2Cl$, $CH_2Cl$, $N=C=O$; $CH_3(CH_2)_{16}C(CH_3)_2$; $CH_3(CH_2)_{17}CHCH_3$;

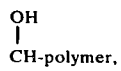

CONH-polymer, $SO_2NH$-polymer, $NHSO_2$-polymer, $CO_2CH_2$-polymer, $Si(CH_3)_2O$-polymer, where "polymer" is p-substituted polystyrene cross-linked with zero to 25% divinyl benzene, or silicas.

Z = H, $SO_2C_6H_4CH_3$-p.

The above compounds I and II are unique in their structures and in their uniquely cooperating molecular properties, making them useful for a wide variety of purposes as will be described below. In this description, definitions are useful.

The systematic names of most of the compounds described are too complicated for ready translation into structural formulas. Therefore structural formulas will be assigned unique numbers, and the specific compounds will be coupled to their structures by these numbers. All of the multiheteromacrocycles (referred to frequency as macrocycles) contain 1,1'-binaphthyl units which are non-superimposable on their mirror images, and are therefore "handed", or chiral. Even through chiral or asymmetric, many of the compounds contain symmetry elements, such as $C_2$ axes. A $C_2$ axis is an axis passed through a molecular structure such that rotation of the structure about that axis by 180° reproduces the exact structure. A consequence of a chiral macrocycle possessing a $C_2$ axis is that the same structure is produced when a second chiral special complexes either the top or bottom face of the macrocycle. Such a cycle in effect lacks sidedness. The term "face" refers to the best plane of the macrocycles' oxygen. A $C_3$ axis is an axis passed through a molecular structure such that rotation of the structure 120° about that axis reproduces the exact structure. The hole of the macrocycle is the space enclosed by the oxygens of the macrocycle when those oxygens are turned inward, and are close to being coplaner. The terms "monolocular", "dilocular" and "trilocular" refer to how the space above (or below) the face of a multiheteromacrocycle is divided. When the space is broken by only one unit that protrudes above or below the face of the macrocycle, the system is monolocular. When the space is divided into two parts, the system is dilocular. When the space is divided into three parts, the system is trilocular. In the compounds described here, the space is divided both above and below the two faces by 1,1'-binaphthyl units, whose naphthalene rings are perpendicular to the faces, and which act as walls, or barriers. Since the 1,1'-binaphthyl units are chiral, the barriers are chiral barriers. The spaces between naphthalene rings of different units are referred to as cavities. Cavities can be chiral if their dimensions are defined by chiral barriers. The term "host molecule" refers to a macrocycle capable of complexing a guest molecule or ion. The term "chiral recognition" refers to the ability of a chiral host of a given configuration to recognize through differential complexation the configuration of a chiral guest entity. Chiral recognition arises from a complementary vs a non-complementary steric fit of host to guest in a complex. The symbols L, M and S attached to an asymmetric center of a potential guest molecule refer to the relative size of the three substituents as large, medium and small, respectively. The symbols L', M', and S' refer to the relative sizes of cavities of the host molecules.

Each cycle's oxygens provide neutral ligands for metal, alkyl or arylammonium, aryldiazonium or aryloxycarbonium cations. When complexed, the oxygens of the host turn inward, and are roughly coplaner. In this state, the hole diameter of I and II varies with n and m. Unique to the 1,1'-binaphthyl-containing macrocycles of this invention, the hole diameter within a specific macrocycle also varies by an estimated 0.5 to 0.7 A per binaphthyl unit. The 1-naphthyl-1'-naphthyl bond acts as a hinge, and variation of the dihedral angle between the planes of each naphthlene varies the diameter of the hole. This adaptive structural feature lends unique properties to the macrocycles. The macrocyclic ring is attached at the two 2-positions of each binaphthyl unit. The two 3-positions of each binaphthyl unit direct the attached side chains or arms under, over and around the hole, and further define the shapes of the cavities.

Carboxyl groups terminating the X-chains of I and II can center above and below the hole, and at least one of them can act as an internal counter-ion for complexed cations. Amino groups or a second carboxyl group terminating the X-chains act as additional neutral ligands, or as sites for hydrogen bonding or ion-pairing with the carboxyl group of a complexed amino acid. The binaphthyl and methylene units of the ring and X-side chains shape the cavity, and provide a lipophylic skin for involved (complexed) hydrophylic substances such as metal alkyl or arylammonium, aryldiazonium or aryloxycarbonium cations, or amino acids. Qualitative observations correlate hole and cavity sizes of I and II taken with the number of potential cationic sites of the X-side chains with the size and ionic sites of candidate substances for complexation. The above uniquely cooperating molecular properties of I and II lead to their further use as agents for optical resolution by differential complexation between I and II and such substances as α- or β-aminoacids or primary amine salt racemates. In turn, racemates of I or II can be resolved by optically active aminoacids, or primary amine salts. This phenomenon, making use of diastereomeric differential complexation in solution or at phase interfaces can be effected with I and II in a variety of environments, and is akin to the complexation-decomplexation reactions between organic entities that are necessary stages in enzyme-catalyzed reactions.

The absolute configurations of the optically active host molecules are known. Because of the complementary stereochemical structures of host and guest in the more stable diastereomeric complex, the absolute configurations of guest or host entities can be determined from knowledge of the absolute configuration of one of them. By use of multiplate complexation-decomplexation processes both optically pure enantiomers can be produced from appropriate racemates, and criteria for optical purity developed.

SYNTHESES OF THE POLYHETEROMACROCYCLES

The primary starting materials for all systems were 2,2'-dihydroxy-1,1'-binaphthyl (1) in a racemic or optically pure state, or 3,3'-dicarboxy-2,2'-dihydroxy-1,1'-binaphthyl (2) in a racemic or optically pure state, or 2,2'-dithiol-1,1'-binaphthyl (1c'), or 2,2'-diamino-1,1'-binaphthyl (1d') in a racemic or optically pure state, and usually ethyleneglycol or polyethyleneglycol ditosylates. Compound 1 was converted to 1c' by a general procedure described previously [J. Org. Chem., 31, 3980 (1966)] for converting phenols to arylthiols. The absolute configurations and maximum rotations of 1, and 1d' and 2 have been established [Tetrahedron, 27 5999 (1971)] and are formulated both in a conventional and in a cross-sectional way which will be useful for depiction of configuration. Optically pure forms of 1 proved stable to ring-closing conditions (alkali metal bases such as sodium hydride, sodium or potassium alkoxides or carbonate in an inert solvent such as tetrahydrofuran or dimethylformamide). The six simplest monolocular macrocycles, 3, 4, 4', 5, 6, and 7 involved 1 and ethyleneglycol, diethyleneglycol, triethyleneglycol, tetraethyleneglycol, pentaethyleneglycol and hexaethyleneglycol ditosylates, respectively. Optically pure (−)-(S)-6 was optically stable when heated for 6 hours at 205°.

Useful intermediates in the syntheses of monolocular and other systems were 1a and 1b'. A mixture of 1 with two moles of sodium hydroxide and the monopyranyl ether of diethyleneglycol monochloride gave a bispyranyl ether, cleavage of which with traces of acid gave the diol, tosylation of which produced 1a. Treatment of 1 with liquid ethylene oxide and anhydrous potassium carbonate gave the diol, tosylation of which produced 1b'.

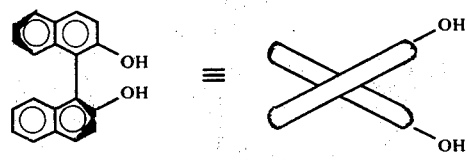

(−)-(S)-1

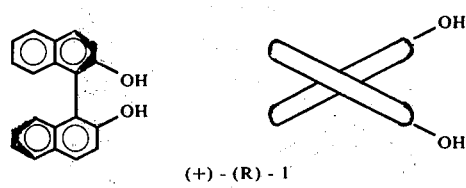

(+)-(R)-1

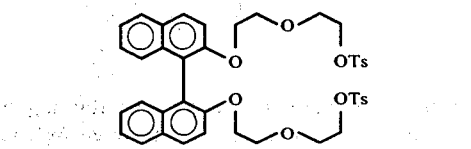

89a tosylate, where each X and Y is hydrogen

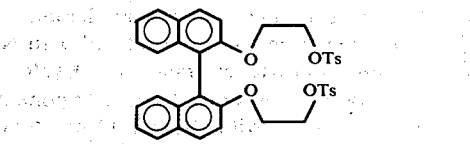

1b'

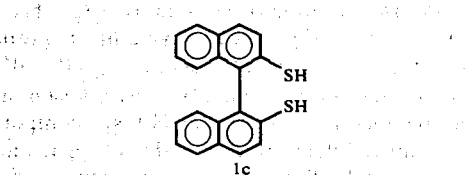

1c

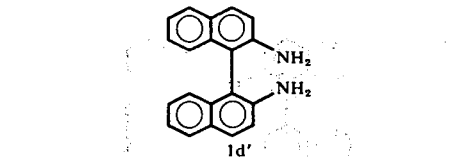

1d'

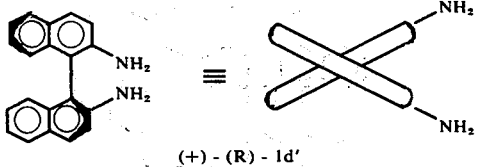

(+)-(R)-1d'

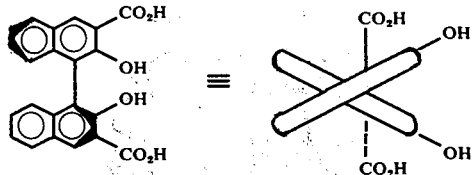

(−)-(S)-2

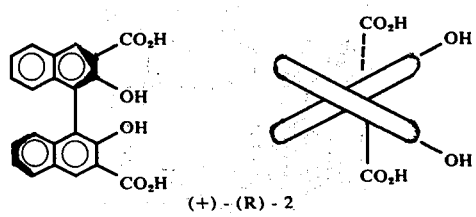

(+)-(R)-2

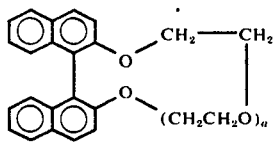

| | |
|---|---|
| 3, | a = 0 |
| 4, | a = 1 |
| 4a, | a = 2 |
| 5, | a = 3 |
| 6, | a = 4 |
| 7, | a = 5 |

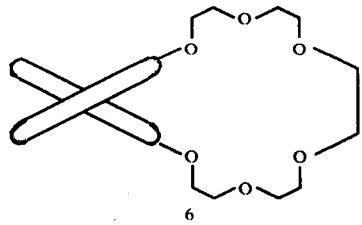

6

Examples of monolocular systems containing sulfur and nitrogen are compounds 6a' through 6g'. Compound 6a' was prepared from 1a and sodium sulfide monohydrate. Compound 6b' was produced from 1a and 1,2'-ethanedithiol. Compound 6c' resulted from reaction of 1a with N,N'-ditosylethylenediamine. Compound 6d' involved 1a and N-tosylethanolamine. Compound 6e' resulted from treatment of 1b' with N,N',-N'',N'''-tetratosyltriethylenetetraamine. Cycle (−)-(R)-6f' was produced as one of the components of reaction of (+)-(R)-1 with N, O, O'-tris-tosyldiethanolamine. Racemic 6f' was obtained from 1b' and tosylamide. Detosylation of 6f' with hydrogen bromide in phenol-acetic acid gave 6g'. Cycle 6h' is prepared from the N,N'-ditriflate of diamine (−)-(R)-1d' and pentaethyleneglycol ditosylate. Base was present in the ring-closing reactions. With the N-tosyl compounds, the base removed the proton from the nitrogen, and the highly nucleophilic R-NTs species was generated.

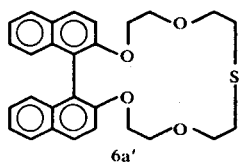

6a'

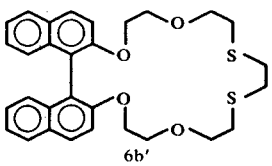

6b'

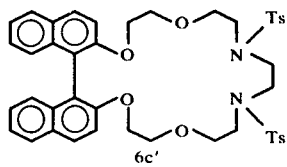

6c'

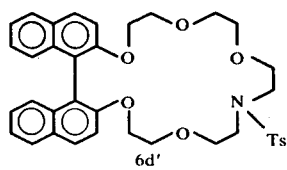

6d'

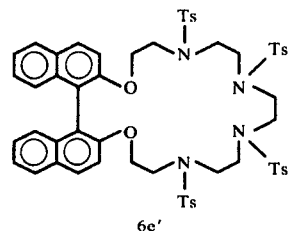

6e'

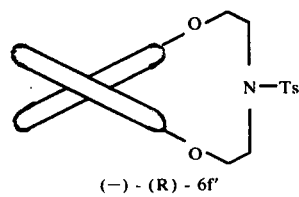

(−) - (R) - 6f'

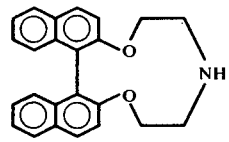

6g'

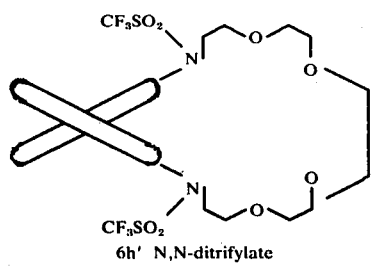

6h' N,N-ditrifylate

The simplest dilocular system, 8, was the major product from 1 and diethyleneglycol ditosylate, with 4 as the minor. Macrocycle 8 was obtained mainly as the (SS)(RR)-isomer with the (SR)-isomer (meso form) as a minor product when (S)(R)-1 was used. With (S)-1 as starting material, only (S)-4 and (SS)-8 were produced. System (SS)-8 was optically stable when heated for 12 hours at 200°.

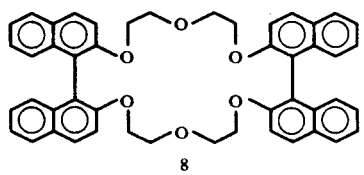

8

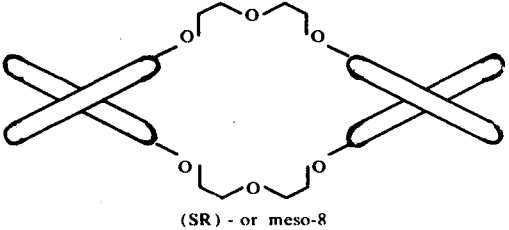

(SR) - or meso-8

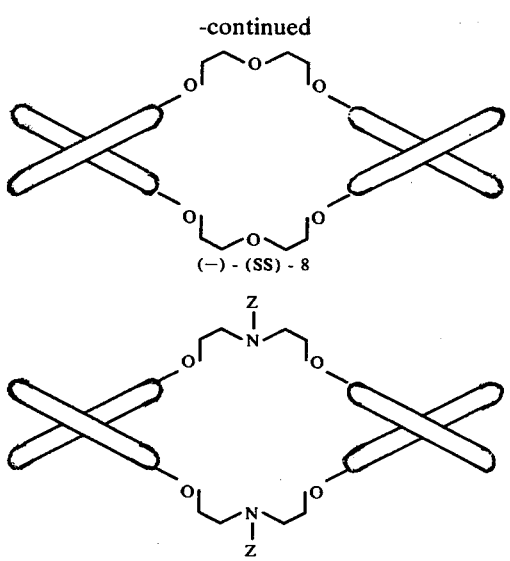

(−) - (SS) - 8

-continued
(−) - (RR) - 8a′, Z = Ts
(+) - (RR) - 8b′, Z = H

The dilocular system (−)-(RR)-8a′ was obtained by the base-catalyzed reaction of (+)-(R)-1 with N,O,O′-tristosyldiethanolamine along with (−)-(R)-6f′. Detosylation of (−)-(RR)-8a′ with hydrogen bromide in acetic acid gave (+)-(RR)-8b′. Retosylation of (+)-(RR)-8b′ gave (−)-(RR)-8a′ of the same rotation as the original material, a fact that demonstrated no racemization or epimerization occurred during the detosylation.

A second dilocular system (12) was generated by the less direct route formulated. When (S)(R)-1 (racemic 1) was employed, a mixture of (SR)-12 (meso form) and (SS)-(RR)-12 (racemate) was obtained. Only (SS)-12 was produced with (S)-1 as starting material.

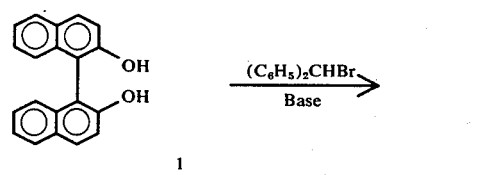

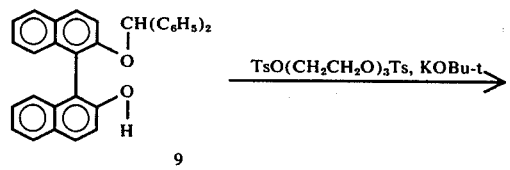

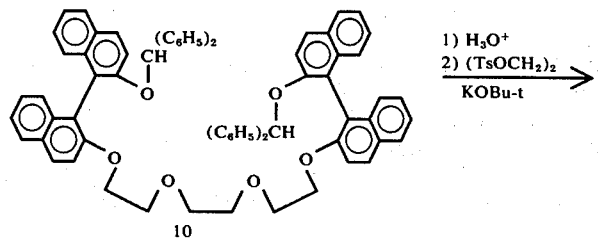

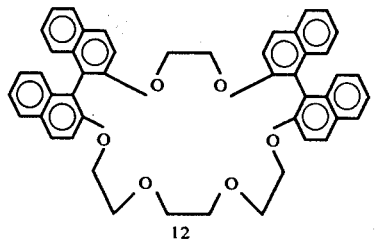

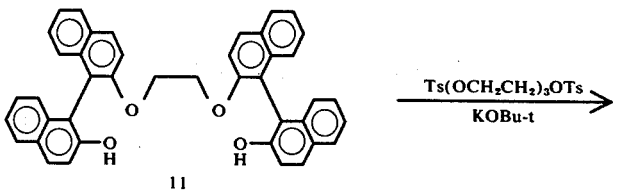

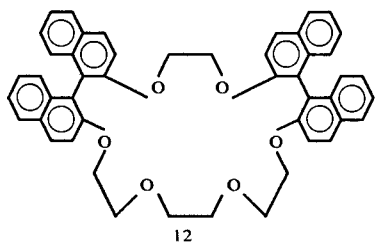

12

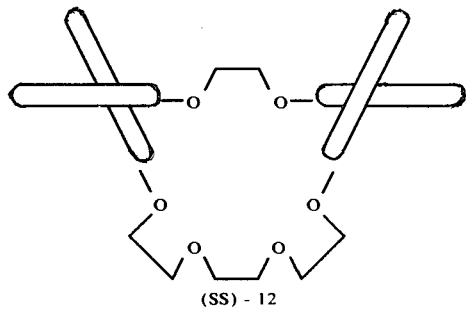

(SS) - 12

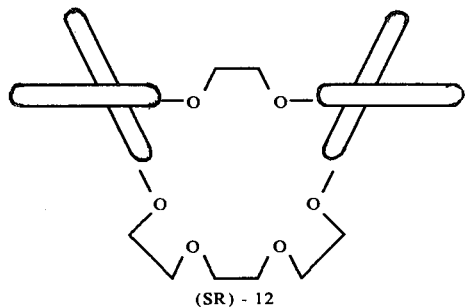

(SR) - 12

The three binaphthyl units of trilocular system 15 were incorporated into the macrocycle by two methods. In the first of these, the multistage reaction of (S)(R)-1 with ethylglycol ditosylate gave a mixture of the five compounds, (S)(R)-3, (S)(R)-13, (S)(R)-14, (SSR)(RRS)-15 and (SSS)(RRR)-15, which were all isolated in a pure state. Use of optically pure (S)-1 gave only (S)-3, (S)-13 and (SSS)-15. A comparison of the compounds obtained from (S)(R)-1 and from (S)-1 identified those products that contained binaphthyl units of the (R)-configuration. The possible (SS)(RR)-14 (isomer) was not observed among the products from (S)(R)-1.

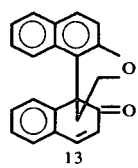

13

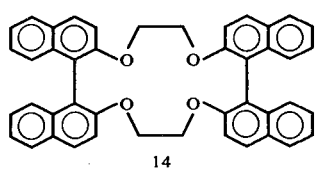

14

-continued

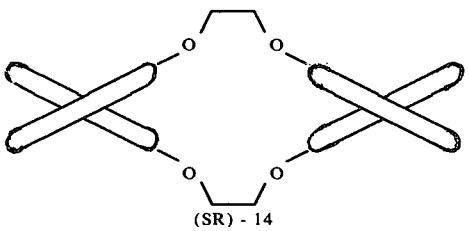

(SR) - 14

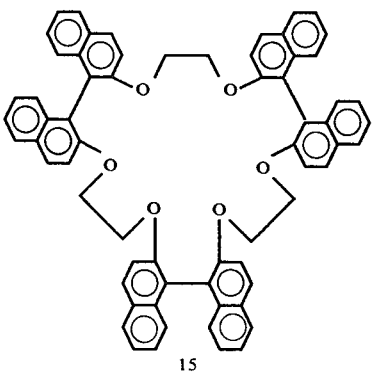

15

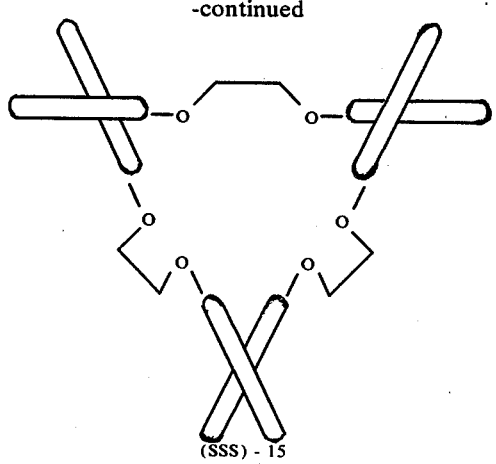

(SSS) - 15

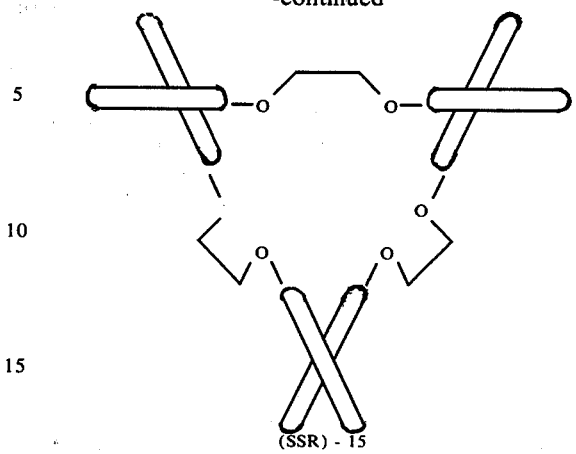

(SSR) - 15

Much better yields of 15 were produced in the stepwise procedure formulated. The great insolubility of the (SSS)-(RRR)-isomer as compared to the (SSR)(RRS) made the two racemates easy to separate. When optically pure (S)-1 was used, only (SSS)-15 was produced. Thus the configurations of the isomers were established. Treatment of 18 with ethyleneglycol ditosylate or of ditosylate 19 with ethyleneglycol and potassium carbonate in diethylformamide provide alternative routes to dilocular system 12.

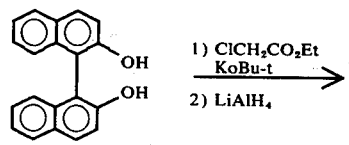

1

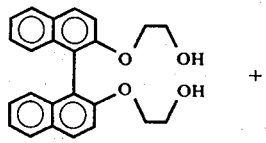

16

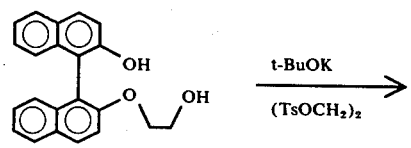

17

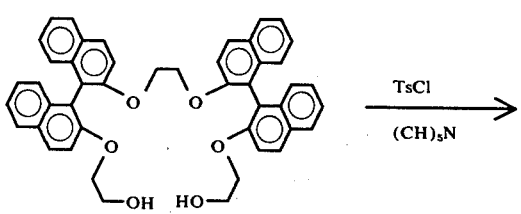

18

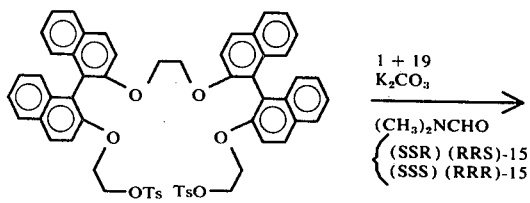

When either (SSR)(RRS)-15 or (SSS)(RRR)-15 were heated at 350° for 0.5 hour under nitrogen, a quantitative yield of an equilibrium mixture of the two was obtained in which [(SSS)(RRR)]/[(SSR)(RRS)]~1.0.

Starting materials for similar ring closures to give mono, di and trilocular systems with substituents X of I and II in place on the 3- and 3'-positions of the binaphthyl units of the starting materials were prepared as follows. A Mannich reaction (160°) with 1 and O(CH$_2$CH$_2$)$_2$NCH$_2$OBu gave 20 and 21. Use of (CH$_3$)$_2$NCH$_2$OCH$_2$CH(CH$_3$)$_2$ gave 22. When heated in acetic anhydride, 20 gave tetracetate 23 and monoacetate, 24, reduction of which with lithium aluminum hydride gave tetrol 25 and triol 26, respectively. Similarly, 21 gave triol 27.

Catalytic reduction of tetrol 25 in ethanol with hydrogen and a palladium-carbon catalyst gave an easily separated mixture of diol 25a' and triol 25b'. The same compounds were produced when 20 was similarly reduced in glacial acetic acid. Another route to 25a' involved treatment of tetrol 25 with dry hydrogen bromide in acetic acid to give 25c', which in turn was reduced to 25a' with lithium aluminum hydride. Diol 25a was resolved through the cinchonine salt of its phosphoric acid diester, which after resolution was reduced with lithium aluminum hydride to optically active diol, (+)-25a'. Ditosylate 25d' was prepared by a procedure modeled after the preparation of ditosylate 1a from 1.

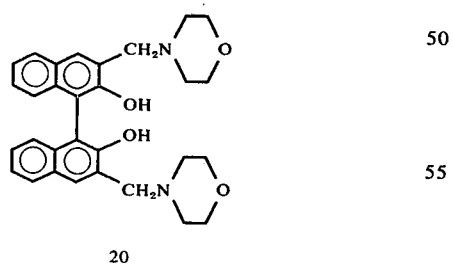

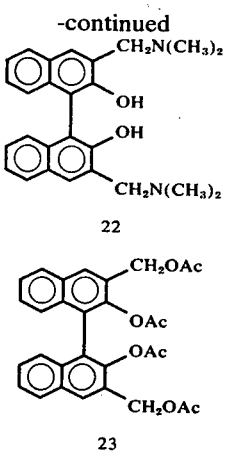

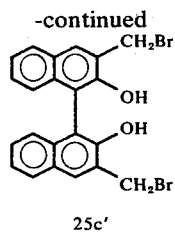

25c'

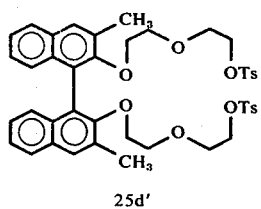

25d'

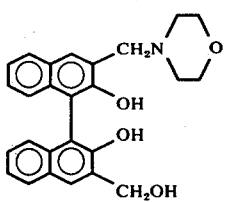

26

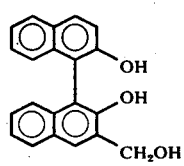

27

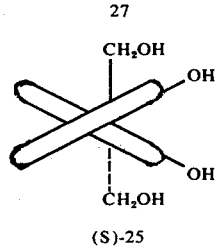

(S)-25

Binaphthol 1 with its 3 and 3'-positions substituted with H, $CH_2N(CH_2CH_2)_2O$, $CH_2N(CH_3)_2$ or $CH_2OH$ or combinations thereof were submitted to ring closures with di- or triethyleneglycol, tetraethyleneglycol, pentaethyleneglycol or hexaethyleneglycol ditosylates and base to give macrocycles with X and X' groups substituted in the 3 and 3'-positions of the binaphthyl units of I. Thus monolocular macrocycles 28, (S)-28, 31, 32, 34, 37, 40, (S)-40, 43, and (R)-43 and 47 were prepared and characterized, as were dilocular macrocycles 46 and 48. Macrocycle 33 was also produced, but not isolated pure or characterized. Macrocycles 28, 34, 37, 40 and 43 were treated with

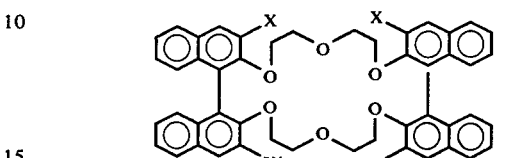

| | b | X | X' |
|---|---|---|---|
| 28 | 4 | $CH_2OH$ | $CH_2OH$ |
| 31 | 4 | $CH_2N(CH_2CH_2)_2O$ | $CH_2N(CH_2CH_2)_2O$ |
| 32 | 4 | $CH_2N(CH_3)_2$ | $CH_2N(CH_3)_2$ |
| 33 | 4 | $CH_2N(CH_3)_2$ | $CH_2OH$ |
| 34 | 4 | H | $CH_2OH$ |
| 34a | 3 | H | $CH_2OH$ |
| 37 | 4 | $CH_2N(CH_2CH_2)_2O$ | $CH_2OH$ |
| 40 | 3 | $CH_2OH$ | $CH_2OH$ |
| 43 | 5 | $CH_2OH$ | $CH_2OH$ |
| 47 | 1 | $CH_2N(CH_2CH_2)_2O$ | $CH_2N(CH_2CH_2)_2O$ |

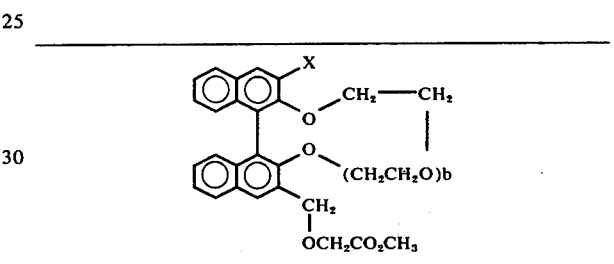

| | X | X' |
|---|---|---|
| 46 | $CH_2N(CH_2CH_2)_2O$ | $CH_2N(CH_2CH_2)_2O$ |
| 48 | $CH_2OH$ | $CH_2OH$ | methyl α-bromoacetate to give the corresponding esters, 29, 35, 38, 41 and 44 which were subsequently hydrolyzed with

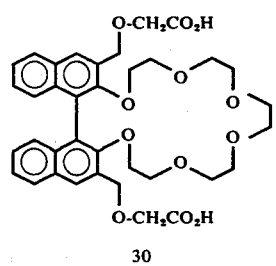

| | b | X |
|---|---|---|
| 29 | 4 | $CH_2OCH_2CO_2CH_3$ |
| 35 | 4 | H |
| 38 | 4 | $CH_2N(CH_2CH_2)_2O$ |
| 41 | 3 | $CH_2OCH_2CO_2CH_3$ |
| 44 | 5 | $CH_2OCH_2CO_2CH_3$ | barium hydroxide. Acidification of the reaction mixtures with hydrochloric acid gave the corresponding carboxylic acids, 30, 36, 39, 42 and 45. Use of optically pure (S)- or (R)-25 (tetrol) in the sequences gave optically pure acids, (S)-30, (S)-42 and (R)-45. Since 2 of maximum rotation and of known absolute configuration was the initial starting material, the maximum rotations and absolute configurations of (S)-30, (S)-42 and (R)-45 are established.

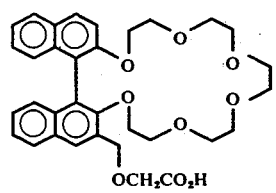

30

36

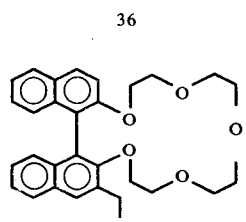

36a

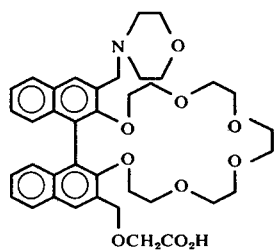

39

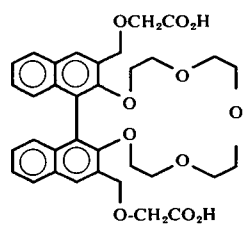

42

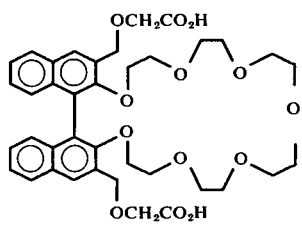

45

Macrocyclic diol 28 served as a starting material for synthesis of a number of additional cycles carrying two arms. With thionyl chloride in benzene, 28 gave the dichloride 28a'. Reaction of 28a' with sodium α-thiolacetate gave 28b', and with sodium β-thiolpropionate gave 28c'. Sodium dimethyl malonate reacted with 28a' to give the corresponding malonate ester, which was hydrolyzed to 28d', which was decarboxylated to give 28e'. When cyclized with pentaethyleneglycol ditosylate, 25b' produced 28f', which was converted to 28g' by a procedure similar to that used to convert 28 to 30. Compound 28h' was prepared from 28 by the same procedure used to prepare 30, except that less methyl α-bromoacetate was employed, the mono and dialkylated materials were separated, and the monoalkylated ester hydrolyzed to 28h'. Compounds 28a', 28b', 28c', 28e' and 28h' were also prepared in an optically pure state.

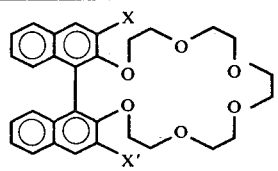

| | X | X' |
|---|---|---|
| 28a' | $CH_2Cl$ | $CH_2Cl$ |
| 28b' | $CH_2SCH_2CO_2H$ | $CH_2SCH_2CO_2H$ |
| 28c' | $CH_2SCH_2CH_2CO_2H$ | $CH_2SCH_2CH_2CO_2H$ |
| 28d' | $CH_2CH(CO_2H)_2$ | $CH_2CH(CO_2H)_2$ |
| 28e' | $CH_2CH_2CO_2H$ | $CH_2CH_2CO_2H$ |
| 28f' | $CH_3$ | $CH_2OH$ |
| 28g' | $CH_3$ | $CH_2OCH_2CO_2H$ |
| 28h' | $C_2OH$ | $CH_2OCH_2CO_2H$ |

Macrocycles 48a' and 48b' were obtained by treating diol 25a' with diethyleneglycol ditosylate. Compound 48a' and the diastereomers of 48b' were separated and characterized. A mixture of racemates, (SS,RR)-48c' and (SR,RS)-48c' was obtained by reaction of 1 with 25d'. Each racemate was isolated and characterized. When optically pure (−)-(S)-1 and racemic 25d' were allowed to react, a mixture of optically pure diastereomers, (−)-(SS)-48c' and (−)-(SR)-48c' was obtained. Each isomer was isolated and characterized. The compound with the lower rotation was assigned the (−)-(SR)-48c' structure because it is the more meso-like. Comparisons of the nmr spectra of the two racemates and the two optically pure diastereomers allowed structures to be assigned to the racemates. Macrocycles (SS,RR)-48d' and (SR,RS)-48d' were prepared from 25 and ditosylate 1a, and were separated. Similarly, from (+)-(R)-25 and (+)-(R)-1a, (+)-RR)-48d' was prepared, whose nmr spectral properties were the same as those of (SS,RR)-48d', a fact used to identify the latter. From (SR,RS)-48d' was prepared (SR,RS)-48e' which was converted to (SR,RS)-48f'. The reactions used were similar to those employed for the conversions of 28 to 29 to 30. Similarly, (+)-(RR)-48e' was prepared from (+)-(RR)-48d'.

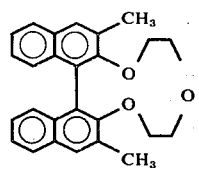

48a'

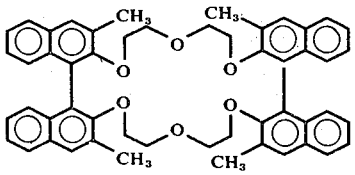

(SS,RR)-48b'
(SR)-48b'

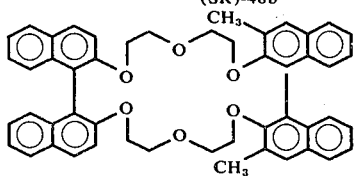

-continued (SS,RR)-48c'
(SR,RS)-48c'

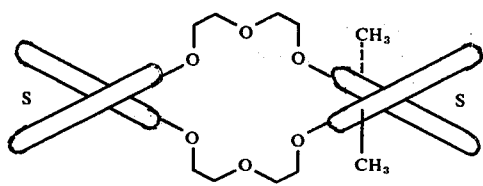

(-)-(SS)-48c'

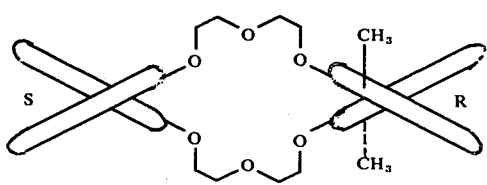

(-)-(SR)-48c'

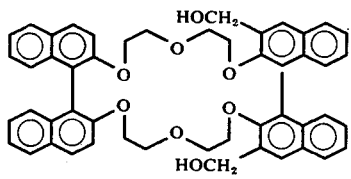

(SS,RR)-48d'
(SR,RS)-48d'

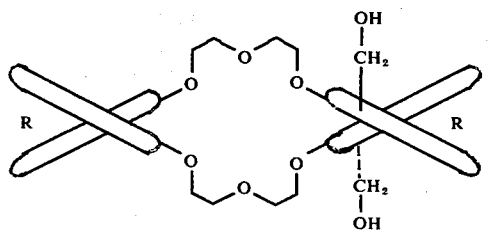

(+)-(RR)-48d'

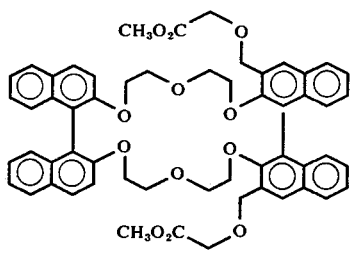

(SS,RR)-48e'
(SR,RS)-48e'

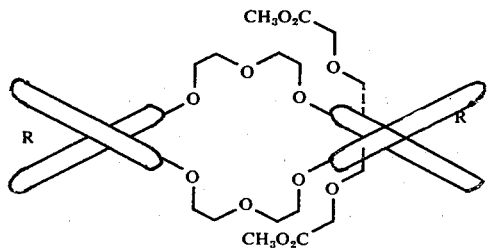

(+)-(RR)-48e'

-continued

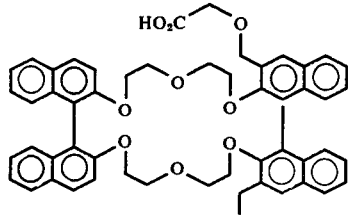

(SR,RS)-48f'

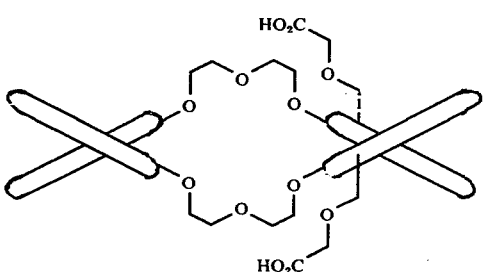

(+)-(RR)-48f'

Macrocycles 28 through 48 serve as starting materials for further elaboration of the arms (X groups) $CO_l$. For example, HCO 29 can be reduced with lithium aluminum hydride to the corresponding diol 49, which with thionyl chloride gives dichloride 50. This dichloride can be converted to a macrocycle whose arms are terminated by sulfonic cid groups 51 by treatment with sodium hydrogen sulfide followed by oxidation. Terminal phosphoric acid groups are introduced to give 52 by the conventional sequence:

$$\sim CH_2Cl \xrightarrow[-20°]{BuLi} \sim CH_2Li \xrightarrow{(CH_2O)_2POCl}$$

$$\sim CH_2PO(OCH_3)_2 \xrightarrow[2)\ H+]{1)\ NaOH} \sim CH_2PO(OH)_2$$

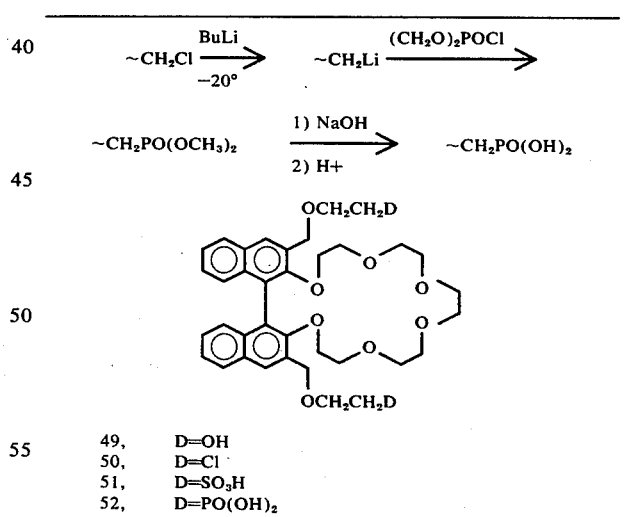

| 49, | D=OH |
| 50, | D=Cl |
| 51, | D=SO$_3$H |
| 52, | D=PO(OH)$_2$ |

Introduction of other arms (X groups) involve modifications of the macrocyclic diol, 28. Treatment of 28 with thionyl chloride gave dichloride 53, reduction of which with lithium aluminum hydride gives 54. Methanolysis of dichloride 53 gives 55. Treatment of 53 with sodium azide followed by reduction with lithium aluminum hydride gives diamine 56, acetylation of which gives diamide 57.

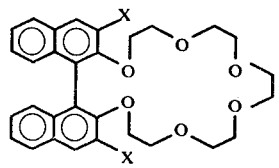

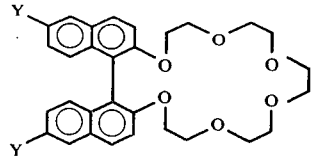

| | | | | | |
|---|---|---|---|---|---|
| 6, | Y=H | 70, | Y=NH$_2$ | 74b', | Y=CH$_2$OCH$_2$CO$_2$H |
| 63, | Y=Br | 71' | Y=CH$_2$OH | | |
| 65, | Y=CH$_3$CO | 72' | Y=CH$_2$Cl | | |
| 66, | Y=SO$_3$H | 73, | Y=CH$_2$CO$_2$H | | |
| 68, | Y=CO$_2$H | 74, | Y=CH=CH$_2$ | | |
| 69, | Y=N=C=O | 74a' | Y=CH$_2$SCH$_2$CO$_2$H | | |

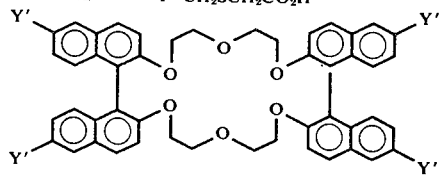

| | | | (SS) (RR) |
|---|---|---|---|
| 8, | Y'=H | 67b', | Y'=CO$_2$H |
| 64, | Y'=Br | 67c', | Y'=Si(CH$_3$)$_2$OCH$_3$ |
| 67, | Y'=SO$_3$H | 67d', | Y'=C(CH$_3$)$_2$(CH$_2$)$_{16}$CH$_3$ |
| 67a', | Y'=CH$_3$CO | 67e', | Y'=CH(CH$_3$)(CH$_2$)$_{17}$CH$_3$ |

| | | | |
|---|---|---|---|
| 53, | X=CH$_2$Cl | 58, | X=CH$_2$SO$_3$H |
| 54, | X=CH$_3$ | 59, | X=CH$_2$PO(OH)$_2$ |
| 55, | X=CH$_2$OCH$_3$ | 60, | X=CH$_2$CO$_2$H |
| 56, | X=CH$_2$NH$_2$ | 61, | X=CH$_2$CH$_2$OH |
| 57, | X=CH$_2$NHCOCH$_3$ | 62, | X=CH$_2$CH$_2$Cl |

Arms with X=CH$_2$SO$_3$H and X=CH$_2$PO(OH)$_2$ in 58 and 59 are prepared by the conventional sequence mentioned above in connection with making compounds with X=CH$_2$OCH$_2$CH$_2$SO$_3$H and X=CH$_2$OCH$_2$CH$_2$PO(OH)$_2$. Dichloride 53 through carbonation of its Grignard reagent gives diacid 60. Reduction of 60 with lithium aluminum hydride gives diol 61, which with thionyl chloride gives 62. This substance (62) treated as was 53 provides macrocycles with X=CH$_2$CH$_3$, CH$_2$CH$_2$OCH$_3$, CH$_2$CH$_2$NH$_2$, CH$_2$CH$_2$NHAc, CH$_2$CH$_2$SO$_3$H and CH$_2$CH$_2$PO(OH)$_2$. Dichloride 62 treated with dimethylamine or morpholine provides macrocycles with X=CH$_2$CH$_2$N(CH$_3$)$_2$ and X=CH$_2$N(CH$_2$CH$_2$)$_2$O, respectively. Dichloride 62 submitted to the same sequences as was dichloride 53 provides macrocycles with X=CH$_2$CH$_2$CO$_2$H, CH$_2$CH$_2$CH$_2$OH, CH$_2$CH$_2$CH$_2$Cl, CH$_2$CH$_2$CH$_3$, CH$_2$CH$_2$CH$_2$OCH$_3$, CH$_2$CH$_2$CH$_2$NH$_2$, CH$_2$CH$_2$CH$_2$NHAc, CH$_2$CH$_2$CH$_2$SO$_3$H, CH$_2$CH$_2$CH$_2$PO(OH)$_2$, CH$_2$CH$_2$CH$_2$N(CH$_3$)$_2$ CH$_2$CH$_2$CH$_2$N(CH$_2$CH$_2$)$_2$O.

A variety of Y-substituted derivatives of 1 are available in the literature. These substituents can also be introduced after the macro ring systems of compoudns I are prepared. For example, 6 was treated with bromine to give dibromide 63. Likewise 8 gave 64. When treated with acetyl chloride and aluminum chloride, 6 gave 65. With chloromethoxymethane and stannic chloride in chloroform, 6 produced 72', which served as a starting material for preparation of 74a', by a procedure similar to that employed for conversion of 28 to 28a'. With sulfuric acid, 6 gives disulfonic acid 66 and 8 gives tetrasulfonic acid 67.

Substituents Y = Br, SO$_3$H and CH$_3$CO provided starting materials for compounds with other Y substituents. For Y = CO$_2$H (68'), 65 was treated with sodium hypobromite (haloform reaction) and acidified. Likewise, 67a' gave 67b'. For Y = N=C=O, 68' is converted to its amide by conventional means, which is submitted to the Hofmann rearrangement, which can be interrupted before the isocyanate 69 hydrolyzes. Hydrolysis of the isocyanate gives the substance with Y = NH$_2$ (70). Reduction of 68' with lithium aluminum hydride gave the corresponding alcohol, 71', which with thionyl chloride gave 72'. Diol 71' was used to prepare 74a' by a procedure similar to that employed for the conversion of 28a' to 28b'. Diacid 74b' was prepared from 71' by a procedure similar to that used for the conversion of 28 to 30. Compound 67d' is prepared by alkylation of 8 with CH$_3$(CH$_2$)$_{16}$C(CH$_3$)$_2$Cl and an aluminum chloride catalyst. Compound 67e' is prepared by treating 67a' with CH$_3$(CH$_2$)$_{17}$MgBr, decomposing the adduct with acid, and catalytically reducing the olefinic mixture produced with palladium and hydrogen. Compound 65, submitted to the Willgerodt reaction provides acid 73. Reduction of 73 with lithium aluminum hydride gives the corresponding alcohol (Y = CH$_2$CH$_2$OH), which when tosylated and treated with base undergoes elimination to give Y = CH=CH$_2$ (74).

These simple Y substituents were used to graft the multiheteromacrocycles to solid supports. For example, metallation of optically pure (RR)-64 with butyllithium, treatment of the product with dichlorodimethylsilane, followed in turn by very dry silica of very large surface area, and then dry methanol, gave (RR)-64a', which by combustion analysis was ~4.6% by weight multiheteromacrocycle, and 95% silica. Treatment of dry (RR)-64a' with trimethylsilyl chloride gave (RR)-64b'.

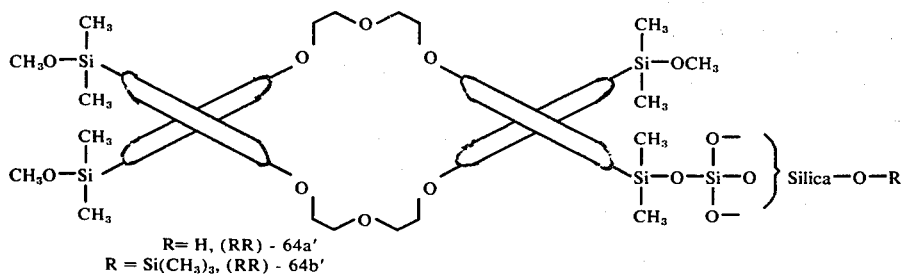

R = H, (RR) - 64a'
R = Si(CH₃)₃, (RR) - 64b'

Further examples follow. Metallation of 64 with butyllithium at low temperatures gives the corresponding organometallic, which when treated with p-aledhydopolystyrenes gives

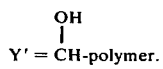

Y' = CH-polymer.

When 68 is converted to its acid chloride and that derivative is mixed with p-aminopolystyrenes, the product with Y = CONH-polymer is obtained. When 67 (or Y = SO₃H) is treated with phosphorus pentachloride, the arylsulfonyl chloride produced (Y=Y' = SO₂Cl) can be grafted to p-aminopolystyrenes to provide Y=Y' = SO₂NH-polymer. When the acid chloride prepared from 68' (Y'=CO₂H) is mixed with p-hydroxymethylenepolystyrene, graft material with Y=Y' = CO₂CH₂-polymer is produced. Styrene and 74 (Y = CH=CH₂) or (Y' = CH=CH₂) copolymerize to give polymer containing the multiheteromacrocycle directly incorporated into the polymer backbone.

The above conversions described for Y-substituted compounds can be applied equally well to Y'-substituted compounds to produce derivatives in which Y' = CH₃CO, Br and SO₃H (as noted above) and also Y' = COOH; N=C=O; NH₂; CH₂OH; CH₂Br; CH₂CO₂H; CH=CH₂.

For example ketone 67a' was oxidized with sodium hypobromite to produce acid 67b'. Bromide 64 was lithiated with butyllithium, the organometallic was treated with excess dichlorodimethylsilane and the product was esterified with methanol to give 67c'. Similarly from 12, 12a can be prepared in which Y = Br; SO₃H; CH₃CO; CO₂H; N=C=O; NH₂; CH₂OH; CH₂Br; CH₂CO₂H; CH=CH₂. Similarly from 15, 15a can be prepared in which Y = Br; SO₃H; CH₃CO; CO₂H; N=C=O; NH₂; CH₂OH; CH₂Br; CH₂CO₂H; CH=CH₂.

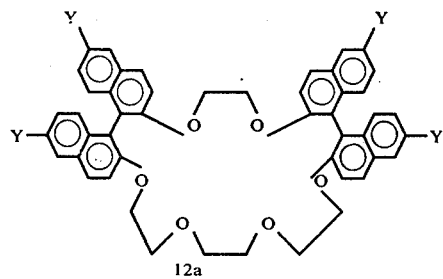

12a

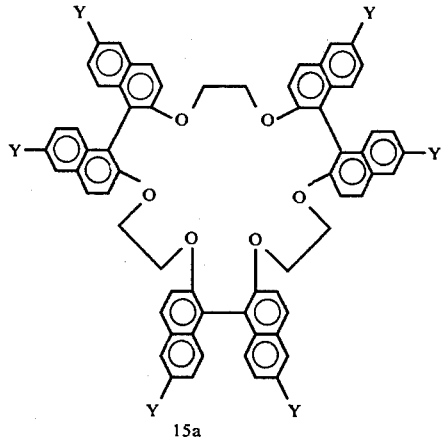

15a

Thus compounds I are prepared from racemic or optically pure 1a as the key starting materials with X = H, X = CH₃, CH₂OH or CH₂N(CH₂CH₂)₂O, and Y = H or Br. By the reactions illustrated above, 1a can be converted to key intermediates 11a, 16a, 16a-ditosylate, 17a, 18a, and 19a. By a combination of the reactions illustrated above and below, key intermediates 89a and 75a also can be prepared. By treatment in an inert atmosphere with base and the appropriate mono or polyethyleneglycol ditosylate in tetrahydrofuran or dimethyl formamide, 1a, 16a, 17a and 89a can be converted to compounds 6a, and 1a to compounds 8a.

Similarly compounds 11a and 18a can be converted to 12b. By treatment in an inert atmosphere with base and the appropriate mono or polyethyleneglycol in tetrahydrofuran or dimethyl formamide, 16a-ditosylate or 75a can be converted to 6a. Similarly, ditosylates 19a can be converted to 12b. In the same media, conditions and bases, 1a and 75a, or 16a and 16a-ditosylate react with one another to give 8a. Similarly, 1a and 19a, or 11a and 16a-ditosylate react with one another to give 15, NH$_2$, Multiheteromacrocycles 6a, 8a, 12b and 15b with X = H, CH$_3$, CH$_2$OH or CH$_2$N(CH$_2$CH$_2$)$_2$O and Y = H or Br are then converted by the reactions illustrated above to 6a, 8a, 12b and 15b wherein: X = (CH$_2$)$_v$R where $v$ = 1 to 3 and R = H, CO$_2$H, SO$_3$H, PO(OH)$_2$mNH$_2$, N(CH$_3$)$_2$,

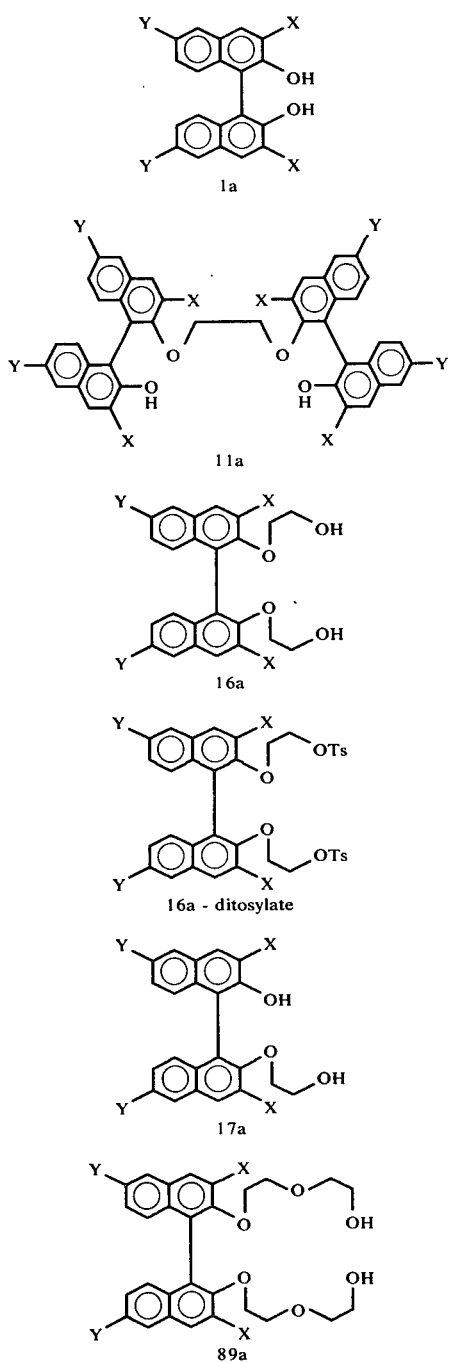

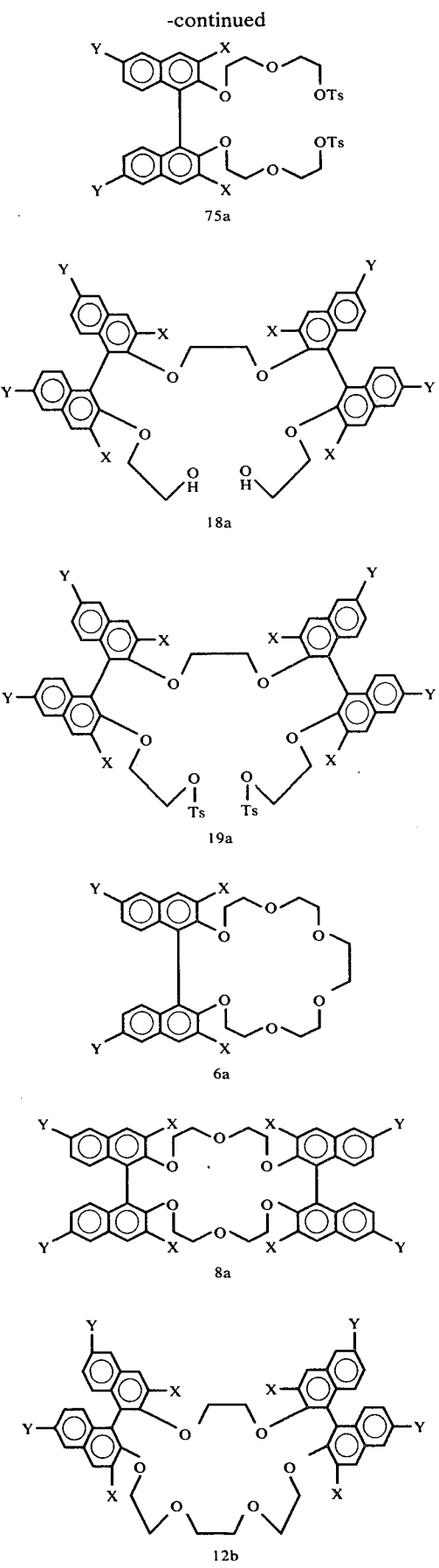

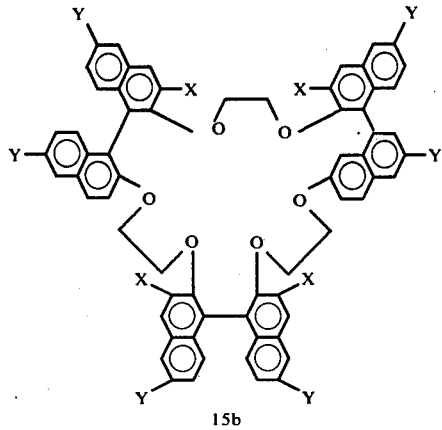

15b

N(CH$_2$CH$_2$)$_2$O, OH, OCH$_3$, NHOCH$_3$, CH$_2$OCH$_2$CO$_2$H, CH$_2$OCH$_2$CO$_2$CH$_3$, CH$_2$OCH$_2$CH$_2$PO(OH)$_2$, CH$_2$OCH$_2$CH$_2$SO$_3$H; and wherein Y = H, Br, NH$_2$, CO$_2$H, SO$_3$H, CH=CH$_2$, CH$_2$OH, CH$_2$CO$_2$H, Si(CH$_3$)$_2$Cl, CH$_2$Cl, N=C=O,

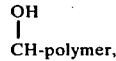
CH-polymer,

CONH-polymer, SO$_2$NH-polymer, NHSO$_2$-polymer, CO$_2$CH$_2$-polymer, Si(CH$_3$)$_2$O-polymer, where "polymer" is p-substituted polystyrene cross-linked with zero to 25% divinylbenzene, or silicon-substituted silica.

Examples of the syntheses of specific compounds which fit into class structure 6a are compounds 6i', 6j' and 6k'. When compound 28a' was treated with chloromethoxymethane and stannic chloride in chloroform, the tetra-substituted compound 6i' was produced. Acetolysis of 6i' followed by reduction of the tetraacetate with lithium aluminum hydride gave 6j'. Treatment of 6i' with sodium thiolacetate in tetrahydrofuran produced tetraacid, 6k'.

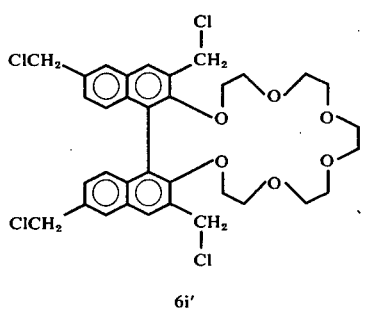

6i'

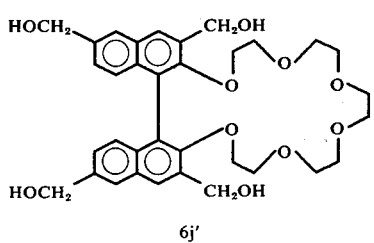

6j'

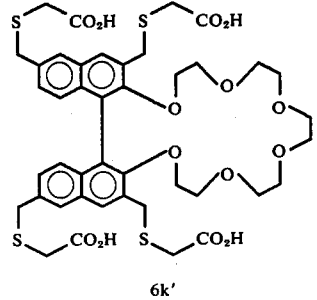

6k'

The large ring systems of compounds II were prepared in stepwise fashion. Ditosylates 75 and 76 were employed as key intermediates. Ditosylate 75 is the same as 1a. Ditosylate 76 was prepared from catechol the same way 75 was prepared from 1. Compound 75 with catechol, o-mercaptophenol or o-dimercaptobenzene, with two moles of sodium hydroxide in a solvent such as butanol gave macrocycles 77, 78, and 79, respectively. Alternatively 77 was constructed from 76 and 1.

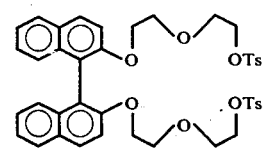

75 (same as 1a)

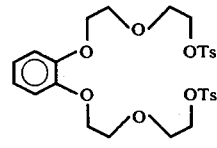

76

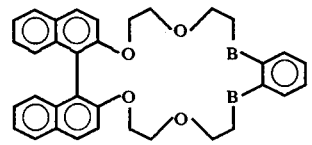

77, B=B=O
78, B=O, B=S
79, B=B=S

Illustration of the way compounds were prepared in which two sulfur atoms are attached directly to the binaphthyl group involves the reaction of 76 with 1c' and base. The product was 79a'. With similar procedures, the compounds of the I series could also be prepared with two sulfurs as part of the macrocycle attached to the binaphthyl unit.

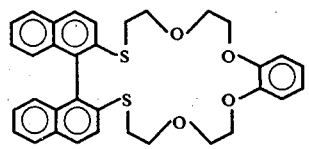

-continued

79a'

Substituents X and Y on the binaphthyl units of II are introduced as they are in I. Substituents X and Y on the benzene unit similarly can be introduced.

This produces 77a.

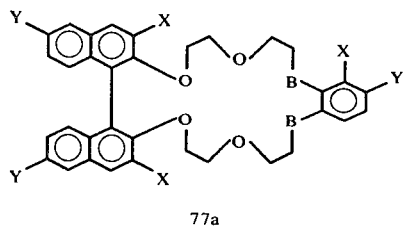

77a

Alternative routes are available for the synthesis of compounds II with substituents X or Y on the benzene ring in place, and modifiable. For example, treatment of ditosylate 75 with 3-propenylcatechol gave macrocycle 80, and with 4-(3'-hydroxypropyl)catechol gave 81. These compounds served as starting materials for compounds 82–88. Ozonolysis of 80 gave aldehyde 82, reduction of which

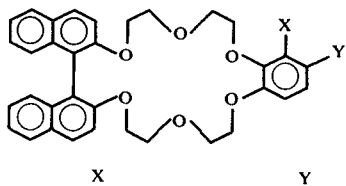

| | X | Y |
|---|---|---|
| 80 | CH=CHCH$_3$ | H |
| 81 | H | (CH$_2$)$_3$OH |
| 82 | CHO | H |
| 83 | CH$_2$OH | H |
| 84 | CH$_2$Cl | H |
| 85 | CH$_2$N$_3$ | H |
| 86 | CH$_2$NHCOCH$_3$ | H |
| 87 | H | (CH$_2$)$_3$Cl |
| 88 | H | (CH$_2$)$_3$CO$_2$H |

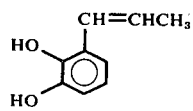

3-Propenylcatechol

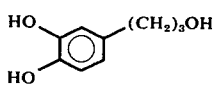

4-(3'-Hydroxypropyl)catechol with lithium aluminum hydride gave 83. Treatment of 83 with thionyl chloride gave 84, which with sodium azide gave 85, which upon reduction with lithium aluminum hydride and acetylation of the amine produced gave amide 86. Macrocycle 81 with thionyl chloride gave 87, whose Grignard reagent when carbonated gave 88.

In the above compounds, insertion of X and Y substituents on the binaphthyl unit as described above leads to the fully substituted structure 77b. In the above reactions involving

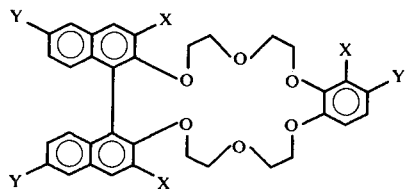

77b ditosylate 75, ditosylate 19a can be substituted to form II where $n=2$ and $m=(0,0)$, (0,0), i.e. 90a and 90b.

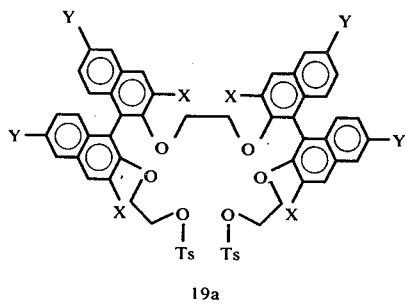

19a

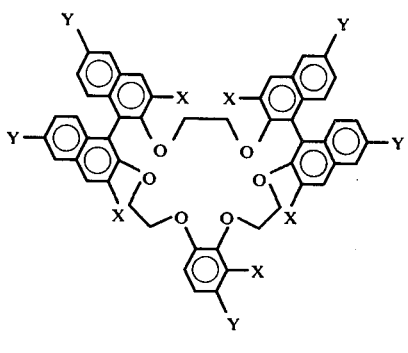

90a

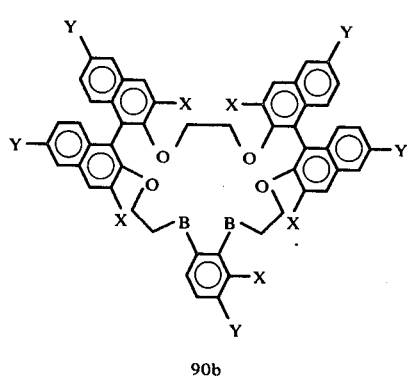

90b

ROLES PLAYED BY STRUCTURAL PARTS OF THE MULTIHETEROMACROCYCLES

The distinctive properties and uses of I and II derive from their unusual ability to complex both simple organic and inorganic entities. Each characteristic part of the host molecule plays a role in selecting and binding guest entities. The hydrocarbon parts give shape to the cavity of the host, both in a general and a sterochemical sense. For example, the binaphthyl unit is asymmetric, and is optically stable in the multiheteromacrocycles of this invention at working temperatures. Thus the cavities are chiral, and have the ability to complex selectively with enantiomers of racemates of certain classes of compounds. This property is referred to as chiral recognition. The binaphthyl units provide hinges that allow the diameter of the hole to accommodate somewhat to the size of the guest entity. The size of the cavity is grossly varied by changes in values of $m$ and $n$ in I and II as described above, thus providing further tailoring of the host to the dimensions of the guest entity. The ether oxygens and B units contain unshared pairs of electrons that stabilize electrostatically the guest entities, many of which are positively charged. The oxygen and B units and their attached methylenes provide the scaffold that partially embraces the guest entities. The X substituents other than hydrogen act as arms attached to the rigid hydrocarbon units, and the term "arm" is used herein in that sense. They are oriented along side, above or below the cavities of the host molecules. These arms provide further shape to the cavities. Except for the alkyl groups the arms are terminated with functional groups that act as additional complexing sites to bind guest to host. These functional groups can carry charges to neutralize the charge of guest entities. The X substituents can also play a steric role in extending the chiral barrier, and in inhibiting complexation with unwanted guest entities. The Y substituents aside from hydrogen can tie the host molecule to a solid support such as by grafting to polymers as described above, by copolymerization, or by direct polymerization. They can also be used to regulate molecular weight, lipophilicity-hydrophilicity relationships and solubility.

The compounds claimed in this application, i.e. I and II are host molecules, capable of complexing in a structurally definable sense, guest molecules or ions. The first family of uses involves complexation by I and II of primary alkyl- and arylammonium salts, aminoacids, aminoesters, aminoamides, aryldiazonium salts, aryloxycarbonium salts, sulfoxides, alcohols, aldehydes and ketones. The compounds I and II are especially useful in resolving aminoesters, amine salts and aminoacids and the like that contain chiral elements. When resolved by differential complexation with optically pure host molecules of established absolute configuration, the optical purity and absolute configuration of guest molecules can be determined. Conversely, the host molecules can be optically resolved by differential complexation with optically active guest molecules. When resolved with guest molecules of established absolute configuration, the optical purity and absolute configuration of host molecules can be determined. Host-guest configurationally complementary relationships for differential complexation frequently can be predicted and verified from examination of their CPK molecular models. The complexes are held together by hydrogen bonds, ion pairing and ion-dipole interactions.

Structures 91 and 92 exemplify diastereomerically related complexes in which little chiral recognition is expected. Thus interchange of the positions of L (large group) and M (medium sized group) in the guest produces little difference in steric compatibility between host and guest. The asymmetric carbon of the guest molecule is free to rotate to seek the lowest energy conformation for each diastereomeric complex, with the small group (S) oriented toward the chiral barrier as drawn.

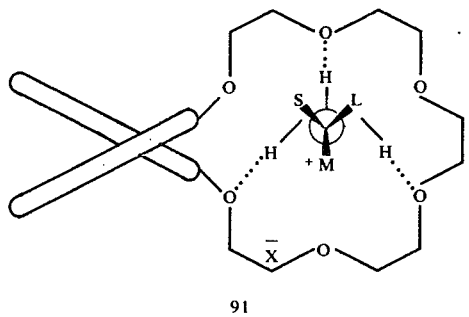

91

Diastereomeric complex (looking down C-N bond) between monolocular system (S)-6 and generalized alkylammonium salts of configuration

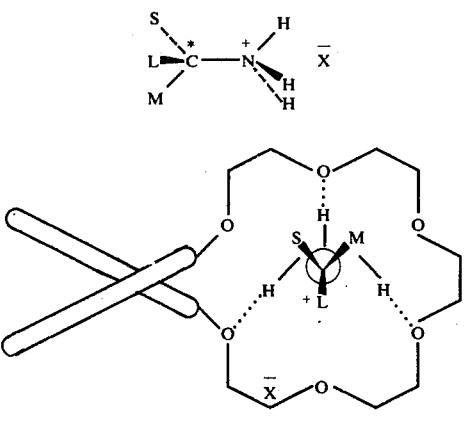

92

Diastereomeric complex (looking down C-N bond) between monolocular system (S)-6 and generalized alkylammonium salts of configuration Structures 93 and 94 exemplify diastereomerically related complexes of a monolocular system in which substantial chiral recognition is expected and observed. Both host and guest entities contain carboxyl groups that hydrogen bond one another to form more structured entities than with 91 and 92. As a result, in diastereomer 93, the S group is close to the chiral barrier, but has adaquate room. In diastereomer 94, the L group is close to the chiral barrier, and the room is less adaquate. Thus diastereomer 93 was found to be more stable than 94. The fact that host and guest are bound to one another at two general sites ($\overset{+}{N}H_3$ to 0's of cycle and

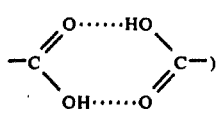

provides only one conformation for each diastereomer. The attraction of $CO_2^-$ for $\overset{+}{N}H_3$ provides a third binding feature of a less structuring variety. Notice (S)-30 possesses a $C_2$ axis, and hence it does not matter which of its two faces is complexed.

same structure. The presence of one side chain that placed a counterion for the ammonium cation under the hole would increase the complexing ability, but not the chiral recognition. The complexing ability of systems can be adjusted by the absence or presence of the counterion in the host molecule.

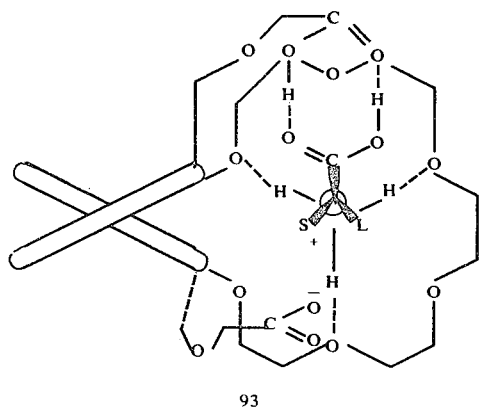

93

Favored diastereomeric complex between monolocular system (S)-30 and generalized α-aminoacids of configuration

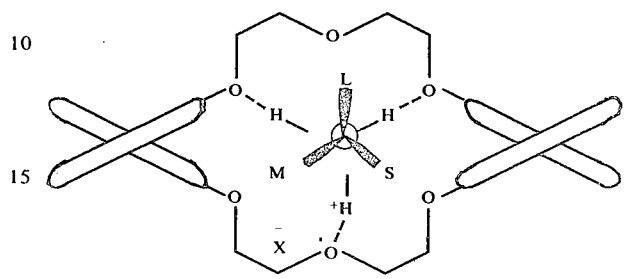

95

Favored diasteromeric complex between dilocular system (SS)-8 and generalized chiral alkylammonium salt of configuration

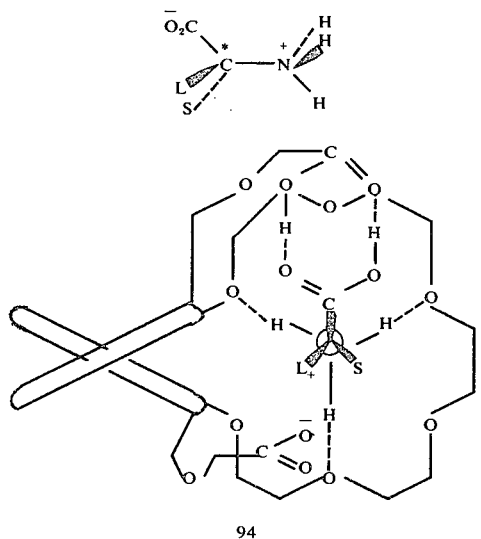

94

Disfavored diastereomeric complex between monolocular system (S)-30 and generalized α-aminoacid of configuration Introduction of two binaphthyl units of the same configuration into a multiheteromacrocycle produces a chiral dilocular system containing two chiral cavities. The dilocular feature provides substantial chiral recognition in molecular complexing of enantiomeric primary alkyl-ammonium ions. One diastereomeric complex has a complementary fit of cavity shape to L, M and S, and the other has a non-complementary fit. These relationships are illustrated with three dilocular systems, 95–96, 97, and 98. In 97, the $CH_3$ groups act only as a means of extending the chiral barrier of the binaphthyl units, and accentuate the chiral recognition by decreasing the space available for L, M and S. All three dilocular hosts formulated contain $C_2$ axes, and therefore complexation at either face products the

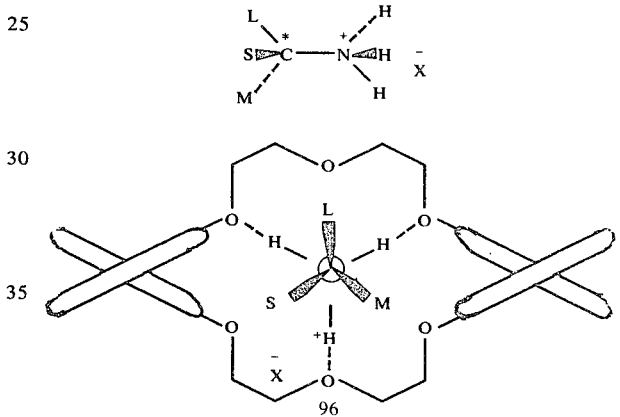

96

Disfavored diastereomeric complex between dilocular system (SS)-8 and generalized chiral alkylammonium salt of configuration

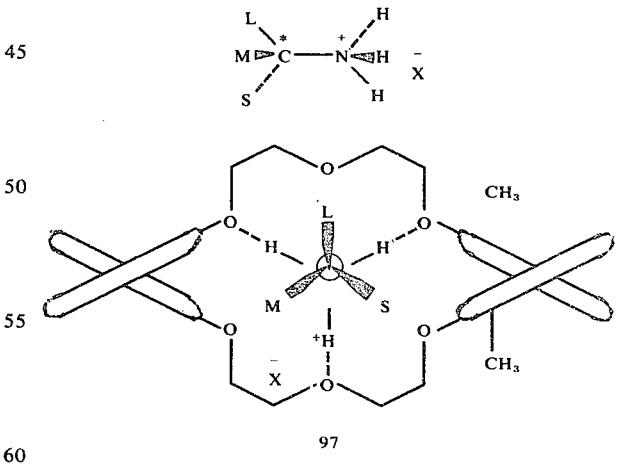

97

Favored diastereomeric complex between dilocular system (SS)-48c' and generalized chiral alkylammonium salt of configuration

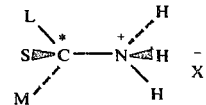

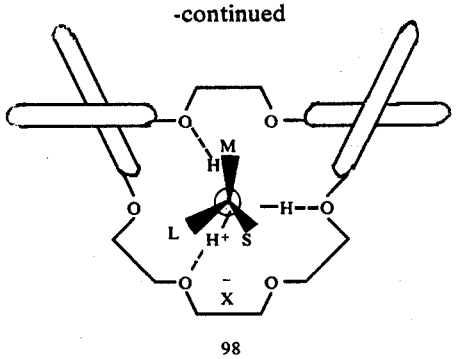

Favored diastereomeric complex between dilocular system (SS)-12 and generalized chiral alkylammonium salt of configuration

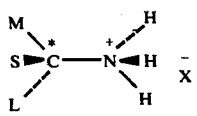

When aminoesters complex with dilocular systems of which 8 is the prototype, two kinds of complexes are possible. One kind resembles 95 or 96, in which three hydrogen bonds only hold to guest. In the second kind, the carbonyl group of the ester is attracted by one of the more basic ($CH_2OCH_2$) oxygens by a dipole-dipole interaction, which provides a fourth binding site. Formulas 95a and 95b depict the four-point binding diastereomeric complexes. In these complexes, $CO_2CH_3$ is the M group of 95 and 96. In comparisons of 95 and 95a, steric effects are pitted against electronic effects, and the relative stabilities of the two diastereomeric complexes depend on the acid-base relationships of host and guest, as well as on the sizes of S and L. Examples will be sited in Detailed Description of Invention in which with one aminoester, 95 was the more stable, and with another aminoester, 95a was the more stable.

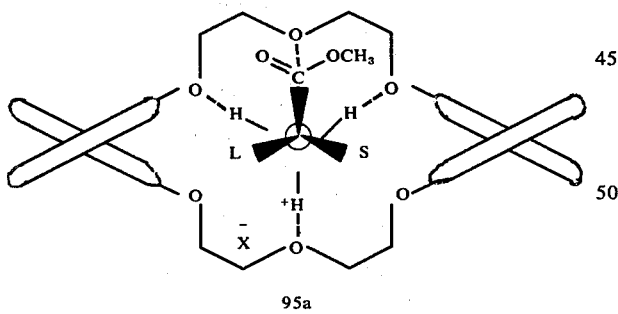

95a

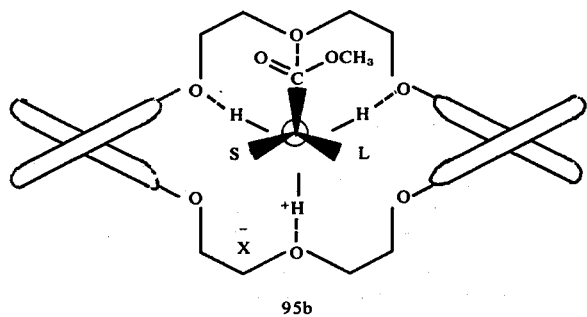

95b

Introduction of three binaphthyl units into a multiheteromacrocyle divides the available space above and around the hole into three cavities to give trilocular systems. When all three binaphthyl units possess the same configuration, the three cavities are equally sized (M'), but are chiral. If two of the binaphthyl units possess one configuration and the third the opposite, then the available space is divided into a large (L'), a medium (M'), and a small cavity (S'). Chiral trilocular system (SSS)-15 possesses three $C_2$ axes, and one $C_3$ axis (perpendicular to th oxygen's plane, 120° rotation gives

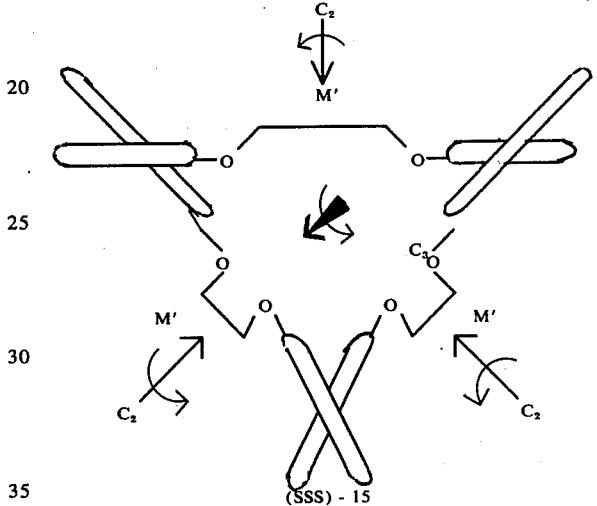

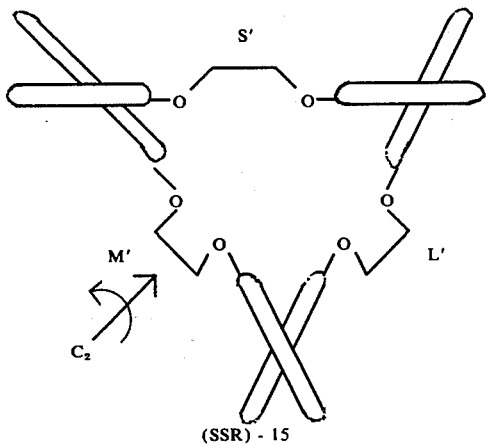

a superimposable structure) to give overall $D_3$ symmetry. Chiral trilocular system (SSR)-15 possesses a $C_2$ axis. Both systems present the same faces to potential guest molecules. System (SSS)-15 possesses chiral recognition properties for primary amine salts whose asymmetric center is β to the ammonium group. Structure 99 formulates the preferred diastereomeric complex. System (SSR)-15 possesses chiral recognition for primary amine salts whose asymmetric center is α to the ammonium group. Structure 100 formulates the preferred diastereomeric complex.

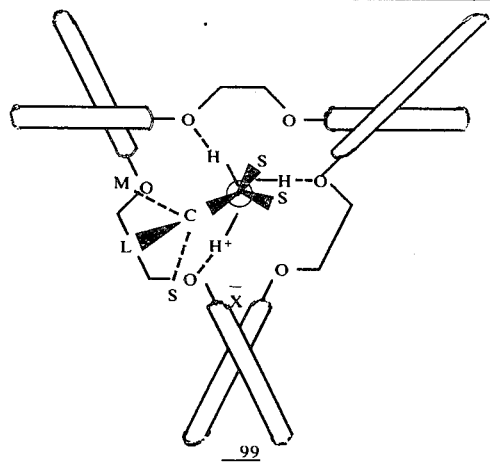

Favored diastereomeric complex between trilocular system (SSS)-15 and generalized chiral alkylammonium salt with a β-asymmetric center of configuration

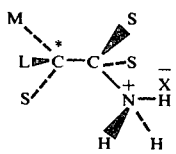

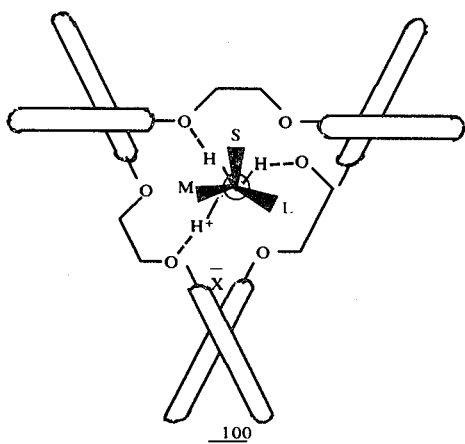

Favored diastereomeric complex between trilocular system (SSR)-15 and generalized chiral alkylammonium salt with an α-asymmetric center of configuration

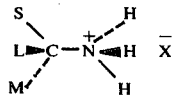

Chiral recognition can and has been used to resolve racemic multiheteromacrocycles into enantiomers with optically active primary amines, aminoesters or aminoacids, or to resolve racemic primary amines, aminoesters or aminoacids into enantiomers with optically active multiheteromacrocycles. The starting material that is optically active remains in phase A, and the two enantiomers to be resolved are distributed due to differential complexation between phase A and a second phase B. Phases A and B can be two immisible liquids, a solid and a liquid, a solid and a gas, or a liquid and a gas. When a solid phase is involved, the optically active resolving material might be covalently bound to, or complexed with a solid support such as a polymer. When the optically active resolving component is the macrocycle, the attachment to the solid support is through the remote Y groups. Complete resolution is accomplished by multiplate processes in which resolving agent and racemate are repeatedly exposed to one another. Thus liquid-liquid, liquid-solid, gas-liquid or gas-solid chromatographic processes can be used. These continuous processes can be preceeded with single plate experiments in which conditions are found to maximize chiral recognition. In the Detailed Description of the Invention, examples are given for the first complete resolution of a primary amine salt by an optically active macrocycle, and for the first complete resolution of a racemic macrocycle by an optically active aminoacid. The relative configurational relationships of the more stable diastereomers of the host-guest complexes are compatible with conclusions drawn from an examination of molecular models. These same principles can be applied to separations of diastereomers which differ in configuration at a center close to an amine, an aminoacid, an aminoester or an aminoamide functional group.

The complexing power of the alkylammonium ion increases as the acidity of that ion increases. The complexing power of the host molecules increases with increasing basicity of the oxygens. Aliphatic oxygens ($CH_2OCH_2$) are more basic than those bonded to aryl groups ($ArOCH_2$). Thus the monolocular systems are stronger complexers than the dilocular, and the dilocular are stronger complexers than the trilocular. With NH in place of O bound to aryl in host molecules, complexation power toward alkylammonium ion increases. With NH in place of O bound only to methylene (e.g. as in 8b′), the protons are transferred from guest to host, and the conjugate acid of the host molecule is intramolecularly hydrogen bonded. As a result, little complexation occurs.

Chiral recognition can and has been amplified by the device of arranging for it to occur in each of two equilibrating phases, but in opposite configurational directions. Pseudo-enantiomerically related multiheteromacrocycles are required whose remote Y groups differ so as to locate one exclusively in one phase, and the other in the other phase of the two phase system. For example, one pseudoenantiomer (through its Y group) can be bound to a solid support, whereas the other's Y group allows it to dissolve in the liquid phase to be used in contact with the solid phase. In a second example, one pseudo-enantiomer can have Y groups that permit it to dissolve only in a polar (e.g. water) phase, whereas the other pseudo-enantiomer has Y groups that solubulize it only in a non-polar (e.g. chloroform) phase, the two phases being immiscible.

Examples are as follows. Optically active (RR)-64a′ was prepared as a fine powder, and was packed into a chromatographic column. Its pseudo-enantiomer, (SS)-8, was dissolved in chloroform to act as a mobile phase for chromatographing apart the enantiomers of chiral alkylammonium salt. Thus (RR)-64a′ complexed preferentially and held to the solid stationary phase one enantiomeric salt, and (SS)-8 complexed preferentially and held in the liquid mobile phase the other enantiomeric salt. The preferred complexes are formulated as 95c′ and 95d′.

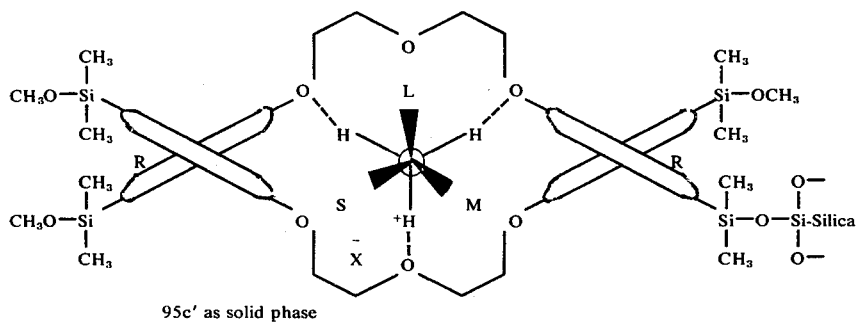

95c' as solid phase

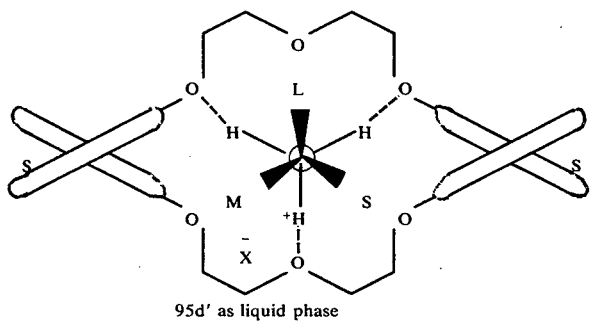

95d' as liquid phase

In a second example, optically active (SS)-67b' was prepared, and its lithium salt dissolved in water is essentially unextractable into chloroform. Its pseudo-enantiomer, (RR)-8, dissolved in chloroform, cannot be extracted into water. Racemic amine salts can be distributed between the aqueous and chloroform phases, and chiral recognition occurs in the opposite direction in each of the two phases. The preferred complexes are formulated as 95e' and 95f'.

type are complexed selectively. An example of scavenging by selective complexation of trace amounts of $Sr^{++}$ from bulk barium hydroxide by diacid 30 has been accomplished. The strontium complex (103) is more stable than either the calcium or barium complexes (102 and 104, respectively), a fact that correlates the ionic diameter of $Sr^{++}$ with the hole size of 30.

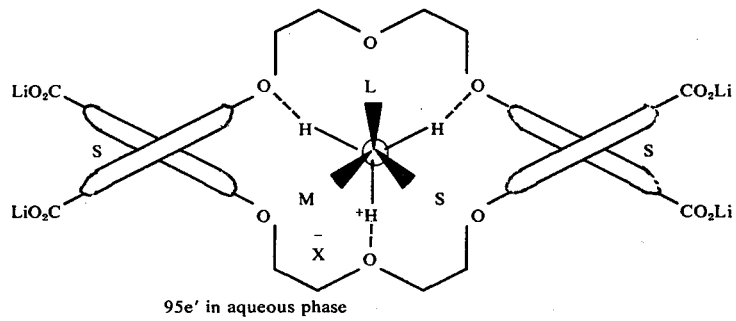

95e' in aqueous phase

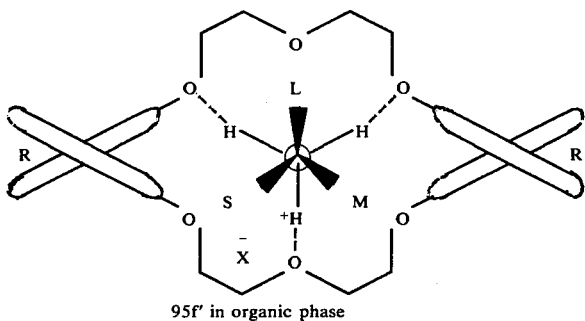

95f' in organic phase

The second family of uses involves selective complexation by I and II of metal cations. Depending on the size of the hole and the number of counterions in the host molecule, metal ions of different size and charge

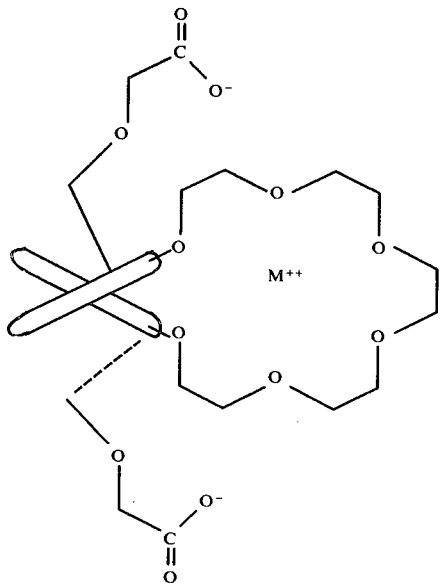

102, M = Ca
103, M = Sr
104, M = Ba

This is but an example of the versatile selective complexation of metals from an environment containing other metals having chemical and physical properties so similar that effective separation has heretofore been tedious and difficult if not impossible. Their use in scavenging metal components causing undesirable physiologic or catalytic effects is accomplished by referring to the properties of the candidate guest metal cations and selecting I or II having the appropriate values for the parameters.

The third family of uses of I and II involves their lipophilization of hydrophilic guest entities, e.g. some of I and II visibly dissolved crystalline potassium permanganate in benzene. Alkyl- and arylammonium salts and aryldiazonium salts, soluble per se only in water or water-alcohol mixtures, can be solubilized in chloroform, dichloromethane or ether using host molecules, I or II. Thus diazonium coupling or substitution reactions (Sandmeyer reactions) can be carried out in non-polar media. Aminoacids can be solublised in chloroform-acetic acid mixtures by appropriate host molecules. Aminoesters and aminoamide salts can be solublized in organic solvents. Barium ion complexed by two host entities (aminoacid 39) per barium ion was stable to chromatography on silica gel, and is soluble in chloroform. This complex (105) was so stable that BaSO₄ was not precipitated by addition of sulfuric acid to the complex dissolved in methanol-water. Potassium ion has been extracted from water into chloroform by aminoacid 39 to form complex 106. This lipophilization of metal, aryl- and alkylammonium ions allows them to pass through lipophilic membranes, and the ions delivered to places otherwise heretofore denied them. Applications include drug delivery, desalination, scavenging of toxic metal ion ($Sr^{++}$ from milk), fermentation aids, antielectrostatic agents, in separating and purifying organic compounds by differential extraction, and making homogeneous and therefore more efficient reactions that must otherwise be conducted heterogeneously.

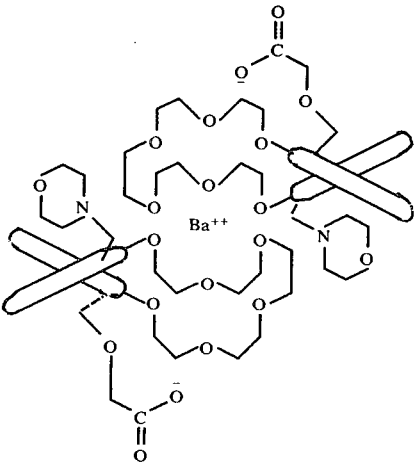

105

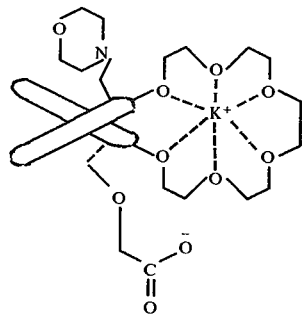

106

DETAILED DESCRIPTION OF THE INVENTION
EXPERIMENTAL

General. Racemic 2,2'-dihydroxy-1,1'-binaphthyl (1) was resolved as before [Tetrahedron Lett., 3617 (1971)] to give optically pure (+)-(R)-1, m.p. 207.5°–208.5°, $[\alpha]_D^{25}$ +34.1° (C 1.0, $(CH_2)_4O$), and (−)-(S)-1, m.p. 207°–208°, $[\alpha]_D^{25}$ −34.3° (C 1.0, $(CH_2)_4O$). The absolute configurations of these isomers are established (Tetrahedron, 27, 5999 (1971)) and are formulated in a conventional and a more illustrative form, which will be used here and elsewhere. Although optically stable at 100° for 24 hours as a solution in dioxane-water (−)-1 racemized 72% with HCl (~1.2 N) present in the same solution at 100° for 24 hours, and 69% in butanol-0.67 M in potassium hydroxide at 118° for 23 hours. The optical stability of 1 and of its derived products are important to some of their uses.

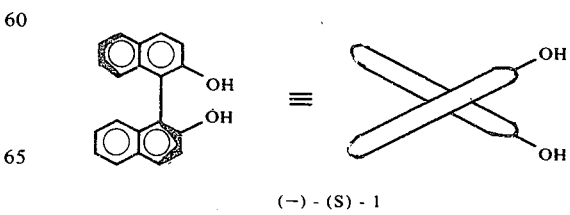

(−) - (S) - 1

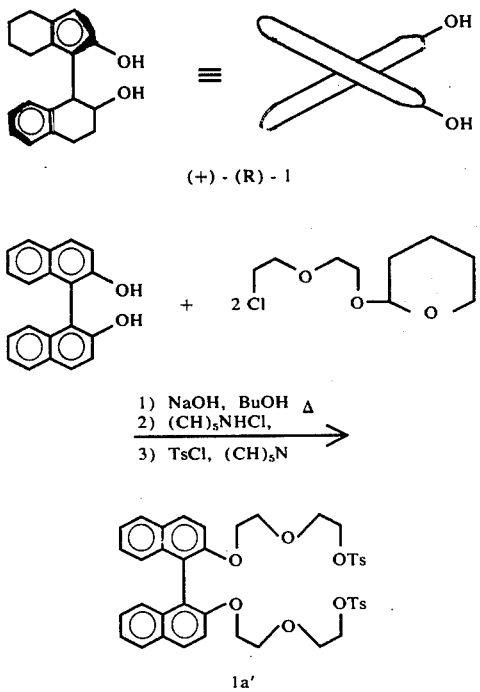

The preparation of racemic 1a' involved preparation of 2-(2'-chloroethoxy)ethyl 2''-tetrahydropyranyl ether, which was prepared as follows. To a stirred, boiling solution of 1.5 kg. (14.1 mol) of diethyleneglycol and 1.1 l. of pyridine in 4.8 l. of benzene was added 450 g. (4.1 mol) of thionyl chloride over a period of 16 hours. The reaction mixture was refluxed with stirring for 17 hours, cooled and the two layers were separated. The lower layer was distilled, first to remove the pyridine and then to collect the crude chloroalcohol, b.p. 95°–105° at 20 mm.

This material was dissolved in 1.5 l. of ether and extracted five times with 200 ml. portions of 3 N hydrochloric acid. The resulting solution was dried, concentrated, and the residue was distilled under vacuum to give 215 g. (42% based on thionyl chloride) of 2-(2'-chloroethoxy)ethanol, b.p. 55°–60° at 5 mm. To 200 g. (1.61 mol) of this chloroalcohol was added 202 g. of dihydropyran and one drop of concentrated hydrochloric acid, whereupon an immediate exothermic reaction occurred. The reaction mixture was allowed to stand for 1 hour, and enough tribenzylamine was added to raise the pH from 5 to 6.5. The resulting solution was distilled under vacuum to give 322 g. (96%) of the tetrahydropyranyl ether as a colorless liquid, b.p. 87°–88° at 0.5 mm.

Anal. Calcd for $C_9H_{17}ClO_3$: C, 51.79; H, 8.21. Found: C, 51.70; H, 8,32.

Intermediate 1a' was prepared as follows. A solution of 120 g. (575 mmol) of 2-(2'-chloroethoxy)ethyl 2''-tetrahydropyranyl ether in 700 ml. of butanol was added (15 min.) to a stirred, boiling mixture of 60 g. (0.217 mol) of binaphthol 1 and 20 g. (0.500 mol) of sodium hydroxide in 700 ml. of butanol. The resulting mixture was stirred and refluxed for 10 hours (pH 7–8), and then 6.0 g. (0.15 mol) more of sodium hydroxide and 60 g. (0.278 mol) of the chloroether in 100 ml. of butanol was added. The mixture was stirred at reflux for an additional 10 hours. The procedure was repeated with 6.0 (0.15 mol) of sodium hydroxide and 20 g. (0.096 mol) of the chloroether in 50 ml. of butanol, and a 15 hour reflux period. The reaction mixture was cooled, filtered, and the filtrate was concentrated under vacuum, ultimately at 150° at 50μ to remove the excess chloroether. The residue (140 g.) was heated to 100° and 5 g. (0.044 mol) of pyridine hydrochloride was added. The resulting mixture was heated at 190° at 50μ with stirring for 2 hours to give, upon cooling, 98.3 g. of a light brown glass (diol precursor to 1a'). A solution of 104 g. (0.545 mol) of tosyl chloride in 300 ml. of dry pyridine at 0° was added to 98.3 g. (0.210 mol) of this diol dissolved in 400 ml. of dry pyridine at 0°. The reaction mixture was allowed to stand at 0° for 24 hrs., poured onto 2 Kg of ice water and stirred for 2 hours. The mixture was extracted with 2 l. portions of dichloromethane. The extracts were combined, washed with two 1 l. portions of cold 6 N hydrochloric acid, and 100 ml. of brine, and dried. The solvent was evaporated to give 138 g. of a brown glass which was chromatographed on 2 Kg of silica gel with chloroform as eluent. Elution with 4 l. of solvent brought 6 g. of material off the column which was discarded. Elution with an additional 16 l. of solvent gave upon evaporation ditosylate 1a', which was pure by tlc. The material was film dried at 105° at 50μ for 24 hours to give 101 g. (63% based on 1) of 1a'. The 100 MHz pmr spectrum in $CDCl_3$ gave signals at δ 7.7 (m, ArH, 8H), 7.2 (m, ArH, 12H), 3.95 (m, $CH_2$, 4H), 3.61 (m, $CH_2$, 4H), 3.30 (m, $CH_2$, 4H), 2.95 (m, $CH_2$, 4H) and 2.35 (s, $CH_3$, 6H).

Anal. Calcd for $C_{42}H_{42}O_{10}S_2$: C, 65.44; H, 5.49. Found: C, 65.64; H, 5.36.

A somewhat different procedure was applied to the synthesis of (−)-(S)-1a'. To a solution of 50.0 g. of optically pure (−)-(S)-1, $[\alpha]_D^{25}$= −34.0° (C 1.0, $(CH_2)_4O$), in one liter of dry dimethylformamide was added 19.5 g. of sodium hydride (50% oil dispersion). The mixture was heated to 70° with stirring under nitrogen. After one hour, 2-(2'-chloroethoxy)-ethyl 2''-tetrahydropyranyl ether (see above for synthesis) 83.2 g, was added. The reaction mixture was stirred at 70° for 48 hours under nitrogen, cooled, and shaken with 2 liters of water. The mixture was extracted with dichloromethane, and the combined organic layers were washed with water, dried and evaporated. The residue in 1:1 pentane-dichloromethane was filtered through 250 g. of basic alumina, which was washed with additional solvent. The eluant was concentrated, and the oil was dissolved in 300 ml. of dichloromethane to which was added 150 ml. of methanol and 10 ml. of concentrated hydrochloric acid. The solution was stirred for 1 hour at 25°, neutralized with aqueous $NaHCO_3$, and the organic layer was separated and combined with dichloromethane washes of the aqueous layer. The organic layer was dried, evaporated, and the oil was washed with pentane to remove the mineral oil. The oil was dried at 90° at 0.1 mm to give 57.4 g. (70%) of diol as a gum. This material, 31.7 g., in 300 ml. of dry pyridine was cooled to −20°, and 30.0 g. of tosyl chloride was added in small portions during 15 minutes, during which time and for an additional 1.5 hours the mixture was cooled and stirred. After standing at −20° for 24 hours, the mixture was stirred into 1000 g. of ice. The water was decanted, and the residual oil was shaken with dichloromethane and 10% aqueous hydrochloric acid. The organic layer was washed with the same acid, then with 10% aqueous $NaHCO_3$, and water. The solution was dried, evaporated at 25° under vacuum, and dried at 0.01 mm (25°) to give 41.5 g. (80%) of (—)-(S)-1a as a gum. This material possessed a pmr (100 MHz) spectrum identical to racemic 1a (see above).

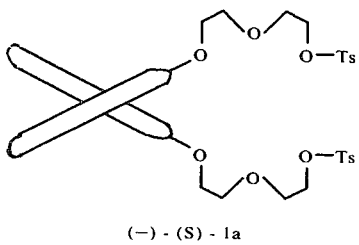

(—) - (S) - 1a

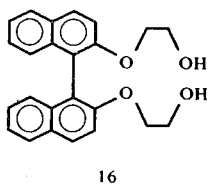

16

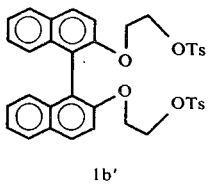

1b'

Ditosylate 1b' and diol 16 (see Example 3, Procedure 2) were prepared as follows. Liquid ethylene oxide (30 ml.) was added to a stirred slurry of 28.7 g. of racemic 1 and 18 g. of anhydrous potassium carbonate held at —20° under nitrogen. Over a period of 2 hours, the reaction mixture was warmed gradually to 90°, where it was held for 16 hours. The excess ethylene oxide was allowed to evaporate during this period. The product was cooled, mixed with ice and dilute hydrochloric acid, and collected. The filter cake was washed with water, dissolved in 250 ml. of dichloromethane, and the solution was washed with 4 portions of 100 ml. of 4N aqueous NaOH, and once with brine. The solution was dried, evaporated, and the residual oil was crystallized from benzene and cyclohexane to give 34.5 g. (92%) of 16, m.p. 101°–104°, whose pmr (60 MHz) spectrum was identical to that of material reported in Example 3, Procedure 2. This diol (9.0 g.) was ditosylated by the same procedure used to prepare 1a (see above). The crude product was recrystallized from methanol to give 13.6 g. (86%) of 1b', m.p. 130.5°–131.5°. The pmr (60 MHz) of 1b' in CDCl₃ gave the following signals: δ 2.33 (s, ArCH₃, 6H), 4.10 (m, OCH₂, 8H), 7.0–8.0 (m, ArH, 20H).

Anal. Calcd for $C_{38}H_{34}O_8S_2$: C, 66.84; H, 5.02, Found: C, 66.70; H, 5.15.

Dithiol 1c' was prepared by a procedure modeled after that for converting phenols to thiophenols [J. Org. Chem., 31, 3980 (1966)]. To a stirred solution under nitrogen of 60 g. of 1 in 450 ml. of dry dimethyl formamide at 0° was added (2 hr) 20.2 g. of a 50% dispersion of sodium hydride in mineral oil. To the resulting mixture was added 52 g. of N,N-dimethylthiocarbamoyl chloride. The stirred mixture was warmed over an hour period to 85°, and after an hour at 85° the slurry was cooled and shaken with 1500 ml. of 1% KOH in water. The solid that separated was collected, dried at 25°, and recrystallized from benzene-cyclohexane to give 83.5 g. (86%) of O,O-bis(N,N-dimethylthiocarbamoyl)-1,1'-binaphthol, m.p. 208°–209.5°, molecular ion in mass spectrum (70 ev), m/e = 460.

Anal. Calcd for $C_{26}H_{24}O_2S_2N_2$: C, 67.79; H, 5.25. Found: C, 68.01; H, 5.07.

The above material, 75.3 g., was heated at 280° for 40 min. A high boiling liquid refluxed. The melt was cooled, dissolved in 500 ml. of chloroform, and chromatographed through a silica gel column. The column was washed with 4 liters of chloroform, and the desired product eluted with 7 liters of 1%-methanol-99%-chloroform. Evaporation of this eluate and crystallization and recrystallization of the residue from chloroform gave 30.5 g. (40%) of bis-(N,N-dimethyl-S-aryl-thiocarbamoyl)-binaphthol, m.p. 245°–247°, mass spectral molecular ion (70 ev) m/e = 460.

Anal. Calcd for $C_{26}H_{24}O_2S_2N_2$: C, 67.79; H, 5.25. Found: C, 67.74; H, 5.24.

A slurry of 18.9 g. of this material in 500 ml. of methanol was refluxed under nitrogen for 0.5 hr. A 10% sodium hydroxide solution (100 ml, oxygen-free) was added (0.5 hr), and the mixture was refluxed under nitrogen for an additional 9 hr, cooled and concentrated. The solid produced was dissolved in 250 ml. of oxygen-free water, washed with dichloromethane, acidified carefully with 15 ml. of concentrated sulfuric acid, crystallized, collected, and dried. This material was recrystallized twice from benzene to give 7.1 g. (55%) of white 1c', m.p. 152.5°–153.5°, pmr (60MHz, CDCl₃) δ, 7.95–6.85 (m, ArH, 12H), 3.2 (s, SH, 2H).

Anal. Calcd for $C_{20}H_{14}S_2$: C, 75.43; H, 4.43. Found: C, 75.38; H, 4.31.

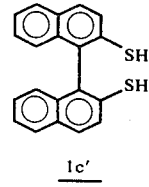

1c'

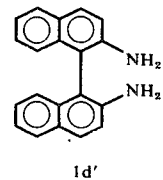

1d'

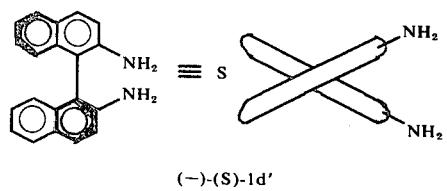

(—)-(S)-1d'

Racemic 1d' was resolved with d-10-camphorsulfonic acid [Ann. Chem., 470, 183 (1927)] to give (+)-(R)-1d', m.p. 243°–244°, $[\alpha]_D^{25}$ +157° (c 3.8, pyridine), and (—)-(S)-1d', m.p. 243°–244°, $[\alpha]_D^{25}$ —156° (c 4.0, pyridine)[see these references for comparable properties, J. Amer. Chem. Soc., 63, 923 (1941); ibid., 90, 4561 (1968)]. The absolute configurations of these substances have been determined [*J. Amer. Chem. Soc.*, 80, 480 (1958); ibid. 80, 2027 (1958); *Angew. Chem.*, 70, 683 (1958); *Tetrahedron*, 27, 5999 (1971)].

Racemic 3,3'-dicarboxy-2,2'-dihydroxy-1,1'-binaphthyl (2) was resolved as before (*Rec. Trav. Chim.*, 48, 1035 (1929); *Helv. Chim. Acta* 27, 1648 (1944); *J. Appl. Chem.*, London, 2, 565 (1952)), and the enantiomers brought to optical purity. Enantiomer (−)-(S)-2 gave m.p. >285°, $[\alpha]_{578}^{25}$ −198° (C 1.1, $(CH)_5N$), (+)-(R)-2 gave m.p. >285°, $[\alpha]_{578}^{25}$ +195° (C 1.1, $(CH)_5N$). The absolute configurations of these isomers are established (*Tetrahedron*, 27, 5999 (1971)), and are formulated both in a conventional and a more illustrative form, which will be used here and elsewhere.

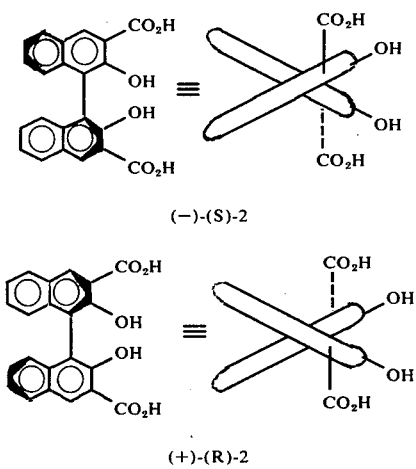

(−)-(S)-2

(+)-(R)-2

Throughout this Experimental, the multiheteromacrocycles will be referred to by formula and by individual compound number. The numbering system is consistent throughout. The systematic names of the individual multiheteromacrocycles are too complicated and arbitary to be of practical use. Temperatures herein are in degrees C.

EXAMPLE 1

Preparation of Cycles with One Binaphthyl Unit.

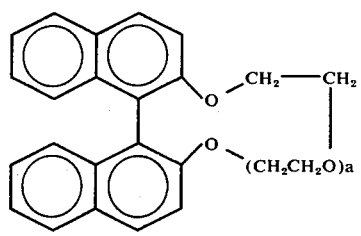

| | |
|---|---|
| 3, | a=0 |
| 4, | a=1 |
| 4a', | a=2 |
| 5, | a=3 |
| 6, | a=4 |
| 7, | a=5 |

-continued

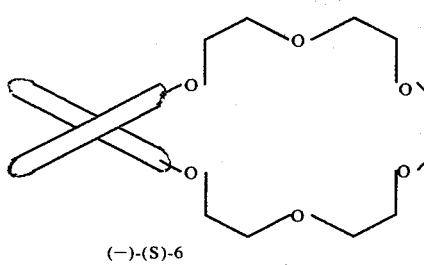

(−)-(S)-6

Procedure 1

The procedure is illustrated with the preparation of (−)-(S)-6. Potassium t-butoxide (2.36 g., 21 mmole) was added to a stirred solution under nitrogen of 3.00 g. (10.5 mmol) of optically pure (−)-(S)-1 (the binaphthol, see above) dissolved in 140 ml. of pure tetrahydrofuran. To the resulting suspension was added 5.72 g. (10.5 mmol) of pentaethyleneglycol ditosylate. (This ditosylate was prepared from pentaethyleneglycol, b.p. 149°–151° at 0.03 mm, and tosyl chloride and pyridine by conventional methods). The mixture produced was heated at reflux for 5 hours, and evaporated under reduced pressure. The residue was shaken with water and dichloromethane, and the organic layer was washed with brine and dried with magnesium sulfate. Evaporation of the solvent gave 6.1 g. of pale brown oil which was absorbed on 23 g. of alumina and placed on the top of a chromatograph column prepared from a slurry of alumina and ether. The (−)-(S)-6 was eluted with ether, and evaporation of the eluate gave a colorless oil, which was dried as a foam for 24 hours at 35° and 0.07 mm, wt. 3.1 g., 64%. The proton magnetic resonance (pmr) spectrum ($CDCl_3$, 100 MHz) gave signals at δ 7.83 (m, aromatic, 4H), 7.26 (m, aromatic, 8H), 4.04 (m, $ArOCH_2$, 4H) and 3.5 (complex m, $CH_2OCH_2$, 16H). The base peak in the mass spectrum (70 ev) was the molecular ion, m/e 488.

Anal. Calcd for $C_{30}H_{32}O_6$: C, 73.76; H, 6.60. Found: C, 73.62; H, 6.45.

The optical rotation of (−)-(S)-6 was $[\alpha]_{546}^{25}$ −89.8° $[\alpha]_D^{25}$ −70.5° (C 1.0, $(CH_2)_4O$). When dissolved in oxygen-free diethyleneglycol and heated in a sealed tube at 205°, the compound underwent 0% rotational loss in 6 hours, and 9% in 202 hours. When the above preparation of (−)-(S)-6 was carried out at 25° for 16 hours, a 52% yield of product of identical physical properties was obtained. Clearly, both 1 and 6 were optically stable to both sets of reaction conditions.

Racemic 6 was similarly prepared from reacemic 1 in 60% yield, m.p. 130°–130.5°.

Anal. Calcd for $C_{30}H_{32}O_6$: C, 73.75; H, 6.60. Found: C, 73.88; H, 7.76.

Optically pure (−)-(S)-4a' was prepared similarly from (−)-(S)-1 and triethyleneglycol ditosylate (m.p. 81°–82°) in 65% yield as a gum, molecular ion (70 ev),, m/e = 400, $[\alpha]_{589}^{25}$ −127° (C 0.91, $CHCl_3$).

Anal. Calcd for $C_{26}H_{24}O_4$: C, 78.00; H, 6.00. Found: C, 78.04; H, 5.96.

Optically pure (−)-(S)-5 was prepared (52%) similarly from (−)-(S)-1 and tetraethyleneglycol ditosylate as a gum, $[\alpha]_{589}^{25}$ −63°, $[\alpha]_{578}^{25}$ −67° (C 1.89, $CHCl_3$).

Anal. Calcd for $C_{28}H_{28}O_5$: C, 75.68; H, 6.31. Found: C, 75.75; H, 6.31.

Racemic 5 was similarly prepared from racemic 1 and tetraethyleneglycol ditosylate in 45% yield, m.p. 107°–108.5°.

Anal. Calcd for $C_{28}H_{28}O_5$: C, 75.68; H, 6.31. Found: C, 75.82; H, 6.28.

Racemic 7 was similarly prepared from racemic 1 and hexaethyleneglycl ditosylate in 48% yield, oil.

Anal. Calcd for $C_{32}H_{36}O_7$: C, 72.16; H, 6.81. Found: C, 72.04; H, 6.87.

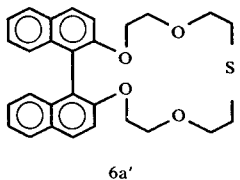

6a'

Procedure 2

This procedure is illustrated by the preparation of racemic 6a'. A solution of 1.25 g. of racemic ditosylate 1a in 400 ml. of 1-butanol and 40 ml. of dioxane was stirred under nitrogen at reflux, and 0.391 g. of disodium sulfide nonahydrate in 15 ml. of distilled water and 100 ml. of 1-butanol was added. The mixture was refluxed under nitrogen for 17 hours, concentrated under reduced pressure, and the residue was triturated with chloroform. The mixture was filtered, the filtrate evaporated, and chromatographed on 200 g. of silica gel. Product was eluted in fractions 10–14 of 100 ml. each of 2% ethyl acetate-98% chloroform to give after recrystallization from methanol, 0.386 g. (52%) of 6a', m.p. 125°–127°. A recrystallized sample gave: m.p. 127°–128°; pmr spectrum (60 MHz) in $CDCl_3$, δ 8.0–7.7 (m, Ar, 4H), 7.5–7.0 (m, ArH, 8H), 4.5–3.8 (m, ArOCH$_2$, 4H), 3.8–3.3 (m, ROCH, 8H), 3.0–2.1 (m, SCH$_2$, 4H); mass spectrum molecular ion (70 ev) m/e = 460.

Anal. Calcd for $C_{28}H_{28}O_4S$: C, 73.01; H, 6.13. Found: C, 72.97; H, 5.98.

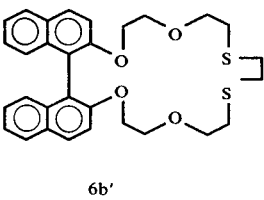

6b'

Procedure 2 is further illustrated by the preparation of racemic 6b'. To a solution of ditosylate 1a (10.0 g.) and 1,2-ethanedithiol (1.22 g.) in 800 ml. of tetrahydrofuran under nitrogen was added 1.04 g. of sodium hydroxide in 10 ml. of water. The mixture was refluxed for 40 hours, concentrated to 200 ml. and partitioned between 500 ml. of dichloromethane and 600 ml. of water. The layers were separated, and the aqueous phase was extracted with two 200 ml. portions of dichloromethane. The combined organic phases were dried, evaporated, and the residue was chromatographed on 150 g. of basic alumina. The column was washed with benzene (2 liters), 49:1 benzene-ether, 48:2 benzene-ether and 19:1 benzene-ether (2 liters each), 9:1 benzene-ether (3liters) to give 1.05 g. (16%) of 6b' in the final eluate, m.p. 85°–90°. Recrystallization of this material gave: m.p. 85°–90°; mass spectrum (70 ev) molecular ion, m/e = 520; pmr spectrum (60 MHz) in $CDCl_3$, δ 7.96–7.00 (m, ArH, 12H) and 4.30–2.30 (m, OCH$_2$, SCH$_2$, 2OH).

Anal. Calcd for $C_{30}H_{32}O_4S_2$: C, 69.22; H, 6.20. Found: C, 69.01; H, 6.12.

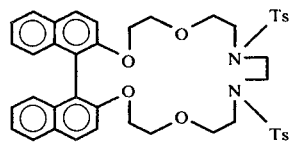

6c'

Procedure 3

Procedure 3 is illustrated by the synthesis of racemic 6c'. To a solution of N,N-ditosylethylenediamine (2.86 g, m.p. 69°–71°) in 75 ml. of dry dimethyl formamide was added 0.80 g. of sodium hydride (50% oil dispersion), and the solution was stirred for one hour. Ditosylate 1a (6.0 g) was added, and the solution was stirred at 50° for 20 hrs. under nitrogen. The solution was poured into 300 ml. of ice water, and the brown precipitate that separated was collected, washed with water and dried (6.4 g.). This material was chromatographed on 200 g. of silica gel, with 2.5% isopropyl alcohol in dichloromethane, as solvent. Fractions (175 ml. each) 6–11 provided 6c', which was recrystallized from acetonitrile-methanol to give 1.7 g. (20%) of a white powder as a solvate, m.p. 130°–202° (solvent was given off). This material after drying at 110° at 50μ gave a molecular ion in its (70 ev) mass spectrum, m/e 794, and a pmr spectrum (60 MHz, CDCl$_3$) as follows: δ 2.2 (s, CH$_3$Ar, 6H), 3.0–4.2 (m, CH$_2$, 20H), 7.0–8.0 (m, ArH, 20H).

Anal. Calcd for $C_{44}H_{46}N_2O_8S_2$: C, 66.48; H, 5.83. Found: C, 66.45; H, 5.81.

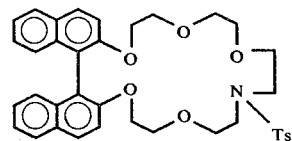

6d'

Compound 6d' was prepared from 1a and N-tosylethanolamine by the same procedure (Procedure 3) used to prepare 6c'. From 2.6 g of N-tosylethanolamine and 9.0 g of 1a was obtained 2.3 g. (31%) of 6d', m.p. 119°–170° (solvate from acetonitrile-methanol). After drying at 100° and 10μ, the material gave a molecular ion in its mass spectrum (70 ev), m/e = 641, and a 60 MHz pmr spectrum in CDCl$_3$: δ 2.4 (s, ArCH$_3$, 3H), 3.4 (m, CH$_2$, 16H), 4.1 (m, CH$_2$, 4H), 7.5 (m, ArH, 16H).

Anal. Calcd for $C_{37}H_{39}NO_7S$: C, 69.25; H, 6.13. Found: C, 69.44; H, 6.36.

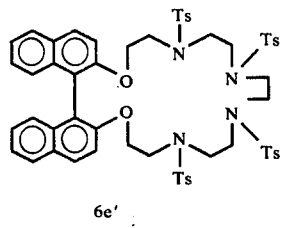

6e'

Procedure 3 is further illustrated by the preparation of racemic 6e'. A solution of 80 g of p-tosyl chloride in 300 ml. of dry pyridine was cooled to 0° and added to a cooled, stirred solution of triethylenetetramine (MCB, technical) in 50 ml. of dry pyridine over a period of 3 hr. The solution was kept at 0° during addition. The solution was allowed to stand at 0° for 24 hrs, and mixed with 100 ml. of concentrated hydrochloric acid and 1 kg. of crushed ice. The resulting aqueous solution was decanted, and the oily residue was triturated with methanol, filtered, and recrystallized twice from 50 ml. of dimethyl formamide and 300 ml. of 95% ethanol to give N,N',N'',N'''-tetratosyltriethylenetetramine, 28.8 g. (38%), m.p. 211°–213°. The analytical sample was dried at 180° for 14 hrs at 10μ.

Anal. Calcd for $C_{34}H_{42}N_4O_8S_4$: C, 53.52; H, 5.55. Found: C, 53.63; H, 5.76.

To a stirred solution of 7.63 g. of this tetratosylate in 100 ml. of dry dimethyl formamide under nitrogen was added 0.6 g. of sodium hydride (50% dispersion in hydrocarbon). After 0.5 hours, a solution of 6.51 g. of racemic ditosylate 1b' in 50 ml. of dry dimethyl formamide was added. The mixture was stirred at 25° for 3 hours, and then an additional 0.6 g. of sodium hydride dispersion was added. After 16 hours, the temperature was raised to 70° and held there for 9 hours. Finally the still basic mixture was cooled to 25° and mixed with crushed ice and 2N hydrochloric acid. The precipitate was collected, and washed throughly with water, pentane, and was dissolved in dichloromethane. The organic layer was washed with a 0.5M solution of sodium hydroxide in a 1:1 methanol-water solution four times, with water twice and dried. The solution was evaporated to give 6.6 g (60%) of crude product. This material was triturated with dichloromethane, filtered, and the filtrate was evaporated. The residue was extracted with 50 ml. of toluene and filtered. The residue (1.6 g.) was dissolved in 10 ml. of hot dimethyl formamide, the solution was filtered and diluted with 10 ml. of hot 95% ethanol. Product 6e' separated as colorless flakes, 1.26 g. (11%), m.p. 259°–261°. An additional 205 was recovered by reworking the various solutions and residues, m.p. 259°–261°. An analytical sample was dried at 180° for 10 hours at 10μ, and gave a mass spectrum (70 ev) with the molecular ion at m/e = 1100.

Anal. Calcd for $C_{58}H_{60}N_4O_{10}S_4$: C, 63.35; H, 5.50. Found: C, 63.31; H, 5.57.

The synthesis of (−)-(R)-6f' is described under Example 2, Procedure 3.

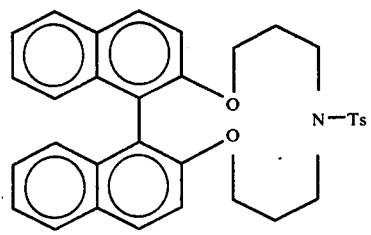

6f'

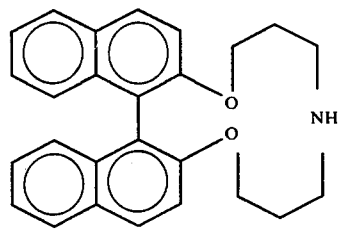

6g'

Procedure 3 is further illustrated by the preparation of racemic 6g'. Racemic 6f' was prepared in 42% yield from ditosylate 1b' and tosylamide with sodium hydride (added in two batches) as base, m.p. 239°–240° (from acetonitrilemethanol). The mass spectrum (70 ev) of the substance gave a molecular ion at m/e = 509, and the pmr spectrum (60 MHz) in CDCl$_3$ gave: δ 7.93–7.00 (m, ArH, 16H), 4.48 (m, CH$_2$O, 4H), 3.33 (m, CH$_2$NTs, 4H), 2.37 (s, ArCH$_3$, 3H).

Anal. Calcd for $C_{31}H_{27}NO_4S$: C, 73.06; H, 5.34. Found: C, 73.09; H, 5.48.

Racemic 6f' was detosylated as follows. A solution of 5.1 g. of racemic 6f', 3.0 g. of phenol and 30% hydrogen bromide in acetic acid (50 ml.) was prepared under nitrogen, and heated and stirred at 110° for 4 hours. The solution was cooled, diluted with 150 ml. of ether, and the precipitate that separated was collected and washed with ether to give 4.1 g. of crude salt. This material was mixed with 50 ml. of 2N sodium hydroxide in 2:1 water-methanol, and the free amine that separated was collected, washed with water and recrystallized from 95% ethanol to give 1.78 g. (50%) of 6g', m.p. 226°–228°. Material dried at 180° at 10μ gave a molecular ion in its mass spectrum (70 ev), m/e = 355, and a pmr spectrum (60 MHz) in CDCl$_3$, δ, 8.0–6.8 (m, ArH, 12H), 4.21 (m, OCH$_2$, 4H), 2.76 (pseudo-t CH$_2$NH, 4H), 1.66 (s, NH, 1H).

Anal. Calcd for $C_{24}H_{21}NO_2$: C, 81.10; H, 5.96. Found: C, 80.89; H, 5.80.

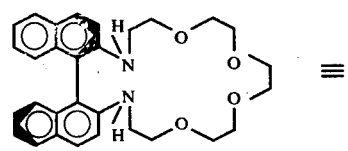

(R)-6h'

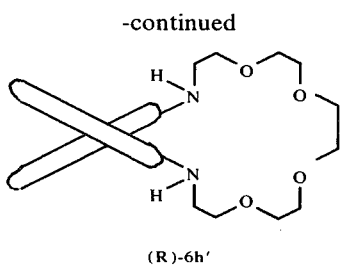

(R)-6h'

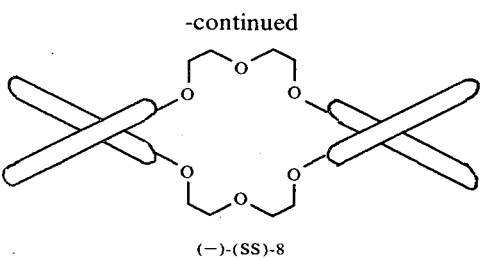

(−)-(SS)-8

Procedure 4

Procedure 4 is illustrated by the preparation of the starting material for cycle (R)-6h', namely the compound (−)-(R)-N,N'-bis-trifluoromethylsulfonyl-2,2'-diamino-1,1'-binaphthyl. To a solution of 2.85 g. of (+)-(R)-1d' and 2.7 g. of dry triethylamine in 100 ml. of dichloromethane (distilled from phosphorus pentoxide) kept at −78° under dry nitrogen was added dropwise (1 hour) a solution of 1.1 g. of trifluormethylsulfonic anhydride [*J. Chem. Soc.*, 4069 (1957)] dissolved in 50 ml. of dry dichloromethane. After 5.5 hours, the temperature was allowed to reach 0°, and the yellow solution was washed with 200 ml. of water (three times), 50 ml. of brine, and dried. The solvent was evaporated under vacuum, 100 ml. of ether was added to the residue, and the solution was evaporated to give 5.95 g. of a gum. This material was chromatographed on 130 g. of silica gel with dichloromethane as the mobile phase. The (−)-(R)-N,N'-bis-trifluoromethylsulfonyl-2,2'-diamino-1,1'-binaphthyl (4.0 g, 73%) was obtained as a yellow glass after complete evaporation of the solvent at 25° and 10μ. The mass spectrum (70 ėv) gave a molecular ion at m/e = 548, and the pmr (60 MHz) in CDCl$_3$ gave δ 8.25–6.90 (m, ArH, 12H), 6.6–5.5 (broad s, NH, 2H), and $[\alpha]_D^{25}$ −148° (C 1, 0, pyridine).

Anal. Calcd for $C_{22}H_{14}F_6N_2O_4S_2$: C, 48.18; H, 2.57. Found: C, 48.09; H, 2.43.

EXAMPLE 2

Preparation of Cycles with Two Binaphthyl Units

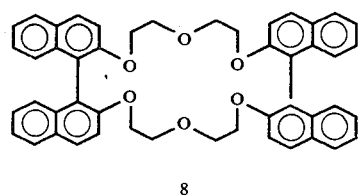

8

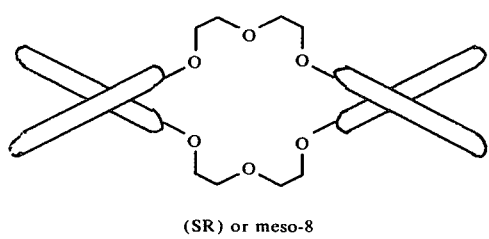

(SR) or meso-8

Procedure 1

With racemic 1 (the binaphthol) and diethyleneglycol ditosylate, (SS) (RR)-8 and (SR)-8 were produced, with (S)(R)-4 as a biproduct. With optically pure (−)-(S)-1 as starting material, (−)-(SS)-8 was obtained, with (+)-(S)-4 as biproduct. Procedure 1 is illustrated with the preparation of the optically active isomer. A solution of 14.5 g. (35.0 mmol) of diethyleneglycol ditosylate in 150 ml. of tetrahydrofuran was added during 10 minutes to a boiling solution of a mixture of 10.0 g. (35.0 mmol) of optically pure (−)-(S)-1 and 8 g. of potassium t-butoxide in 250 ml. of tetrahydrofuran and 2 ml. of water. The resulting mixture was refluxed for 12 hours, cooled, neutralized with concentrated hydrochloric acid and filtered. The filtrate was concentrated and chromatographed on 1 kg. of neutral alumina with benzene-ether (9 to 1, v/v) as eluting solvent, cut in one liter fractions. Fractions 2–4 contained only (−)-(SS)-8 (3.9 g.,), whereas fractions 5–14 contained mixtures of (−)-(SS)-8 and of cycle (+)-(S)-4, (2.0 g.). By fractional recrystallization of the mixture from benzenecyclohexane and combining appropriate fractions, 4.3 g. of white needles of (−)-(SS)-8 were obtained as a solvate of 0.5 mole of benzene and 0.5 mole of cyclohexane, as shown by integration of the substance's pmr spectrum (100 MHz), m.p. 123°–126°.

Anal. Calcd for $C_{48}H_{40}O_6.0.5C_6H_{12}.0.5C_6H_6$: C, 81.69; H, 6.22. Found: C, 81.71; H, 6.06.

The solvate was heated at 170° at 50 μ for 17 hours to give 3.9 g. (31%) of pure (−)-(SS)-8 as a colorless glass, $[\alpha]_{578}^{25}$ −220°, $[\alpha]_{546}^{25}$ −262°, $[\alpha]_{436}^{25}$ −599° (C 1.10, CH$_2$Cl$_2$). The rotations of this substance were the same before and after heating at 170° when correction was made for the presence of the solvate. The base peak in the pass spectrum (70 ev) was that of the molecular ion, m/e 712. The pmr spectrum of this material was identical to that of racemic 8 (see below). From the filtrates of the fractional recrystallization of (−)-(SS)-8 was isolated by fractional sublimation, 0.24 g. (2%) of (+)-(S)-4, m.p. 31°–132°, $[\alpha]_{578}^{25}$ +72°, $[\alpha]_{546}^{25}$ +78°, $[\alpha]_{436}^{25}$ +40° (C 0.88, CH$_2$Cl$_2$). The base peak in the mass spectrum (70 ev) was that of the molecular ion at m/e 356.

Anal. Calcd for $C_{24}H_{20}O_3$: C, 80.88; H, 5.66. Found: C, 80.81; H, 5.55.

The pmr spectrum was identical to that of (S)(R)-4 (see below).

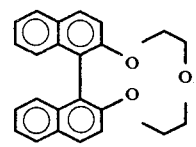

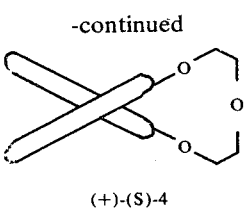

(+)-(S)-4

Application of procedure 1 to racemic 1 gave a mixture of (SS)(RR)-8, (SR)-8 and (S)(R)-4, which were separated by a combination of chromatographic, fractional crystallization and sublimation techniques. The (SR)-8 isolated (2%) gave m.p. 283°–284° after solvent was removed at 165° at 50 μ for 48 hours. Its pmr spectrum (100 MHz) in CDCl$_3$ gave absorptions at δ 7.76 (m, aromatic, 4H), 7.20 (complex m, aromatic, 8H), 3.90 (m, ArOCH$_2$, 4H) and 3.29 (m, CH$_2$OCH$_2$, 4H). The base peak in the mass spectrum (70 ev) was that of the molecular ion, m/e 712.

Anal. Calcd for C$_{48}$H$_{40}$O$_6$: C, 80.88; H, 5.66. Found: C, 80.88; H, 5.84.

The (SS)(R)-8 isolated (15%) gave m.p. 244°–251° (phase change). Its pmr spectrm (100 MHz) in CDCl$_3$ gave absorptions at δ 7.83 (m, aromatic, 4H), 7.2 (complex m, aromatic, 8H), 3.81 (m, ArOCH$_2$, 4H) and 3.18 (m, CH$_2$OCH$_2$, 4H). The base peak in the 70 ev mass spectrum provided the molecular ion at m/e 712.

Anal. Calcd for C$_{48}$H$_{40}$O$_6$: C, 80.88; H, 5.66. Found: C, 81.05; H, 5.92. Racemic or (S)(R)-4 (4%) gave m.p. 226°–227°. The pmr spectrum (100 MHz) in CDCl$_3$ exhibited absorptions at δ 7.8 (m, aromatic, 4H), 7.2 (complex m, aromatic, 8H), and an ABX$_2$ pattern with absorptions at δ 4.32 (8 lines, 2H), 4.01 (8 lines, 2H) and 3.5 (m, 4H). The base peak in the 70 ev mass spectrum was due to the molecular ion, m/e 356.

Anal. Calcd for C$_{24}$H$_{20}$O$_3$: C, 80.88; H, 5.66. Found: C, 81.01; H, 5.77.

→ (−)-(SS)-8. Compound (+)-(S)-9 was prepared as follows. To a solution of 28.6 g. of optically pure (−)-(S)-1, 11.76 g. of potassium tert-butoxide and 750 ml. of pure tetrahydrofuran stirred under nitrogen was added 26 g. of benzhydryl bromide dissolved in 250 ml. of tetrahydrofuran. The resulting solution was stirred and refluxed for 12 hrs. The solvent was evaporated under vacuum, and the residue was shaken with 500 ml. of ice water and 500 ml. of dichloromethane. The organic layer was washed with 10% aqueous sodium hydroxide solution to remove any unused 1. The organic layer was washed with water, dried, evaporated and chromatographed on 700 g. of alumina. The column was washed with 2.3 liters of 15% dichloromethane in pentane, and the product eluted with dichloromethane-pentane (4 liter, 1:1), dichloromethane (1 liter) and 5% ethanol in dichloromethane (2 liters) to give 33 g. (73%) of (+)-(S)-9 as a foam, [α]$_{589}^{25}$ +18.7°, [α$_{578}^{25}$ +19.6°, [α]$_{546}^{25}$ +21.3° (C 0.55 CHCl$_3$).

Anal. Calcd for C$_{33}$H$_{24}$O$_2$: C, 87.58; H, 5.35. Found: C, 87.49; H, 5.57.

Compound (−)-(SS)-10a' was prepared as follows. A solution of 9.05 g. of the above sample of (+)-(S)-9, 4.14 g. of diethyleneglycol ditosylate, 1.45 g. of potassium hydroxide in 5 ml. of water, all in 200 ml. of tetrahydrofura was stirred under nitrogen at reflux for 36 hr. The solution was cooled slightly, and 50% aqueous potassium hydroxide (2 ml.) and 2.0 g. of diethyleneglycol ditosylate were added. The solution was refluxed for an additional 12 hours. The mixture was cooled, filtered, and the filtrate was evaporated under vacuum. The residue was chromatographed on a 4 by 35 cm column of alumina, and the column was washed with three successive one liter fractions of 10, 20 and 30% dichloromethane in pentane. The product was eluted wit 40% dichloromethane-60% pentane in fractions 4 and 5 (one liter fractions were taken), 7.15 g. (73%), as a white foam, [α]$_{578}^{25}$ −3.04°, [α]$_{546}^{25}$ −5.18°, [α]$_{436}^{25}$ −30.25° (c 1.0, CHCl$_3$). The substance gave a mass

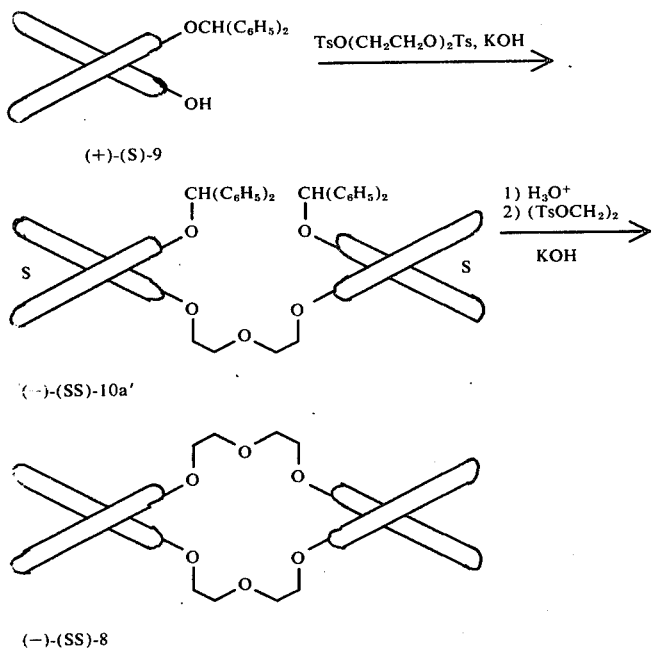

The compound, (−)-(SS)-8 was also prepared by the multistage procedure, (+)-(S)-9 → (−)-(SS)-10a' spectrum (70 ev) that contained the molecular ion, m/e = 974, and a pmr spectrum (100 MHz) in CDCl$_3$δ 2.82

(t, OCH₂, 4H), 3.54 (t, ArOCH₂, 4H), 6.00 (s, Ar₂CH, 2H), 6.8–7.3 and 7.5–7.9 (m, m, ArH, 44H).

Anal. Calcd for $C_{70}H_{54}O_5$: C, 86.21; H, 5.58. Found: C, 86.08; H, 5.69.

A solution of 4.35 g. of the above material ((−)-(SS)-10a′) in 50 ml. of dichloromethane, 50 ml. of methanol and 5 ml. of concentrated hydrochloric acid was stirred for 8 hours at 25°, during which time the cloudy solution became clear. The mixture was shaken with 200 ml. each of ice water and dichloromethane, the organic phase was washed with water, dried, and evaporated under vacuum. The resulting mixture of diphenylmethoxymethane and the phenol was mixed with 200 ml. of tetrahydrofuran, 1.85 g. of diethyleneglycol ditosylate and 0.65 g. of potassium hydroxide in 1 ml. of water. The solution was heated under nitrogen at reflux for 24 hours. The mixture was cooled, filtered, and the residue was dissolved in dichloromethane. The solution was washed with water, dried, evaporated under vacuum, and the residue was chromatographed over 200 g. of alumina. Elution of the column with 1 liter of 1:9 dichloromethanepentane gave 1.51 g. (85%) of diphenylmethoxymethane. Elution of the column with 1:1 dichloromethane-pentane gave nothing in the first liter, but gave (−)-(SS)-8 (1.48 g. or 47%) in the second liter, which was crystallized from 1:1 benzene-cyclohexane and whose pmr spectrum after drying was superimposable on that of authentic material, $[\alpha]_{578}^{25}$ 215°, $[\alpha]_{546}^{25}$ −255° (c 0.31, $CH_2Cl_2$).

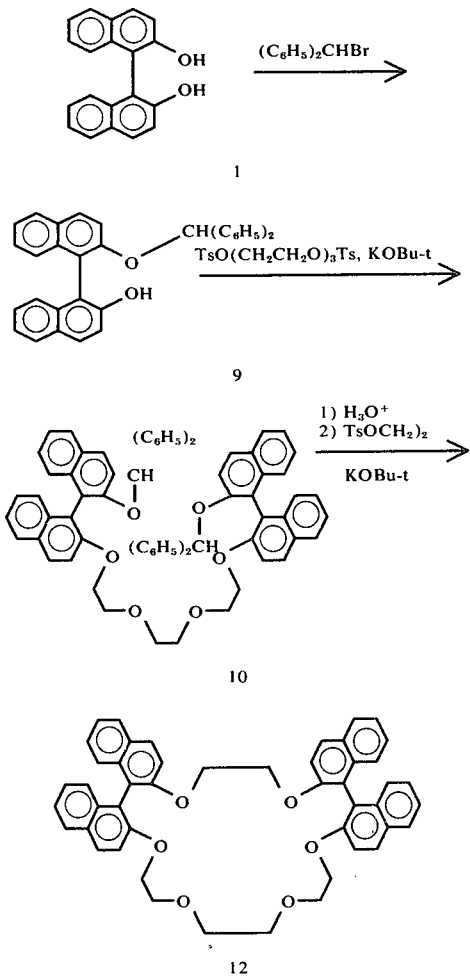

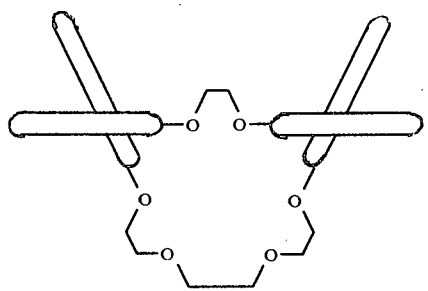

(SR)-or meso-12

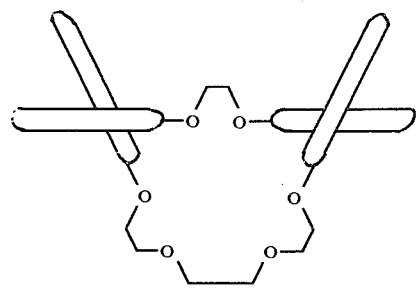

(SS)-12

Procedure 2

In procedure 2, the cyclic ether 12 was prepared with two binaphthyl units separated by one ethyleneglycol unit on one side and by a triethyleneglycol unit on the other. The sequence used was 1 → 9 → 10 → 12. Racemic 1 as starting material gave rise to a mixture of (SR)-12 and (SS)(RR)-12. Use of optically pure (S)-1 provides only (SS)-12.

Benzhydryl ether 9 was prepared as follows. A mixture of 28.6 g. (0.10 mole) of binaphthol (1), 300 ml. of tetrahydrofuran and 12.0 g. (0.11 mole) of potassium t-butoxide was stirred for 5 minutes, and benzhydryl bromide (27.1 g. or 0.11 mole) in 200 ml. of tetrahydrofuran was added. The mixture was heated at reflux for 24 hours, cooled, and evaporated under vacuum. The residue was partitioned between dichloromethane and 10% sodium hydroxide solution. The aqueous layer upon acidification gave 4 g. of recovered 1. The dichloromethane layer was washed with water, with brine, and was dried ($MgSO_4$). Evaporation of this solution gave an oil which crystallized as a monoetherate of 9 when dissolved in 200 ml. of ether, weight 31.6 g. (60%), m.p. 103°–105° (bubbles).

Anal. Calcd for $C_{33}H_{24}O_2 \cdot C_4H_{10}O$: C, 84.38; H, 6.51. Found: C, 84.27; H, 6.35.

When recrystallized from pentane, pure 9 was obtained, melting behavior, translucent at 62°, cloudy at 84°, liquid at 138°–140°. A 100 MHz pmr spectrum of this material ($CCl_4$) gave signals at δ 7.68 and 7.00 (multiplets, ArH, 22H), 6.03 (s, OCH, 1H), 4.74 (s, OH, 1H). A 70 ev mass spectrum of 9 gave a molecular ion at m/e=452.

Anal. Calcd for $C_{33}H_{24}O_2$: C, 87.58; H, 5.35. Found: C, 87.73; H, 5.37.

Compound 9 was converted to 10 as follows. To a stirred mixture of 10.5 g. (0.02 mole) of 9, 100 ml. of tetrahydrofuran and 10 ml. of water containing 1.5 g. of potassium hydroxide was added 4.6 g. (0.01 mole) of triethyleneglycol ditosylate in 90 ml. of tetrahydrofuran. The resulting solution was refluxed for 16 hours, filtered, and the filtrate was evaporated to dryness under vacuum. The residue was dissolved in dichloromethane, the solution was washed with water, dried and evaporated to give 12.5 g. of a yellow semisolid. This material was chromatographed on 400 g. of alumina made up in one-to-one pentanedichloromethane. The column was washed with 200 ml. of the same solvent to give 200 mg. of tetraphenylethylene. Product 10 was eluted with 2 liters of pure dichloromethane, evaporation of which gave 5 g. (50%) of a mixture of (SR) and (SS)(RR)-10, m.p. 75°–81°. A 70 ev mass spectrum of this material gave the molecular ion at m/e = 1018. A 100 MHz pmr spectrum in CDCl$_3$ gave signals at $\delta$ 6.8–7.9 (complex m, ArH, 44H), 6.06 (s, ArCH, 2H), 3.85 and 3.16 (m, ArOCH$_2$CH$_2$, 8H), 2.70 (s, CH$_2$OCH$_2$CH$_2$OCH$_2$, 4H).

Anal. Calcd for C$_{72}$H$_{58}$O$_6$: C, 84.84; H, 5.73. Found: C, 84.88; H, 5.84.

The two benzhydryl protecting groups of 10 were cleaved with acid, and the diphenolic product was converted to multiheteromacrocycle 12 as follows. A solution of 4.9 g. of the above mixture of (SR) and (SS)(RR)-10 in 300 ml. of tetrahydrofuran and 100 ml. of concentrated hydrochloric acid was allowed to stand at 25° for 16 hours. The solution was evaporated under vacuum until it became turbid, at which point it was shaken with 200 ml. of water and 200 ml. of dichloromethane. The aqueous phase was extracted with additional dichloromethane, and the combined organic layers were washed with water and evaporated. Toluene (150 ml.) and enough concentrated ammonium hydroxide to neutralize the residue was added, and the solution was evaporated under vacuum. The toluent-ammonium hydroxide-evaporative treatment was repeated, and the phenolic oil produced was used directly in the next step. This material was dissolved in 100 ml. of tetrahydrofuran, and 3 g. of potassium hydroxide dissolved in 15 ml. of water was added. To the resulting mixture was added 3.7 g. of ethyleneglycol ditosylate in 75 ml. of tetrahydrofuran. The solution was refluxed for 36 hours, and an additional 1.5 g. of potassium hydroxide and 1.5 g. of ethyleneglycol ditosylate was added. The resulting mixture was refluxed for an additional 12 hours, filtered, and shaken with 200 ml. of dichloromethane and 200 ml. of water. The organic phase was washed with 10% sodium hydroxide solution, water, and brine. The solution was dried, evaporated, and the resulting oil was chromatographed on neutral alumina (500 g.) made up in one-to-one dichloromethane-pentane. The column was washed with the same solvent mixture, and 75 ml. fractions were cut. Multiheteromacrocycle 12 was eluted in fractions 5–14, 1.7 g. (50%) as a 3-to-7 mixture of (SR) and (SS)(RR)-isomers. A sample of this material was molecularly distilled at 250° at 10μ to give material for analysis. The 70 ev mass spectrum of the material gave a molecular ion at m/e = 712.

Anal. Calcd for C$_{48}$H$_{40}$O$_6$: C, 80.87; H, 5.66. Found: C, 80.59; H, 5.94.

A solution of 100 mg. of the (SR), (SS)(RR)-12 mixture was submitted to thick layer chromatography on silica gel (1 mm thick plate) with chloroform-cyclohexane as developer (6 times). The bands were scraped from the plate, and the products recovered by repeated washing of the silica gel with one-to-three methanol-chloroform. The (SR)-isomer (R$_f$ = 0.13, SiO$_2$-chloroform) was crystallized from ethanol, m.p. 118°–121° (bubbles at 180°). The (SS)(RR)-isomer (R$_f$ = 0.28, SiO$_2$-chloroform) was crystallized and recrystallized from ethanol, m.p. 132°–135° and after recrystallization (bubbles at 180°).

The pmr spectra (CDCl$_3$, 100 MHz) of dried (SS)(RR)-isomer gave signals at $\delta$, 7.03–8.0 (complex m, Ar-H, 22H), 6.75 and 6.86 (d, Ar-$^3$H, 2H), 2.9–4.0 (m, OCH$_2$CH$_2$O, 16H). The pmr spectra of other multiheteromacrocycles contained two binaphthyl units of the same configuration separated by a single ethylenedioxy unit exhibit signals at ca. $\delta$ 6.76 and 6.86, and are assigned to those protons (one per binaphthyl unit) at the 3-positions of the naphthalene rings that thrust into the face of a naphthalene ring of the attached binaphthyl unit. The dried (SR)-isomer gave signals at $\delta$ 6.9–7.9 (complex m, Ar-H, 24H), 3.0–4.0 (m, OCH$_2$CH$_2$O, 16H, with sharp peaks at 3.0 and 3.9).

Isomer (SS)-12 was prepared by a similar procedure as follows. Compound (+)-(S)-9 was prepared as in Example 2, Procedure 1. Compound (−)-(SS)-10 was obtained from (+)-(S)-9 in 73% yield as a foam, mass spectrum (70 ev) molecular ion m/e = 1018, $[\alpha]_{589}^{25}$ −3.04°, $[\alpha]_{578}^{25}$ −3.4°, $[\alpha]_{548}^{25}$ −5.25 (C 1.1, CHCl$_3$), pmr spectrum (100 MHz) in CDCl$_3$ $\delta$ 7.9–6.8 (m, ArH, 44H), 6.04 (s, Ar$_2$CH, 2H), 3.84 (m, ArOCH$_2$, 4H), 3.15 (pseudo-t, ArOCH$_2$CH$_2$-O, 4H), 2.67 (s, CH$_2$OCH$_2$CH$_2$OCH$_2$, 4H).

Anal. Calcd for C$_{72}$H$_{58}$O$_6$: C, 84.84; H, 5.73. Found: C, 85.01; H, 5.67.

Compound (−)-(SS)-10 was converted to (−)-(SS)-12 in 60% yield, and was obtained as a foam mass spectrum (70 ev) molecular ion, m/e = 712, $[\alpha]_{589}^{25}$ −212°, $[\alpha]_{578}^{25}$ −223°, $[\alpha]_{546}^{25}$ −265° (c 4.5, CHCl$_3$), pmr, identical to that of (SS,RR)-12.

Anal. Calcd for C$_{48}$H$_{40}$O$_6$: C, 80.88; H, 5.66. Found: C, 80.96; H, 5.95.

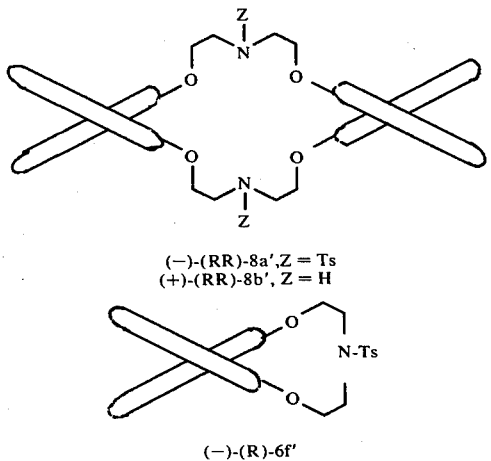

(−)-(RR)-8a′, Z = Ts
(+)-(RR)-8b′, Z = H (−)-(R)-6f′

Procedure 3

Procedure 3 is illustrated with the preparation of (−)-(RR)-8a′ and (+)-(RR)-8b′, with (−)-(R)-6f′ as a byproduct. In dry pyridine at 0°, N,N-bis-(2-hydroxyethyl)-p-toluenesulfonamide (m.p. 96°–99°) was tosylated with tosyl chloride by the standard method to give N,O,O′-tritosyldiethanolamine, m.p. 85°–87°. [Can. J. Chem. 45, 1555 (1967) gives 78°–79°].

Anal. Calcd for C$_{25}$H$_{29}$NO$_8$S$_3$: C, 52.89; H, 5.14. Found: C, 52.80; H, 4.96.

A solution of 11.45 g. of optically pure (+)-(R)-1 in 50 ml. of dry dimethyl formamide was stirred with 2.8 g. of finely ground anhydrous potassium carbonate for 40 min. at 25° under nitrogen. A solution of 5.7 g. of the above tritosylate in 25 ml. of dry dimethyl formamide was added over a 1 hour period, and the mixture was held at 60° for another hour. This sequence of additions (2.8 g. of potassium carbonate and 5.7 g. of tritosyl compound) was repeated three times with an interval of 3 hours for the mixture to warm from 25° to 70°. After the fourth cycle, the reaction mixture was stirred for 11 hours at 70°, and given an additional treatment with 2.8 g. of potassium carbonate and 5.7 g. of tritosyl compound. The reaction mixture was stirred for an additional 5 hours at 70°, and stirred with 1.5 liter of crushed ice. The precipitate was collected, washed with water, and dissolved in 100 ml. of toluene. The toluene phase was washed 4 times with 50 ml. of 1:1 methanol-water, 0.5M in sodium hydroxide at 0°, and the washes were back extracted with 50 ml. of toluene. The combined toluene layer was washed with brine, dried, evaporated under vacuum, and the crude product was chromatographed on 600 g. of silica gel with 1:1 benzene-dichloromethane as the mobile phase. After 1.4 liter of solvent appeared as eluate, 250 ml. fractions were collected. Fractions 3–9 contained 9.9 g. of (−)-(R)-6f′ (49%), fractions 14–20, 4.0 g. of (−)-(RR)-8a′ (20%), and fractions 21–28, 2.0 g. (10%) of a mixture of (−)-(RR)-8a′ and tritosyl compound. The (−)-(R)-6f′ was recrystallized (with filtration) from 50 ml. of hot acetonitrile, to give 6.6 g. (33%) of product dried at 78° and 50μ, m.p. 280°–281°, $[\alpha]_{589}^{25}$ −59.6°, $[\alpha]_{578}^{25}$ −60.5°, $[\alpha]_{546}^{25}$ −64.3° (C 1.0, $CH_2Cl_2$). Additional material (1.42 g. of 7%) was recovered from the filtrates. The mass spectrum (70 ev) gave a molecular ion at m/e = 509, and the pmr spectrum (60 MHz) in $CDCl_3$ gave, δ 7.93–7.00 (m, ArH, 16H), 4.48 (m, $OCH_2$, 4H), 3.33 (m, $CH_2NTs$, 4H), and 2.37 (s, $ArCH_3$, 3H). This material was sublimed at 5μ without change of optical rotation.

Anal. Calcd for $C_{31}H_{127}NO_4S$: C, 73.06; H, 5.34. Found: C, 72.90; H, 5.52.

The material from fractions 14–20 was dissolved in 450 ml. of hot ethanol, filtered, and (−)-(RR)-8a′ crystallized, weight 2.33 g. (11.3%), m.p. 130°–220° (solvent of crystallization slowly lost). This material after drying at 117° at 20μ for 6 hours gave: a molecular ion in its 70 ev mass spectrum of m/e = 1018; a pmr spectrum (60 MHz) in $CDCl_3$ of δ 7.90–6.64 (m, ArH, 32H), 3.66 (pseudo-t, $OCH_2$, 8H), 2.66 (pseudo-t, $CH_2NTs$, 8H), 2.20 (s, $ArCH_3$6H); $[\alpha]_{589}^{25}$ −104.2°, $[\alpha]_{578}^{25}$ −108.2°, $[\alpha]_{546}^{25}$ −123.6° (C 1.0, $CH_2Cl_2$).

Anal. Calcd for $C_{62}H_{54}N_2O_8S_2$: C, 73.06; H, 5.34. Found: C, 72.83; H, 5.54.

Detosylation of (−)-(RR)-8a′ was accomplished as follows. A solution prepared from 0.538 g. of this material (see above) and 0.190 g. of phenol in 15 ml. of acetic acid was heated to 90°, and a slow stream of hydrogen bromide gas was bubbled through the solution for 10 minutes. The colorless liquid underwent an exothermic reaction and started to reflux. After the reaction subsided, more hydrogen bromide was added, and the material was maintained at 75° for two additional hours. The solution was cooled, 200 ml. of dry ether was added, and the solution was made alkaline with solid sodium carbonate. The organic phase was washed with 2N sodium hydroxide solution and brine, and then extracted twice with 2N hydrochloric acid that was 30% ethanol. The combined acid solution was made basic with sodium hydroxide, extracted with dichloromethane, and the dichloromethane solution was washed with brine, dried and evaporated under vacuum. The creamy residue was recrystallized from ether-cyclohexane to give 0.18 g. (48%) of (+)-(RR)-8b′ as a glass, $[\alpha]_{589}^{25}$ +181°, $[\alpha]_{578}^{25}$ +191°, $[\alpha]_{546}^{25}$ +228° (C 0.96, $CH_2Cl_2$), pmr (60 MHz) in $CDCl_3$, δ 8.05–6.95 (m, ArH, 24H), 3.80 (pseudo-t, $OCH_2$, 8H), 2.37 (pseudo-t, $CH_2$-N, 8H) and 1.43 (S, NH, 2H). The 70 ev mass spectrum gave a molecular ion, m/e = 710.

Anal. Calcd for $C_{48}H_{42}N_2O_4$: C, 81.10; H, 5.96. Found: C, 80.91; H, 6.09.

To determine if any material racemized or epimerized during the detosylation of (−)-(RR)-8a′, a solution of the above sample of (+)-(RR)-8b′ (0.18 g.) in 5 ml. of dry pyridine at −20° was treated with 0.2 g. of tosyl chloride. After warming to 0° and standing at this temperature for 24 hours, the product was isolated as usual to give 0.065 mg. (25%) of (−)-(RR)-8a′, $[\alpha]_{589}^{25}$ −103°, $[\alpha]_{578}^{25}$ −106°, $[\alpha]_{546}^{25}$ −122° (C 1.2, $CH_2Cl_2$). Clearly little change occurred in the rotation during the cycle, (−)-(RR)-8b′ → (+)-(RR)-8b′ → (−)-(RR)-8a′.

EXAMPLE 3

Preparation of Cycles with Three Binaphthyl Units

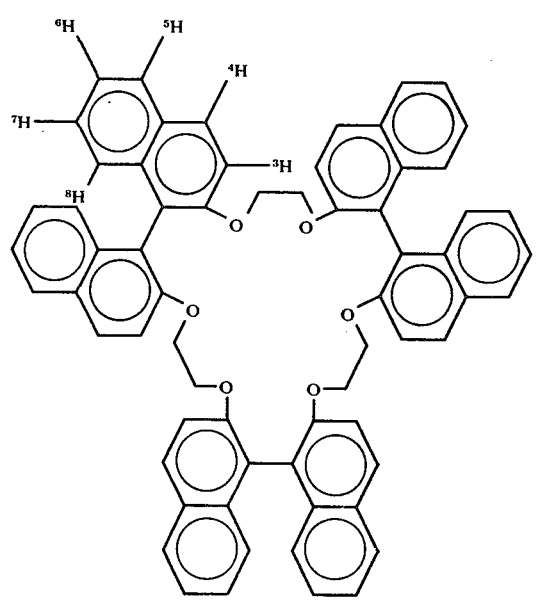

15

-continued

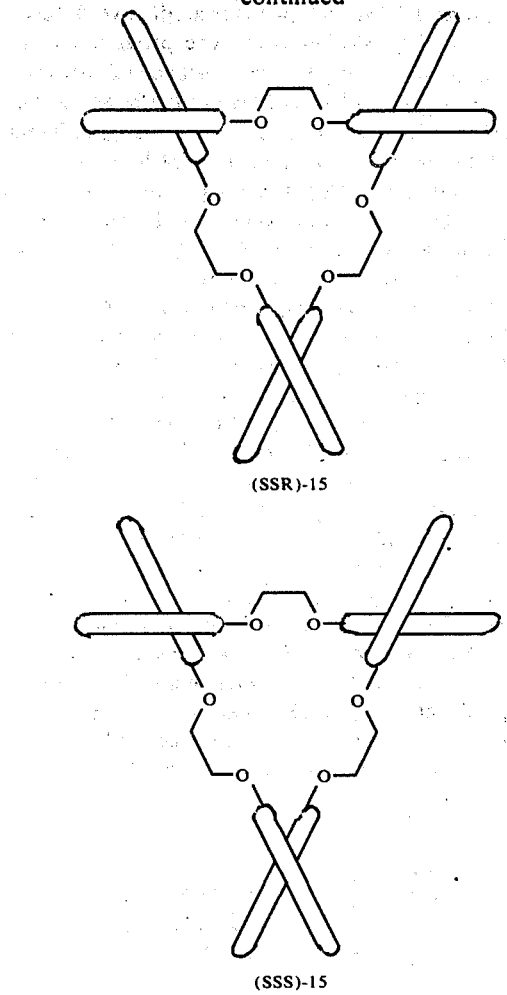

(SSR)-15

(SSS)-15

Procedure 1

In procedure 1, the three binaphthyl units were incorporated into a multiheteromacrocycle in one multistage reaction. To a solution of 10 g. (34.9 mmol) of binaphthol (racemic 1) in 400 ml. of pure tetrahydrofuran stirred under nitrogen was added 7.83 g. (69.8 mmol) of potassium t-butoxide and 100 ml. of pure tetrahydrofuran, and the solution was stirred for 30 min. To the resulting mixture as added ethyleneglycol ditosylate, 12.93 g. (34.9 mmol), dissolved in 200 ml. of tetrahydrofuran. The mixture was held at reflux temperature for 44 hours, cooled and evaporated. The residue was shaken with a mixture of 200 ml. of water, 50 ml. of methanol and 200 ml. of dichloromethane. The aqueous phase was separated and washed with two successive portions of 200 ml. of dichloromethane. The organic layers were combined, washed with brine, dried with magnesium sulfate, and evaporated to give 11.2 g. of a light tan solid. This material dissolved in 100 ml. of dichloromethane was filtered through 100 g. of neutral alumina, and the column was washed with 300 ml. of additional dichloromethane. The eluate was concentrated, and the 10.1 g. of solid was chromatographed on 150 g. of silica gel. Fractions (250 ml.) of eluate were collected as follows with various eluting solvents: pentane, fractions 1–4; pentane-ether (98:2), fractions 5–10; pentane-ether (96:4), fractions 11–50; pentane-ether (94:6), fractions 51–86; pentane-benzene (1:1), fractions 87–90; benzene, fractions 91–94. Fractions 16–58 contained cycle 3, fractions 59–66 contained a mixture of 3 and 13, fractions 67–86 contained 13, whereas fractions 87–94 contained a mixture of 13, of (SR)-14, of racemic (SSR)(RRS)-15, and of racemic (SSS)(RRR)-15 (detected by tlc). These compounds were separated and characterized as follows.

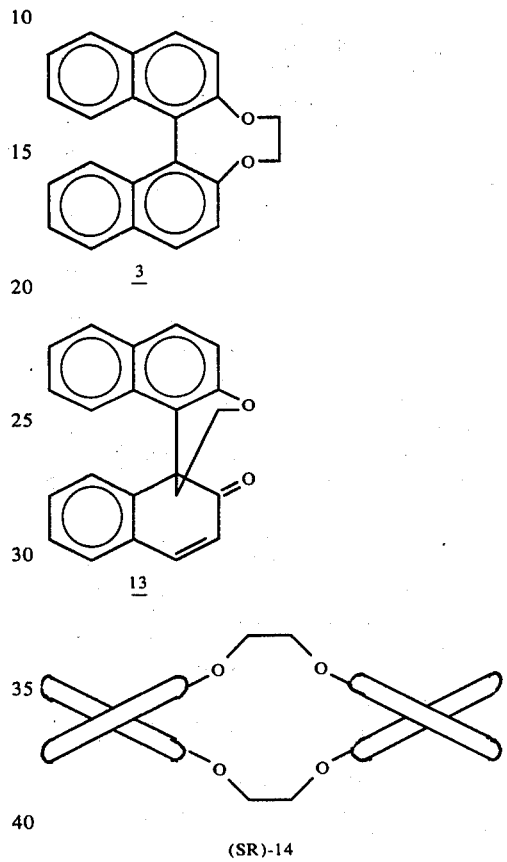

3

13

(SR)-14

Recrystallization of the residue of fractions 16–58 from ether-pentane gave 2.46 g. (22%) of 3, m.p. 222°–223°. Sublimation of this material at 200° and 5 μ did not change its m.p. The mass spectrum at 70 ev gave a molecular ion at m/e 312, and a Rast molecular weight of 319. The pmr spectrum (100 MHz) in $CDCl_3$ showed signals at δ 7.76–7.92 (m, aromatic, 4H), 4.02–7.40 (complex multiplet, aromatic, 8H), 4.0–4.36 (m, $OCH_2CH_2O$, 4H). The uv spectrum in dichloromethane gave shoulders at 317 and 291 nm, λmax 325 nm (ε 5.71 × $10^3$), and λmax 298 (ε 1.17 × $10^4$).

Anal. Calcd for $C_{22}H_{16}O_2$: C, 84.59; H, 5.16. Found: C, 84.52; H, 5.33.

Recrystallization of the residues of fractions 67–86 from ether-pentane gave ketone 13, 4.8 g (43%), m.p. 196.5°–198°. Sublimation of this material at 200° and 5 μ gave light yellow crystals, m.p. 198°–200°. The mass spectrum at 70 ev gave a molecular ion at m/e 312, and a Rast molecular weight gave 338. The pmr spectrum in $CDCl_3$ (100 MHz) gave the following signals: δ 6.68–7.70 (broad m, aromatic, 10H) 6.22–6.50 (m, CH=CH, 2H), and two symmetrical multiplets centered at 4.18 ($OCH_2$, 2H) and at 2.22 ($C-CH_2$, 2H). The ir spectrum (KBr) gave a strong band at 1660 $cm^{-1}$ (C=O stretch). The uv spectrum in dichloromethane gave shoulders at 331 and 268 nm, with λmax 304 (ε 1.20 × 10⁴), λmax 289 (ε 1.26 × 10⁴) and λmax 278 (ε 1.01 × 10⁴).

Anal. Calcd for $C_{22}H_{16}O_2$: C, 84.59; H, 5.16. Found: C, 84.61; H, 5.30.

The material from fractions 87–94 (3.6 g.) was rechromatographed on 300 g. of silica gel with benzene as eluting solvent (250 ml. fractions were cut). Fractions 2–5 contained a mixture of 433 mg. of (SR)-14 and (SSR)(RRS)-15, which when recrystallized from dichloromethane gave (SR)-14. This material was sublimed at 250° and 5 μ to give 85 mg. (~ 1%) of pure substance, m.p. 355° (dec). The uv spectrum of the compound in dichloromethane gave a shoulder at 273 nm, and λmax 336 nm (ε 1.14 × 10⁴), 323 nm (ε 1.05 × 10⁴), 292 nm (ε 1.80 × 10⁴) and 282 nm (ε 2.08 × 10⁴). The 70 ev mass spectrum gave a molecular ion peak at m/e 624.

Anal. Calcd for $C_{44}H_{32}O_4$: C, 84.59; H, 5.16. Found: C, 84.54; H, 5.03.

Fractions 6–11 of the second chromatograph column contained a mixture of (SSR)(RRS)15 and (SSS)(RRR)-15, 179 mg. Preparative thin layer chromatography (silica gel, 4:6 dichloromethane-pentane) on this and the material from the filtrates of crystallization of (SR)-14 gave (SSR)(RRS)-15, which when recrystallized from dichloromethane-pentane gave 55 mg. (~ 0.5%) of pure material, m.p. 188°–190°. Its pmr spectrum (100 MHz) in CDCl₃ showed a broad multiplet at δ 6.52–7.96 (aromatic, 36 H) and another multiplet at 3.63–4.02 (CH₂CH₂, 12H). The uv spectrum in dichloromethane showed a shoulder at 273 nm, with λmax 335 (ε 1.41 × 10⁴), 324 (ε 1.37 × 10⁴), 292 (ε 2.42 × 10⁴) and 282 (ε 2.78 × 10⁴). The 70 ev mass spectrum gave a molecular ion at m/e 937.

Anal. Calcd for $C_{66}H_{48}O_6$: C, 84.59; H, 5.16. Found: C, 84.49; H, 5.08.

Also isolated by thin layer chromatography (tlc) was (SSS)(RRR)-15, which was recrystallized from a large volume of ether to give 52 mg. (~.5%) of pure compound, m.p. 338°–342° (dec). This compound was too insoluble to get a good pmr spectrum. Its uv spectrum in methylene chloride gave a shoulder at 273 nm,, with λmax at 335 (ε 1.53 × 10⁴), 325 (ε 1.49 × 10⁴), 293 (ε 2.56 × 10⁴) and 282 (ε 2.87 × 10⁴). The 70 ev mass spectrum gave a molecular ion at 937 m/e.

Anal. Calcd for $C_{66}H_{48}O_6$: C, 84.59; H, 5.16. Found: C, 84.32; H, 5.32.

The stereoisomeric identification of (S)-3, (S)-13 and (SSS)-15 was accomplished through their synthesis from optically pure (S)-1 (the binaphthol). The reaction was conducted as before, but only 500 mg. was used. Three products were separated by preparative thick layer chromatography on silica gel plates with dichloromethane:pentane (4:6) as eluent. Cycle (S)-3, 113 mg. (21%) gave m.p. 216.5°–217°, $[\alpha]_{578}^{25}$ +546°, $[\alpha]_{546}^{25}$ +628°, $[\alpha]_{436}^{25}$ +1,116° (C 0.93, CH₂Cl₂), and spectra and tlc behavior identical to that of (S)(R)+3. Optically active ketone, (+)-(S)-13, 221 mg. (40%), gave m.p. 187°–188°, $[\alpha]_{578}^{25}$ +247°, $[\alpha]_{546}^{25}$ +314°, $[\alpha]_{436}^{25}$ +1,323 (C 1.0, CH₂Cl₂), and spectra and tlc behavior identical to that of (S)(R)-13. Cycle (SSS)-15, 9 mg. (~2%) gave tlc behavior identical to (SSS)(RRR)-15, and gave a 100 MHz spectrum in CDCl₃ as follows: δ7.83 (d, Ar-⁵H, 6H), $J_{5,6}$=9Hz, 7.59 (d, Ar-⁴H, 6H), $J_{3,4}$=9Hz, 7.16 (m, Ar-H, 18H), 6.65 (d, Ar-⁸H, 6H), $J_{7,8}$=9Hz, 3.74 (s, CH₂CH₂, 12H).

The five compounds isolated from the reaction involving (S)(R)-1 as starting material all gave different and characteristic tlc behavior. The product mixture obtained from (S)-1 showed the presence of only three of these components by tlc. Since in the later reaction no (R)-1 was present, no product containing an R-unit was possible. Since (SR)-14 contains both an S and an R unit, its production from (S)(R)-1 and the absence of (SS)-14 when (S)-1 was employed differentiates it from (SS)(RR)-14. Had the isomer of 14 obtained from (S)(R)-1 been (SS)(RR)-14, then (S)-1 would have produced (SS)-14, which was absent. Hence only (SR)-14 is produced in detectable quantities from (S)(R)-1, although in principle, both (SS)(RR)-14 and (SR)-14 were possible.

Similarly, the structures of the two racemates, (SSR)(RRS)-15 and (SSS)(RRR)-15 were differentiated. Both enantiomers of the former contain (S) and (R)-units, but the enantiomers of the latter contain either only (S)- or only (R)-units. Thus when only (S)-units were available, as when (S)-1 was the starting material, neither (SSR)-15 nor (RRS)-15 could be produced. The only isomer produceable from (S)-1 was (SSS)-15, and only one was observed. The identical tlc behavior of (SSS)-15 with one of the components produced from (S)(R)-1 identified that component as (SSS)(RRR)-15. Thus the isomeric component produced from (S)(R)-1 must have been (SSR)(RRS)-15.

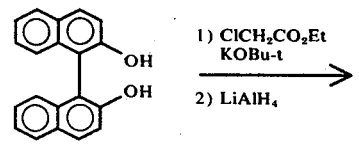

-continued

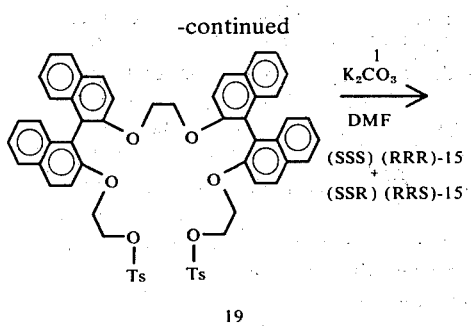

19

Procedure 2

In procedure 2, better yields of 15 were obtained by the sequence 1 → 16 + 17 → 18 → 19 → 15. Compounds 16 and 17 were prepared as follows. Potassium t-butoxide (23.5 g. 0.21 mol) was added to a stirred solution under nitrogen of 50 g. (0.175 mol) of 1 in 1 l. of tetrahydrofuran. To the refluxing mixture was added during 30 min. a solution of ethyl chloroacetate (25.8 g., 0.21 mol) in 30 ml. of tetrahydrofuran. The mixture was refluxed for 14 hours, the solvent was evaporated, and the residue was dissolved in 600 ml. of ether and 400 ml. of water. The layers were separated, and the ether layer was washed with water and dried with magnesium sulfate. The ether solution was concentrated to 300 ml. and added dropwise to a slurry of lithium aluminum hydride (7.0 g., 0.184 mol) in 1500 ml. of anhydrous ether. The mixture was stirred at 25° for 12 hours. After excess reducing agent was destroyed with 3 ml. of ethyl acetate, 400 ml. of a 6N hydrochloric acid was added, and the mixture was stirred for an additional 4 hours. The insoluble material (17) was filtered. The filtrate layers were separated, and the ether layer was extracted with several 80 ml. portions of a 2N potassium hydroxide solution in 2:1 water-methanol. The aqueous solution was acidified with concentrated hydrochloric acid solution, and the precipitate was filtered and sucked as dry as possible. This solid was dissolved in a minimum amount of hot tetrahydrofuran, and the resulting solution was poured into three volumes of ether. The precipitate, mainly 17, was collected. The filtrate was evaporated and the residue again dissolved in a minimum of tetrahydrofuran, and additional 17 was precipitated by addition of ether. From the filtrate was recovered 10 g. (20%) of 1. The combined samples of 17 were recrystallized from ethanoltetrahydrofuran to give 23.2 g. (40%) of 17, m.p. 209°–211°, whose pmr spectrum (60 MHz) in $CD_3SOCD_3$ gave the following signals: δ3.32 (m, $OCH_2$, 2H), 3.92 (m, $OCH_2$, 2H), 3.9 (s, OH, 2H), 6.7–7.9 (m, ArH, 12H).

Anal. Calcd for $C_{22}H_{18}O_3$: C, 79.98; H, 5.49. Found: C, 79.77; H, 5.49.

The ether layers from the above basic extraction were washed with water, dried with magnesium sulfate and concentrated. Recrystallization of the residue from benzene-hexane gave 9.8 g. (15%) of 16 as a cotton-like solid, m.p. 112°–113°, whose mr (60MHz) spectrum in $CDCl_3$ gave the following signals: δ2.27 (s, OH, 2H), 3.50 (m, $OCH_2$, 4H), 4.04 (m, $OCH_2$, 4H), 7.0–8.0 (m, ArH, 12H).

Anal. Calcd for $C_{24}H_{22}O_4$: C, 76.99; H, 5.92. Found: C, 76.81; H, 5.76.

Compounds 18 and 19 were prepared as follows. Potassium t-butoxide (6.5 g., 0.058 mol) was added to a stirred solution of 17 (18.9 g., 0.057 mol) in 600 ml. of tetrahydrofuran. The mixture was stirred under nitrogen for 30 min., a solution of ethyleneglycol ditosylate (10.7 g., 0.029 mol) in 100 ml. of tetrahydrofuran was added, and the mixture was refluxed for 28 hours. The solvent was evaporated and the oily residue dissolved in an ether-dichloromethane (4:1) mixture. The organic layer was washed with 3 portions of a 2N potassium hydroxide solution in water-methanol (2:1), then with water, and dried ($MgSO_4$). Evaporation of the solvent gave an oil, which when film dried gave 18 as a foam, 18.3 g. (93%), whose 60 MHz pmr spectrum in $CDCl_3$ gave the following signals: δ2.0 (s, OH, 2H); 3.35 (m, $OCH_2$, 4H), 3.8 (m, $OCH_2$, 4H), 6.7–8.0 (m, ArH, 24H). This material (18) was converted directly to 19 as follows. To a solution of the above crude 18 (10.0 g., 14.6 mmol) in 80 ml. of dry pyridine at −3° was added tosyl chloride (8.3 g., 43 mmol). The solid was stirred into solution at 0°, and the resulting solution was allowed to stand at 0° for 1 week. The solution was then stirred for 45 min. with 500 ml. of ice water. The precipitate was collected, washed with water and dried under vacuum over solid potassium hydroxide. This crude material (12.5 g.) was dissolved in 450 ml. of dichloromethane and rapidly chromatographed over 70 g. of silica gel with dichloromethane as solvent. Evaporation of the column eluate gave 7.6 g. (52%) of 19 as a white powder, m. p. 175°–190°, a mixture of two diastereomers, (SR)(RS)-19, and (SS)(RR)-19. This material gave a pmr spectrum (60 MHz) in $CDCl_3$ as follows: δ2.30 (s, $ArCH_3$, 6), 3.9 (m, $OCH_2$, 12H), 6.8–8.0 (m, ArH, 32H). An analytic sample was prepared by recrystallizing a portion of this material from chloroform-ethanol,, m.p. 190°–196°.

Anal. Calcd for $C_{60}H_{50}O_{10}S_2$: C, 72.42; H, 5.06. Found: C, 72.36; H, 5.00.

The isomers of 15 were prepared from 1 and the isomeric mixture, 19. A mixture of 1.5 g. (5.25 mmol) of 1, 0.75 g. (5.5 mmol) of potassium carbonate and 50 ml. of dimethylformamide was heated under nitrogen with stirring at 80°. This mixture was added in one portion to a warm solution of 5 g. (5.0 mmol) of crude 19 dissolved in 350 ml. of dimethylformamide. The mixture was stirred for 30 hours at 80°, and the solvent was evaporated under vacuum. The residue was dissolved in 400 ml. of dichloromethane and chromatographed over 150 g. of silica gel. The column eluate was evaporated to give 3.4 g. (68%) of a mixture of diastereomers of 15. The white solid was extracted with three 20 ml. portions of dichloromethane, leaving 0.6 g. (12%) of (SSS)(RRR)-15, which was dissolved in 100 ml. of hot dioxane. This solution was cooled and diluted with 100 ml. of ether. Pure (SSS)(RRR)-15 separated, m.p. 335°–340°, undepressed by admixture with the same material prepared directly from 1 and ethyleneglycol ditosylate. The 70 ev mass spectrum of this compound gave a molecular ion at m/e 936.

Anal. Calcd for $C_{66}H_{48}O_6$: C, 84.59; H, 5.16. Found: C, 84.49; H, 5.08.

The dichloromethane extract of the diastereomeric mixture was concentrated and chromatographed on 300 g. of silica gel with dichloromethane as developer, with 50 ml. fractions cut. The later fractions contained 0.2 g. (4%) of (SSS)(RRR)-15. The first fractions contained 2.0 g. (40%) of pure (SSR)(RRS)-15, m.p. 185°–187°, undepressed by admixture of a sample prepared directly from 1 and ethyleneglycol ditosylate. An analytical sample was prepared by recrystallization of the material from chloroform-ethanol. This material gave a 70 ev mass spectrum with a molecular ion at m/e 936, and a 60 MHz pmr spectrum (CDCl$_3$) as follows: δ 3.72 (m, OCH$_2$, 12H), 6.5–8.0 (m, ArH, 36H).

Anal. Calcd for C$_{66}$H$_{48}$O$_6$: C, 84.59; H, 5.16. Found: C, 84.32; H, 5.32.

The mixture of (SR)- and (SS)(RR)-18 were separated through their 3,5-dinitrobenzoates as follows. A solution of diols 18 (8.5 g.) in 30 ml. of benzene was added to a solution of 3,5-dinitrobenzoyl chloride in 100 ml. of benzene. The mixture was refluxed for 24 hours, the solvent evaporated, and the residual oil was chromatographed on 400 g. of silica gel in dichloromethane, 125 ml. fractions being collected. Fractions 6–11 (9.6 g.) contained both isomers, whereas 12–20 contained only (SS)(RR)-diester, (2.7 g.). The mixture was again chromatographed on 400 g. of silica gel to give 4.1 g. of (SR)-diester and 3.4 g. of (SS)(RR)-diester. Each isomer was recrystallized from acetone-ether to give 4.0 g. (30%) of (SS)(RR)-diester and 2.8 g. (21%) of (SR)-diester. The (SS)(RR)-diester gave m.p. 174°, pmr spectrum (60 MHz) in CDCl$_3$, δ 3.95 (s, OCH$_2$, 4H), 4.28 (m, OCH$_2$, 8H), 6.82–8.0 (m, ArH, 24H), 9.10 (t, ArH, 6H).

Anal. Calcd for C$_{60}$H$_{42}$O$_{16}$N$_4$: C, 67.03; H, 3.94. Found: C, 67.01; H, 3.80.

The (SR)-diester gave m.p. 124°–126°, pmr (60 MHz) in CDCl$_3$, δ 4.05 (m, CH$_2$O, 12H), 6.80–8.0 (m, ArH, 20H), 8.60 (d, ArH, 4H), 9.10 (t, ArH, 6H).

Anal. Calcd for C$_{60}$H$_{42}$O$_{16}$N$_4$: C, 67.03; H, 3.94. Found: C, 66.78; H, 4.01.

Each of these diesters was hydrolyzed to diols 18 with potassium hydroxide in water-tetrahydrofuran by the usual method. From the (SS)(RR)-diester, (SS)(RR)-18 was obtained in 91% yield as a foam, pmr spectrum (60 MHz) in CDCl$_3$, δ 2.08 (s, OH, 2H), 3.45 (m, OCH$_2$, 4H), 3.82 (s, OCH$_2$, 4H), 3.98 (m, OCH$_2$, 4H), 6.78–8.0 (m, ArH, 24H).

Anal. Calcd for C$_{46}$H$_{38}$O$_6$: C, 80.44; H, 5.58. Found: C, 79.70; H, 5.50.

The (SR)-18 was obtained in 92% yield from its diester, as a foam, pmr (60 MHz) in CDCl$_4$, δ 1.80 (s, OH, 2H), 3.32 (m, OCH$_2$, 4H), 3.81 (m, OCH$_2$, 8H), 6.80–8.0 (m, ArH, 24H).

Anal. Calcd for C$_{46}$H$_{38}$O$_6$: C, 80.44; H, 5.58. Found: C, 80.30; H, 5.60.

The ditosylate, (SS)(RR)-19, was prepared in 50% yield, m.p. 204°–205.5°, pmr spectrum (60 MHz) in CDCl$_3$, δ 2.30 (s, ArCH$_3$, 6H), 3.90 (m, OCH$_2$, 12H), 6.8–8.0 (m, ArH, 32H).

Anal. Calcd for C$_{60}$H$_{50}$O$_{10}$S$_2$: C, 72.42; H, 5.06. Found: C, 72.38; H, 4.97.

The ditosylate, (SR)-19, was prepared in 52% yield, m.p. 217°–219°, and was too insoluble in organic solvents for a pmr spectrum.

Anal. Calcd for C$_{60}$H$_{50}$O$_{10}$S$_2$: C, 72.42; H, 5.06. Found: C, 72.25; H, 5.03.

The diastereomeric structures of the isomers of 18 and 19 were assigned by the numbers of different products produced when each reacted with (R)(S)-1 to give the diastereomers of 15 (see above procedures). Thus (SR)-19 gave the single product (SSR)(RRS)-15 (65%), whereas (SS)(RR)-19 gave two products as a mixture (72%) of (SSR)(RRS)-15 and (SSS)(RRR)-15, which were separated as before and characterized.

The diastereomeric structures of the stereoisomers of 18, 19 and 15 were assigned accordingly.

By the above procedures, optically pure (−)-(S)-1 [[α]$_{546}^{25}$ −50.4°, C 1.0 (CH$_2$)$_4$O] was converted to (+)-(S)-16 [19%, m.p. 133°–134°, [α]$_{546}^{25}$ +23.2° (C 1.1, (CH$_2$)$_4$O)], (+)-(S)-17 [43%, oil, [α]$_{546}^{25}$ +12.9° (C 1.2, (CH$_2$)$_4$O)] and (−)-(S)-1 [35% recovered, [α]$_{546}^{25}$ −49.5° (C 1.0, (CH$_2$)$_4$O)]. The three compounds were separated by chromatography on silica gel. The fact that optically pure 1 was recovered indicates no racemization occurred during reaction. By the above procedures, the above (+)-(S)-17 as converted to (−)-(SS)-18 [85%, foam, [α]$_{546}^{25}$ −55.8° (C 1.0, (CH$_2$)$_4$O)] which in turn was transformed into (+)-(SS)-19 [37%, m.p. 172°–174° [α]$_{546}^{25}$ +68.2° (C 1.0, (CH$_2$)$_4$O)]. By the above procedures, (+)-(SS)-19 was converted (using very dry pyridine and optically pure (+)-(R)-1) to (−)-(SSR)-15, [58%, m.p. 247°–249°, [α]$_{546}^{25}$ −141.0° (C 1.0, (CH$_2$)$_4$O)]. Similarly, (+)-(SS)-19 and optically pure (−)-(S)-1 was converted to optically pure (−)-(SSS)-15 [46%, m.p. 170°–190° (series of phase transitions), [α]$_{546}^{25}$ −175° (C 1.0, (CH$_2$)$_4$O)].

The pmr spectra of (SSR)-15 and (SSS)-15 show large differences, the most notable of which is a high upfield doublet in the aromatic region. Integration showed it to be due to 2 protons in (SSR)-15, and 6 protons in (SSS)-15. This difference is probably due to the H$^3$ aromatic proton of the binaphthyl. When two (R) or two (S) units are connected, the H$^3$ protons of one naphthalene are shielded by the ethyleneglycol-connected naphthylene. When (S) and (R) units are connected, the H$^3$ protons are deshielded.

EXAMPLE 4

Synthesis of Binaphthyl Units with Functional Groups in Place for Building Arms

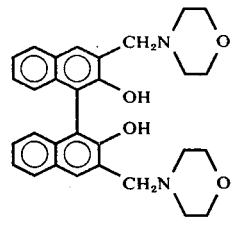

20

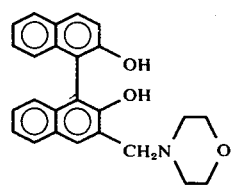

21

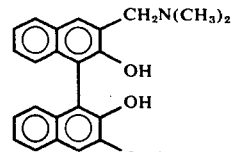

22

-continued

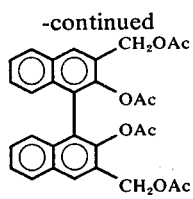

23

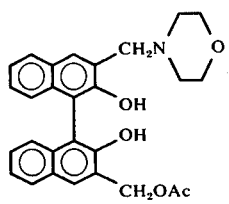

24

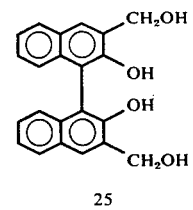

25

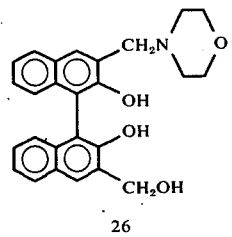

26

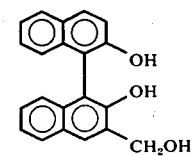

27

(S)-25

Procedure 1

Compound 20 was produced from binaphthol 1 and 4-(n-butoxymethylene)morpholine [*J. Chem. Eng. Data*, 7, Pt. 2, 575 (1962)]. A solution of 100 g. (0.35 mole) of 1 in 850 g. (4.9 moles) of 4-(n-butoxymethylene)morpholine was heated at 160° under nitrogen for 5 days (a precipitate of 20 started to form after 6 hours). The reaction mixture was cooled, 300 ml. of benzene was added with stirring, and the suspension stood at 25° for 10 hours. The solid was collected, washed with 300 ml. of ether and dried at 25° (30 mm) to give 104 g. (61%) of 20. A sample of 5 g. of this material was recrystallized from chloroform and ethyl acetate to give 4.5 g. of 20, m.p. 300° dec. The pmr spectrum (60 MHz) in CDCl$_3$ gave signals at δ 760 (m, ArH, 4H), 7.05 (m, ArH, 6H), 3.98 (AB quartet, $J_{AB}$=14Hz, ArCH$_2$N, 4H), 3.65 (m, OCH$_2$, 8H) and 2.60 (m, NCH$_2$, 8H). The base peak in the 70 ev mass spectrum was the molecular ion, m/e 484.

Anal. Calcd for C$_{30}$H$_{32}$N$_2$O$_4$: C, 74.36; H, 6.66; N, 5.78 Found: C, 74.23; H, 6.75; N, 5.66.

From the filtrate of the original reaction by chromatography was obtained 21 in 15% yield, m.p. 226°–228°.

Anal. Calcd for C$_{25}$H$_{23}$O$_3$N: C, 77.90; H, 6.01. Found: C, 77.84; H, 5.99.

Application of procedure 1 to 1 (42.9 g, 0.15 mol) and 131 g. of isobutoxymethylenedimethylamine (1 mole), [*J. Chem. Soc.*, 532 (1923)] in 400 ml. of isobutyl alcohol gave after 9 days at 160°, 19.8 g. (33%) of diamine 22, m.p. 256°–258°. The mass spectrum (70 ev) gave the molecular ion at m/e = 400.

Anal. Calcd for C$_{28}$H$_{28}$N$_2$O$_2$: C, 77.97; H, 7.05. Found: C, 78.20; H, 6.88.

Procedure 2

Tetrol (S)(R)-25 and triol 26 were prepared from 20 as follows. A solution of 50 g. (105 mmol) of 20 in 1200 ml. of acetic anhydride was refluxed for 8 days. The solution was cooled, evaporated at 30 mm, and the residue was dissolved in 150 ml. of benzene. The product mixture was chromatographed on 1 Kg. of silica gel in hexane-benzene (2:1). Elution of the column with 1 l. hexane-benzene (2:1), 2 l. hexane-benzene (1:1), 5 l. benzene and 3 l. 2% ether-benzene produced crude tetraacetate, 23. The combined fractions were evaporated, the residue was dissolved in 200 ml. of ether, which on concentration produced 24.5 g. (46%) of tetraacetate, m.p. 113°–114°.

Anal. Calcd for C$_{30}$H$_{26}$O$_8$: C, 70.03; H, 5.09. Found: C, 70.18; H, 5.18.

Further elution of the column with 5 l. 5% ether-benzene and 5 l. 10% ether-benzene produced monoacetate 24, isolated as follows. The combined fractions were evaporated, the residue was dissolved in hot benzene (75 ml.), which was cooled and 200 ml. of ether added. Evaporation of the solution at 25° produced 16.5 g. (39%) of 24, m.p. 115°–117°.

Anal. Calcd for C$_{28}$H$_{27}$NO$_5$: C, 75.31; H, 5.95. Found: C, 73.72; H, 6.04.

Procedure 3

Reduction of the tetraacetate 23 gave 25 as follows. To a refluxing suspension of 10.0 g. (210 mmol) of lithium aluminum hydride in 1.5 l. of dry ether was added dropwise 18.5 g. (36 mmol) of tetraacetate dissolved in tetrahydrofuran. The mixture was refluxed for 6 hours, cooled, and the excess reducing was destroyed by dropwise addition of ethanol at 0°. To the solution was added 400 ml. of 15% hydrochloric acid and 300 ml. of tetrahydrofuran. The mixture was stirred for 12 hours, the organic layer was washed with water and 10% sodium bicarbonate solution, and dried over magnesium sulfate. The ether was evaporated at 30 mm and the concentrated solution (250 ml.) was refluxed with continuous replacement of the tetrahydrofuran by benzene. Tetrol (S) (R)-25 crystallized from the hot benzene solution to give 12.5 g. (98%), m.p. 222°–224°, reported [*J. Org. Chem.*, 29 1394 (1964)] m.p. 231°. The base peak in the 70 ev mass spectrum was the molecular ion, m/e 346.

Anal. Calcd. for $C_{22}H_{18}O_4$: C, 76.29; H, 5.24. Found: C, 76.44; H, 5.35.

Procedure 3 applied to monoacetate 24 gave triol 26 (75%), m.p. 190°–192°. The 70 ev mass spectrum of this material gave a molecular ion at m/e 415.

Anal. Calcd for $C_{26}H_{25}O_4N$: C, 75.16; H, 6.06. Found: C, 75.07; H, 5.95.

Procedures 2 and 3 applied in sequence with 21 as starting material gave triol 27 in 80% overall yield, m.p. 206°–207°. The 70 ev mass spectrum of this material gave a molecular ion at m/e 316.

Anal. Calcd for $C_{21}H_{16}O_3$: C, 79.73; H, 5.10. Found C, 79.70; H, 5.29.

Optically pure (S)- and (R)-25 were prepared from optically pure diacids (S)- and (R)-2 of established absolute configuration [Tetrahedron, 27, 5999 (1971)]. A solution of optically pure (R)-2 (7.49 g., 20 mmol) in 60 ml. of tetrahydrofuran was added to a suspension of lithium aluminum hydride (6.08 g., 160 mmol) in 200 ml. of tetrahydrofuran, and the mixture was refluxed for 9 hours. The cooled reaction mixture was stirred with 90 ml. of 50% hydrochloric acid and 100 ml. of ether. The organic layer was separated, and the aqueous layer was extracted with a mixture of ether-tetrahydrofuran. The combined organic layers were washed with brine and dried over magnesium sulfate. Evaporation of the solvent with added benzene gave a yellow solid. This solid was recrystallized from tetrahydrofuran and benzene to give a solvate (prisms) which when dried at 138° at 0.05 mm for 24 hours gave (R)-25, 5.35 g. (77%), m.p. 192°–195°, $[\alpha]_{548}^{25}$ +78.7° (C 1.2, $(CH_2)_4O$).

Anal. Calcd. for $C_{22}H_{18}O_4$: C, 76.28; H, 5.24. Found: C, 76.39; H, 5.36.

A similarly conducted reduction of optically pure (S)-2 gave optically pure tetrol (S-25) in 79% yield, m.p. 190°–193°, $[\alpha]_{546}^{25}$ −77.8° (C 1.1, $(CH_2)_4O$). This material gave the same pmr spectrum (100 MHz) in $CD_3COCD_3$ as (S) (R)-25 as follows: δ 7.98 (s, Ar-$^4$H, 2H), 7.80 (m, Ar-$^5$H, 2H), 7.18 (m, Ar-H, 6H) and 4.92 (s, $CH_2$, 4H). The base peak in the 70 ev mass spectrum was the molecular ion, m/e 346.

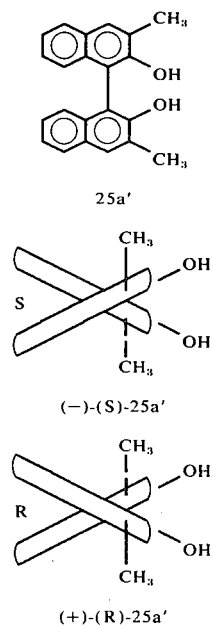

Procedure 4

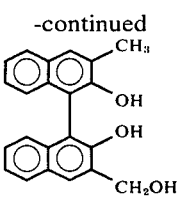

25b'

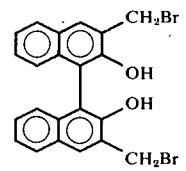

25c'

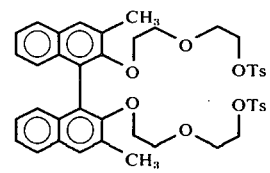

25d'

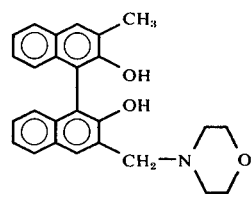

25e'

Procedure 4

Procedure 4 is illustrated by the preparation of racemic 25a' through 25c' as intermediates. A slow stream of dry hydrogen bromide was bubbled through a stirred suspension of 8.5 g. of tetrol 25 ml in 120 ml. acetic acid. After 10 minutes, the mixture became clear, the temperature increased, and a heavy precipitate formed. The HBr addition was stopped, the mixture was allowed to stand for 1 hour, the precipitate was collected, and the filtrate concentrated. The residue and precipitate were combined and dissolved in 500 ml. of ether, the solution was washed with water, and then with a saturated solution of sodium bicarbonate. The solution was dried and evaporated to give 11g. of solid. One recrystallization of this material from benzene gave 9.5 g. (85%) of white crystals of 25c', m.p. 215°–216°, pmr (100 MHz) in $CD_3COCD_3$, δ 8.05 (s, ArH$^4$, 2H), 7.84 (q, ArH$^5$, 2H), 7.22 (m, ArH$^{6,7}$, 4H), 6.94 (m, ArH$^8$, 2H), 4.84 (s, ArCH$_2$Br), 4H), mass spectrum (70 ev) molecular ion m/e = 472.

Anal. Calcd for $C_{22}H_{16}O_2Br_2$: C, 55.96; H, 3.41. Found C, 55.94; H, 3.53.

To a suspension of 3 g. of LiAlH$_4$ in 350 ml. of dry ether was added 7.08 g. of 25c' in 100 ml. of tetrahydrofuran. The mixture was refluxed for 4 hours and stirred at 25° for 12 hours. At 0°, 25 ml. of 95% ethanol was added, followed by 300 ml. of 15% hydrochloric acid and 100 ml. of tetrahydrofuran. The layers were separated, and the organic layer was washed twice with 10% sodium bicarbonate solution, with water, and was dried and evaporated. The residue was crystallized from benzene to give 4.7 g. (98%) of 25a', m.p. 205°. The pmr spectrum (100 MHz) in CDCl$_3$ gave δ 7.76 (m, ArH$^{4,5}$, 4H), 7.17 (m, ArH, 6H), 5.05 (s, OH, 2H) and 2.47 (s, CH$_3$, 6H), and the mass spectrum (70 ev) gave a molecular ion at m/e = 314.

Anal. Calcd for C$_{22}$H$_{18}$O$_2$: C, 84.05; H, 5.77. Found: C, 83.98; H, 5.85.

Procedure 4 is further illustrated. Diol 25a' and triol 25b' were produced by catalytic reduction of tetrol 25. A solution of 6.0 g. of 25 in 60 ml. of 95% ethanol was stirred with 3 g. of 10% palladium on charcoal under one atmosphere of hydrogen for 8 hours. The mixture was filtered, the filtrate was concentrated under vacuum and chromatographed on 100 g. of silica gel. Elution of the column with benzene gave 25a', 1.83 g. (33%), m.p. 205° (undepressed by admixture with an authentic sample). Elution with 1:1 benzene-dichloromethane gave 1.9 g. (32%) of triol 25b', m.p. 204° (from benzene). The compound's mass spectrum (70 ev) gave a molecular ion at m/e = 330, and pmr spectrum (100 MHz) in CDCl$_3$ gave δ 7.82 (m, ArH$^{4,5}$, 4H), 7.16 (m, ArH, 6H), 4.93 (s, ArCH$_2$, 2H) and 2.50 (s, CH$_3$, 3H).

Anal. Calcd for C$_{22}$H$_{18}$O$_3$: C, 79.98; H, 5.49. Found: C, 79.96; H, 5.68.

Elution of the column with 98:2 dichloromethaneisopropanol gave 1.0 g. (17%) of starting tetrol, 25.

Procedure 4 is further illustrated. Reduction of diamine 20 gave 25a' and 25e'. A mixture of 2.0 g. of 20, 80 ml. of glacial acetic acid, 120 ml. of 95% ethanol and 1 g. of 10% palladium on charcoal was stirred under one atmosphere of hydrogen for 15 hours. The product was isolated as before, and chromatographed on 100 g. of silica gel. Benzene eluted 25e', 0.56 g. (44%), m.p. 206° (undepressed by admixture with an authentic sample). Elution with 1:1 benzene-dichloromethane gave 0.280 g. (20%) of 25e', m.p. 185° (from dichloromethane-ether). The mass spectrum of the substance (70 ev) contained the molecular ion, m/e = 399, and the 100 MHz pmr spectrum in CDCl$_3$ gave δ 7.72 (m, ArH$^{4,5}$, 4H), 7.16 (m, ArH, 6H), 3.96 (s, ArCH$_2$-N, 2H), 3.66 (t, CH$_2$O, 4H), 2.60 (t, CH$_2$N, 4H) and 2.49 (s, CH$_3$, 3H).

Anal. Calcd for C$_{26}$H$_{25}$O$_3$N: C, 78.17; H, 6.31. Found: C, 78.09; H, 6.37.

Procedure 4 is further illustrated. Racemic 25a' was resolved into its enantiomers is as followed. A slurry of 146 g. of 25a', 750 ml. of dichloromethane and 84.5 g. of POCl$_3$ was stirred under nitrogen, and 111.3 g. of triethylamine was slowly added at a rate that maintained gentle reflux. After addition was complete, the solution was stirred an additional hour, and extracted twice with 300 ml. of water. The solution was dried, evaporated, and the crude chlorophosphat was stirred with 750 ml. of tetrahydrofuran and 200 ml. of water at 50° for 1 hour. To this solution, 700 ml. of ethyl acetate was added, the layers were separated, the organic layer was washed with 200 ml. of water, with 200 ml. of brine, dried with magnesium sulfate and evaporated under vacuum to produce white crystals of the phosphoric acid diester of 25a', weight 129 g. (75%), m.p. >300°. This material gave a molecular ion in its mass spectrum (70 ev), m/e = 376.

A mixture of 3.4 g. of the above acid ester, 2.65 g. of cinchonine and 45 ml. of methanol was warmed to reflux, and to the solution was added 8 ml. of water. The solution was cooled to 25°, and the crystalline salt that separated was collected, washed and dried to give 2.88 g. of salt (47% based on racemate = 100%). This material was recrystallized from 30 ml. of methanol and 5.5 ml. of water to give 2.3 g. of salt, [α]$_{578}^{25}$ −291°, [α]$_{546}^{25}$ −339°, [α]$_{436}^{25}$ −632° (C 1.1, dimethylformamide). The original mother liquors were evaporated to dryness to give a powder, 2.9 g. of salt of the other diastereomer, [α]$_{436}^{25}$ +526° (C 1.0, dimethylformamide).

The (−)-salt (see above, 0.50 g.) was dissolved in 13 ml. of hot ethanol, and 5.0 ml. of concentrated hydrochloric acid was added. The solution was cooled to 0°, and the crystals that separated were collected to give 0.20 g. (72%) of (−)-diester acid, [α]$_{578}^{25}$ −520°, [α]$_{546}^{25}$ −604°, [α]$_{436}^{25}$ −1116° (c 0.5, CH$_3$OH). The (+)-salt (see above, 0.50 g.) was similarly treated to give, after one recrystallization from methanol-water, 0.10 g. (36%) of (+)-diester acid, [α]$_{578}^{25}$ +492°, [α]$_{546}^{25}$ +552, [α]$_{436}^{25}$ +1008° (c 0.5, CH$_3$OH).

The above (−)-diester acid (0.50 g.) was dissolved in 50 ml. of tetrahydrofuran and 0.1 g. of LiAlH$_4$ was cautiously added, followed by an additional 20 ml. of tetrahydrofuran. The mixture was stirred under nitrogen at 25° for 18 hours, 20 ml. of 10% hydrochloric acid was added with cooling, 100 ml. of ether was added, and the layers were separated. The organic layer was washed with water three times, once with brine, was dried and evaporated. The residue was recrystallized from benzene to give 0.29 g. (70%) of (+)-(R)-25a', m.p. 199–200°, [α]$_{578}^{25}$ +28.2°, [α]$_{546}^{25}$ +35.3°, [α]$_{436}^{25}$ +101° (C 0.5, CHCl$_3$). The pmr spectrum of this material was identical to that of racemic 25a'. A similar reduction of the above (+)-diester acid gave (60%) (−)-(S)-25a', m.p. 199°–200°, [α]$_{578}^{25}$ −27°, [α]$_{546}^{25}$ −34°, [α]$_{436}^{25}$ −99° (C 0.5, CHCl$_3$).

The absolute configurations of (+)- and (−)-25a' were assigned on the basis of comparisons of the CD spectra of (+)-25a', (+)-(R)-1 and (+)-(R)-2. All three compounds exhibit a positive Cotton effect at ∼315nm. Thus (+)-25a' possesses the (R)-, and (−)-25a' the (S)-configurations.

Procedure 4 was further illustrated. The synthesis of 25d' from 25a' was patterned after the synthesis of (−)-(S)-1a' from (−)-(S)-1 described under Experimental, General. From 25a', 3,3'-dimethyl-2,2'-bis(-diethylenoxytetrahydropyran)-1.1'-binaphthyl was produced as an oil in 65% yield. This bis-pyranyl ether was cleaved with acid to give the corresponding diol as an oil in 90% yield. This material was tosylated to give 25d' as a glass in 90% yield. The pmr spectrum of this material (100 MHz) in CDCl$_3$ gave δ 7.70 (m, ArH, 8H), 7.28 (m, ArH, 6H), 7.05 (q, ArH, 4H), 3.86 (q, CH$_2$OTs, 4H), 3.49 (m, OCH$_2$CH$_2$OT$_s$, 4H), 3.10 (m, ArOCH$_2$CH$_2$O, 8H), 2.46 (s, CH$_3$-naphthyl, 6H) and 2.37 (s, CH$_3$C$_6$H$_4$, 6H).

Anal. Calcd for C$_{44}$H$_{46}$O$_{10}$S$_2$: C, 66.15; H, 5.80. Found: C, 66.40; H, 6.16.

EXAMPLE 5

Synthesis of Macrocycles with Arms on Binaphthyl Units

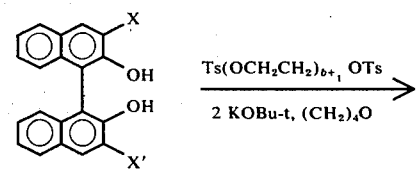

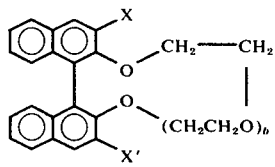

Procedure 1

Procedure 1 is illustrated for preparation of monolocular systems with the conversion of tetrol 25 to macrocycle 28. A solution of 12.6 g. (37 mmol) of tetrol 25 in 900 ml. of tetrahydrofuran was stirred at 25° under nitrogen for 30 min. To the clear solution was added 4.5 g. (80 mmol) of potassium hydroxide dissolved in 80 ml. of water. The mixture was warmed to 65° (homogeneous) and with stirring 26 g. (39 mmol) of pentaethyleneglycol) ditosylate dissolved in 100 ml. of tetrahydrofuran was added. The solution was refluxed for 48 hours, cooled, concentrated to 200 ml. at 30 mm and partitioned between water and dichloromethane. The water layer was extracted with additional dichloromethane. The combined dichloromethane extracts were dried with magnesium sulfate and concentrated to 100 ml. This solution was chromatographed on 500 g. of neutral alumina packed in dichloromethane. Elution of the column with 2 l. dichloromethane, 2 l. of 1% isopropanoldichloromethane and 2 l. of 2% isopropanol-dichloromethane gave side products. Elution of the column with 6 l. of 4% isopropanol-dichloromethane produced after removal of solvents, 12.0 g. (60%) of 28 as a colorless glass, which tenaciously retains solvent. When heated as a thin film at 145° and 0.05 mm for 6 hours, solvent evaporates. A crystalline sample of 28 was obtained by concentrating an isopropyl alcohol solution (1 g. in 50 ml.) at 25°. The solid material after drying at 25° for 48 hours and 0.1 mm still contained a trace (pmr) of isopropanol. The pmr spectrum of 28 (100 MHz) in $CDCl_3$ gave signals at $\delta$ 7.90 (s, Ar-$^4$H, 2H), 7.85 (m, Ar-$^5$H, 2H), 7.28 (m, Ar-H, 6H), 4.95 (AB quartet, $J_{AB}$ = 13Hz, $ArCH_2O$, 4H), and 7.28 (complex m, $OCH_2$, 20H). The base peak in the 70 ev mass spectrum was the molecular ion, m/e 548 (see Table 1 for analysis).

TABLE 1

$M = N(CH_2CH_2)_2O$     $P = OCH_2CO_2CH_3$     $T = OCH_2CO_2H$

| COMPOUND NUMBERS | | PRO-CEDURE | | PRODUCT | | | | | Analyses (%) | | | |
|---|---|---|---|---|---|---|---|---|---|---|---|---|
| Product | Start. Mat. | No. | b | X | X' | mp | Yld % | (C 1, $(CH_2)_4O$) $[\alpha]_{546}^{25}$ | Calc'd for Formula | C | H | Found C | H |
| (S)-28 | (S)-25 | 1 | 4 | $CH_2OH$ | $CH_2OH$ | glass | 55 | −34.0° | $C_{32}H_{36}O_8$ | 70.05 | 6.61 | 69.89 | 6.82 |
| 28 | 25 | 1 | 4 | $CH_2OH$ | $CH_2OH$ | 132–134° | 60 | — | $C_{32}H_{36}O_8$ | 70.05 | 6.61 | 69.91 | 6.70 |
| (S)-29 | (S)-28 | 2 | 4 | $CH_2P$ | $CH_2P$ | glass | 44 | −25.7° | $C_{38}H_{44}O_{12}$ | 65.87 | 6.40 | 65.99 | 6.27 |
| 29 | 28 | 2 | 4 | $CH_2P$ | $CH_2P$ | glass | 60 | — | $C_{38}H_{44}O_{12}$ | 65.87 | 6.40 | 65.63 | 6.27 |
| (S)-30 | (S)-29 | 3 | 4 | $CH_2T$ | $CH_2T$ | glass | 90 | −24.4° | $C_{36}H_{40}O_{12}$ | 65.05 | 6.07 | 65.00 | 6.23 |
| 30 | 29 | 3 | 4 | $CH_2T$ | $CH_2T$ | glass | 80 | — | $C_{36}H_{40}O_{12}$ | 65.05 | 6.07 | 64.87 | 6.28 |
| 31 | 20 | 1 | 4 | $CH_2M$ | $CH_2M$ | glass | 65 | — | $C_{40}H_{50}N_2O_8$ | 69.95 | 7.34 | 69.71 | 7.38 |
| 32 | 22 | 1 | 4 | $CH_2N(CH_3)_2$ | $CH_2N(CH_3)_2$ | glass | 64 | — | $C_{36}H_{48}N_2O_8$ | 71.73 | 7.69 | 71.70 | 7.62 |
| 34 | 27 | 1 | 4 | H | $CH_2OH$ | 136–137° | 50 | — | $C_{31}H_{34}O_7$ | 71.80 | 6.61 | 71.57 | 6.64 |
| 34a | 27 | 1 | 3 | H | $CH_2OH$ | 151–152° | 31 | — | $C_{29}H_{30}O_6$ | 73.39 | 6.37 | 73.33 | 6.26 |
| 35 | 34 | 2 | 4 | H | $CH_2P$ | glass | 70 | — | $C_{34}H_{38}O_9$ | 69.14 | 6.48 | 68.95 | 6.71 |
| 36 | 35 | 3 | 4 | H | $CH_2T$ | glass | 70 | — | $C_{33}H_{36}O_9$ | 68.74 | 6.29 | 68.95 | 6.63 |
| 36a | 34a | 2,3 | 3 | H | $CH_2T$ | 128–130° | 35 | — | $C_{31}H_{32}O_8$ | 69.91 | 6.05 | 70.09 | 6.26 |
| 37 | 26 | 1 | 4 | $CH_2M$ | $CH_2OH$ | glass | 55 | — | $C_{36}H_{43}NO_8$ | 70.00 | 7.02 | 69.76 | 7.22 |
| 38 | 37 | 2 | 4 | $CH_2M$ | $CH_2P$ | glass | 35 | — | $C_{39}H_{47}NO_{10}$ | 67.91 | 6.87 | 67.98 | 6.89 |
| 39 | 38 | 3 | 4 | $CH_2M$ | $CH_2T$ | glass | 65 | — | $C_{38}H_{45}NO_{10}$ | 67.53 | 6.71 | 67.41 | 6.74 |
| (S)-40 | (S)-25 | 1 | 3 | $CH_2OH$ | $CH_2OH$ | glass | 6 | −56.1° | $C_{30}H_{32}O_7$ | 71.41 | 6.39 | 71.45 | 6.45 |
| 40 | 25 | 1 | 3 | $CH_2OH$ | $CH_2OH$ | glass | 10 | — | $C_{30}H_{32}O_7$ | 71.41 | 6.39 | 71.21 | 6.53 |
| (S)-41 | (S)-40 | 2 | 3 | $CH_2P$ | $CH_2P$ | glass | 51 | −95.7° | $C_{36}H_{40}O_{11}$ | 66.65 | 6.22 | 66.50 | 6.05 |
| 41 | 40 | 2 | 3 | $CH_2P$ | $CH_2P$ | glass | 55 | — | $C_{36}H_{40}O_{11}$ | 66.65 | 6.22 | 66.46 | 6.15 |
| (S)-42 | (S)-41 | 3 | 3 | $CH_2T$ | $CH_2T$ | glass | 65 | −107.4° | $C_{34}H_{36}O_{11}$ | 65.79 | 5.85 | 65.86 | 5.94 |
| 42 | 41 | 3 | 3 | $CH_2T$ | $CH_2T$ | glass | 85 | — | $C_{34}H_{36}O_{11}$ | 65.79 | 5.85 | 65.92 | 5.87 |
| (R)-43 | (R)-25 | 1 | 5 | $CH_2OH$ | $CH_2OH$ | glass | 57 | −16.4° | $C_{34}H_{40}O_9$ | 68.90 | 6.80 | 69.02 | 6.80 |
| 43 | 25 | 1 | 5 | $CH_2OH$ | $CH_2OH$ | glass | 50 | — | $C_{34}H_{40}O_9$ | 68.90 | 6.80 | 68.73 | 6.98 |
| (R)-44 | (R)-43 | 2 | 5 | $CH_2P$ | $CH_2P$ | glass | 54 | −19.5° | $C_{40}H_{48}O_{13}$ | 65.20 | 6.57 | 65.05 | 6.50 |
| 44 | 43 | 2 | 5 | $CH_2P$ | $CH_2P$ | glass | 50 | — | $C_{40}H_{48}O_{13}$ | 65.20 | 6.57 | 65.06 | 6.39 |
| (R)-45 | (R)-44 | 3 | 5 | $CH_2T$ | $CH_2T$ | glass | 50 | −15.0° | $C_{38}H_{44}O_{13}$ | 64.39 | 6.26 | 64.18 | 6.06 |
| 45 | 44 | 3 | 5 | $CH_2T$ | $CH_2T$ | glass | 75 | — | $C_{38}H_{44}O_{13}$ | 64.39 | 6.26 | 64.14 | 6.42 |
| 28a' | 28 | 4 | 4 | $CH_2Cl$ | $CH_2Cl$ | glass | 91 | — | $C_{32}H_{34}Cl_2O_6$ | 65.61 | 5.86 | 65.89 | 5.91 |
| (S)-28a' | (S)-28 | 4 | 4 | $CH_2Cl$ | $CH_2Cl$ | glass | 81 | −9.5° | $C_{32}H_{34}Cl_2O_6$ | 65.61 | 5.86 | 65.87 | 6.01 |
| 28b' | 28a' | 5 | 4 | $CH_2SCH_2CO_2H$ | $CH_2SCH_2CO_2H$ | glass | 96 | — | $C_{36}H_{40}O_{10}S_2$ | 62.06 | 5.79 | 61.90 | 6.16 |
| (S)-28b' | (S)-28a' | 5 | 4 | $CH_2SCH_2CO_2H$ | $CH_2SCH_2CO_2H$ | glass | 72 | −12.0° | $C_{36}H_{40}O_{10}S_2$ | 62.06 | 5.79 | 62.21 | 6.01 |
| 28c' | 28a' | 5 | 4 | $CH_2SCH_2-CH_2CO_2H$ | $CH_2SCH_2-CH_2CO_2H$ | glass | 97 | — | $C_{38}H_{44}O_{10}S_2$ | 62.98 | 6.12 | 62.86 | 6.15 |
| (S)-28c' | (S)-28a' | 5 | 4 | $CH_2SCH_2-CH_2CO_2H$ | $CH_2SCH_2-CH_2CO_2H$ | glass | 58 | −33.6° | $C_{38}H_{44}O_{10}S_2$ | 62.98 | 6.12 | 62.67 | 6.27 |
| 28d' | 28a' | 6 | 4 | $CH_2CH(CO_2H)_2$ | $CH_2CH(CO_2H)_2$ | 140° | 91 | — | $C_{38}H_{40}O_{14}$ | 63.33 | 5.59 | 63.15 | 5.82 |
| 28e' | 28d' | 6 | 4 | $CH_2CH_2CO_2H$ | $CH_2CH_2CO_2H$ | glass | 92 | — | $C_{36}H_{40}O_{10}$ | 68.34 | 6.37 | 68.30 | 6.51 |
| (S)-28e' | (S)-28a' | 6 | 4 | $CH_2CH_2CO_2H$ | $CH_2CH_2CO_2H$ | glass | 85 | −94° | $C_{36}H_{40}O_{10}$ | 68.34 | 6.37 | 68.10 | 6.40 |
| 28f' | 25b' | 1 | 4 | $CH_3$ | $CH_2OH$ | 159° | 59 | — | $C_{32}H_{36}O_7$ | 72.16 | 6.81 | 72.12 | 7.06 |
| 28q' | 28f' | 2,3 | 4 | $CH_3$ | $CH_2T$ | glass | 85 | — | $C_{34}H_{38}O_9$ | 69.14 | 6.48 | 69.78 | 6.47 |
| 28h' | 28 | 7 | 4 | $CH_2OH$ | $CH_2T$ | glass | 77 | — | $C_{34}H_{38}O_{10}$ | 67.31 | 6.31 | 67.63 | 6.29 |
| (R)-28h' | (R)-28 | 7 | 4 | $CH_2OH$ | $CH_2T$ | glass | 82 | −24.2° | $C_{34}H_{38}O_{10}$ | 67.31 | 6.31 | 67.30 | 6.21 |

*C 1.0, $CHCl_3$

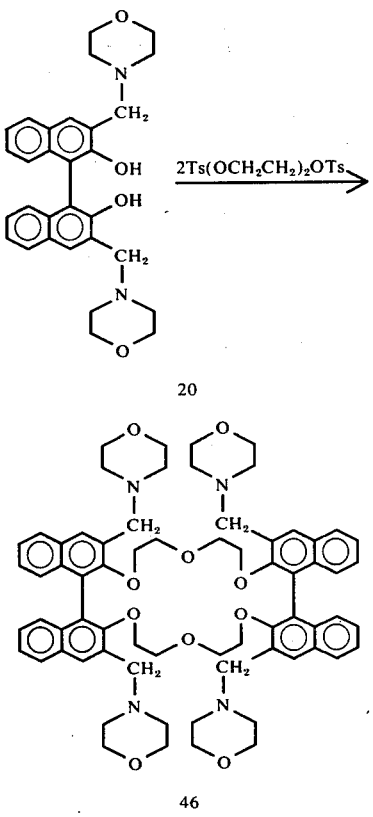

20

46

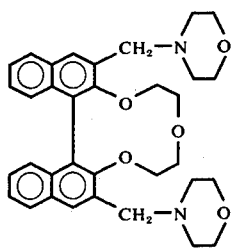

47

Procedure 1 is illustrated for the preparation of dilocular systems by conversion of 20 to 46. A solution at 50° was prepared from 800 ml. of tetrahydrofuran, 19.36 g. (40 mmol) of 20 and 9 g. (80 mmol), of potassium t-butoxide. To the solution under nitrogen was added with stirring 16.56 g. (40 mmol) of diethyleneglycol ditosylate. The resulting mixture was stirred at 25° for 12 hours and at reflux for 90 minutes. The mixture was filtered, the filtrate evaporated, and the residue (34.8 g.) was chromatographed on 900 g. of neutral alumina, with products eluted with ether, with 500 ml. fractions collected. Fractions 3–7 contained 8.4 of 47 (product of reaction of one mole each of 20 and diethyleneglycol ditosylate) which was purified by a second chromatogram to give 7.9 g. (36%) of pure material (oil) dried as a film at 60° and 20 mm for 24 hours. The 70 ev mass spectrum gave a molecular ion at 554.

Anal. Calcd for $C_{34}H_{38}O_5H_2$: C, 73.64; H, 6.86. Found: C, 73.92; H, 7.08.

Fractions 9–14 contained 46 which precipitated as a microcrystalline material on evaporation of an ether solution, wt 11.2 g. (51%), m.p. 130°–132° (one component on tlc). This material gave a 70 ev mass spectrum with a parent ion at m/e 1108.

Anal. Calcd for $C_{68}H_{76}O_{10}N_4$: C, 73.64; H, 6.86. Found: C, 73.72; H, 7.16.

The absence of a second isomer coupled with the great predominance of the (SS) (RR) over the (SR)-isomer in preparation of the parent system (8) indicates this material also has the (SS) (RR)-configuration. Molecular models suggest this isomer can better template around potassium ion than the (SR)-isomer.

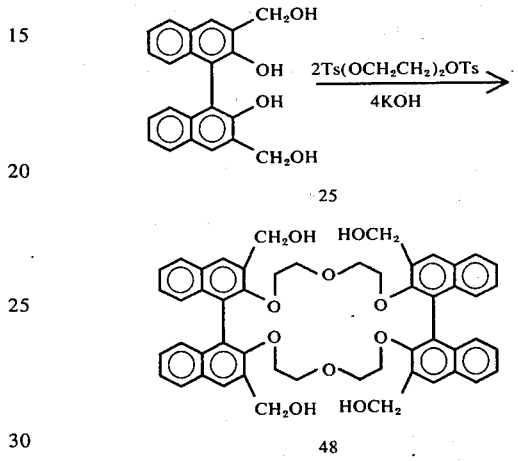

48

Procedure 1 as applied to a dilocular system is further illustrated by conversion of tetrol 25 to (SR) (RS-48. From 3.5 g. (10.1 mmol) of tetrol, 4.1 g. (10 mol) of diethyleneglycol ditosylate and 1.14 g. (20.3 mmol) of potassium hydroxide was obtained, after the usual extraction and evaporation procedure, a material that was chromatographed on silica gel. With 95% ether-5% methanol and 94% ether-6% methanol was eluted a material which after further chromatography on alumina gave 0.50 g. (10%) of (SS) (RR)-48, m.p. 168°–170° (with bubbles). The 60 MHz pmr spectrum in CDCl$_3$ gave the following signals: δ 7.76 (m, ArH, 8H), 7.10 (m, ArH, 12H), 4.76 (s, ArCH$_2$, 8H), 3.36–2.96 (m, OCH$_2$CH$_2$O, 16H). The 70 ev mass spectrum of the substance gave a molecular ion minus two moles of water at m/e = 796.

Anal. Calcd for $C_{52}H_{48}O_{10}$: C, 74.98; H, 5.81. Found: C, 74.86; H, 6.00.

Elution of the original silica gel column with 92% ether-8% methanol gave 0.52 g. (10%) of (SR)-48 m.p. 168°–170° (with bubbles). The 60 MHz pmr spectrum in CDCl$_3$ gave the following signals: δ 7.80 (m, ArH, 8H), 7.10 (m, ArH, 12H), 4.80 (broad s, ArCH$_2$, 8H), 3.83–2.48 (complex m, OCH$_2$CH$_2$O, 16H). The 70 ev mass spectrum of the substance gave a molecular ion minus two moles of water at m/e = 796.

Anal. Calcd for $C_{52}H_{48}O_{10}$: C, 74.98; H, 5.81. Found: C, 75.14; H, 6.00.

The structures of these two steroisomers were distinguished as follows. That they are different is shown by their different pmr spectra, and the fact they depress each others melting points (m.m.p. 148°–160°, bubbles). The (SS) (RR)-isomer (83 mg.) was distributed between the two layers formed by adding 20.2 mg. of optically pure (+)-α-phenylethylammonium bromide and 10 mg. of NaPF$_6$ to 0.20 ml. of CDCl$_3$, 0.40 ml. of CD$_3$CO$_2$D and 0.11 ml. of D$_2$O. After shaking, the two layers separated. Examination of the 100 MHz pmr spectrum of each layer indicated the macrocycle to be distributed 40% in the aqueous and 60% in the chloroform layer, but the amine salt to be essentially completely in the aqueous layer. The macrocycle in each layer was isolated and the optical rotations of each sample taken. The material from the chloroform layer gave $[\alpha]_{578}^{25}$ +0.1 ±0.05° (C2, CHCl$_3$), and that from the water layer gave $[\alpha]_{578}^{25}$ −0.2 ±0.1° (C2, CHCl$_3$). A similar experiment performed with the (SR)-isomer gave rotations of 0.00° for the material in each layer. Thus the material that eluted from the original chromatograph column first must have been a racemate ((SS) (RR)-48), and the material that eluted second must have been a meso compound ((SR)-48).

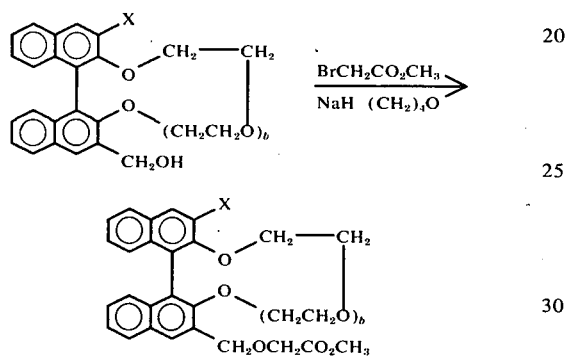

Procedure 2

Procedure 2 is illustrated with the conversion of diol (S)-28 to diester (S)-29. To a solution of optically pure (S)-28 (5.8 g., 10.5 mmol) in 250 ml. of tetrahydrofuran was added sodium hydride as a 50% suspension in oil (2.4 g., 50 mmol), and the mixture was stirred at 25° for 2 hr. Methyl bromoacetate (7.6 g., 50 mmol) was added to the above suspension, and the mixture was heated to reflux for 6.5 hours. The reaction mixture was cooled, filtered, and the filter cake was washed with tetrahydrofuran. The combined filtrate was evaporated to an oil that was chromatographed on 150 g. of silica gel. Elution of the column with 1.4 l. of dichloromethane gave non-naphthalene containing products (pmr). Elution with 3.5 l. of 2% methanol-ether gave (S)-29. The eluate was evaporated to give 3.2 g. (44%) of a glass, which was dried at 165° under 0.07 mm for 1 hour, $[\alpha]_{546}^{25}$ −25.7° (C 1.0, (CH$_2$)$_4$O). The 70 ev mass spectrum of the material gave a parent ion at m/e 692. A 100 MHz pmr spectrum in CDCl$_3$ gave the following signals: δ 7.7–8.05 (m, ArH, 4H), 7.0–7.5 (m, ArH, 6H), 5.0 (s, ArCH$_2$O, 4H), 4.35 (s, OCH$_2$CO$_2$, 4H), 3.80 (s, OCH$_3$, 6H), 2.8–3.8 (m, OCH$_2$CH$_2$O, 2OH). Table I records the analysis.

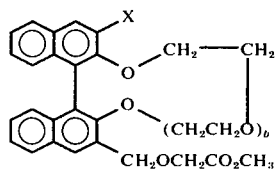

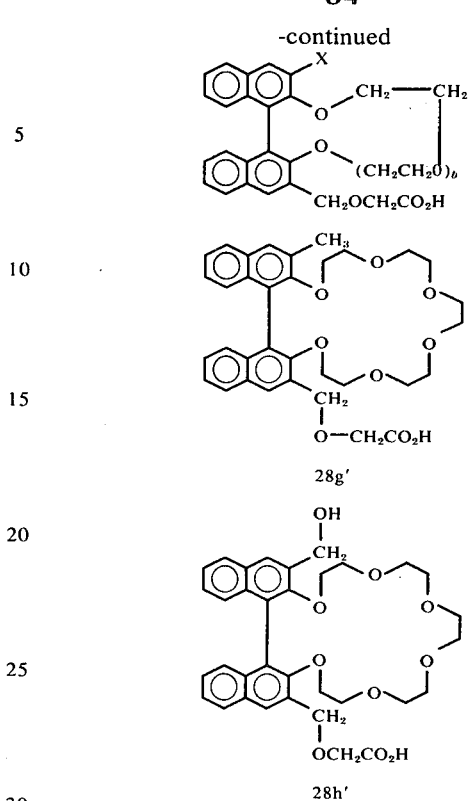

Application of procedure 2 to monool 28f' gave (72%) of the methyl ester of 28g' as a glass. The mass spectrum (70 ev) gave a molecular ion at m/e = 604. The pmr spectrum (60 MHz) in CDCl$_3$ gave δ 8.10–6.84 (m, ArH, 10H), 4.98 (s, ArCH$_2$, 2H), 4.32 (s, CH$_2$CO$_2$, 2H), 4.05–2.76 (m, CH$_2$O, 20H), 3.72 (s, OCH$_3$, 3H) and 2.55 (s, ArCH$_3$, 3H).

Anal. Calcd for C$_{35}$H$_{40}$O$_9$: C, 69,52; H, 6.67. Found: C, 69.29; H, 6.48.

Application of a modified procedure 2 to diol 28 gave the methyl ester of monoacid 28h'. To a solution of 5.5 g. of 28 in 500 ml. of tetrahydrofuran under nitrogen was added 3.0 g. of sodium hydride (50% mineral oil dispersion). The mixture was heated to reflux and 2.2 g. of methyl bromoacetate in 25 ml. of tetrahydrofuran was added, and the mixture was refluxed for 12 hours, cooled, filtered and evaporated under vacuum. The residue was shaken with 400 ml. each of water and dichloromethane, and the organic layer was dried and concentrated. The residue was chromatographed on 200 g. of silica gel, and the column was washed with 2 liters of dichloromethane, 2 liters of dichloromethane-methanol (99:1), and 2 liters of dichloromethane-methanol (49:1). Then 2 liters of 19:1 dichloromethane-methanol gave 2.2 g. (35%) of diester 29, identified by tlc and pmr. Elution of the column with 2 liters of 9:1 and 3 liters of 4:1 dichloromethane-methanol gave upon evaporation and drying 0.60 g. (10%) of the ester of mono-acid 28h'. The mass spectrum (70 ev) showed a molecular ion at m/e 620. The pmr spectrum (60 MHz) in CDCl$_3$ gave δ 8.02 (s, ArH$^{4'}$, 1H), 7.86 (s, ArH at ArH$^4$, 1H), 7.95–6.85 (m, ArH, 8H), 4.88 (s, ArCH$_2$O, 2H), 4.90 (AB q, CH$_2$OH, 2H), 4.26 (s, OCH$_2$CO$_2$, 2H), 3.75 (s, OCH$_3$, 3H) and 3.92-2.80 (m, OCH$_2$, 20H).

Anal. Calcd for C$_{35}$H$_{40}$O$_{10}$: C, 67.73; H, 6.50. Found: C, 67.90; H, 6.51.

Application of this same procedure to optically pure (+)-(R)-28 gave (14%) the ester of mono-acid, (−)-(R)-28h', identified by the tlc and pmr spectral comparisons with racemic ester.

Procedure 3

Procedure 3 is illustrated with the conversion of diester (S)-29 to diacid (S)-30. A mixture of (S)-29 (5.2 g., 7.5 mmol) and barium hydroxide octahydrate (7.1 g., 22.5 mmol) and 250 ml. of methanol was heated at reflux for 4 hours, and evaporated to dryness. The residue was dissolved in water, and the aqueous solution was washed with a mixture of dichloromethane and ether. The aqueous layer was filtered and acidified with hydrochloric acid to pH = 1 to give a milk-like emulsion, which was extracted twice with dichloromethane. The combined extracts were washed once with 5% aqueous hydrochloric acid, three times with water, and dried over magnesium sulfate. Evaporation of the dichloromethane gave 4.65 g. (90%) of optically pure (S)-30 as a glass. A sample dried as a thin film at 165° under 0.07 mm for 1 hour gave $[\alpha]_{546}^{25}$ −24.4° (C 1.0, $(CH_2)_4O$). The 70 ev mass spectrum gave a molecular ion at m/e 664. A 100 MHz pmr spectrum in $CDCl_3$ gave the following signals: $\delta$ 7.7–8.1 (m, ArH, 4H), 6.9–7.5 (m, ArH, 6H), 4.97 (s, $ArCH_2O$, 4H), 4.30 (s, $OCH_2CO_2$, 4H), 3.0–4.0 (m, $OCH_2CH_2O$, 20H). The analysis is given in Table I.

Procedure 3 when applied to the hydrolysis of the methyl ester of 28g' gave (85%) 28g' as a glass. The mass spectrum (70 ev) gave a molecular ion at m/e = 590. The pmr spectrum (60 MHz) in $CD_3CO_2D$ gave $\delta$ 8.15 –6.95 (m, ArH, 10H), 5.10 (s, $ArCH_2$, 2H), 4.42 (s, $CH_2CO_2$, 2H), 4.20–2.95 (m, $OCH_2$, 20H) and 2.60 (s, $ArCH_3$, 3H). Table I records the analysis.

Procedure 3 when applied to the methyl ester of monoacid 28h' gave (77%) acid 28h', a glass. The mass spectrum (70 ev) of this material gave a molecular ion of m/e = 606, and a pmr spectrum (60 MHz) in $CDCl_3$ of $\delta$ 8.07 (s, $ArH^{4'}$, 1H), 7.96 (s, $ArH^4$, 1H), 7.95–6.88 (m, ArH, 8H), 4.90 (m, $ArCH_2OH$ and $ArCH_2OCH_2$, 4H), 4.25 (s, $OCH_2CO_2$, 2H) and 3.92–2.80 (m, $OCH_2$, 20H).

Procedure 3 applied to the methyl ester of mono-acid (+)-(R)-28h' gave (82%) (+)-(R)-28h' as a glass, $[\alpha]_{578}^{25}$ −68.3°, $[\alpha]_{546}^{25}$ −80.4° (C 1.0, $CHCl_3$) and $[\alpha]_{578}^{25}$ +20.7° and $[\alpha]_{546}^{25}$ +24.2° (C 1.0, $(CH_2)_4O$). Table I records the analysis.

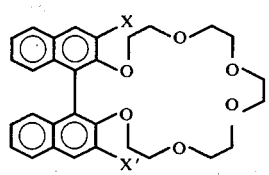

| | X | X' |
|---|---|---|
| 28a' | $CH_2Cl$ | $CH_2Cl$ |
| 28b' | $CH_2SCH_2CO_2H$ | $CH_2SCH_2CO_2H$ |
| 28c' | $CH_2SCH_2CH_2CO_2H$ | $CH_2SCH_2CH_2CO_2H$ |
| 28d' | $CH_2CH(CO_2H)_2$ | $CH_2CH(CO_2H)_2$ |
| 28e' | $CH_2CH_2CO_2H$ | $CH_2CH_2CO_2H$ |
| 28f' | $CH_3$ | $CH_2OH$ |
| 28g' | $CH_3$ | $CH_2OCH_2CO_2H$ |
| 28h' | $CH_2OH$ | $CH_2OCH_2CO_2H$ |

Procedure 4

Procedure 4 is illustrated by the conversion of 28 to 28a'. To a suspension of 4.0 g. of 28 in 50 ml. of benzene was added 4.0 g. of thionyl chloride at 25°. The mixture became homogeneous, and after stirring at 25° for 8 hours, the solvent was evaporated under vacuum and the residue was dissolved in 100 ml. of dichloromethane. The solution as extracted with a 100 ml. portion of sodium bicarbonate-saturated water, and the water layer was washed with 50 ml. of dichloromethane. The combined organic extracts were dried, evaporated and chromatographed on 100 g. of silica gel. The column was washed with 500 ml. of dichloromethane and 500 ml. of dichloromethaneether (19:1). Product (28a') was eluted with 2 liters of dichloromethane-ether (9:1) and 1 liter of 4:1 dichloromethane-ether as an oil, weight 3.9 g. (91%). The mass spectrum (70 ev) of the material gave a molecular ion at m/e = 584, and the pmr spectrum (60 MHz) in $CDCl_3$ gave $\delta$ 8.05 (s, $ArH^4$, 2H) 7.98–7.14 (m, ArH, 8H), 5.50 (ABq, $CH_2Cl$, 4H) and 3.93–2.75 (m, $OCH_2$, 20H). Table I reports the analysis. Optically pure enantiomer (−)-(S)-28a', similarly prepared from optically pure (S)-28 gave $[\alpha]_{578}^{25}$ −7.0°, $[\alpha]_{546}^{25}$ −9.5°, $[\alpha]_{436}^{25}$ −38.4° (C 1.0, $CHCl_3$).

Procedure 5

To a stirred solution of racemic 28a' (2.0 g.) and 3.7 g. of thioglycolic acid in 200 ml. of tetrahydrofuran under nitrogen was added 3.2 g. of sodium hydroxide dissolved in 30 ml. of water. The mixture was refluxed for 20 hours, cooled and concentrated under vacuum to 20 ml. The solution was diluted to 100 ml. with water, and 6N hydrochloric acid was added until a pH of one was obtained. An oil separated, and the mixture was allowed to stand at 25° for 10 hours. The aqueous solution was decanted, and the oily residue was washed three times with 50 ml. of water. The residue was dissolved in 150 ml. of dichloromethane, and the solution was washed with water, dried and evaporated under vacuum. The residue was dried at 95° (5$\mu$) for 1 hour to give 2.3 g. (96%) of 28b' as a glass. The mass spectrum (70 ev) of the material gave a molecular ion at m/e = 696. The pmr spectrum (60 MHz) in $CD_3CO_2D$ gave $\delta$ 8.02 (s, $ArH^4$, 2H), 8.00-6.90 (m, ArH, 8H), 4.22 (ABq, $ArCH_2S$, 4H), 3.40 (s, $SCH_2CO_2$, 4H) and 4.10–2.90 (m, $OCH_2$, 20H). Table I records the analysis.

Optically pure (+)-(S)-28b' was similarly prepared, $[\alpha]_{546}^{25}$ +204° (C 1.3, $CHCl_3$) and $[\alpha]_{546}^{25}$ +12.0° (C 1.0, $(CH_2)_4O$). Table I records the analysis.

Racemic 28c' was similarly prepared except $\beta$-mercaptopropionic was substituted for thioglycolic acid. The product gave a mass spectrum (70 ev) containing a molecular ion at m/e = 724, and a pmr spectrum (60 MHz) in $CD_3CO_2D$ with $\delta$ 8.02 (s, $ArH^4$, 2H), 8.02–6.90 (m, ArH, 8H), 4.18 (ABq, $ArCH_2$, 4H), and 4.20–2.50 (m, $OCH_2$, $SCH_2CH_2CO_2$, 28H). Table I records the analysis.

Optically pure (-)-(S)-28c' prepared from optically pure (S)-28a' gave $[\alpha]_{546}^{25}$ +61.5° (C 1.15, $CHCl_3$) and $[\alpha]_{546}^{25}$ −33.6° (C 1.21, $(CH_2)_4O$).

Procedure 6

Procedure 6 is illustrated by the conversion of racemic 28a' to 28e'. To a solution under nitrogen of 3.0 g. of 28a' and 2.0 g. of dimethyl malonate in 100 ml. of dry toluene was added with stirring 0.720 g. of sodium hydride (50% mineral oil dispersion). The mixture was stirred for 1 hour at 25°, at reflux for 2 hours and an additional 6 hours at 25°. The solution was cooled and shaken with 200 ml. of dichloromethane and 200 ml. of water. The aqueous layer was extracted with 50 ml. of dichloromethane, and the combined organic layers were dried and evaporated under vacuum. The residue was chromatographed on 100 g. of silica gel. The column was washed with 1 liter of dichloromethane, 1 liter of 49:1 dichloromethane-ether, and 1 liter of 19:1 of dichloromethane-ether. Elution of the product (tetraester) came with 2 liters of 9:1 and 2 liters of 4:1 dichloromethane-ether, wt 2.6 g. (65%) of a glass. The mass spectrum (70 ev) gave a parent ion at m/e 776, and the pmr spectrum (60 MHz) in $CDCl_3$ gave $\delta$ 7.92–6.90 (m, ArH, 10H), (m, C$\underline{H}$($CO_2CH_3$)$_2$, 2H) and 3.90–2.70 (m, ARCH$_2$, OCH$_2$, OCH$_3$, 36H).

Anal. Calcd for $C_{42}H_{48}O_4$: C, 64.94; H, 6.23. Found: C, 64.85; H, 6.16.

To a solution of 2.0 g. of the above tetraester in 100 ml. of ethanol was added 2.0 g. of sodium hydroxide in 15 ml. of water. The mixture was refluxed for 8 hours, concentrated under vacuum to 10 ml. and diluted with 75 ml. of water. The solution was acidified with 6N hydrochloric acid to a pH of one. The tetraacid 28d' that crystallized was collected, washed with water and vacuum dried at 25° to give 1.7 g. (91%) of white solid, m.p. 140°, with loss of carbon dioxide. The pmr spectrum (60 MHz) in $D_6$-DMSO gave $\delta$8.04°–6.80 (m, ArH, 10H) and 4.20–3.16 (m, $CH_2O$, $CH_2CH(CO_2H)_2$, 26H). Table I records the analysis.

Tetraacid 28d', 0.36 g., was heated at 160° at 30 mm pressure for 2 hours. The resulting oil was cooled, dissolved in 50 ml. of dichloromethane, and the solution was washed with water and dried. The solution was evaporated under vacuum and dried to give 0.30 g. (92%) of 28e' as a glass. The mass spectrum (70 ev) of this material gave a molecular ion at m/e = 632, and the pmr spectrum (100 MHz) in $CD_3CO_2D$ gave $\delta$ 8.0–6.8 (m, ArH, 10H) and 4.5–2.60 (m, $CH_2O$, $ArCH_2CH_2CO$, 2H). Table I records the analysis.

By Procedure 6 optically pure (−)-(S)-28a' was converted to optically pure (−)-(S)-28e'. The tetraester intermediate was obtained in 44% yield (glass), $[\alpha]_{578}^{25}$ −64.7°, $[\alpha]_{546}^{25}$ −75.7°, $[\alpha]_{436}^{25}$ −152.4°, (C 1.0, $CHCl_3$).

Anal. Calcd for $C_{42}H_{48}O_4$: C, 64.94; H, 6.23. Found: C, 64.85; H, 6.16.

The above tetraester was hydrolyzed to the tetraacid, (−)-(S)-28d' in 90% yield, m.p. 125° (with $CO_2$ evolution), $[\alpha]_{578}^{25}$ −31.3°, $[\alpha]_{546}^{25}$ −35.6° and $[\alpha]_{436}^{25}$ −66.1° (C 1.0, $CH_3CO_2H$).

This tetraacid, (−)-(S)-28d', was decarboxylated to give (85%) (−)-(S)-28e' as a glass, $[\alpha]_{578}^{25}$ +80° and $[\alpha]_{546}^{25}$ +94° (C 1.0, $CHCl_3$). Table I records the analysis.

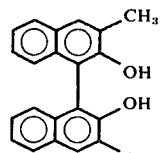

25a'

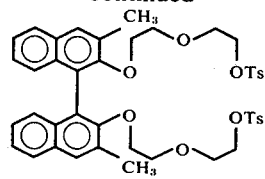

25d'

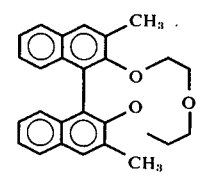

48a'

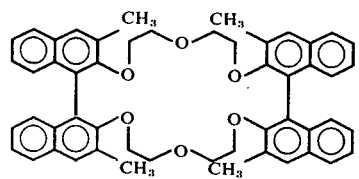

(SS)(RR)-48b'
(SR)-48b'

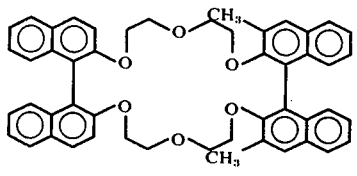

(SS)(RR)-48c'
(SR)(RS)-48c'

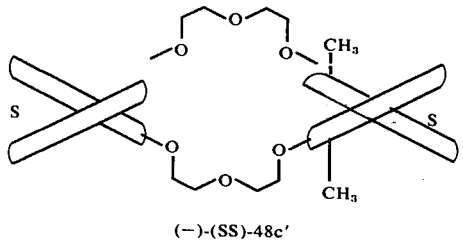

(−)-(SS)-48c'

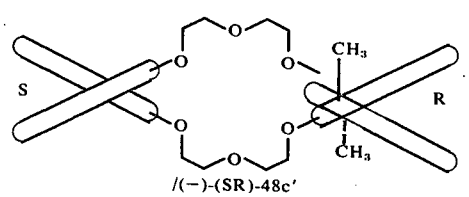

/(−)-(SR)-48c'

Procedure 7

Procedure 7 is illustrated by the synthesis of dilocular systems (SS)(RR)-48b' and (SR) -48b' from 25a' and 25d'. A mixture of 0.942 g. of 25a', 10 ml. of tetrahydrofuran and 0.377 g. of potassium hydroxide in 1 ml. of water was stirred under nitrogen at 65°. A solution of 2.4 g. of ditosylate 25d' in 50 ml. of tetrahydrofuran was added, and the solution was refluxed for 40 hours. The mixture was cooled, evaporated, and the residue was shaken with dichloromethane and water. The dichloromethane solution was washed with water, with brine, was dried and evaporated. The residue was chromatographed on 400 g. of silica gel. The (SR)-48b' was eluted with benzene, and recrystallized from benzene to give 0.155 g. (7%), m.p. 314°–315°. This substance gave a mass spectrum (70 ev) with a molecular ion at m/e = 768, and a pmr spectrum (100 MHz) in CDCl$_3$ of δ7.73 (d, ArH$^{4,5}$, 8H), 7.10 (m, ArH, 12H), 3.68 (m, CH$_2$O, 8H), 3.26 (m, CH$_2$O, 4H), 2.86 (m, CH$_2$O, 4H) and 2.52 (s, CH$_3$, 12H).

Anal. Calcd for C$_{52}$H$_{48}$O$_6$: C, 81.22; H, 6.29. Found: C, 81.01; H, 6.28.

Elution of the column with benzene-ether (20:1) gave (SS) (RR)-48b', which after recrystallization from dichloromethane-ether gave 0.22 g. (10%), m.p. 158°–160°. This material gave a mass spectrum (70 ev) with a molecular ion at m/e = 768, and a pmr spectrum (100 MHz) in CDCl$_3$ with δ7.70 (m, ArH$^{4,5}$, 8H), 7.12 (m, ArH, 12H), 3.50 (m, CH$_2$O, 8H), 2.92 (m, CH$_2$O, 8H), 2.45 (d, CH$_3$, 12H).

Anal. Calcd for C$_{52}$H$_{48}$O$_6$: C, 81.22; H, 6.29. Found: C, 80.93; H, 6.28.

The configurational assignments of the isomers of 48b' were made based on pmr and chromatographic behavior analogies between these isomers and those of 8, 48, and 48c', whose configurations were unequivocally demonstrated. When 25a' and diethyleneglycol ditosylate were used as starting materials (Procedure 1), (SR)-48b' was produced in 4% yield, m.p. 314°–315°, (SS) (RR)-48b' in 5% yield, m.p. 158°–160°, and monolocular system 48a' was produced in 8% yield, m.p. 285° (from benzene). This material gave a mass spectrum (70 ev) with a molecular ion at m/e = 384 and a pmr spectrum (100 MHz) in CDCl$_3$ of δ7.72 (m, ArH$^{4, 5}$, 4H), 7.20 (m, ArH, 6H), 4.06 (m, CH$_2$O, 4H), 3.28 (t, CH$_2$O, 4H) and 2.58 (s, CH$_3$, 6H).

Anal. Calcd for C$_{26}$H$_{24}$O$_3$: C, 81.22; H, 6.29. Found: C, 81.45; H, 6.44.

Procedure 7 is further illustrated by the synthesis of the isomers of 48c' from 25d' and 1. To a solution of 0.570 g. of 1 in 15 ml. of dry dimethyl formamide stirred at 25° under nitrogen was added 0.22 g. of sodium hydride (57% dispersion in mineral oil), followed by 1.6 g. of ditosylate, 25d' in 25 ml. of dry dimethyl formamide. The mixture was stirred at 45° until it became homogeneous, and then at 60° for 48 hours. The mixture was then cooled, the solvent was evaporated under reduced pressure, and the residue was shaken with dichloromethane and water. The organic layer was washed with water, with brine, was dried and evaporated, and the residue was dried as a foam at 80° and 50μ for 3 hours, wt 1.3 g. This material was chromatographed on 200 g. of silica gel. Hexane eluted unreacted 1 (0.13 g. or 23%), whereas 2:3 hexane-dichloromethane eluted first (SR) (RS)-48c' (m.p. 249°, 0.176 g., 12%, from dichloromethane-hexane), then a mixture of diastereomers (0.12 g., 8%) and finally (SS) (RR)-48c' (m.p. 222°–223°, 0.147 g., 10%, from dichloromethane-hexane). Both diastereomers gave mass spectra (70 ev) with molecular ions at m/e = 740. The pmr spectrum (100 MHz) in CDCl$_3$ of the (SR) (RS) -isomer gave δ7.72 (m, ArH, 8H), 7.36 (s, ArH, 2H), 7.12 (m, ArH, 12H), 3.96 (m, CH$_2$O, 4H), 3.69 (m, CH$_2$O, 4H), 3.33 (m, CH$_2$O, 4H), 2.88 (m, CH$_2$O, 4H), and 2.50 (s, CH$_3$, 6H); that of the (SS) (RR)-isomer gave δ 7.80 (m, ArH, 8H); 7.38 (s, ArH, 2H), 7.09 (m, ArH, 12H), 4.00 (m, OCH$_2$, 4H), 3.50 (m, CH$_2$O, 8H), 3.04 (m, CH$_2$O, 4H) and 2.40 (s, CH$_3$, 6H).

Anal. of (SR) (RS)-48c' Calcd for C$_{50}$H$_{44}$O$_6$: C, 81.06; H, 5.98. Found: C, 80.84; H, 6.23.

Anal. of (SS) (RR)-l48c' Calcd for C$_{50}$H$_{44}$O$_6$: C, 81.06; H, 5.98. Found: C, 80.63; H, 6.12.

The above procedure was repeated with 1.80 g. of optically pure (−)-(S)-1 and 5.10 g. of racemic ditosylate, 25d', to give 1.45 g. (30%) of a mixture of the two optically pure diastereomers, which were separated by chromatography to give (−)-(SR)-48c', 0.48 g. (10%), m.p. 195°–196°, [α]$_D^{25}$ −35.8°, [α]$_{546}^{25}$ −47.0° and [α]$_{436}^{25}$ −125° (C 1.0, CHCl$_3$), and (−)-(SS)-48c', 0.72 g. (15%), glass, [α]$_D^{25}$ −144°, [α]$_{546}^{25}$ −178°, [α]$_{436}^{25}$ −400° (C 1.0, CHCl$_3$). The configurations of the two optically pure diastereomers were assigned from the fact that (−)-(S)-1 was a starting material, coupled with the fact that the negative Cotton effect in the 315 to 320 nm region of the CD spectrum of each isomer was of much higher intensity for one isomer ((SS)-48c') than the other ((SR)-48c'). The rotational contributions of the two binaphthyl units should reinforce one another in the (SS)-isomer, but somewhat cancel one another in the (SR)-isomer, as was observed. The pmr spectra of (SR) (RS)-48c' and (SR)-l48c' were identical, as were the pmr spectra of (SS) (RR)-48c' and (SS)-48c'. The configurational assignments to the two racemates were made accordingly. These configurational assignments were confirmed by a rational synthesis of (RR)-48c' (see below).

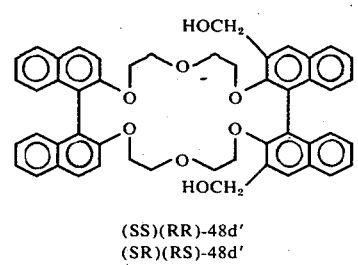

(SS)(RR)-48d'
(SR)(RS)-48d'

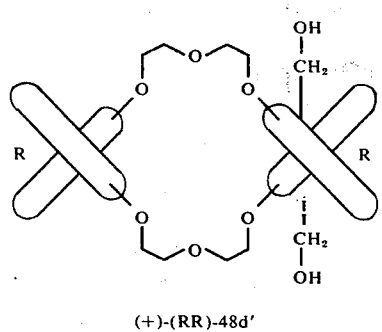

(+)-(RR)-48d'

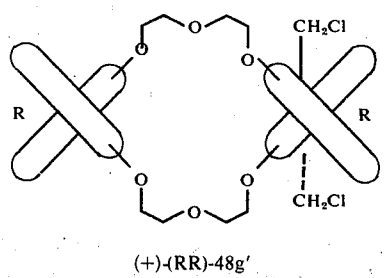

(+)-(RR)-48g'

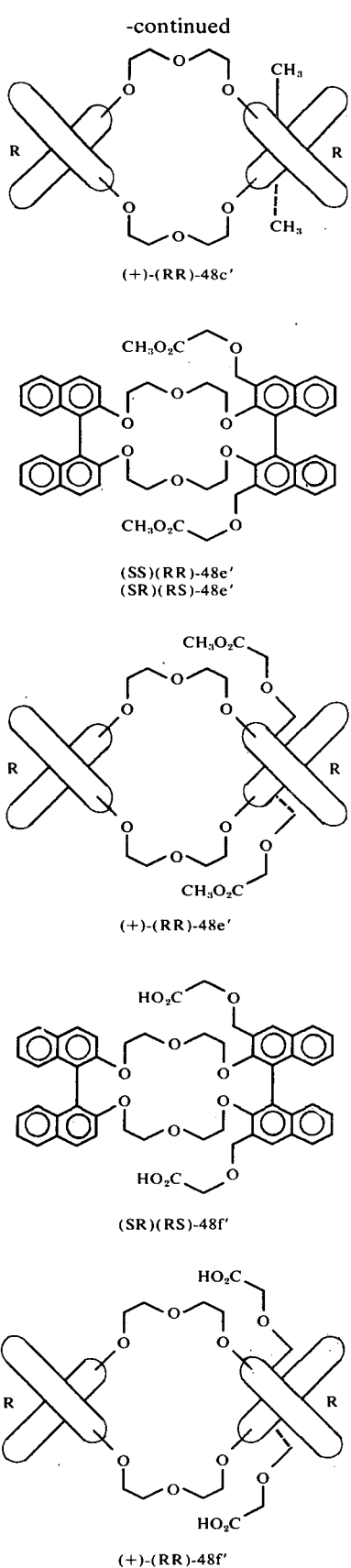

(+)-(RR)-48c'

(SS)(RR)-48e'
(SR)(RS)-48e'

(+)-(RR)-48e'

(SR)(RS)-48f'

(+)-(RR)-48f'

Procedure 7 is further illustrated by the synthesis of diol (SS) (RR)-48d' and (SR) (RS)-48d' from racemic ditosylate 1a racemic tetraol 25. A solution of 23 g. of 25 in 2 liters of tetrahydrofuran, 5.4 g. of sodium hydroxide in 60 ml. of water and 56 g. of 1a in 500 ml. of tetrahydrofuran was stirred under nitrogen at reflux for 100 hours. The crude product was isolated in the usual way, and chromatographed on 1.5 kg. of alumina. The column was washed with 3 liters of ether, and then product was eluted with ether-isopropyl alcohol mixtures, 4 liters of 99.5:0.5, 4 liters of 99:1, 2 liters of 49:1 to give 17.0 g. (33%) of a mixture of the diastereomers, 48d'. The faster eluting isomer was fractionally crystallized from dichloromethane-ethyl acetate to give (SR) (RS)-48d', 4.25 g. (8%), m.p. 197°–198°. The mass spectrum (70 ev) gave a molecular ion at m/e = 772, and the pmr spectrum (60 MHz) in CDCl$_3$ gave δ8.00–6.98 (m, ArH, 22H), 4.94 (m, ArCH$_2$, 4H), and 4.40–2.70 (m, OCH$_2$, 16H).

Anal. Calcd for C$_{50}$H$_{44}$O$_8$: C, 77.70; H, 5.74. Found: C, 77.50; H, 5.96.

Fractional crystallization of the slower moving racemate from dichloromethane and ethyl acetate gave 8.5 g. (16%) of (SS) (RR)-48d', m.p. 230°–231°. The mass spectrum (70 ev) gave a molecular ion at m/e = 772. The pmr spectrum (60 MHz) in CDCl$_3$ gave δ7.80 (m, ArH, 8H), 7.18 (m, ArH, 14H), 4.70 (m, ArCH$_2$, 4H) and 4.22 –3.78 (m, OCH$_2$, 16H).

Anal. Calcd for C$_{50}$H$_{44}$O$_8$: C, 77.70; H, 5.74. Found: C, 77.48; H, 6.01.

By the same procedure from optically pure (+)-(R)-25 and optically pure (+)-(R)-1a was produced (+)-(RR)-48d' in 28% yield as a glass, pure to tlc and pmr, $[\alpha]_{578}^{25}$ +120°, $[\alpha]_{546}^{25}$ +115°, $[\alpha]_{436}^{25}$ +318° (C 1, CHCl$_3$). The pmr spectrum was identical to that of the (SS) (RR)-48d' prepared above, and the configurational assignment of the two racemates of 48d' was assigned accordingly.

Anal. Calcd for C$_{50}$H$_{44}$O$_8$: C, 77.70; H, 5.74. Found: C, 77.72; H, 5.87.

Procedure 7 is further illustrated by the conversion of (+)-(RR)-48d' to (+)-(RR)-48g'. To a solution of 0.90 g. (1.2 mmole) of (+)-(RR)-48d' in 40 ml. of benzene was added 4.0 g. (34 mmole) of thionyl chloride in a single portion. The solution was stirred at 25°for 10 hrs. and evaporated at 30 mm pressure and 60°. The residue was dissolved in 50 ml. of dichloromethane, and the solution was extracted with 30 ml. of 10% sodium bicarbonate. The organic layer was dried (MgSO$_4$), concentrated to 15 ml, and the residue was chromatographed on 50.0 g. of silica gel. Elution of the column with 2 liters of dichloromethane gave 0.72 g. (76%) of (+)-(RR)-48g' as a glass, which was dried at 50$\mu$ and 50° for 10 hrs. The compound gave a pmr spectrum (60 MHz) in CDCl$_3$: δ8.05–6.90 (m, ArH, 22H), 4.70 (AB quartet, ArCH$_2$, 4H) and 4.16-2.78 (m, OCH$_2$CH$_2$O, 16H). The substance had the following rotations: $[\alpha]_{589}^{25}$ +116°, $[\alpha]_{578}^{25}$ +122°, $[\alpha]_{546}^{25}$ +145° and $[\alpha]_{436}^{25}$ +335°.

Anal. Calcd for C$_{50}$H$_{42}$Cl$_2$O$_6$: C, 74.15; H, 5.24. Found: C, 74.50; H, 5.26.

Procedure 7 is further illustrated by the conversion of (+)-(RR)48g' to (+)-(RR)-48c'. To a solution of 1.5 g. (39 mmoles) of lithium aluminum hydride in 150 ml. of tetrahydrofuran under nitrogen was added 0.7 g. (0.87 mmoles) of (+)-(RR)-48g' in 20 ml. of tetrahydrofuran (all at once). The mixture was refluxed for 3 hours, cooled to 5°, and the excess lithium aluminum hydride was decomposed by dropwise addition of water. Diethyl ether (150 ml.) and 100 ml. of 6N hydrochloric acid were added and the resulting mixture was stirred at 25° for 6 hours. The organic layer was separated, and the aqueous phase was extracted with 100 ml. of diethyl ether. The combined organic extracts were washed with 100 ml. of 10% sodium bicarbonate solution, dried (MgSO$_4$) and concentrated to 30 ml. The residue was chromatographed on 50 g. of neutral alumina. Elution of the column with 2.5 liters of diethyl ether gave 0.51 g. (80%) of (+)-(RR)-48c' as a colorless glass, dried at 50μ and 100° for 5 hours. The pmr spectrum (60 MHz) of the substance in CDCl$_3$ gave δ8.00–6.90 (m, ArH, 22H), 4.24–2.90 (m, OCH$_2$, 16H) and 2.40 (s, CH$_3$, 16H). The compound gave the following optical rotations: $[\alpha]_{589}^{25}$+145°, $[\alpha]_{578}^{25}$ +152°, $[\alpha]_{546}^{25}$ +180° and $[\alpha]_{436}^{25}$ +405°.

Anal. Calcd for C$_{50}$H$_{44}$O$_6$: C, 81.06; H, 5.99. Found: C, 81.10; H, 6.13.

By Procedure 2, (SS)(RR)-48d' was converted (71%) to (SS)(RR)-48e' (glass), whose mass spectrum (70 ev) contained a molecular ion at m/e 916, and whose pmr spectrum (60 MHz) in CDCl$_3$ gave δ 7.90 (m, ArH, 8H), 7.20 (m, ArH, 14H), 4.72 (s (broad), ArCH$_2$, 4H), 4.03 (s, OCH$_2$CO$_2$, 4H), 3.63 (s, OCH$_3$, 6H) and 4.22–2.90 (m, OCH$_2$, 16H).

Anal. Calcd for C$_{56}$H$_{52}$O$_{12}$: C, 73.35; H, 5.72. Found: C, 72.29; H, 5.75.

By Procedure 2, (SR)(RS)-48d' was converted (50%) to (SR)(RS)-48e' (glass), whose mass spectrum (70 ev) gave a molecular ion at m/e = 916, and whose pmr spectrum (60 MHz) in CDCl$_3$ gave δ 8.07–6.85 (m, ArH, 22H), 4.97 (s, ArCH$_2$, 4H), 4.20 (s, CH$_2$CO$_2$CH$_3$, 4H), 3.66 (s, OCH$_3$, 6H) and 4.40–2.50 (m, OCH$_2$, 16H).

Anal. Calcd for C$_{56}$H$_{52}$O$_{10}$: C, 73.35; H, 5.72. Found: C, 73.30; H, 5.60.

By Procedure 2, (+)-(RR)-48d' was converted (97%) to (+)-(RR)-48e', a glass, $[\alpha]_{589}^{25}$ +109.6°, $[\alpha]_{578}^{25}$ +115.8°, $[\alpha]_{546}^{25}$ +137.3° and $[\alpha]_{436}^{25}$ +311.2° (C 1.0, CHCl$_3$). The pmr spectrum of (+)-(RR)-48e', was identical to that of (SS)(RR)-48e'.

Anal. Calcd for C$_{56}$H$_{52}$O$_{12}$: C, 73.35; H, 5.72. Found: C, 73.19; H, 5.59.

By Procedure 3, (SR)-RS)-48e' was converted (94%) to (SR)(RS)-48f', a glass, whose pmr spectrum (60 MHz) in CDCl$_3$ gave δ 8.10–6.90 (m, ArH, 22H), 5.00 (s broad, ArCH$_2$, 4H), 4.22 (s broad, OCH$_2$CO$_2$, 4H), and 4.30–2.80 (m, OCH$_2$, 16H).

Anal. Calcd for C$_{54}$H$_{48}$O$_{12}$: C, 72.96; H, 5.44. Found: C, 72.90; H, 5.32.

By Procedure 3, (+)-(RR)-48e' was converted (94%) to (+)-(RR)-48f', glass, $[\alpha]_{589}^{25}$ +104°, $[\alpha]_{578}^{25}$ +110°, $[\alpha]_{546}^{25}$ +131°, $[\alpha]_{436}^{25}$ +304° (C 1.0, (CH$_2$)$_4$O). The pmr spectrum (60 MHz) in CDCl$_3$ gave δ 8.15–6.35 (m, ArH, 22H), 4.68 (s (broad), ArCH$_2$, 4H), 3.98 (s (broad), OCH$_2$CO, 4H) and 4.30–2.80 (m, OCH$_2$CH$_2$O, 16H).

Anal. Calcd for C$_{54}$H$_{48}$O$_{12}$: C, 72.96; H, 5.44. Found: C, 73.10; H, 5.56.

EXAMPLE 6

Direct Substitution of Binaphthyl Units of Cycles

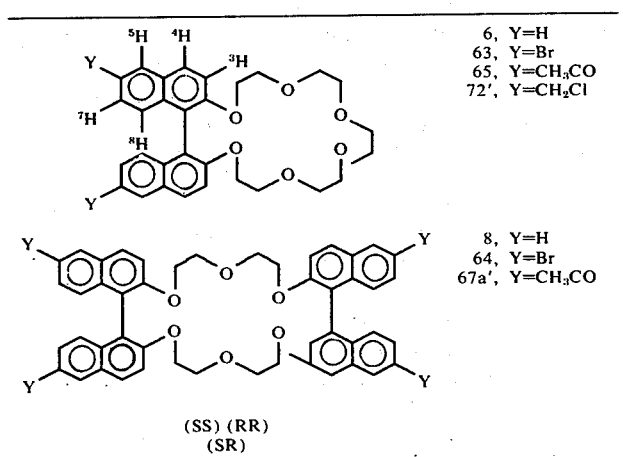

6, Y=H
63, Y=Br
65, Y=CH$_3$CO
72', Y=CH$_2$Cl

8, Y=H
64, Y=Br
67a', Y=CH$_3$CO (SS) (RR)
(SR)

Procedure 1

Bromination of 6 gave 63 as follows. To 3 g. (6.15 mmol) of 6 dissolved in 100 ml. of dichloromethane was added 0.3 ml. (5.88 mmol) of bromine, and the reaction mixture was heated to reflux. After one hour, 0.35 ml. (6.86 mmol) more bromine was added, and the solution was refluxed an additional 7.5 hours. The solution was cooled and shaken with 25 ml. of a 10% sodium bisulfite solution. The organic phase was separated, washed successively with water, saturated sodium bicarbonate solution, brine, and dried over magnesium sulfate. Evaporation of the solvent left 4.17 g. of an orange oil. This material was dissolved in ether, and the solution was cooled to give 2.65 g. (67%) of 63, m.p. 138°–139.5°. The pmr spectrum of this material in CDCl$_3$ (100 MHz) gave signals at δ 3.40–3.62 (m, CH$_2$OCH$_2$, 16H), 3.86–4.26 (m, ArOCH$_2$, 4H), 7.40 (Ar-$^3$H), 7.76 (Ar-$^4$H), J$_{3,4}$ = 9Hz, 7.93 (Ar-$^5$H), 7.20 (Ar-$^7$H), J$_{5,7}$ = 2Hz, 6.90 (Ar-$^8$H), J$_{7,8}$ = 9Hz. This pmr spectrum is uniquely consistent with the bromines being substituted in the 6 and 6'-positions of 63. The various hydrogens are identified by number in the general formula.

Anal. Calcd for C$_{30}$H$_{30}$O$_6$Br$_2$: C, 55.74; H, 4.68. Found: C, 55.98; H, 4.55.

Adaptation of Procedure 1 to (SS)(RR)-8 gave (SS)-(RR)-64 in 52% yield, m.p. 299°–300°.

Anal. Calcd for C$_{48}$H$_{36}$O$_6$Br$_4$: C, 56.06; H, 3.53. Found: C, 56.25; H, 3.50.

Adaptation of Procedure 1 to (SR)-8 gave (SR)-64 in 90% yield, m.p. 334°–335° (from chloroform-heptane). The mass spectrum (70 ev) gave a molecular ion at m/e = 1024.

Anal. Calcd for C$_{48}$H$_{36}$O$_6$Br$_4$: C, 56.06; H, 3.53. Found: C, 56.30; H, 3.57.

Adaptation of Procedure 1 to (+)-(RR)-8 gave (+)-(RR)-64 in 91% yield, m.p. 179°–180° (from chloroform-heptane), $[\alpha]_{589}^{25}$ +108°, $[\alpha]_{578}^{25}$ +124°, $[\alpha]_{546}^{25}$ +148° (C 1.0, CHCl$_3$).

Anal. Calcd for C$_{48}$H$_{36}$O$_6$Br$_4$: C, 56.06; H, 3.53. Found: C, 56.27; H, 3.12.

Procedure 2

Acetylation of 6 gave 65 as follows. Aluminum chloride (4.55 g., 34.1 mmol) was added to 21.6 ml. of nitrobenzene, and the mixture was cooled to 0°. Acetyl chloride (2.52 g., 32.1 mmol) and 6 (2.01 g., 4.1 mmol) were then added in rapid succession, and the mixture was stirred at 0° for 1 hour. The cold mixture was stirred into an ice-concentrated hydrochloric acid mixture, which was subsequently extracted with dichloromethane. The organic phase was washed successively with water, saturated sodium bicarbonate solution, brine and dried over magnesium sulfate. Solvent was evaporated under reduced pressure to give an oil that was chromatographed on 100 g. of neutral alumina. Fractions were collected (100 ml.) of eluent. After 500 ml. of ether eluate, 1% ethanol in ether brought off the desired product in fractions 13–17, which on evaporation gave 0.982 g. of 65, m.p. 107°–109°. Recrystallization of this material from acetone-hexane gave 0.86 g. (36%), m.p. 103°–104°. The ir spectrum (KBr) gave a strong band at 1675 cm$^{-1}$ (C=O). The pmr spectrum (100 MHz) in CDCl$_3$ gave δ 2.5 (s, CH$_3$, 6H), 3.30–3.58 (m, CH$_2$OCH$_2$, 16H), 3.92–4.34 (m, ArOCH$_2$, 4H), 7.50 (Ar-$^3$H), 8.04 (Ar-$^4$H), J$_{3,4}$ = 9Hz, 8.46 (Ar-$^5$H), 7.72 (Ar-$^7$H), J$_{5,7}$ = 2Hz, 7.10 (Ar-$^8$H), J$_{7,8}$ = 9Hz.

Anal. Calcd for C$_{34}$H$_{36}$O$_8$: C, 55.74; H, 4.68. Found: C, 55.98; H, 4.55.

Procedure 2 was further illustrated by the acetylation of (SS)(RR)-8, which gave (SS)(RR)-67a' in 74% yield, m.p. 340°–341° (in a capillary, decomposition). The ir spectrum of this material (KBr pellet) gave a carbonyl absorption at 1680 cm$^{-1}$.

Anal. Calcd for C$_{48}$H$_{40}$O$_6$: C, 76.35; H, 5.49. Found: C, 76.10; H, 5.64.

Procedure 3

Chloromethylation of 6 to give 72' illustrates this procedure. To 2.0 g. of 6 and 10 g. of chloromethyl methyl ether in 25 ml. of chloroform stirred at −60° was added (15 minutes) 3 ml. of anhydrous stannic chloride. The solution was stirred for 1 hour at −60°, and shaken with 50 ml. of water and 100 ml. of dichloromethane. The organic layer was washed with 100 ml. of saturated sodium bicarbonate solution, dried and concentrated. The residue was chromatographed on 75 g. of silica gel, and the column was washed with 500 ml. of dichloromethane and 500 ml. of 19:1 dichloromethane-ether. Product was eluted with 1 liter of 4:1 and 2 liters of 1:1 dichloromethane-ether to give 1.2 g. (50%) of 72' as a glass. The mass spectrum (70 ev) gave a molecular ion at m/e = 584, and the pmr spectrum (60 MHz) in CDCl$_3$ gave δ 7.90–7.02 (m, ArH, 10H), 4.62 (s, ArCH$_2$, 4H), 4.02 (m, ArOCH$_2$, 4H) and 3.70–3.18 (m, OCH$_2$, 16H).

Anal. Calcd for C$_{32}$H$_{34}$Cl$_2$O$_6$: C, 65.61; H, 5.86. Found: C, 65.58; H, 5.80.

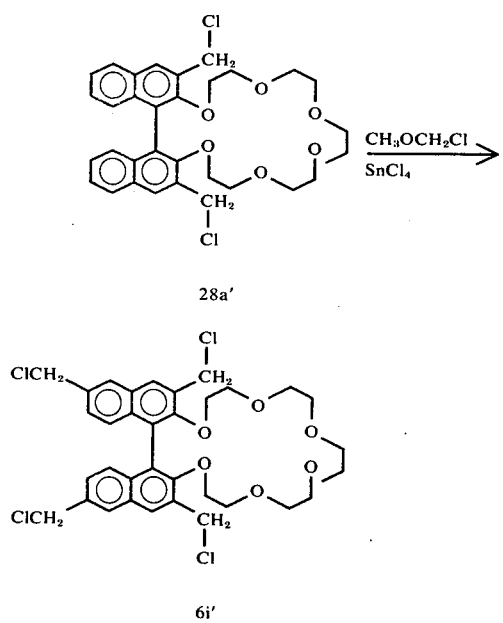

Procedure 3 was further illustrated by the conversion of 28a' to 6i' in 82% yield, which was isolated as a glass. The mass spectrum of 6i' (70 ev) gave a molecular ion at m/e = 680, and the pmr spectrum (60 MHz) in CDCl$_3$ gave δ 8.00 (s, ArH$^4$, 2H), 7.80 (s broad, ArH$^5$, 2H), 7.34–6.90 (m, ArH$^{7,8}$, 4H), 4.98 (ABq, 3,3'-CH$_2$Cl, 4H), 4.64 (s, 6,6'-CH$_2$Cl, 4H), and 4.05–2.90 (m, OCH$_2$, 2OH).

Anal. Calcd for C$_{34}$H$_{36}$Cl$_4$O$_6$: C, 59.83; H, 5.33. Found: C, 61.01; H, 5.67.

EXAMPLE 7

Modifications of the Side Chains Attached to Binaphthyl Units in the 6,6'-Positions

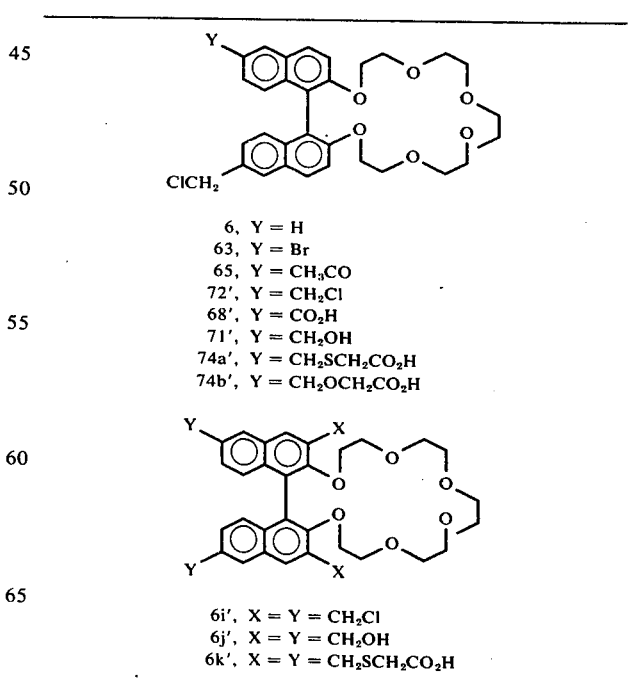

6, Y = H
63, Y = Br
65, Y = CH$_3$CO
72', Y = CH$_2$Cl
68', Y = CO$_2$H
71', Y = CH$_2$OH
74a', Y = CH$_2$SCH$_2$CO$_2$H
74b', Y = CH$_2$OCH$_2$CO$_2$H

6i', X = Y = CH$_2$Cl
6j', X = Y = CH$_2$OH
6k', X = Y = CH$_2$SCH$_2$CO$_2$H

-continued

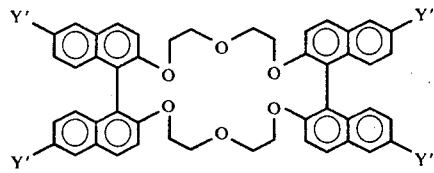

8, Y' = H
64, Y' = Br
67a', Y' = CH$_3$CO
67b', Y' = CO$_2$H
67c', Y' = Si(CH$_3$)$_2$OCH$_3$

Procedure 1

Oxidation of the two acetyl groups of 65 to the two carboxyl groups of 68' was accomplished as follows. To a solution of 32 g. of potassium hydroxide in 100 ml. of water at 5° was added 24 g. of bromine. A solution of 4.5 g. of 65 in 200 ml. of tetrahydrofuran was added, and the resulting mixture was held at reflux for 12 hours with vigorous stirring. The reaction mixture was cooled, 100 ml. of 10% sodium bisulfite solution was added, and the solution was concentrated under vacuum to 150 ml. The aqueous solution was diluted with 300 ml. of water, washed with 200 ml. of ether, and acidified with 6N HCl to pH 1. The product that separated was collected, washed with water and dried (50$\mu$) at 100° to give 3.8 g. (84%) of 68', which gave m.p. 291°–292° (from methanol). The pmr spectrum (100 MHz) in (CD$_3$)$_2$SO gave $\delta$ 7.70 (m, ArH$^3$ and ArH$^7$, 4H), 8.24 (d, ArH$^4$, $J_{3,4}$ = 9Hz, 2H), 8.61 (d, ArH$^5$, $J_{5,7}$ = 2Hz, 2H), $\kappa$ 6.98 (d, ArH$^8$, $J_{7,8}$ = 9Hz, 2H), $\delta$ 4.16 (m, ArOCH$_2$, 4H), and $\delta$ 3.36 (m, CH$_2$O, 16H).

Anal. Calcd for C$_{32}$H$_{32}$O$_{10}$: C, 66.66; H, 5.59. Found: C, 66.53; H, 5.63.

Procedure 1 was further illustrated by the conversion of (SS)(RR)-67a' to (SS)(RR)-67b' in 100% crude yield. The tetraacid was purified through its tetramethyl ester as follows. Crude (SS)(RR)-67b', 1.10 g. was heated at reflux in dry methanol (350 ml.) containing 56 drops of concentrated sulfuric acid for 5 days. As esterification proceeded, the tetraacid slowly dissolved, and the tetraester crystallized. The mixture was cooled, diluted with 350 ml. of ether, filtered and washed. The filtrate was evaporated and shaken with water, dichloromethane and the filter cake. The dichloromethane layer was washed with dilute sodium hydroxide, with water, was dried and evaporated. The residue was chromatographed on 300 g. of silica gel, and eluted with dichloromethane (100 ml. fractions). Fractions 12–45 contained the tetraester, pure to tlc, which was recrystallized from dichloromethane-acetone to give 0.95 g. (86%), dried at 110° and 20$\mu$ for 16 hours, m.p. 300°–301°. The tetraester gave a mass spectrum (70 ev) containing a molecular ion at m/e = 944, and a pmr spectrum (100 MHz) in CDCl$_3$, $\delta$ 7.30 (d, ArH$^3$, $J_{3,4}$ = 9Hz, 4H), 8.04 (d, ArH$^4$, 4H), 8.60 (d, ArH$^5$, $J_{5,7}$ = 2Hz, 4H), 7.72 (d, ArH$^7$, $J_{7,8}$ = 9Hz, 4H), 7.02 (d, ArH$^8$, 4H), 3.87 (m, ArOCH$_2$, 8H), 3.17 (m, OCH$_2$, 16H), and 3.88 (s, CH$_3$, 12H).

Anal. Calcd for C$_{56}$H$_{48}$O$_{14}$: C, 71.17; H, 5.12. Found: C, 71.08; H, 5.10.

This tetraester was hydrolyzed to 67b' as follows. A solution of 0.769 g. of the ester dissolved in 10 ml. of purified dioxane was added to 100 ml. of 0.6 M lithium hydroxide, and the mixture was refluxed for 60 hours. The mixture was concentrated under vacuum and acidified with 50% hydrochloric acid. The precipitate was collected, washed with 1M hydrochloric acid, acetone and ether, and then dissolved in 10 ml. of 0.25 M sodium hydroxide, and reprecipitated with 1 M hydrochloric acid. The product (67b') was collected, washed with dilute hydrochloric acid, acetone, ether and was dried for 24 hours at 36$\mu$, wt 0.678 g. (94%), m.p. 380° (decomposition). This material in 0.1 M NaOD in D$_2$O gave the following pmr (60 MHz) spectrum: $\delta$ 8.54 (d, H$^5$ J, 5,7 = 1.3, 4H), 8.28 (d, H$^4$ $J_{3,4}$ = 9, 4H), 7.63 (d of d, H$^7$ $J_{7,8}$ = 9, 4H) 7.40 (d, H$^8$ $J_{7,8}$ = 9, 4H), 6.98 (d, H$^3$ $J_{3,4}$ = 9, 4H), 3.70 (m, ArCH$_2$O, 8H), 2.89 (m, CH$_2$OCH$_2$, 8H).

Anal. Calcd for C$_{52}$H$_{40}$O$_{14}$: C, 70.26; H, 4.54. Found: C, 70.28; H, 4.71.

Procedure 2

Diacid 68' was reduced to diol 71' as follows. To a refluxing solution of 3.8 g. of lithium aluminum hydride in 300 ml. of tetrahydrofuran was added, via soxhlet extraction, 4.0 g. of 68'. The mixture was refluxed for 16 hours, cooled, and ethanol cautiously added. The mixture was shaken with 500 ml. of ether and 200 ml. of 6N hydrochloric acid, and the resulting mixture was stirred for 8 hours. The ether layer was separated and the aqueous layer extracted with two 200 ml. portions of ether. The combined organic layer was washed with 100 ml. of saturated aqueous sodium bicarbonate, dried and concentrated. The residue was chromatographed on 150 g. of alumina. The column was washed with 2 liters of ether, and the product eluted with ether-isopropyl alcohol, 2 liters of 49:1 and 2 liters of 19:1, to give 2.8 g. (74%) of 71' as a glass. The mass spectrum (70 ev) gave a molecular ion at m/e 548, and the pmr spectrum (60 MHz) in CDCl$_3$ gave 67 7.88–7.00 (m, ArH, 10H), 4.62 (s, ArCH$_2$, 4H) and 4.22–3.05 (m, OCH$_2$CH$_2$O, 2OH).

Anal. Calcd for C$_{32}$H$_{36}$O$_8$: C, 70.06; H, 6.61. Found: C, 70.22; H, 6.59.

Procedure 3

Tetrachloro compound 6i' was acetolyzed to produce the derived tetraacetate which was reduced to tetrol 6i'. To an acetic acid solution (150 ml.), 1 M in potassium acetate, was added 5.50 g. of 6i', and the solution was refluxed for 18 hours. The solution was cooled, shaken with a mixture of 400 ml. each of water and dichloromethane, and the organic layer was washed with two 100 ml. portions of sodium bicarbonate-saturated water, dried and evaporated. The product was chromatographed on 100 g. of silica gel, and the column was washed with 250 ml. of dichloromethane, and dichloromethane-ether, 0.5 liter (19:1) and 0.5 liter (9:1). The tetraacetate was eluted with dichloromethaneether, 1 liter of 4:1 and 2 liters of 1:1 to give 4.8 g. (76%) of the tetraacetate of 6i' as a glass. The mass spectrum (70 ev) gave a molecular ion at m/e = 776, and the pmr spectrum (60 MHz) in CDCl$_3$ gave, $\delta$ 7.98 (s, ArH$^4$, 2H), 7.83 (s broad, ArH$^5$, 2H), 7.10 (m, ArH$^{7,8}$, 4H), 5.50 (s, 3,3'-ArCH$_2$, 4H), 5.20 (s, 6,6'-ArCH$_2$, 4H), 3.82–2.80 (m, OCH$_2$CH$_2$O, 2OH), 2.18 (s, 3,3'-COCH$_3$, 6H), and 2.05 (s, 6,6'-COCH$_3$, 6H).

Anal. Calcd for C$_{42}$H$_{48}$O$_{14}$: C, 64.94; H, 6.23. Found: C, 64.90; H, 6.15.

To a refluxing solution of 3.8 g. of lithium aluminum hydride in 300 ml. of tetrahydrofuran under nitrogen was added dropwise a solution of 4.8 g. of tetraacetate in 150 ml. of tetrahydrofuran. The mixture was refluxed for 8 hours, cooled to 5°, ethanol was cautiously added, and the mixture was shaken with 200 ml. of 6 N hydrochloric acid and 300 ml. of ether. The aqueous layer was washed with three 150 ml. portions of 2:1 ether-tetrahydrofuran, and combined with the original organic layer. The solution was dried, and evaporated under reduced pressure to give 3.4 g. (90%) of 6i' as a glass. The mass spectrum (70 ev) gave a molecular ion at m/e = 608, and the pmr spectrum (60 MHz) in $CDCl_3$ gave, δ 7.82 (s, $ArH^4$, 2H), 7.72 (s, broad, $ArH^5$, 2H), 7.00 (m, $ArH^{7,8}$, 4H), 4.82 (ABq, 3,3'-$ArCH_2$, 4H), 4.63 (s, 6,6'-$ArCH_2$, 4H) and 4.20–2.70 (m, $OCH_2CH_2O$, 2OH).

Anal. Calcd for $C_{34}H_{40}O_{10}$: C, 67.09; H, 6.62. Found: C, 66.82; H, 6.90.

Procedure 4

By a method modeled after Example 5, Procedure 5, dichloride 72' was converted to diacid 74a' in 75% yield, which was an oil. The mass spectrum (70 ev) gave a molecular ion at m/e = 696, and the pmr spectrum (60 MHz) in $CD_3CO_2D$ gave δ 8.00–6.85 (m, ArH, 10H), 3.96 (s, $ArCH_2$, 4H), 4.15 (m, $ArOCH_2$, 4H), 3.50 (m, $OCH_2$, 16H) and 3.18 (s, $CH_2CO_2$, 4H).

Anal. Calcd for $C_{36}H_{40}O_{10}S_2$: C, 62.06; H, 5.79. Found: C, 61.94; H, 5.71.

By the same procedure (except the relative amount of thioglycolic acid was "increased"), tetrachloride 6i' was converted to tetraacid 6k' in 96% yield as a glass. The mass spectrum did not give a molecular ion probably due to a lack of volatility. The pmr spectrum (60 MHz) in $CD_3CO_2D$ gave δ 8.02 (s, $ArH^4$, 2H), 7.86 (s, $ArH^5$, 2H), 7.40–6.90 (m, $ArH^{7,8}$, 4H), 4.20 (s, 3,3'-$ArCH_2$, 4H), 3.95 (s, 6,6'-$ArCH_2$, 4H), 3.40 (s, 3,3'-$CH_2CO_2$, 4H), 3.18 (s, 6,6'-$CH_2CO_2$, 4H) and 4.30–2.62 (m, $OCH_2$, 2OH).

Anal. Calcd for $C_{42}H_{48}O_{10}S_4$: C, 55.73; H, 5.35. Found: C, 56.04; H, 5.43.

Procedure 5

By a method modeled after Example 5, Procedure 2, diol 71' was converted to the dimethyl ester of diacid 74b' in 55% as a glass. The mass spectrum (70 ev) showed a molecular ion at m/e = 692. The pmr spectrum (60 MHz) in $CDCl_3$ gave δ 7.98–7.04 (m, ArH, 10H), 4.72 (s, $ArCH_2$, 4H), 4.16 (s, $CH_2CO_2$, 4H), 3.73 (s, $OCH_3$, 6H) and 4.24–3.10 (m, $OCH_2CH_2O$, 2OH).

Anal. Calcd for $C_{38}H_{44}O_{12}$: C, 65.88; H, 6.40. Found: C, 65.85; H, 6.60.

By a method modeled after Example 5, Procedure 3, the dimethyl ester of diacid 74b' was converted in 75% yield to diacid 74b' as a glass. The mass spectrum of (70 ev) gave a parent ion at m/e = 664, and the pmr spectrum (60 MHz) in $CDCl_3$ gave δ 7.98–7.00 (m, ArH, 10H), 4.70 (s, $ArCH_2$, 4H), 4.10 (s, $CH_2CO_2$, 4H) and 4.20–3.20 (m, $OCH_2CH_2O$, 2OH).

Anal. Calcd for $C_{36}H_{40}O_{12}$: C, 65.05; H, 6.07. Found: C, 65.20; H, 6.11.

Procedure 6

Tetrabromide (SR)-64 was converted to tetra-(dimethylmethoxysilyl) derivative (SR)-67c' as follows. In a dry system under pure, dry nitrogen was placed 250 ml. of pure, dry 1,2-dimethoxyethane, distilled from calcium hydride, containing a trace amount of triphenylmethane indicator. A few drops of butyllithium solution in hexane were added until a pink color persisted. Then 6 ml. of a 2.2 molar solution of butyllithium in hexane (13.2 mmole) was added dropwise under nitrogen while the solution was stirred at −75°. Tetrabromide (SR)-64 was added (2.05 g.) and the resulting mixture was stirred for 3 hours at −75°, and added rapidly under nitrogen to dichlorodimethylsilane (12 g.) stirred at −75°. The stirred mixture was allowed to warm to 25°, and after 4 hours at 25° was refluxed for 10 hours. The mixture was cooled, filtered, the filter cake was washed with dry 1,2-dimethoxyethanol, and the solvent was evaporated under reduced pressure to produce a glass, which was quenched with dry methanol to give crude (SR)-67c'. This material was chromatographed on silica gel with dichloromethane as eluting agent to give pure material, m.p. 95°–96°, wt 1.8 g. (84%). The mass spectrum (70 ev) gave a weak molecular ion at m/e = 1064.

Anal. Calcd for $C_{60}H_{72}Si_4O_{10}$: C, 67.67; H, 6.77. Found: C, 67.45; H, 6.89.

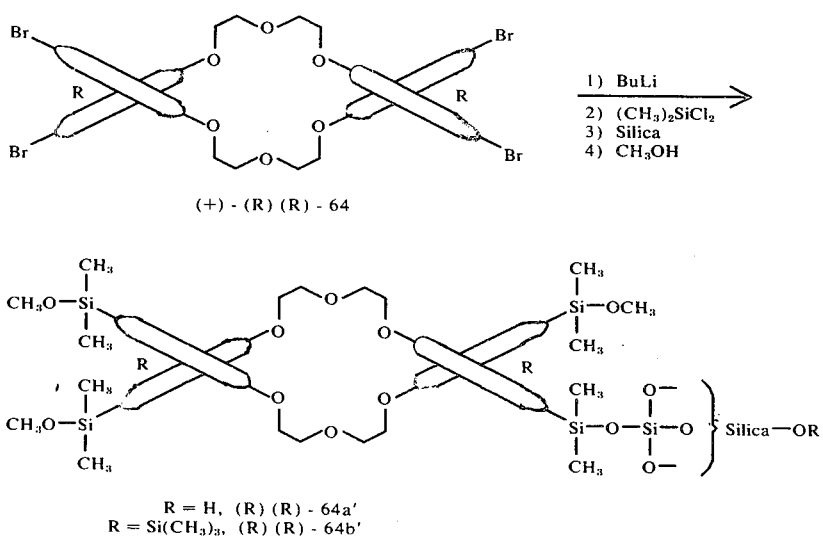

Procedure 7

Procedure 7 illustrates the attachment of optically active dilocular system 8 to a solid support by covalent bonds. To a dry solution of 2.11 g. of optically pure (+)-(RR)-64 in 200 ml. of 1,2-dimethoxyethane stirred under pure, dry nitrogen at −75° was added a trace of triphenylmethane, followed by dropwise addition of 10 ml. of a 2.2 M solution of butyllithium in hexane. The mixture was stirred at −75° for 2 hours, and the reaction mixture was added with stirring under pure, dry nitrogen to 12 g. of dichlorodimethylsilane. The reaction mixture was stirred and allowed to warm to 25°, stirred for 4 hours, refluxed for 10 hours, cooled, and diluted with 100 ml. of chloroform distilled from $P_2O_5$. Silica (100 to 325 mesh, Davidson No. 56), was dried in a muffle furnace at 300° for 36 hours to constant weight. A 40.0 portion of this material was stirred with 300 ml. of chloroform distilled from $P_2O_5$ under dry nitrogen. The chlorosilated multiheteromacrocycle was filtered quickly under dry nitrogen into the stirred slurry of silica and chloroform, while the HCl gas evolved was being purged from the system with dry nitrogen. After stirring for 4 hours, the mixture was filtered under nitrogen, and the solid was washed well with dry chloroform, methanol, benzene and again chloroform, and dried at 90° at 10μ for 18 hours to constant weight, 41.6 g. Combustion analysis of this material ((RR)-64a′) gave 3.08% carbon by weight, or 4.6% of the total solid was multiheteromacrocycle, or the solid contained 0.044 mmole of cycle per g. of solid. In other words, the multiheteromacrocycle had an average molecular weight of ~23,000. This material was stirred under dry nitrogen with 300 ml. of chloroform (distilled from $P_2O_5$), and 10 g. of chlorotrimethylsilane in 100 ml. of dry chloroform was added with stirring. The mixture was stirred at 25° for 3 hours while the flask was purged with dry nitrogen, filtered under dry nitrogen, and the filtrate was washed thoroughly with dry chloroform, and dried at 90° at 10μ to give 41.7 g. of (RR)-64b′. This material on combustion analysis gave 4.28% carbon by weight, which indicates the silica was about 0.33 mmole in $(CH_3)_3Si$ groups per g.

The filtrates from the original washings of the silica-bound multiheteromacrocycle were combined and evaporated to give 1.0 g. of residue, which was dissolved in dichloromethane, filtered, and evaporated to give 0.80 g. of a white solid which was chromatographed on 50 g. of silica gel to give 0.20 g. of dimethyldibutylsilane (pmr spectrum was used for identification) and 0.16 g. of a glass whose pmr spectrum was superimposable on that of (+)-(RR)-8, $[\alpha]_D^{25}$ +164° (C 1.0, $CHCL_3$). This material was recrystallized from benzene-cyclohexane and dried to give optically pure (+)-(RR)-8, $[\alpha]_D^{25}$ +220° (C 1.0, $CHCl_3$). This material must have arisen by protonation with adventitious water of the tetralithium derivative of 8. The near optical purity of this material suggests that Procedure 7 does not lead to racemization of the materials used and produced.

EXAMPLE 8

Synthesis of Macrocycles Containing Binaphthyl and Aryl Units.

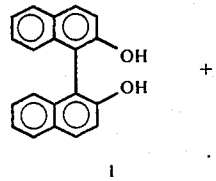

1

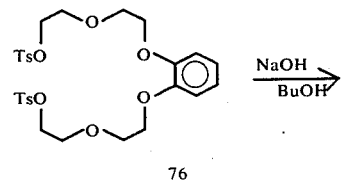

76

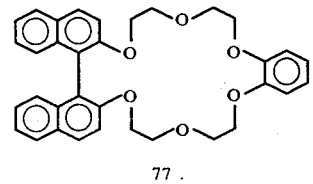

77 .

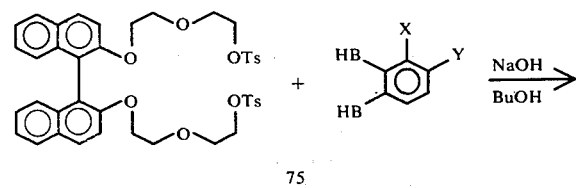

75

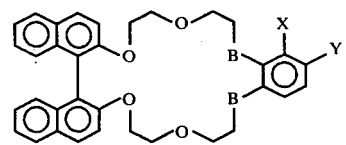

77, B=B=O, X=Y=H
78, B=O, B=S, X=Y=H
79, B=B=S, X=Y=H
80, B=B=O, X=CH=CHCH₃, Y=H
81, B=B=O, X=H, Y=(CH₂)₃OH

Procedure 1

Procedure 1 is illustrated by the sequence, 1 + 76 → 77. Ditosylate 76 was prepared, (47%) from catechol as a viscous oil by the same kind of procedure used to convert racemic 1 to 1a′.

Anal. Calcd for $C_{28}H_{34}O_{10}S_2$: C, 56.55; H, 5.75. Found: C, 56.24; H, 5.90.

A solution of 20.8 g. (35 mmol) of ditosylate 76 was added to a mixture of 10 g. (35 mmol) of binaphthol 1, 2.88 g. (70 mmol) of sodium hydroxide and 70 ml. of butanol held at reflux temperature. The reaction mixture was refluxed for 20 hours, the solvent was evaporated, and the residue was partitioned between 200 ml. of chloroform, and 200 ml. of water. The chloroform layer was dried with magnesium sulfate, evaporated, and the residue was chromatographed on 800 g. of neutral alumina. The column was washed with 2 l. of benzene, and the product (77) was eluted with 6 l. of benzene-ether (3:2). The solvent was evaporated, and the crystals that separated were recrystallized from benzene-cyclohexane to give 9.3 g. (50%) of pure 77, m.p. 147°–148°. The base peak in the 70 ev mass spectrum was the molecular ion, m/e 536. The pmr spectrum (100 MHz) in $CDCl_3$ gave signals at δ 7.8 (m, naphthyl ArH, 4H), 7.2 (complex m, naphthyl ArH, 8H), 6.84 (narrow m, benzo ArH, 4H), 4.0 (complex m, ArOCH$_2$, 8H), and 3.6 (m, CH$_2$OCH$_2$, 8H).

Anal. Calcd for $C_{34}H_{32}O_6$: C, 76.10; H, 6.01. Found: C, 75.78; H, 5.99.

Procedure 1 applied to 75 and catechol gave a 41% yield of 77, m.p. 147°–148°, undepressed by admixture with the sample of 77 prepared above.

Procedure 1 is further illustrated by the preparation of cycle 80. A solution of 38.3 g. (50 mmol) of ditosylate 75 dissolved in 200 ml. of purified dioxane was added (15 min.) to a refluxing and stirred (under nitrogen) mixture of 8.0 g. (53 mmol) of 3-allylcatechol (*Indian J. Chem.*, 2, 323 (1964)), 6.9 g. (107 mmol) of 85% potassium hydroxide and 400 ml. of butanol. The resulting mixture was refluxed for 7 hours, cooled and filtered. The filtrate was concentrated to give 37 g. of oil which was chromatographed on 1 kg. of neutral alumina. Elution of the column with 10 l. of benzene-ether (7:3) gave on concentration and drying at 100° (50μ) for 24 hours, 11.7 g. (41%) of macrocycle. The 100 MHz pmr spectrum of this material in $CDCl_3$ gave a multiplet at δ 4.95 (C=CH$_2$) as well as a doublet of doublets at δ 1.81, whose integration indicated the presence of 71% of the allyl and 29% of the 1-propenyl derivative. Accordingly, the mixture was dissolved in 700 ml. of dry benzene which was mixed at 25° with 10 ml. of 1 M potassium t-butoxide in t-butyl alcohol for 6 hours, conditions that completed the isomerization of the allyl to the propenyl derivative. The solution was extracted with three 200 ml. portions of 0.5 M hydrochloric acid, dried, concentrated and film dried at 100° (50μ) for 24 hours to give 11.1 g. (95%) of cycle 80 as a colorless glass. The 70 ev mass spectrum gave a molecular ion at m/e 576. The pmr spectrum (100 MHz) in $CDCl_3$ gave signals at δ 7.8 (m, naphthyl ArH, 4H), 7.5 to 6.5 (complex m, naphthyl and benzo ArH and olefinic CH, 12H), 6.2 (m, olefinic CH, 1H), 4.0 (m, ArOCH$_2$, 7H), 3.6 (m, CH$_2$OCH$_2$, 9H), and 1.84 (doublet of doublets, $J_1$ = 7Hz, $J_2$ = 2Hz, CH$_3$, 3H).

Anal. Calcd for $C_{37}H_{36}O_6$: C, 77.06; H, 6.29. Found: C, 77.11; H, 6.25.

Procedure 1 applied to 4-(3'-hydroxypropyl)catechol gave cycle 81 in 46% yield as a colorless glass. The pmr spectrum (100 MHz) in $CDCl_3$ gave signals at δ 7.8 (m, naphthyl ArH, 4H), 7.2 (complex m, naphthyl ArH, 8H), 6.7 (m, benzo ArH, 3H), 4.0 (complex m, ArOCH$_2$, 8H), 3.5 (complex m, CH$_2$OCH$_2$ and CH$_2$OH, 1OH), 2.57 ) m, aryl-CH$_2$, 2H), and 1.78 (m, CH$_2$CH$_2$CH$_2$OH, 3H).

Anal. Calcd for $C_{37}H_{38}O_7$: C, 74.73; H, 6.44. Found: C, 74.84; H, 6.56.

The 4-(3'-hydroxypropyl)catechol used above was prepared as follows. To a solution of 42.6 g. (239 mmol) of 4-allylveratrole [*J. Chem. Soc.*, 97, 1131 (1910)] in 250 ml. of dry tetrahydrofuran was added 110 ml. of a 0.1M solution of diborane (110 mmol) in tetrahydrofuran, and the solution was stirred for 0.75 hours. A solution of 1 ml. of 3 M aqueous sodium hydroxide in 16 ml. of water was added carefully, followed by 31 ml. of 3 M aqueous sodium hydroxide, followed by careful addition of 42 ml. of a 30% solution of hydrogen peroxide. The resulting mixture was stirred for 1 hour, and 120 g. of potassium carbonate and 100 ml. of water were added, and the mixture was stirred for 1 hour. The layers were separated, the tetrahydrofuran layer was dried and concentrated to give 43.9 g. of an oil. This material was distilled under vacuum to give three fractions: F1, 0.64 g., b.p. 60°–110° at 50μ; F2, 34.5 g., b.p. 110°–112° at 50μ; F3, 4.9 g., b.p. 112°–113° at 50μ. F2 was shown by its pmr spectrum to be a 9:1 mixture of primary to secondary alcohol, and F3 contained <0.5% secondary alcohol by pmr. F$_2$ and F$_3$ together provided 39.4 g. (84%) of a 9.15:0.85 mixture of the primary to secondary alcohol.

Anal. Calcd for $C_{11}H_{16}O_3$: C, 67.32; H, 8.22. Found: C, 67.35; H, 8.12.

This veratrole derivative was demethylated as follows. A solution of 104 g. (415 mmol) of boron tribromide in 150 ml. of dry dichloromethane was added to 35.0 g. (178 mmol) of the above mixture of alcohols dissolved in 400 ml. of dry dichloromethane at −77° under nitrogen. The resulting solution was warmed to 25° over 1 hour, poured into 1 Kg. of ice water, and stirred vigorously for 12 hours. The layers were separated and the dichloromethane solution was dried and concentrated to give 3.5 g. of olefinic material derived from the unwanted secondary alcohol. The aqueous layer was extracted with five 600 ml. portions of ether, the combined extracts were dried, concentrated and dried as a film at 110° (50μ) for 15 hours, wt 21.5 of viscous oil. This material was pure to tlc. Its pmr spectrum (60 MHz) in $CD_3COCD_3$ containing several drops of $D_2O$ gave signals at δ 6.7 (m, ArH, 3H), 3.58 (t, J = 6.5Hz, C$\underline{H}_2$OH(D), 2H), 2.57 (m, ArCH$_2$, 2H) and 1.83 (m, CH$_2$C$\underline{H}_2$CH$_2$, 2H). There was no trace of a doublet in the region of δ 1.2, attributable to a methyl group of a secondary alcohol. The 70 ev mass spectrum gave a molecular ion at m/e 168.

Anal. Calcd for $C_9H_{12}O_3$: C, 64.27; H, 7.19. Found: C, 64.18; H, 7.24.

Application of procedure 1 to 75 and o-mercaptophenol gave 78 in 38% yield, m.p. 111°–113°. The 100 MHz pmr spectrum of 78 in $CDCl_3$ gave signals at δ 6.68–8.0 (m, ArH, 16H), 3.86–4.2 (m, ArOCH$_2$, 6H), 3.2–3.75 (m, ROCH$_2$, 8H), 2.5–3.2 (m, ArSCH$_2$, 2H). The 70 ev mass spectrum of 78 gave the molecular ion at m/e 552.

Anal. Calcd for $C_{34}H_{32}O_5S$: C, 73.88; H, 5.84. Found: C, 73.93; H, 5.86.

Application of procedure 1 to 75 and o-dimercaptobenzene gave 79 in 72% yield, m.p. 150°–151°. The 100 MHz pmr spectrum of 79 in $CDCl_3$ gave signals at δ 7.6–7.9 (m, ArH, 4H), 6.9–7.4 (m, ArH, 12H), 3.7–4.1 (m, ArOCH$_2$, 4H), 3.2–3.5 (m, ROCH$_2$, 8H), 2.7–3.0 (m, ArSCH$_2$, 4H). The 70 ev mass spectrum gave a parent ion at m/e 568.

Anal. Calcd for $C_{34}H_{32}O_4S_2$: C, 71.79; H, 5.67. Found: C, 72.00; H, 5.53.

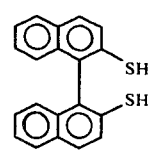

lc'

105
-continued

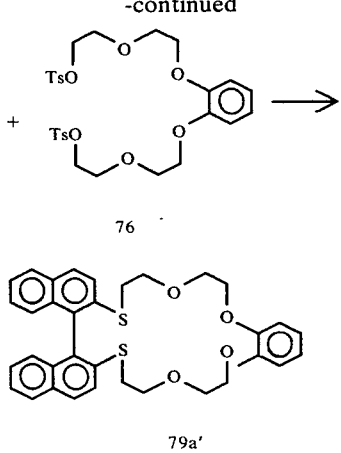

Procedure 2

Procedure 2 is illustrated by the reaction of 1c' with ditosylate 76. To a solution of 1.0 g. of 1c' in one liter of pure tetrahydrofuran stirred under pure nitrogen was added a solution of 0.434 g. of potassium hydroxide in 40 ml. of distilled water. To this solution stirred under nitrogen was added a solution of 1.86 g. of 76 dissolved in 200 ml. of pure tetrahydrofuran and 28 ml. of pure dioxane. The resulting solution had a pH of 7 to 8, and after refluxing for 15 hrs. had a pH of 5 to 6. The solution was evaporated under reduced pressure, and the residue was mixed with 50 ml. of dichlormethane. The potassium tosylate that separated was collected (0.903 g. or 69%), and the filtrate was washed with 10% potassium hydroxide, water and brine. The solution was dried, evaporated under reduced pressure, and the residue was crystallized from benzene, and recrystallized from 1:1 benzene-cyclohexane to give 1.14 g. of a solvate, m.p. 154°–155°, which after drying at 81° and 50μ for 24 hours, gave 1.10 g. (58%) of 79a', m.p. 167°–168°. The mass spectrum (70 ev) gave a molecular ion at m/e = 568, and a pmr spectrum (60 MHz) in CDCl$_3$, δ 8.1–6.9 (m, naphtho-H, 12H), 6.85 (s, benzo-H, 4H), 4.2–3.9 (m, ArOCH$_2$, 4H), 3.9–3.6 (m, CH$_2$OCH$_2$, 8H), 3.3–2.9 (m, ArSCH$_2$, 4H).

Anal. Calcd. for C$_{34}$H$_{32}$O$_4$S$_2$: C, 71.79; H, 5.67. Found: C, 71.65; H, 5.85.

EXAMPLE 9
Modification of Side Chains of Macrocyclic Ethers

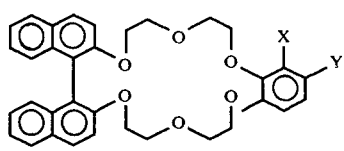

| Compound No. | X | Y |
|---|---|---|
| 80 | CH=CHCH$_3$ | H |
| 82 | CHO | H |
| 83 | CH$_2$OH | H |
| 84 | CH$_2$Cl | H |
| 85 | CH$_2$N$_3$ | H |
| 86 | CH$_2$NHCOCH$_3$ | H |
| 81 | H | (CH$_2$)$_3$OH |
| 87 | H | (CH$_2$)$_3$Cl |
| 88 | H | (CH$_2$)$_3$CO$_2$H |

The aromatic rings and ether linkages of the parent systems are stable to a variety of reaction conditions that modify the functional groups attached to the arms of the cyclic ethers. Two reaction sequences are exemplified in this section.

Procedure 1

Procedure 1 involved the sequence 80 → 82 → 83 → 84 → 85 → 86. Ozonolysis of 80 to give 82 was conducted as follows. Into 500 ml. of dichloromethane at −77° was bubbled an ozone-oxygen mixture until the deep blue color did not intensify. This solutin was added to a stirred solution of 5.8 g. (10 mmol) of 80 in 125 ml. of dry dichloromethane at −77°. The colorless solution was stirred for 0.3 hours, 1.8 g. (28 mmol) of zinc was added, and the stirred solution was slowly warmed (5 hours) to 25°. The solution was concentrated and the residue dissolved in dry tetrahydrofuran, whereupon a solid separated. A portion of this material (aldehyde 82) was purified as follows, and the remainder was used directly in the next reaction (82 → 83). The white solid (0.15 g.) was recrystallized from tetrahydrofuran to give cubic crystals of a 1:1 solvate (pmr), m.p. 100°–110° (bubbles, solidification and remelting at 159°–160°). The solid was heated at 100°–110° at 50μ for 24 hours, and the amorphous aldehyde (82) characterized. The ir spectrum in CDCl$_3$ gave a C=O band at 1695 cm$^{-1}$. The 100 MHz pmr spectrum in CDCl$_3$ gave signals at δ 10.36 (s, O=CH, 1H), 7.8 (m, naphthyl ArH, 4H), 7.5 to 6.9 (complex m, naphthyl and benzo ArH, 11H), 4.1 and 3.6 (overlapping complex m, OCH$_2$, 16H).

Anal. Calcd for C$_{35}$H$_{32}$O$_7$: C, 74.45; H, 5.71. Found: C, 74.22; H, 5.80.

Aldehyde 82 gave alcohol 83 as follows. The remaining unpurified aldehyde (last paragraph) in 150 ml. of tetrahydrofuran was slowly added to 380 mg. (400 mmol of H$^-$) of lithium aluminum hydride in 150 ml. of dry tetrahydrofuran. The mixture was refluxed for 0.5 hours, treated with 2.5 ml. of water, filtered and concentrated. The residue was chromatographed on 300 g. of silica gel with chloroformethanol (49:1) as eluent.

Alcohol 83 was eluted with 12 l. of solvent, which when evaporated gave a glass. This material was film dried at 100° and 50μ for 24 hours to give 4.4 g. (80% based on olefin 80) of 83. The ir spectrum in KBr gave an OH band at 3440 cm$^{-1}$. The 100 MHz pmr spectrum in CDCl$_3$ gave signals at δ 7.8 (m, naphthyl ArH, 4H), 7.2 (complex m, naphthyl ArH, 8H), 6.8 (m, benzo ArH, 3H), 4.72 and 4.34 (AB quartet, J$_{AB}$ = 12 Hz, CH$_2$OH, 2H) and 4.2 to 3.1 (complex m, CH$_2$O and OH, 7H).

Anal. Calcd for C$_{35}$H$_{34}$O$_7$: C, 74.19; H, 6.05. Found: C, 74.03; H, 5.97.

This material crystallized as a solvate form tetrahydrofuran, m.p. 90°–100° (bubbles).

Alcohol 83 gave chloride 84 as follows. A solution of 5.8 g. (49 mmol) of thionyl chloride in 210 ml. of dry benzene was added dropwise to a solution of 12.8 g. (22.6 mmol) of 83 in 620 ml. of dry benzene and 4 ml. of dry pyridine. The mixture was refluxed for 1 hour, filtered, concentrated, and the residue was dissolved in 500 ml. of dichloromethane. The solution was washed with water, dried (MgSO$_4$) and concentrated to give 13.2 g. (100% crude) of 84 as a yellow glass film dried at 70° (50μ) for 1 hour. A 100 mg. sample was crystallized and recrystallized from tetrahydrofuran to give a 1:1 solvate, m.p. 90°–100° (bubbles).

Anal. Calcd for $C_{35}H_{33}ClO_6 \cdot C_4H_8O$: C, 71.27; H, 6.29. Found: C, 71.27; H, 6.42.

The sample when heated at 100° (50μ) for 48 hours gave 84 as a glass.

Anal. Calcd for $C_{35}H_{33}ClO_6$; C, 71.86; H, 5.69. Found: C, 71.74; H, 5.69.

Chloride 84 gave azide 85 as follows. A mixture of 12.8 g. (21.5 mmol) of 84, 14 g. of sodium azide and 700 ml. of 95% ethanol was stirred at reflux for 15 hours and concentrated. The residue was partitioned between 500 ml. of dichloromethane and 150 ml. of water. The organic layer was washed with water, dried ($MgSO_4$) and concentrated to give after film drying at 100° and 50μ (2 hours) 10.1 g. (80%) of a glass. A 150 mg. sample was chromatographed on neutral alumina with benzene-ether (4:1) as eluent to give azide 85 as a glass, whose ir spectrum ($CDCl_3$) showed a strong band at 2105 $cm^{-1}$ ($N_3$ asymmetric stretch).

Anal. Calcd for $C_{35}H_{33}N_3O_6$: C, 71.05; H, 5.58. Found: C, 71.00; H, 5.62.

Azide 85 gave amide 86 as follows. A solution of 9.8 g. of crude azide 85 (last paragraph) in 500 ml. of dry tetrahydrofuran was added slowly to 2.5 g. (264 mmole $H^-$) of lithium aluminum hydride in 100 ml. of dry tetrahydrofuran. The resulting mixture was refluxed for 0.5 hours, cooled, treated carefully with 32 ml. of water and 500 ml. of dichloromethane. The mixture was filtered, dried ($MgSO_4$) and concentrated to give a glass. This amine (8.6 g., or 15.2 mmol) was dissolved in 240 ml. of dry dichloromethane and 4.6 g. (46 mmol) of triethylamine, and the solution was treated with a solution of 1.61 g. (20.5 mmol) of acetyl chloride in 100 ml. of dry dichloromethane. The mixture was stirred for 0.5 hours, washed with water, dried and evaporated to give 8.2 g. of a glass. This material was chromatographed on 500 g. of neutral alumina with ether-ethanol (99:1) as eluent. Fractions of 500 ml. were collected. Fractions 12–24 were evaporated to give 5.6 g. of a white solid which was crystallized from ether-benzene. This amide 86 as fine needles was dried at 165° at 50μ for 24 hours to give 5.1 g. (57%) of pure material, m.p. 193°–194°. The ir spectrum ($CDCl_3$) gave an N-H band at 3333 $cm^{-1}$ and a C=O band at 1661 $cm^{-1}$. The 70 ev mass spectrum gave a base peak that was the molecular ion at m/e 607. The pmr spectrum (100 MHz) in $CDCl_3$ gave signals at δ 7.8 (m, naphthyl, ArH, 4H), 7.2 (complex m, naphthyl ArH, 8H), 6.8 (m, benzo ArH and NH, 4H), 4.1 (complex m, $ArOCH_2$ and $ArCH_2N$, 10H), 3.5 (complex m, $CH_2OCH_2$, 8H) and 1.75 (s, $CH_3$, 3H). The base peak in the 70 ev mass spectrum was the molecular ion at m/e=607.

Anal. Calcd for $C_{32}H_{37}NO_7$: C, 73.17; H, 6.14. Found: C, 73.27; H, 6.11.

Procedure 2

Procedure 2 involved the sequence 81 → 87 → 88. Alcohol 81. 4.0 g. (6.74 mmol), in 70 ml. of dry benzene and 2.5 ml. of dry pyridine was treated with 1.6 g. (13.5 mmol) of thionyl chloride in 70 ml. of dry benzene. The resulting mixture was refluxed for 3.5 hours, and stirred at 25° with 1 ml. of water. The benzene layer was concentrated and the residue was chromatographed on 300 g. of silica gel with chloroform as eluting agent. Product was eluted with 3 l. of chloroform, concentration of which gave after drying at 110° (50μ) for 24 hours, 3.9 g. (95%) of chloride 87.

Anal. Calcd for $C_{37}H_{38}ClO_6$: C, 72.71; H, 6.10. Found: C, 72.70; H, 6.05.

Chloride 87 was converted to acid 88 as follows. A solution of 8.0 g. (73 mmol) of ethyl bromide in 100 ml. of dry tetrahydrofuran was added slowly to 2.2 g. (91 mmol) of magnesium turnings covered by 30 ml. of dry tetrahydrofuran under nitrogen. After about half the ethyl bromide had been added, a solution of 4.75 g. (7.76 mmol) of chloride 87 in 20 ml. of dry tetrahydrofuran was added to the remaining ethyl bromide solution, and the addition was completed. The resulting reaction mixture was refluxed for 8 hours, cooled to −25° and dry carbon dioxide gas was bubbled through the reaction mixture for 1 hour. The solution was warmed to 25°, diluted with 10 ml. of brine, and the mixture was shaken. The organic layer was filtered, concentrated, and the residue was dissolved in 200 ml. of dichloromethane. The solution was washed with dilute hydrochloric acid, and the aqueous layer was extracted with dichloromethane. The combined organic layers were dried ($MgSO_4$), concentrated and the residue was chromatographed on 300 g. of silica gel with chloroform-ethanol-acetic acid (98:2:0.2) as eluting agent. Elution of the column with 1.5 l. of solvent gave 0.5 g. of byproducts. Elution with an additional 2 l. of solvent gave product acid 88, obtained as a glass by evaporation of the solvent and film drying at 120° (50μ) for 24 hours, wt 3.6 g. (74%). The ir spectrum ($CDCl_3$) gave a broad OH band at 3000 $cm^{-1}$, and a C=O band at 1720 $cm^{-1}$. The 100 MHz pmr spectrum in $CDCl_3$ gave signals at δ 9.3 (broad s, $CO_2H$, 1H), 7.8 (m, naphthyl ArH, 4H), 7.2 (complex m, naphthyl ArH, 8H), 6.68 )narow m, benzo ArH, 3H), 4.0 and 3.5 (overlapping complex m, $CH_2O$, 16H), 2.56 and 2.31 (overlapping m's; former is phenyl-$CH_2$—, latter is $HO_2CC\underline{H}_2$, 4H) and 1.92 (m, $CH_2C\underline{H}_2CH_2$, 2H). A 70 ev mass spectrum gave a base peak that was the molecular ion at m/e=622. Anal. Calcd for $C_{38}H_{38}O_8$: C, 73.29; H, 6.15. Found: C, 72.99; H, 6.34.

EXAMPLE 10

Criteria for Complexation of Polar Species by Multiheteromacrocycles

Four criteria have been used for complexation of polar species (guest entities) by multiheteromacrocycles (host entities): (1) adsorption of host entities from dichloromethane onto ion exchange polystyrenesulfonate salts; (2) solubilization of crystalline salts by host entities in non-polar media; (3) alteration of distribution of host and gust entities between a polar and a non-polar medium when the two are in the presence of one another; (4) stability of complexes to experimental manipulation. In the use of criteria (2) and (3) particularly, pmr spectral methods were used both to measure relative amounts of host and guest entities in a solution but also to show that the two complexed one another.

Procedure 1

Amberlyst-15,polystyrenesulfonic acid, Rohm and Haas, 40–60 mesh, average pore diameter, 200–600A, was saturated with $H_3O^+$, $Na^+$, $K^+$, $NH_4^+$ or $Cs^+$, and dried for 12 hours at 70° at 5μ. The dry resin (25 to 50 mg.) was mixed with 5 to 12 × $10^5$ M solution of cycle in dry dichloromethane. The optical density of the solution's ultraviolet absorption (uv) spectrum from λ 250 to 340 nm was measured before mixing, and was monitored until constant. During this time (12 hours)

the mixture was shaken at 25°. For each cation and cycle, the resin became saturated with cycle to an extent (±5%) independent of cycle concentration in dichloromethane, and $K_s$ = 100 × (moles adsorbed cycle)/(moles cation present). For tribenzylamine against resin-$H_3O^+$, $K_s$=18.6. Table II lists the values of $K_s$ for the five ions and representative cycles. The low values reflect the steric inaccessability of most of the cations complex better than five, but comparably to seven oxygen, except for —$K^+$ and —$Cs^+$; S substituted for O lowers $K_s$, except for resin-$H_3O^+$; the side chain of 86 decreases $K_s$ for $Cs^+$, increases $K_s$ for —$H_3O^+$ but has little effect on the other three; (SS)(RR)-8 complexes —$H_3O^+$, —$Na^+$ and —$K^+$ better than (SR)-8, but the two diastereomers complex —$NH_4^+$ and —$Cs^+$ comparably.

TABLE II

BN = 2,2'-disubstituted 1,1'-binaphthyl

| Multiheteromacrocycle Structure | Number | resin-$H_3O^+$ | resin-$Na^+$ | resin-$K^+$ | resin-$NH_4^+$ | resin-$C_s^+$ |
|---|---|---|---|---|---|---|
| | 5 | 0.40 | 0.59 | 0.21 | 0.096 | 0.027 |
| | 6 | 0.91 | 0.67 | 0.57 | 0.47 | 0.23 |
| | 7 | 0.92 | 0.61 | 0.49 | 0.45 | 0.29 |
| | (RS)-8 | 0.087 | <0.093 | 0.061 | 0.042 | 0.014 |
| | (SS)(RR)-8 | 0.19 | 0.18 | 0.078 | 0.043 | 0.011 |
| | 77 | 0.54 | 0.55 | 0.43 | 0.30 | 0.095 |
| | 86 | 1.14 | 0.54 | 0.31 | 0.30 | 0.047 |
| | 78 | 0.83 | 0.29 | 0.13 | 0.06 | 0.007 | to the cycles, which possess large cross sections. The trends indicate: aromatic rings decrease $K_s$'s: $K_s$ for resin-$H_3O^+$ > —$Na^+$ > —$K^+$ > —$NH_4^+$ > —$Cs^+$, except, for cycle 5 (—$Na^+$ > —$H_3O^+$): six oxygen cycles Table II' expands the data of Table II, and gives the wave lengths used to determine $K_s$ values. The generalizations drawn from the limited data of Table II apply to the expanded data of Table II', and several new ones emerge.

TABLE II'

| Multihetero-macrocycle No. | UV Measurements made at | | $K_s$ values (saturation constants) for following cations on resin-$SO_3^-$ | | | | |
|---|---|---|---|---|---|---|---|
| | $\lambda_{max}$ (nm) | log E | $H_3O^+$ | $Na^+$ | $K^+$ | $NH_4^+$ | $C_s^+$ |
| 101 | 337 | 3.789 | 0.437 | 0.419 | 0.182 | 0.135 | 0.0073 |
| ($C_6H_5CH_2)_3N$ | — | — | 18.6 | — | — | — | — |
| 5 | 337 | 3.816 | 0.40 | 0.59 | 0.21 | 0.096 | 0.027 |
| 6 | 337 | 3.785 | 0.91 | 0.67 | 0.57 | 0.47 | 0.23 |
| 7 | 337 | 3.766 | 0.92 | 0.61 | 0.49 | 0.45 | 0.29 |
| 6a' | 337 | 3.797 | 0.95 | 0.19 | 0.029 | 0.017 | 0.00 |
| 31 | 285 | 4.017 | 1.97 | 0.74 | 0.69 | 1.25 | 0.61 |
| 32 | 286 | 4.013 | 2.53 | 0.90 | 0.86 | 1.91 | 0.90 |

TABLE II'-continued

| Multihetero-macrocycle No. | UV Measurements made at | | $K_s$ values (saturation constants) for following cations on resin-$SO_3^-$ | | | | |
|---|---|---|---|---|---|---|---|
| | $\lambda_{max}$ (nm) | log E | $H_3O^+$ | $Na^+$ | $K^+$ | $NH_4^+$ | $C_s^+$ |
| 28 | 293 | 4.013 | 1.61 | 1.11 | 1.12 | 0.92 | 0.73 |
| 29 | 293 | 4.013 | 1.27 | 0.77 | 0.74 | 0.61 | 0.43 |
| 30 | 292 | 3.987 | 1.82 | 1.50 | 1.51 | 1.23 | 1.26 |
| 42 | 292 | 3.927 | 1.54 | 1.28 | 1.20 | 0.94 | 0.88 |
| 45 | 292 | 3.949 | 1.54 | 1.09 | 1.39 | 1.28 | 1.21 |
| 36 | 293 | 3.954 | 1.39 | 0.98 | 0.99 | 0.85 | 0.70 |
| 39 | 293 | 3.989 | 1.99 | 1.07 | 1.10 | 1.43 | 1.03 |
| (SR)-8 | 325 | 4.017 | 0.087 | <0.093 | 0.061 | 0.042 | 0.014 |
| (SS)(RR)-8 | 326 | 4.045 | 0.19 | 0.18 | 0.078 | 0.043 | 0.011 |
| (SR)-12 | 336 | 4.013 | 0.15 | 0.14 | 0.076 | 0.027 | 0.0044 |
| (SS)(RR)-12 | 336 | 4.053 | 0.20 | 0.14 | 0.070 | 0.047 | 0.019 |
| (SRR)(RSS)-15 | 335 | 4.164 | 0.012 | 0.00 | 0.00 | 0.00 | 0.00 |
| (SSS)(RRR)-15 | 335 | 4.182 | 0.023 | 0.015 | 0.012 | 0.00 | 0.012 |
| (SS)(RR)-8b' | 337 | 4.097 | 3.68 | — | — | — | — |
| 46 | 293 | 4.283 | 1.01 | 0.33 | 0.31 | 0.69 | 0.37 |
| (SR)-48b' | 324 | 3.664 | 0.333 | 0.21 | 0.084 | 0.040 | 0.009 |
| (SS)(RR)-48b' | 324 | 3.657 | 0.38 | 0.14 | 0.050 | 0.045 | 0.069 |
| (SR)-48 | 326 | 3.785 | 1.18 | 0.89 | 0.87 | 0.90 | 0.80 |
| (SS)(RR)-48 | 326 | 3.755 | 1.086 | 0.83 | 0.85 | 0.83 | 0.81 |
| 86 | 337 | 3.783 | 1.14 | 0.54 | 0.31 | 0.30 | 0.047 |
| 77 | 337 | 3.778 | 0.54 | 0.55 | 0.43 | 0.30 | 0.095 |
| 78 | 337 | 3.775 | 0.83 | 0.29 | 0.13 | 0.06 | 0.007 |
| 79 | 293 | 4.029 | 0.59 | 0.17 | 0.041 | 0.026 | 0.00 |
| 79a' | 302 | 4.140 | 0.72 | 0.26 | 0.150 | 0.071 | 0.011 |

The open-chain, six oxygen ether, 101, is less well bound by all five cations than its cyclic analogue, 6, as is expected. For the six-oxygen cycles, all five cations provide the order, monolocular > dilocular > trilocular systems (6 > 8 ~12 > 15). The binaphthyl groups inhibit binding sterically, and undoubtedly make their attached oxygens less basic by electron delocalization. The two non-substituted dilocular systems 8 and 12 are grossly similar in their $K_s$ values. With most cations and structures, the more configurationally homogeneous dilocular and trilocular systems are more tightly bound than their diastereomers. Thus in general, (RR) (SS)-diastereomers are bound better than (RS)-diastereomers, and (SSS) (RRR)-15 is bound better than (SRR) (RSS)-15, although there are exceptions. The introductions of the methyl groups in the 3- and 3'-positions of the naphthalene rings of 8 to give 48b' results in a small enhancement of binding toward most ions. Apparently the electron-releasing inductive effect of the methyl groups tends to make the aryl-bound oxygen more basic, and this effect outweighs the steric effects of the methyl groups. Introduction of oxygen-or nitrogen-containing side chains into the 3- or 3'-positions of the naphthalene rings of the cycles increases their $K_s$ values toward all cations. For the monolocular six-oxygen cycles, in general the side chains enhance binding toward most cations in the order, $CH_2OCH_2CO_2H \sim CH_2N(CH_3)_2 > CH_2OH - CH_2N(CH_2CH_2)_2O > CH_2OCH_2CO_2CH_3 > H$ (e.g. 30 ~ 32 > 28 ~ 31 > 29 > 6). Two $CH_2OCH_2CO_2H$ side chains (in 30) contribute to binding better than one (in 36). Amino acid cycle 39 is between diamine cycle 31 and diacid cycle 30 in binding power toward most cations. Of the three monolocular diacids with 5-, 6- and 7-oxygens in their cycles, the 7-oxygen ~ 6-oxygen > 5-oxygen in binding power (45 ~ 30 > 42). The four $CH_2OH$ side chains of dilocular systems 48 enhance binding toward all cations over the four $CH_2N(CH_2CH_2)_2O$ side chains of 46, which in turn enhance binding over that of the parent system without side chains (8). Introduction of two amino nitrogens into the cycle in dilocular system 8b' increased its $K_s$ value toward resin-$H_3O^+$ over that of the all-oxygen system 8, as expected. Comparisons of $K_s$'s for 77, 78, 79 and 79a' indicate the effect of replacing the oxygens of 77 with sulfur atoms. Except toward resin-$H_3O^+$, the replacement of oxygen by sulfur atoms decreases $K_s$. The decrease is less marked when the sulfur atoms are bound to the binaphthyl (as in 79a') than when they are bound to the benzo (as in 79).

With no exceptions, resin-$H_3O^+$ was a better cycle-binding ion than resin-$NH_4^+$ or resin-$Cs^+$, and with only two exceptions ((SS)(RR)-48b' and 30), resin-$NH_4^+$ > resin-$Cs^+$ in binding power. With several exceptions, resin-$H_3O^+$ > resin-$Na^+$ or resin-$K^+$ > resin-$NH_4^+$ > resin-$Cs^+$. For six cycles (31, 32, 45, 39, 46, (SR)-48) resin-$NH_4^+$ > resin-$Na^+$ or resin-$K^+$, and in these cases the cycles had substituents,

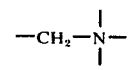

or —$CH_2O$—, in the 3-positions of the naphthalene rings. With all but two cycles, resin-$NA^+ \geq$ resin-$K^+$, the factor between the two $K_s$'s being a maximum of 3. With the four-oxygen, one-sulfur-cycle, 6a', $K_s$ for resin-$Na^+$ exceeded that for resin-$K^+$ by a factor of over 6, and for the four-oxygen, two-sulfur cycle 79, the factor was over 4.

These $K_s$ values measure the multiheteromacrocycles' ability to complex cations at a solid-liquid interface. To the extent that qualitative data are available, the relative $K_s$ values for resin-$Na^+$ correlate with the relative abilities of the cycles to complex alkylammonium ions in solution.

Procedure 2

Tertiary-butylammonium, α-phenylethylammonium, and anilinium tetraphenylborate salts were prepared (Anal. Chem., 28, 1974 (1956)) by adding an aqueous solution of the hydrochloride of the amine to an aqueous solution of sodium tetraphenylborate. The precipitated salt was filtered, water washed and dried at 50° at 50μ. Aryldiazonium tetrafluoroborate salts were prepared by a recorded procedure (Organic Reactions, Vol. VI, 1949, p. 193). In the preparation of 4-methylbenzenediazonium hexafluorophosphate, the appropriate amount of $KPF_6$ was substituted for $NaBF_4$.

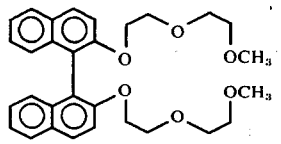

101

Compound 101 was prepared for purposes of comparisons in complexation. Binaphthol 1 (14.3 g., or 0.05 mole) was dissolved in 150 ml. of tetrahydrofuran, and a solution of potassium hydroxide (85% pellets, 7 g.) in 5 ml. of water was added. To the resulting mixture was added with stirring under nitrogen a solution of 27.4 g. (0.1 mole) of 1-tosyloxy-3,6-dioxaheptane dissolved in 60 ml. of tetrahydrofuran. The mixture was heated at 65° for 10 hours, cooled, filtered and evaporated to give 37.6. of oil, which was chromatographed on 500 g. of neutral alumina. Elution of the column with etherpentane (2:3) gave 19.8 g. (81%) of 101, m.p. 55.5°–56.5°. The 100 MHz pmr spectrum in $CDCl_3$ gave signals at $\delta$ 3.06 (s, $C\underline{H}_2CH_2OCH_3$, 8H), 3.16 (s, $CH_3O$, 6H), 3.40 (m, $ArOCH_2C\underline{H}_2O$, 4H), 4.04 (m, $ArOC\underline{H}_2$, 4H), 7.24 (m, ArH, 8H) and 7.81 (m, ArH, 4H).

Anal. Calcd for $C_{30}H_{34}O_6$: C, 73.45; H, 6.99.
Found: C, 73.61; H, 7.02.

The ability of the cyclic ethers to solubilize salts were determined as follows. The cyclic ether (~90 mg) was dissolved in 0.4 ml. of chloroform and its 100 MHz pmr spectrum recorded. Excess salt (3 to 4 moles per mole of cyclic ether) was shaken with this solution which was then filtered, and the pmr spectrum again taken. The relative number of moles of the cyclic ether to the dissolved salt were determined (±5%) by integrating the appropriate signals of the protons of the cycle vs those of the salt. After the spectra were run, all solutions were returned to contact with the excess salt, and the mixtures were shaken intermittently for 24 hours without spectral change. With each salt, a parallel experiment was performed in which the cyclic ether was absent. Unless noted otherwise, no signal was observed for the salt in the absence of the cyclic ether, indicating the salt alone to be too insoluble to be detected. Run 23 involved benzoyl hexafluorophosphate as the guest salt. This material both complexed with and more slowly reacted with (benzoylated) the host cycle. Within 5 minutes, the nmr spectrum of the mixture indicated that 80% of the benzoyl salt originally complexed had reacted. The aryl-diazonium salts were stabilized by complexation, as shown by the decreased rate of nitrogen evolution upon complexation of the more unstable of them. Reactions other than complexation of the diazonium salts with the cyclic ethers were very slow. However, reactions of the complexed diazonium salts with compounds with which they ordinarily react rapidly (e.g., N,N-dimethylaniline, potassium phenoxide, Sandmeyer reaction reagents, hypophosphorous acid) were not inhibited by complexation. For example, when 2.25 g. (10 mmol) of 4-chlorobenzenediazonium tetrafluoroborate was dissolved at 25° in a solution of 4.88 g. (10 mmol) of a cyclic ether 6 in 50 ml. of dichloromethane, cooled to −75°, and N,N-dimethylaniline added, a 95% yield of 4-chloro-4'-(N,N-dimethylamino)-azobenzene was produced.

The results of the experiments on solubilization are summarized in Table III.

In runs 40 and 41, the cyclic ether used contained a carboxyl group. One mole of salt was readily complexed. When the chloroform layer of the complex was washed with an equal volume of water after the runs, the alkyl and arylammonium ions were retained in the chloroform layer. In run 5 (involving the same cation as run 41 but the cyclic ether without the caboxyl groups) the chloroform solution after the run was washed with water. All of the salt was extracted into the water layer. Thus complexation is greatly enhanced when the cyclic ether contains a counter-ion to the charge of the guest ion.

Although the aromatic protons of complexed and uncomplexed crown ethers give different pmr signals, the most dramatic spectral changes involve the chemical shifts of the $ArOCH_2$ protons. For example these protons in uncomplexed 6 occur as a closely packed multiplet at $\delta$ 4.04 that overlaps with the complex multiplet of the $CH_2OCH_2$ protons. When complexed, the $ArOCH_2$ the protons move to about $\delta$ 4.3 to 4.5, and form a better defined multiplet. Probably two of these protons turn inward in uncomplexed material, but when the hole is occupied by a guest entity, the oxygens turn inward and the conformation of the $ArOCH_2$ protons relative to the magnetic field of the aryl group is altered. In solvents such as chloroform, benzene, dichloromethane, carbon tetrachloride or dioxane, the pmr spectra indicate the absence of complexation from the chemical shift of the $ArOCH_2$ protons. In dimethyl sulfoxide, acetonitrile or acetone as solvents, the macrocycles appear complexed from the chemical shifts of the $ArOCH_2$ protons. The $(CH_3)_2S^+-$, $(CH_3)_2C^+-O^-$, and $CH_3C^+=N^-$ dipoles are just what might be expected to make their oxygens protrude into the hole of the macrocycles so the oxygens of the macrocycle can solvate $S^+$ or $C^+$.

TABLE III

| | BN = 2,2'-disubstituted-1,1'-binaphthyl Cyclic Ether | | DNB = 3,5-$(NO_2)_2C_6H_3CO_2$ | PIC = 2,4,6-$(NO_2)_3C_6H_2O$ |
|---|---|---|---|---|
| Run No. | Structure | Number | Salt | Equivalents of salt complexed per equivalent of cyclic ether |
| 1 | BN with cyclic ether structure | 5 | t-$BuNH_3(C_6H_5)_4B$ | 1.0 |
| 2 | | 5 | t-$BuNH_3^+ SCN^-$ | 0 |
| 3 | | 5 | 4-$CH_3C_6H_4\overset{+}{N}\equiv N\ BF_4^-$ | 0 |

TABLE III-continued

| | BN = 2,2'-disubstituted-1,1'-binaphthyl Cyclic Ether | | DNB = 3,5-(NO$_2$)$_2$C$_6$H$_3$CO$_2$ | PIC = 2,4,6-(NO$_2$)$_3$C$_6$H$_2$O |
|---|---|---|---|---|
| Run No. | Structure | Number | Salt | Equivalents of salt complexed per equivalent of cyclic ether |
| 4 | BN-[cyclic ether structure] | 6 | t-BuNH$_3^+$(C$_6$H$_5$)$_4$B | 1.0 |
| 5 | | 6 | C$_6$H$_5$NH$_3^+$Cl | 0.6 |
| 6 | | 6 | C$_6$H$_5$NH$_3^+$OAc | 0.7 |
| 7 | | 6 | 4-BrC$_6$H$_4$NH$_3^+$Br | 0.9 |
| 8 | | 6 | 4-CH$_3$C$_6$H$_4$NH$_3^+$ DNB | 1.0 |
| 9 | | 6 | 4-CH$_3$OC$_6$H$_4$NH$_3^+$ DNB | 1.0 |
| 10 | | 6 | 4-NO$_2$C$_6$H$_4$NH$_3^+$ DNB | 1.0 |
| 11 | | 6 | C$_6$H$_5$CH(CH$_3$)NH$_3^+$ DNB | 0 |
| 12 | | 6 | C$_6$H$_5$CH(CH$_3$)—NH$_3^+$ PIC | 1.0 |
| 13 | | 6 | NH$_4^+$ CNS | 1.0 |
| 14 | | 6 | H$_3$O$^+$ OTs | 1.0 |
| 15 | | 6 | 4-CH$_3$OC$_6$H$_4$N≡N$^+$ BF$_4^-$ | 1.0 |
| 16 | | 6 | 4-CH$_3$C$_6$H$_4$N≡N$^+$ BF$_4$ | 1.0 |
| 17 | | 6 | 4-CH$_3$C$_6$H$_4$N≡N$^+$ PF$_6$ | 1.0 |
| 18 | | 6 | 3,4-(CH$_3$)$_2$C$_6$H$_3$N≡N$^+$ BF$_4$ | 1.0 |
| 19 | | 6 | 2,6-(CH$_3$)$_2$C$_6$H$_3$N≡N$^+$ BF$_4^-$ | 0 |
| 20 | | 6 | C$_6$H$_5$N≡N$^+$ BF$_4$ | 1.0 |
| 21 | | 6 | 4-ClC$_6$H$_4$N≡N$^+$ BF$_4$ | 1.0 |
| 22 | | 6 | 4-NO$_2$C$_6$H$_4$N≡N$^+$ BF$_4$ | 1.0 |
| 23 | | 6 | C$_6$H$_5$C≡O$^+$ PF$_6$ | 0.5 |
| 24 | BN-[cyclic ether structure] | 7 | 4-CH$_3$OC$_6$H$_4$N≡N$^+$ BF$_4$ | 1.0 |
| 25 | BN-[cyclic ether with benzo structure] | 77 | t-BuNH$_3^+$ (C$_6$H$_5$)$_4$B | 1.0 |
| 26 | | 77 | C$_6$H$_5$CH(CH$_3$)—NH$_3^+$ (C$_6$H$_5$)$_4$B | 1.5 |
| 27 | | 77 | NH$_4^+$ CNS | 0.3 |
| 28 | | 77 | H$_3$O$^+$ OTs | 1.0 |
| 29 | BN-[cyclic ether with Ac-NH-CH$_2$-benzo structure] | 86 | t-BuNH$_4^+$ (C$_6$H$_5$)$_4$B$^-$ | 1.0 |

TABLE III-continued

| | BN = 2,2'-disubstituted-1,1'-binaphthyl Cyclic Ether | | DNB = 3,5-$(NO_2)_2C_6H_3CO_2$ | PIC = 2,4,6-$(NO_2)_3C_6H_2O$ |
|---|---|---|---|---|
| Run No. | Structure | Number | Salt | Equivalents of salt complexed per equivalent of cyclic ether |
| 30 | (BN cyclic ether with $HO_2C$ aryl group) | 88 | $NH_4CNS$ | complexed (pmr lines overlapped) |
| 31 | (BN...NB bis-binaphthyl cycle) | (SS)(RR)-8 | $\overset{+}{NH_4}\ \overset{-}{CNS}$ | 0 |
| 32 | | (SS)(RR)-8 | 4-$CH_3C_6H_4\overset{+}{N}\!\!\equiv\!\!N\ \overset{-}{BF_4}$ | 0 |
| 33 | | (SS)(RR)-8 | 4-$CH_3OC_6H_4\overset{+}{N}\!\!\equiv\!\!N\ \overset{-}{BF_4}$ | 0 |
| 34 | | (SS)(RR)-8 | 4-$CH_3OC_6H_4\overset{+}{NH_3}\ \overset{-}{DNB}$ | 0.5 |
| 35 | | (SS)(RR)-8 | t-$Bu\overset{+}{NH_4}\ (C_6H_5)_4\overset{-}{B}$ | 0.26 |
| 36 | (BN cyclic ether with two O—$CH_3$ groups) | 101 | t-$Bu\overset{+}{NH_3}\ (C_6H_5)_4\overset{-}{B}$ | 0.3 |
| 37 | | 101 | 4-$CH_3C_6H_4\overset{+}{NH_3}\ \overset{-}{DNB}$ | 0.2 |
| 38 | | 101 | 4-$CH_3C_6H_4\overset{+}{N}\!\!\equiv\!\!N\ \overset{-}{BF_4}$ | 0 |
| 39 | | 101 | 4-$CH_3C_6H_4\overset{+}{N}\!\!\equiv\!\!N\ \overset{-}{PF_6}$ | 0 |
| 40 | (bis-binaphthyl cycle with $OCH_2CO_2H$) | 36 | t-$Bu\overset{+}{NH_3}\ \overset{-}{Br}$ | 1 |
| 41 | | 36 | $C_6H_5\overset{+}{NH_3}\ \overset{-}{Cl}$ | 1 |

The inability of the open chain ether 101 to complex the aryldiazonium salts of Table III indicates the cyclic structural feature to be a condition necessary to this complexation. However, the open-chain ether did complex the ammonium salts. The ability of the five-oxygen cyclic ether (5) to complex t-butylammonium tetraphenylborate but not aryldiazonium salt correlates with what is suggested by CPK molecular models. The alkylammonium ion complexes by hydrogen bonding the oxygens, and the nitrogen sits well above the best plane of the oxygens. The aryldiazonium ion complexes by insertion of the two nitrogens fully into the hole. The hole diameters with the oxygens turned inward are estimated from CPK models to vary with naphthyl-naphthyl dihedral angles (45°–135°) for the cycles containing one binaphthyl unit as follows: cycle with 5 O's, 1.7 to 2.2 A; cycle with 6 O's, 2.4 to 3.1; cycle with 7 O's, 3.4 to 4.1. The diameter of the nitrogen-nitrogen triple bond carrying a positive charge is estimated to be about 2.8 A, too large for the 5-oxygen cycle. The facts that 3,4-dimethylbenzenediazonium salt complexes the 6-oxygen cycle (run 18) but the 2,6-dimethylbenzenediazonium salt does not (run 19) support this conclusion. In the latter salt, the two methyls inhibit insertion of the two nitrogen atoms into the hole. Attempts to form azobenzenes trapped in the hole failed. It appears that complexed azo compounds are less reactive than the small equilibrium concentration of uncomplexed salt in the medium.

A qualitative experiment with cyclic ether 6 indicated the compound when dissolved in benzene immediately solubilized crystalline potassium permanganate. The permanganate color rapidly diffused into the benzene without any water being present.

Procedure 3

In this procedure, cyclic ether was dissolved in a non-polar medium such as chloroform, benzene, methylene dichloride, ether or similar solvents. These solutions were used to extract salts or other polar species from water or water-polar-organic solvent mixtures into the non-polar solvent. In effect, the water-polar-organic-solvent mixtures overcome the lattice energy of the crystalline polar species, and the oxygens of the cyclic ether in the non-polar medium solvate the polar species competitively with the polar solvent.

In a series of runs, cyclic ethers (∼90 mg.) were dissolved in 0.7 ml. of $CDCl_3$, and shaken with 0.8 ml. of $D_2O$ containing six moles (relative to the cyclic ether) each of potassium thiocyanate and either α-phenylethylammonium bromide, or the hydrobromide of methyl α-phenylglycinate. The organic layer was separated, dried with magnesium sulfate, and the 100 MHz pmr spectrum examined.

The relative amounts of cyclic ether and complexed salt were determined (±5%) by integration of appropriate pmr peaks of the host and guest entities. In parallel runs made without cyclic ether present, or alternatively without the potassium thiocyanate present, peaks due to the salts were absent from the chloroform layer's spectra. Table IV records the results.

$CH_3OD[\delta$ 3.18 (s, $CH_3$, 3H)] and of (RR)-8 [$\delta$ 7.68 (m, $ArH^{4,5}$, 8H), 7.00 (m, $ArH^{3,6,7,8}$, 12H), 3.62 (m, $ArOCH_2$, 12H), 3.00 (m, $CH_2OCH_2$, 8H)].

TABLE IV

BN = 2,2'-disubstituted-1,1'-binaphthyl

| Run No. | Cyclic Ether Structure | Number | Extracted salt's structure | Equivalents of salt complexed per equivalent of cyclic ether |
|---|---|---|---|---|
| 1 | BN with 6-oxygen macrocycle | 6 | $C_6H_5\overset{CH_3}{\underset{\phantom{x}}{CH}}-\overset{+}{N}H_3$ $CNS^-$ | 2.0 |
| 2 | | 6 | $C_6H_5\overset{CO_2CH_3}{\underset{\phantom{x}}{CH}}-\overset{+}{N}H_3$ $CNS^-$ | 0.8 |
| 3 | BN with benzo-fused macrocycle | 77 | $C_6H_5\overset{CH_3}{\underset{\phantom{x}}{CH}}-\overset{+}{N}H_3$ $CNS^-$ | 1.9 |
| 4 | | 77 | $C_6H_5\overset{CO_2CH_3}{\underset{\phantom{x}}{CH}}-\overset{+}{N}H_3$ $CNS^-$ | 0.7 |
| 5 | BN with $HO_2C$-benzo-fused macrocycle | 88 | $C_6H_5\overset{CO_2CH_3}{\underset{\phantom{x}}{CH}}-\overset{+}{N}H_3$ $CNS^-$ | 0.8 |

In run 26 of Table III and runs 1 and 3 of Table IV, evidence indicated that the macrocycles could complex more than one mole of guest alkylammonium ion. Likely one alkylammonium ion is located above and the second below the hole of the macrocycle. The first hydrogen-bonds to three alternate oxygens from the top, and the second hydrogen bonds to the other three alternate oxygens from the bottom.

The following experiment demonstrates the ability of (RR)-8 dissolved in carbon disulfide to complex on a one-to-one molar basis one mole of methanol. A 0.112 M solution of (RR)-8 in carbon disulfide (80 mg. in 1.0 ml.) was cooled to −78° and shaken with 1.5 ml. of a 20% solution (by volume) of $D_2O$ in $CH_3OD$ which was 0.66 M in $LiPF_6$ (152 mg.) at −78°. The layers were carefully separated at this temperature. Integrations of the pmr spectrum of the carbon disulfide layer taken (100 MHz) at 25° gave the relative amounts of

| Integrals | $ArH^{4,5}$ | $ArH^{3,6,7,8}$ | $ArOCH_2$ | $CH_2OCH_2$ + $CH_3OD$ |
|---|---|---|---|---|
| Calcd for one-to-one complex: | 75 | 150 | 75 | 103 |
| Found: | 75 | 150 | 75 | 100 |

Repetition of the experiment except that the (RR)-8 was omitted gave no observable amount of $CH_3OD$ in the carbon disulfide layer, although less than 10% of the observed in the original experiment would have been detected.

Procedure 4

Representative examples of complexes have been prepared and crystallized or precipitated. For example, treatment of a solution of 5-oxygen cycle 5 (44.4 mg.) in 2 ml. of chloroform with 46 mg. of t-butylammonium tetraphenylborate gave a clear solution, which after standing at 25° for 14 hours deposited crystals, wt 75 mg. (80%), m.p. 118°–120°. The pmr spectrum of this material in $DCCl_3$ indicated it to be 1:1.

Anal. Calcd. for $C_{56}H_{60}O_5NB$: C, 80.29; H, 7.17. Found: C, 80.30; H, 7.34.

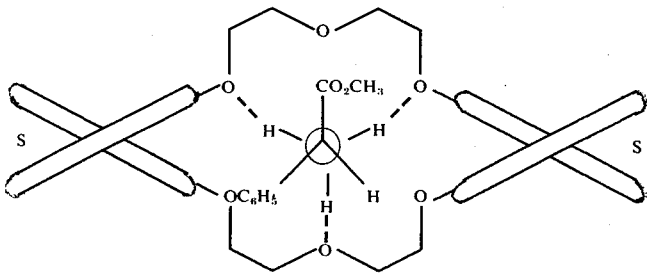

PF$_6^-$ . CHCl$_3$

101a'

A crystalline complex was formed by extracting 1.5 ml. of a D$_2$O solution 4M in lithium hexafluorophosphate (pH 4.0) and 1.2 M in (R)-phenylglycine methyl ester hydrochloride with 3 ml. of an 0.2 M solution of (SS)-8 in CDCl$_3$ at −13°. The chloroform layer was dried, and its pmr spectrum showed it contained a one-to-one complex. After 0.5 hours the complex crystallized and was collected and recrystallized from CHCl$_3$ to give 0.41 g. (75%) of 101a', phase change and bubbles 142°–145° and m.p. 222°–224° (decomposition). The analysis and an X-ray molecular weight determination demonstrated that a one-to-one complex had formed (101a'), and that one mole of chloroform was present as solvate.

Anal. Calcd for C$_{57}$H$_{52}$F$_{6t}$ $_{NO8}$P.HCCl$_3$: C, 60.93; H, 4.67; Cl, 9.30. Found: C, 60.75; H, 4.55; Cl, 8.91.

A solution of 350 mg. (0.5 mmol) of amino ester 38 and 120 mg. (2.1 mmol) of potassium hydroxide in 100 ml. of methanol-water (9:1) was refluxed under nitrogen for 6 hours. The solution was evaporated (30 mm) and the residue was partitioned between 150 ml. of water and 200 ml. of ether. The ether layer was dried (MgSO$_4$), filtered and evaporated to give <10 mg. of material. The aqueous layer was extracted with four 100 ml. portions of chloroform, which were combined, dried (MgSO$_4$) and evaporated to give 50 mg. of material. The pmr spectrum (60 MHz) of this material in CDCl$_3$ gave signals indicative of complexed material: δ 6.98–8.18 (complex m, ArH, 10H), 4.98 (AB quartet, ArCH$_2$O, 2H), 4.20 (s, broad),

2H), 2.85–4.15 (m, OCH$_2$CH$_2$O, ArCH$_2$N and OC$\underline{H}_2$CH$_2$N, 26H) and 2.40–2.70 (m, NC$\underline{H}_2$CH$_2$O, 4H). A 30 ml. portion of the above aqueous solution was brought to ph1 with 6N hydrochloric acid, and continuously extracted with chloroform for 8 hours. The chloroform extract was dried (MgSO$_4$), filtered and evaporated to dryness to give a powder. A 70 ev mass spectrum of the residue (40 mg.) showed a parent molecular ion at m/e = 713 (potassium salt of amino acid), but no peak at 675 (molecular ion of aminoacid 39). The hydrochloride, potassium salt of the amino acid (106) was apparently extracted into chloroform. Neutralization of aminoacid 39 with potassium hydroxide gave the potassium salt of the aminoacid as a powder.

Anal. Calcd for C$_{38}$H$_{44}$O$_{10}$NK: C, 63.94; H, 6.22; K, 5.49. Found: C, 62.21; H, 6.12; K, 5.64.

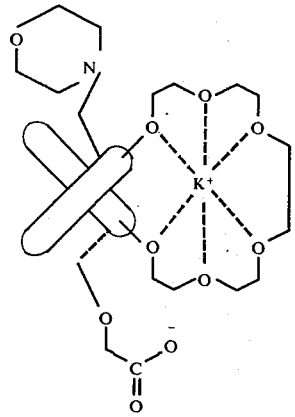

106

A solution of 3.5 g. (5 mmol) of amino ester 38 and 3.2 g. (10 mmol) of barium hydroxide octahydrate in 400 ml. of methanol-water (4:1) under nitrogen was refluxed for 8 hours. The solution was concentrated (30 mm) to 40 ml., and 300 ml. of water and 75 ml. of acetic acid were added to the mixture. The aqueous solution was extracted 3 times with 300 ml. portions of chloroform. The chloroform extracts were dried (MgSO$_4$) and concentrated to 40 ml. The crude product was chromatographed on 200 g. of silica gel made up in benzene. Elution of the column with up to 1:4 isopropanol-ether mixture gave only traces of material. Elution of the column with 3 l. of methanol ether (1:4) and 2l. of methanol-ether (2:3) gave 1.5 g. (40%) of the barium salt of the aminoacid (105) as a powder. The 1 to 2 complex is readily soluble in water, methanol, chloroform and acetic acid, which demonstrates its mixed hydrophilic-lipophilic character. The 100 MHz pmr spectrum in CDCl$_3$ gave signals at δ 6.90–8.20 (complex m, ArH, 10H), 4.82 (AB quartet, $J_{AB}$ = 7Hz, ArCH$_2$O, 2H), 4.72 (s, broad, OCH$_2$CO$_2$, 2H), 2.85–4.10 (m, OCH$_2$, ArCH$_2$N, 24H) and 2.80 (m, NC$\underline{H}_2$CH$_2$O, 4H). The spectrum is dramatically different from that of the uncomplexed aminoacid hydrochloride.

Anal. Calcd for C$_{76}$H$_{88}$O$_{20}$Ba: C, 61.37; H, 5.92; Ba, 9.24. Found: C, 61.98; H, 6.10; Ba, 9.58.

A solution of this complex in methanol-water was acidified with 5% sulfuric acid. No precipitate of BaSO$_4$ was formed. Molecular models of the complex suggest it has structure 105.

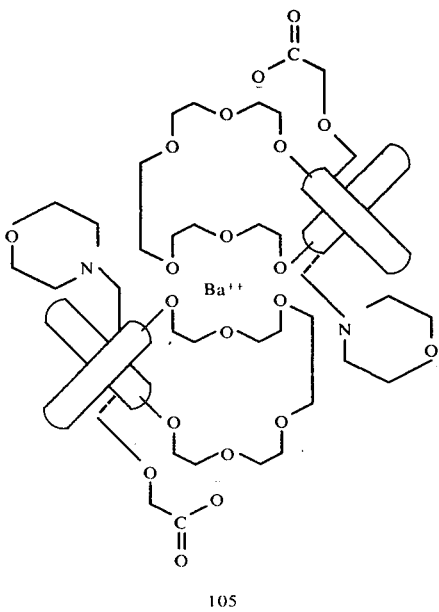

105

The alkaline earth complexes of the diacids containing one binaphthyl unit and 5-, 6- or 7-oxygens (macrocycles 42, 30 and 45, respectively) were prepared by a method illustrated as follows. A solution of 0.70 g. (1 mmol) of dimethyl ester 29 and 2 mmol of M(OH)$_2$(M = Ca, Sr or Ba) in 200 ml. of methanol-water (4:1) was refluxed under nitrogen for 8 hours. The solution was concentrated to about 20 ml. and 150 ml. of water was added. The aqueous solution was extracted with two 50 ml. portions of dichloromethane to remove neutral material. The water layer was then extracted with five 100 ml. chloroform-methanol (3:1) portions to give chloroform solutions of the salts. The combined organic extracts were dried with the metal sulfates corresponding to the M(OH)$_2$ used in the hydrolysis. The dried solutions were evaporated to give the metal salt complexes as white powders. Since BaSO$_4$ was an inefficient drying agent, benzene was added during the evaporation to help dry the solution when M = Ba. The yields of the salts ranged from ~80% for Ca and Sr to ~50% for Ba. The extraction of the barium salt was considerably less efficient than for the other two ions. The pmr spectra (60 MHz) of the salts in CD$_3$CO$_2$D were consistent with highly complexed cyclic ether but the differences for the three complexes were not significant enough to correlate with possible metal positioning within the cycle. The pmr spectrum (60 MHz) of the barium salt (102) in CD$_3$CO$_2$D gave δ 7.00–8.20 (complex m, ArH, 10H), 4.98 (AB quartet, J$_{AB}$ 12Hz, ArC$\underline{H}_2$, rH), 4.38 (broad s, OC$\underline{H}_2$CO$_2$, 4H) and 2.95–4.20 (m, OC$\underline{H}_2$C$\underline{H}_2$, 20 H).

Anal. Calcd for C$_{36}$H$_{38}$O$_{12}$Ba: C, 54.04; H, 4.80; Ba, 17.16. Found: C, 53.68; H, 4.77; Ba, 15.47.

The pmr spectrum (60 MHz) for the strontium salt (103) in CD$_3$CO$_2$D gave δ 7.08–8.22 (complex m, ArH, 10H), 5.04 (AB quartet, J$_{AB}$ = 13Hz, 4H), 4.42 (broad s, OCH$_2$CO$_2$, 4H) and 2.90–4.05 (m, OCH$_2$CH$_2$, 20 H).

Anal. Calcd for C$_{36}$H$_{38}$O$_{12}$Sr: C, 57.63; H, 5.10; Sr, 11.68. Found: C, 57.33; H, 5.84; Sr, 10.88.

The pmr spectrum (60 MHz) for the Ca salt (104) in CD$_3$CO$_2$D gave δ 7.10–8.18 (complex m, ArH, 10H), 4.80 (AB quartet, J$_{AB}$ = 12Hz, ArC$\underline{H}_2$, 4H), 4.22 (broad s, OCH$_2$CO$_2$, 4H) and 2.90–4.20 (m, OC$\underline{H}_2$C$\underline{H}_2$, 20 H).

Anal. Calcd for C$_{36}$H$_{38}$O$_{12}$Ca: C, 61.52; H, 5.45; Ca, 5.70. Found: C, 62.04; H, 6.03.

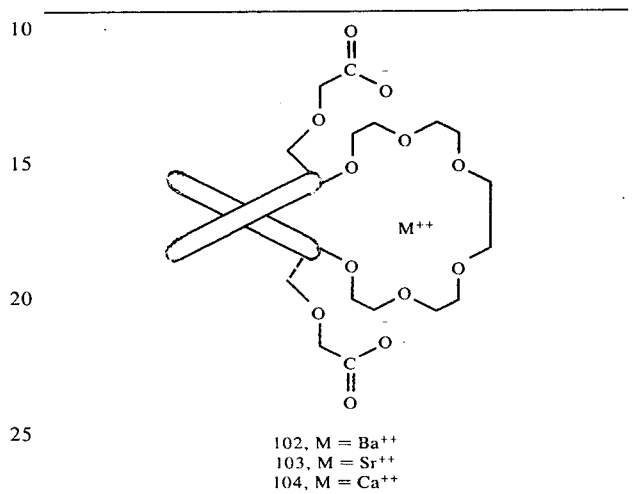

102, M = Ba$^{++}$
103, M = Sr$^{++}$
104, M = Ca$^{++}$

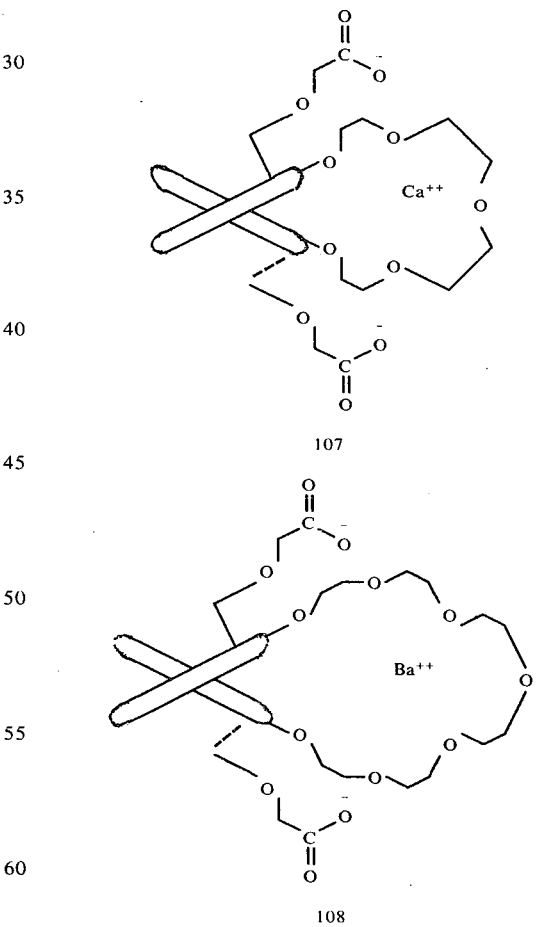

107

108

Application of this same method to diester 41 and calcium hydroxide produced calcium salt 107, ~ 80%.
Anal. Calcd for C$_{34}$H$_{34}$O$_{11}$Ca: C, 61.98; H, 5.21; Found: C, 60.81; H, 5.54;

Application of this same method to diester 44 and barium hydroxide gave barium salt 108 ~ 75%.

Anal. Calcd for $C_{38}H_{42}O_{13}Ba$: C, 54.07; H, 5.02; Ba, 16.27. Found: C, 53.89; H, 5.20; Ba, 16.04.

Application of this method to diester 29 and a 10 mmol of $Ba(OH)_2$ which was 0.8% $Sr(OH)_2$ gave a solution which after hydrolysis and the dichloromethane wash was acidified with excess acetic acid. The solution was extracted by the above method, dried with $MgSO_4$ and evaporated to a gum. The mass spectrum of this material contained the molecular ion of both diacid 30 at m/e = 664, and more interestingly, that of strontium salt 103, at m/e = 750. Thus diacid 30 scavenged strontium from bulk barium, and the strontium was carried through the acidification and extraction procedure.

The most probable diameters (A) in ionic crystals of metals used here are (*Theoret. Chim. Acta* (Berl.), 12, 333 (1968)) $Na^+$, 2.24; $K^+$, 2.88; $NH_4^+$, 3.32; $Cs^+$, 3.68; $Ca^{++}$, 2.36; $Sr^{++}$, 2.64; $Ba^{++}$, 2.98. The hole diameters (A) are estimated from CPK models to vary with naphthyl-naphthyl dihedral angles (45°–135°) as follows: one binaphthyl and four ethyleneglycol units (5 oxygens), 1.77 to 2.2; one binaphthyl and five ethyleneglycol units (6 oxygens), 2.4 to 3.1; one binaphthyl and six ethyleneglycol units (7 oxygens), 3.4 to 4.1. Proper design of hole size, heteroatom type and the number of "built in" counterions provides host multiheteromacrocycles with a wide range of differential complexing abilities of many of the metal cations of the periodic table.

EXAMPLE 11

Complete Optical Resolution by Differential Complexation in Solution Between Chiral Multiheteromacrocycles and Chiral Amines of Amino Acids.

Procedure 1

Racemic α-phenylethylamine (109) was resolved to optical purity with optically pure (SS)-8, by partitioning between chloroform and water. The macrocycle was insoluble in water, and the amine salt was differentially extracted into the chloroform by chiral complexation. Preliminary-one-plate runs established the proper experimental conditions. Run 1. The hydrobromide salt (150 mg.) of optically pure (R)-α-phenylethylamine (*Chem. Ber.*, 87, 690 (1954); ibid., 64, 2827 (1931)) ((R)-109·HBr) was dissolved in 0.8 ml. of $D_2O$ and shaken thoroughly at 25° with 0.7 ml. of $CDCl_3$ containing 90 mg. of optically pure (SS)-8. The 100 MHz pmr spectrum of the dried ($MgSO_4$) $CDCl_3$ layer indicated 109·HBr to be absent. Run 2. This run duplicated 1 except that 125 mg. of $NaPF_6$ was present. The spectrum showed ~ 0.7 mole of (R)-109·HPF$_6$ per mole of macrocycle to be present in the $CDCl_3$ layer. Thus the PF$_6$ ion is necessary for the complexation. Run 3. Duplicated 2 except (S)-109·HBr was substituted for (R)-109·HBr. The spectrum showed ~ 0.5 mole of (S)-109·HPF$_6$ per mole of macrocycle to be present in the $CDCl_3$ layer. Thus (SS)-8 solubilizes by complexation (R)-109·HPF$_6$ more than it does (S)-109·HPF$_6$. Run 4. Duplicated 2 except that (R)(S)-109·HBr was employed. The spectrum showed 0.74 mole of salt per mole of macrocycle in the $CDCl_3$ layer, and two methyl doublets (59% (R)-109·HPF$_6$ at δ 1.40, and 41% (S) 109·HPF$_6$ at δ 1.14). Thus differential extraction occurred when both enantiomers were present. Run 5 duplicated 4 except the extraction temperature was lowered to 0°. The spectrum of the $CDCl_3$ layer showed per mole of macrocycle 0.93 mole of salt, which was 62% (R)-109·HPF$_6$ and 38% (S)-109·HPF$_6$. Thus lowering the temperature increased the amount of salt extracted, as well as the chiral recognition. Run 6. Involved shaking at 0° the mixture formed from 3.00 g. of (SS)-8, 3.9 g. of (R)(S)-109·HCl, 4.2 g. of NaPF$_6$, 25 ml. of chloroform and 30 ml. of water. The chloroform layer was separated, and extracted with three 20 ml. portions of 0.1 M hydrochloric acid. The combined aqueous layers were washed with three 10 ml. portions of dichloromethane, made basic with potassium hydroxide, and the free amine was extracted with three 20 ml. portions of dichloromethane. The combined dichloromethane layers were washed with 10 ml. of brine, dried ($MgSO_4$) and evaporated through a Vigreux column. The residue was vacuum (30 mm) distilled to give 0.333 g. (65%) of α-phenylethylamine, $[\alpha]_{578}^{25}$ +9.41° (c 7.56, $CHCl_3$), 62% (R)-109 and 38% (S)-109. The chiral recognition factor is defined as the ratio of the amounts of the predominant to the subordinate enantiomer observed at equilibrium in the phase where the major amount of complexation occurs. In runs 5 and 6, the factor = [62%(R)-109]/[38%(S)-109]=1.63 for the chloroform phase.

Complete resolution of racemic amine, (R)(S)-109, was accomplished as follows by liquid-liquid chromatography. Celite (60.0 g.) was shaken with 26 ml. of distilled water saturated with chloroform which was 1 M in sodium hexafluorophosphate (4.328 g. or 12.9 mmol). The resulting powder was 30% aqueous by weight, and was packed tightly in portions into a 4 cm diameter column to form an 18 cm long stationary phase. A solution of 0.300 g. (1.5 mmol) of (R)(S)-109·HBr and 0.263 g. (1.56 mmol) of sodium hexafluorophosphate in 0.75 ml. of water saturated with chloroform was mixed thoroughly with 1.6 g. of Celite. This powder was packed on the top of the column to form a 0.5 cm layer. A 0.05 M solution of optically pure (SS)-8 (16.996 g., 23.9 mmol) dissolved in 480 ml. of chloroform saturated with water was cooled to 0°, and was added to the top of the column chilled to 0°. After the addition of 105 ml. of solution (one free volume of the column), eluent appeared at the bottom of the column, and was collected in 10 ml. fractions. Each fraction was tested by silica gel tlc with diethyl ether as solvent. The amine salt moved very slowly on tlc, (rf ~ 0 03) and was visible in fractions 10–27. The intensity of the thin layer spot under a ultraviolet lamp was very light for the sample (one drop) from fraction 10, reached a maximum in fractions 14 and 15, dropped to a very light minimum in fraction 18, reached a second maximum in fractions 23 and 24 and dwindled in the later fractions. Fractions 10–15 were combined and the amine was isolated as in run 6 to give 52 mg. (57% of maximum) of optically pure (R)-109, $[\alpha]_{578}^{25}$ +39.5° (c 7.4, $CHCl_3$).

Fractions 23–27 were combined and the amine was isolated as in run 6 to give 43 mg. (47% of maximum) of essentially optically pure (S)-109, $[\alpha]_{578}^{25}$ −39.1° (c 7.1, $CHCl_3$). The more stable diastereomeric complex is formulated (110).

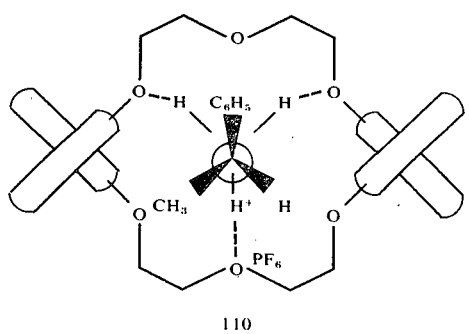

110

Favored diastereomeric complex between (SS)-8 and hexafluorophosphate salt of (R)-α-phenylethylamine (109)

Procedure 2 -

The chiral recognition factors of macrocycles 30, 36, 29, 42, and 45 were determined for valine (111) in a series of runs.

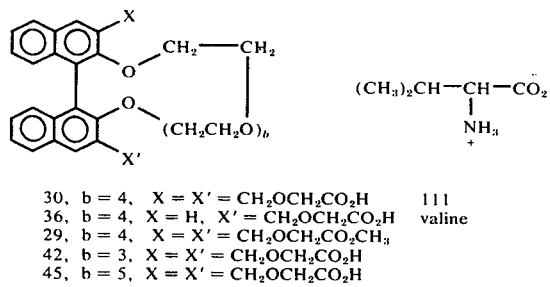

| | | |
|---|---|---|
| 30, b = 4, | X = X' = CH$_2$OCH$_2$CO$_2$H | 111 |
| 36, b = 4, | X = H, X' = CH$_2$OCH$_2$CO$_2$H | valine |
| 29, b = 4, | X = X' = CH$_2$OCH$_2$CO$_2$CH$_3$ | |
| 42, b = 3, | X = X' = CH$_2$OCH$_2$CO$_2$H | |
| 45, b = 5, | X = X' = CH$_2$OCH$_2$CO$_2$H | |

Run 1. The (R)- and (S)-components of racemic 30 (76 mg.) and 11.4 mg. of optically pure (R)-valine ["Chemistry of Amino Acids", John Wiley and Sons, Inc., N.Y., 1961, p. 116] were partitioned at equilibrium between the two layers formed by shaking 0.2 ml. D$_2$O, 0.3 ml. of DCCl$_3$ and 0.6 ml. CD$_3$CO$_2$D (at 30°). The pmr spectra (100 MHz) of the aqueous (~ 0.75 ml.) and chloroform layers (~ 0.25 ml.) indicated the former contained ~50% of 30 and ~95% of the valine used, and the latter, 50% of the 30 and ~5% of the valine used. Changes in the pmr spectral chemical shifts of the ArCH$_2$O protons of the macrocycle in the aqueous layer, and of the CH$_3$ protons of the valine in the chloroform layer indicated these species to be complexed. The aqueous layer was evaporated under vacuum, the residue was shaken with 3 ml. of chloroform and 3 ml. of water. The organic layer was washed twice with 3 ml. of water, and evaporated to dryness (30°, 50μ, 3 hours) to give 30.0.5H$_2$O as a film, wt 33.5 mg. (~ 44%), [α]$_{546}^{25}$ +6.7 (C 1.0, (CH$_2$)$_4$O). A 40 mg. sample of optically pure (S)-30, submitted to the above isolation conditions, gave a 5% weight loss, [α]$_{546}^{25}$ −24.6° (C 1.0, (CH$_2$)$_4$O). Thus the aqueous layer contained 30 of ~ 27% optical purity, rich in the (R)-isomer. Thus a chiral recognition factor of 1.7 was observed for (R)-valine selecting (R)-30 over (S)-30 for complexation in the aqueous phase, where the major amount of complexation occurs. In run 2 carried out similarly but at 0°, and with formic acid substituted for acetic acid, a factor of 1.7 was also observed for preferential complexation of (R) over (S)-30. In run 3, 0.35 ml. of CD$_3$CO$_2$D, 1 ml. of benzene and 0.25 ml. of D$_2$O at 30° with the same amounts of valine and macrocycle as in run 1 gave an aqueous layer (~ 0.5 ml.) that contained >95% of the valine and ~ 50% of the 30, rich in the (R)-isomer by a factor of 1.25. Run 4 was the same as run 1 except that monoacid 36 was substituted for 30. The absolute configuration and maximum rotation of the enantiomers of 36 are unknown. The 36 isolated from the aqueous layer gave [α]$_{546}^{25}$ +1.2° (C 1.0, CHCl$_3$). The magnitudes of rotation of the molecular relatives of 36 suggest this rotation reflects a very small chiral recognition factor. Run 5 was the same as run 1 except diester 29 was substituted for diacid 30. Although (R)-29 dominated in the aqueous layer, the factor dropped to 1.06. Run 6 was the same as run 1 except diacid 42 was substituted for diacid 30. The aqueous layer showed no enrichment in either isomer of 42, and only a trace of valine in the chloroform layer was detected. Run 7 was the same as run 1 except diacid 45 was substituted for diacid 30. The aqueous layer was enriched by a factor of 1.02 in the (R)-isomer. These runs demonstrate that of the five cycles tried, only diacid 30 possesses useful chiral recognition properties. An examination of CPK molecular models of the ten non-enantiomeric complexes of the five macrocycles tested led to the conclusion that only 30 should show chiral recognition toward valine, and that with 30, the (R)(R) or (S)(S)-complex should be more stable than the (R)(S) or (S)(R)-complex. Structure 112 was envisioned for the (S)(S)-complex. Three hydrogen bonds and carboxylate-to-ammonium ion-pairing hold the amino acid to the macrocycle, and carboxyl-to-carboxyl hydrogen bonding presses the hydrogen of the chiral center of the amino acid to the chiral barrier of the macrocycle. Monoacid 36 binds well to amino acids, but the absence of the second carboxyl of the host allows the chiral center of the guest too much conformational flexibility for the diastereomeric complexes to differ much in stability. Complexes of diester 29 are less structured, since they lack two of the three binding features that characterize the complexes of 30. In models, the hole of 42 is too small for firm hydrogen bonding of the ammonium ion to the oxygens of the macrocycle, and little complexation was observed. Models of aminoacid complexes of 45 suggest that the three alternate oxygens remote from the chiral barrier most stably bind the ammonium ion. As a result, the two chiral elements are also remote.

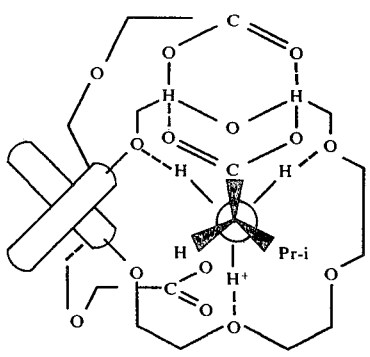

112

Favored diastereomeric complex between (S)-30 and (S)-valine

Run 8 determined the ability of optically pure (S)-30 to discriminate between (R)- and (S)-valine when complexation occurred only in the chloroform layer. A mixture of 400 mg. of (S)-30, 177 mg. (2.5 equivalents) of racemic valine, 1.0 ml. of $CD_3CO_2D$, 1.5 ml. of $CDCl_3$ and 0.5 ml. of $D_2O$ was shaken at 30° to produce two equilibrated layers. The chloroform layer (~ 2.3 ml.) contained >99% of the (−)-(S)-30 and ~ 40% (1.0 equivalent) of the valine fully complexed (pmr spectra, 100 MHz). The chloroform layer was evaporated, and the residue was shaken with 5 ml. of chloroform and 5 ml. of water. The water layer was washed with 5 ml. of chloroform, and evaporated to give 37 mg. of valine, $[\alpha]_{546}^{25}$ +4.0° (C 2.0, 5N HCl). Optically pure valine has $[\alpha]_{546}^{25}$ +32.2° (C 2, 5N HCl ["Chemistry of the Amino Acids", John Wiley and Sons, Inc., N.Y., 1961, p. 116], and the one plate experiment gave 12% optical purity. Thus (S)-30 preferentially complexed (S)-valine over (R)-valine in the chloroform layer by a factor of 1.3.

These one plate experiments established the feasibility of completely resolving by multiplate processes either racemic α-aminoacids by optically active cyclic ethers, or of racemic cyclic ethers by optically active α-aminoacids. An example of the resolution by (S)-valine of racemic 30 by liquid-liquid chromatography to give both enantiomers in an optically pure state is as follows.

A solution of 6 g. of (S)-valine [$[\alpha]_{546}^{25}$ +31.8°, C 2.00, 5N HCl) was dissolved in a mixture of 40 ml. of acetic acid-10 ml. of water-15 ml. of benzene. This homogeneous solution was shaken with 60 g. of Celite to give a uniformly coated powder, which was firmly packed into a chromatograph column to give a 3 by 100 cm. stationary liquid phase. An additional 5 g. of dry Celite was packed on the top of the column. Racemic diacid 30 (1.00 g.) dissolved in 5 ml. of the same acetic acid-water-benzene mixture used to coat the Celite was added at the top of the column. A moving phase of benzene-saturated with 80% acetic acid-20% water was added to the column, and 40 fractions of 40 ml. each were collected. The column required about 90 ml. to fill the free volume. Fractions 8–34 contained 30 and traces of valine. Diacid was isolated as in run 1 from each fraction to give 910 mg. total recovery. Combined fractions 12–16 (some approached optical purity) gave 336 mg. of fully dried (R)-30, $[\alpha]_{546}^{25}$ −69.2° (C 1.0, $CHCl_3$), 90% optically pure, which when rechromatographed on a similar column containing (R)-valine gave 220 mg. of optically pure (R)-30, $[\alpha]_{546}^{25}$ −76.5° (C 1.0, $CHCl_3$). The beginning fractions of this second column gave (R)-30 of lower optical purity. Combined fractions 21–34 of the first column (the last two fractions contained optically pure (S)-30 gave 363 mg. of (S)-30, $[\alpha]_{546}^{25}$ +70.0° (C 1.0, $CHCl_3$), which was 91% optically pure. This material was rechromatographed on a third column identical to the first with (S)-valine in the stationary phase. All but the first fractions gave optically pure (S)-30, $[\alpha]_{546}^{25}$ +76.5° (C 1.0, $CHCl_3$), wt of combined optically pure fractions, 271 mg.

EXAMPLE 12

Comparisons of the Abilities of Chiral Multiheteromacrocycles to Complex Selectively and Resolve by Liquid-Liquid Chromatography Enantiomers of Primary Amine Salts, and Amino Ester Salts These procedures are useful for the optical resolution of racemic guest molecules by optically active host molecules, or racemic host molecules by optically active guest molecules by countercurrent extraction involving two immiscible phases, P (polar) and N (non-polar phase). Several conditions must be met before the following treatment applied strictly. (1) The host molecule must be soluble essentially only in one of two phases. (2) The guest molecule in the absence of the host molecule must be soluble essentially only in the other phase. (3) The complex formed between host and guest must be soluble essentially only in one of the two phases. Provided the proper solubility relationships apply, optically active host molecule can be used to optically resolve racemic guest molecules, or optically active guest molecules to resolve racemic host molecules.

The Chiral Recognition Factor (CRF) was defined as the ratio of the concentrations of the predominant to the subordinate enantiomer observed at equilibrium in the phase containing the complex. This factor is not a constant, but varies with the relative amounts of host and guest used. A more satisfactory measure of chiral recognition is the ratio of the distribution constants, $K_A$ and $K_B$, of enantiomers A and B between the two phases. This ratio is termed the "Enantiomer Distribution Constant". Thus $EDC = K_A/K_B$, where $K_A$ is the distribution constant for A, the enantiomer that is the more complexed, and $K_B$ is the distribution constant of B, the less complexed enantiomer at equilibrium of host, guest and complex in the two phases. By definition, $K_A/K_B$ is always equal to unity (no chiral recognition) or greater than unity (chiral recognition).

Equations (1) and (2) indicate the relationships between CRF, EDC, $K_A$, $K_B$ and the concentrations at equilibrium of guest enantiomers, $[G_A]$ and $[G_B]$, in the case where the host is optically pure, the guest is racemic, complexation occurs in the non-polar phase, N, and noncomplexed guest is stored in the polar phase, P. Equation (2) indicates that as $[G_B]_P/[G_A]_P$ approaches unity, EDC approaches CRF.

$$K_A = \frac{[G_A]_N}{[G_A]_P} \quad K_B = \frac{[G_B]_N}{[G_B]_P} \quad CRF = \frac{[G_A]_N}{[G_B]_N} \quad (1)$$

$$EDC = \frac{K_A}{K_B} = \frac{[G_A]_N [G_B]_P}{[G_B]_N [G_A]_P} = CRF \cdot \frac{[G_B]_P}{[G_A]_P} \quad (2)$$

Equations (3) and (4) indicate the relationships between CRF, EDC, $K_A$, $K_B$, and the concentrations at equilibrium of host enantiomers, $[H_A]$ and $[H_B]$, in the case where the guest is optically pure, the host is racemic, complexation occurs in the polar phase, P, and non-complexed host is stored in the non-polar phase, N.

$$K_A = \frac{[H_A]_P}{[H_A]_N} \quad K_B = \frac{[H_B]_P}{[H_B]_N} \quad CRF = \frac{[H_A]_P}{[H_B]_P} \quad (3)$$

-continued $$EDC = \frac{K_A}{K_B} = \frac{[H_A]_P [H_B]_N}{[H_B]_P [H_A]_N} = CRF \cdot \frac{[H_B]_N}{[H_A]_N} \qquad (4)$$

The other two possible cases are: (1) the host is optically pure, the guest racemic, complexation occurs in the polar phase, P, and non-complexed guest is stored in the non-polar phase, N; (2) the guest is optically pure, the host is racemic, complexation occurs in the non-polar phase, N, and non-complexed host is stored in the polar phase, P. The equations describing these cases are analogous to (1) through (4).

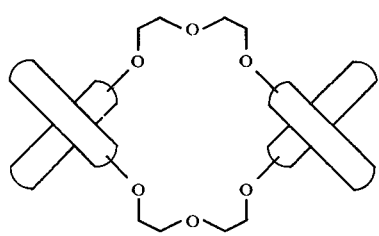

(RR)-8

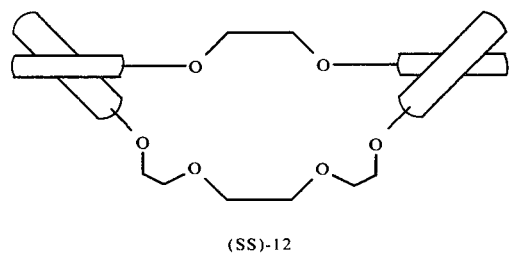

(SS)-12

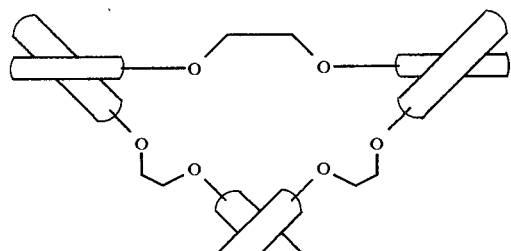

(SSR)-15

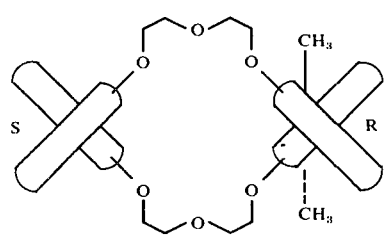

(SR)-48c'

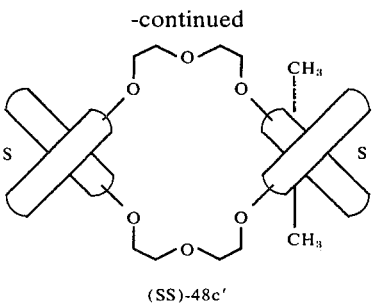

(SS)-48c'

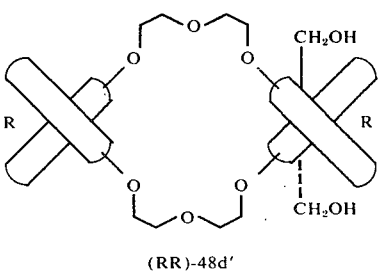

(RR)-48d'

Procedure 1

In Procedure 1, optically active host compounds were used to partially resolve racemic guest compounds by chiral recognition in complexation in the non-polar phase, and the non-complexed guest compounds were stored in the polar phase. The EDC values of (RR)-8, (SS)-12, (SSR)-15, (SR)-48c', (SS)-48c', and (RR)-48d' were measured with one or more of the hexafluorophosphate salts of the amines formulated as guests. The absolute configuration and maximum rotation of amine (+)-(R)-109 has been determined by others [*Chem. Ber.*, 87, 690 (1954); ibid,, 64, 2827 (1937)]. The absolute configurations and maximum rotations of amino ester salts of (−)-(R)-109a', (−)-(R)-109b', (+)-(S)-109c', and (+)-(S)-109d' have been established [*Ann.*, 523, 199 (1936); Tet., 23, 2031 (1967); "Chemistry of the Amino Acids", Wiley, New York, 1961 p. 931]. Optically pure salts were prepared, converted to their amines, and their rotations taken (c 2.0, CH$_2$Cl$_2$). The amines were then converted back to their salts, and their rotation shown not to have changed in the cycle. The maximum rotations and absolute configurations are recorded below the formulas.

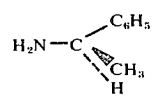

(+)-(R)-109

$[\alpha]_{546}^{25} = +10.8°$ (C 7.5, CHCl$_3$)

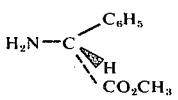

(−)-(R)-109a'

$[\alpha]_{546}^{25} = -185°$ (C 2.0, CH$_2$Cl$_2$)

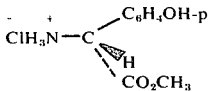

-continued (−)-(R)-109b'

$[\alpha]_{546}^{25} = -173°$ (C 1.0, CH$_3$OH)

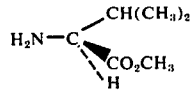

(+)-(S)-109c'

$[\alpha]_{546}^{25} = +50°$ (C 2.0, CH$_2$Cl$_2$)

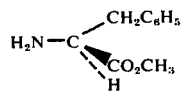

(+)-(S)-109d'

$[\alpha]_{546}^{25} = +20°$ (C 2.0, CH$_2$Cl$_2$)

The non-polar phase, CHCl$_3$ or CDCl$_3$, dissolved the host molecule, which selectively complexed the guest salt, and drew it into the chloroform layer. The polar phase was D$_2$O or H$_2$O in which was dissolved large amounts of LiPF$_6$ or NaPF$_6$. The amine was dissolved as its hydrochloride salt in the aqueous phase, which after equilibration served to store the non-complexed amine salt. The inorganic salts were present in the aqueous layer to "salt out" the complexed guest compound, to depress the melting point of water for extractions at temperatures below 0°, and to provide the PF$_6^-$ counterion for the amine salt extracted. Inorganic salts such as LiAsF$_6$, LiSbF$_6$, NaAsF$_6$ or NaSbF$_6$ gave similar results, but salts containing K$^+$, Cl$^-$, Br$^-$, I$^-$, SCN$^-$, CF$_3$CO$_2^-$, CCl$_3$CO$_2^-$, or ArCO$_2^-$ resulted in lowered chiral recognition. With alkylammonium ions of low acidity and host cycles of low basicity, Na$^+$, K$^+$ and H$_3$O$^+$ competitively complexed the host molecule, but Li$^+$ did not.

Two methods were used to measure the amounts of each enantiomeric guest compound in each phase. In method A, the two phases were separated, the guest compound in each phase was isolated and weighed, and their rotations were taken. From these values, the concentrations of each enantiomer in each phase were calculated. In method B, the two phases were separated. The concentrations of each enantiomer of the guest salt present in the CDCl$_3$ phase relative to the known concentrations of the host cycle were determined from their pmr integrals. Since the enantiomeric guest molecules present in the organic phase were complexed with optically active host molecules, the complexes were diastereomeric, and therefore had different pmr spectra. The assignments of signals to diastereomeric complexes of appropriate configurations were based on the pmr spectra of pure diastereomeric complexes of known configuration, which were prepared, and their pmr spectra taken. The relative concentrations of guest to host, [G]/[H], in the chloroform layer were determined from pmr integrals. The concentrations of the enantiomeric guest compounds remaining in the water layer were calculated by difference from the known original concentrations, and the concentrations of each enantiomer in the chloroform layer.

Table V records the results of runs 1–39, the conditions, materials and methods used, the concentrations, the value of [G]/[H], of EDC, and the direction of chiral recognition.

TABLE V

Enantiomer Distribution Constants (EDC) For Host Cycles (H) and Guest Molecules (G)

| Run No. | T C° | Host Cycle Comp. No. | Concn. (M) | R | RR'CHNH$_3^+$PF$_6^-$ Structure R' | Concn. (M) | Initial equivalents H/G |
|---|---|---|---|---|---|---|---|
| 1 | +25 | (SS)-8 | 0.18 | C$_6$H$_5$ | CH$_3$ | 0.94 | 1.7 |
| 2 | 0 | (SS)-8 | 0.18 | C$_6$H$_5$ | CH$_3$ | 0.94 | 1.7 |
| 3 | +26 | (RR)-8 | 0.18 | C$_6$H$_5$ | CO$_2$CH$_3$ | 0.95 | 6 |
| 4 | −1 | (RR)-8 | 0.18 | C$_6$H$_5$ | CO$_2$CH$_3$ | 0.94 | 6 |
| 5 | −5 | (RR)-8 | 0.17 | C$_6$H$_5$ | CO$_2$CH$_3$ | 1.22 | 6 |
| 6 | −15 | (RR)-8 | 0.17 | C$_6$H$_5$ | CO$_2$CH$_3$ | 0.87 | 3 |
| 7 | −15 | (RR)-8 | 0.18 | C$_6$H$_5$ | CO$_2$CH$_3$ | 0.87 | 3 |
| 8 | +26 | (RR)-8 | 0.20 | C$_6$H$_5$ | CO$_2$CH$_3$ | 1.20 | 3 |
| 9 | +15 | (RR)-8 | 0.20 | C$_6$H$_5$ | CO$_2$CH$_3$ | 1.20 | 3 |
| 10 | +2 | (RR)-8 | 0.20 | C$_6$H$_5$ | CO$_2$CH$_3$ | 1.20 | 3 |
| 11 | −5 | (RR)-8 | 0.20 | C$_6$H$_5$ | CO$_2$CH$_3$ | 1.20 | 3 |
| 12 | −10 | (RR)-8 | 0.20 | C$_6$H$_5$ | CO$_2$CH$_3$ | 1.20 | 3 |
| 13 | −14 | (RR)-8 | 0.20 | C$_6$H$_5$ | CO$_2$CH$_3$ | 1.20 | 3 |
| 14 | −18 | (RR)-8 | 0.20 | C$_6$H$_5$ | CO$_2$CH$_3$ | 1.20 | 3 |
| 15 | −5 | (RR)-8 | 0.16 | p-HOC$_6$H$_4$ | CO$_2$CH$_3$ | 1.9 | 6 |
| 16 | −6 | (RR)-8 | 0.30 | p-HOC$_6$H$_4$ | CO$_2$CH$_3$ | 1.6 | 3 |
| 17 | −15 | (RR)-8 | 0.30 | p-HOC$_6$H$_4$ | CO$_2$CH$_3$ | 1.6 | 3 |
| 18 | −15 | (RR)-8 | 0.30 | p-HOC$_6$H$_4$ | CO$_2$CH$_3$ | 1.3 | 3 |
| 19 | −23 | (RR)-8 | 0.30 | p-HOC$_6$H$_4$ | CO$_2$CH$_3$ | 1.6 | 3 |
| 20 | −1 | (RR)-8 | 0.18 | (CH$_3$)$_2$CH | CO$_2$CH$_3$ | 0.95 | 6 |
| 21 | +26 | (RR)-8 | 0.20 | (CH$_3$)$_2$CH | CO$_2$CH$_3$ | 1.2 | 3 |
| 22 | +1 | (RR)-8 | 0.20 | (CH$_3$)$_2$CH | CO$_2$CH$_3$ | 1.2 | 3 |
| 23 | +1 | (RR)-8 | 0.20 | (CH$_3$)$_2$CH | CO$_2$CH$_3$ | 2.5 | 3 |
| 24 | −10 | (RR)-8 | 0.20 | (CH$_3$)$_2$CH | CO$_2$CH$_3$ | 2.5 | 3 |
| 25 | −10 | (RR)-8 | 0.20 | (CH$_3$)$_2$CH | CO$_2$CH$_3$ | 1.2 | 3 |
| 26 | −10 | (RR)-8 | 0.20 | (CH$_3$)$_2$CH | CO$_2$CH$_3$ | 2.5 | 3 |
| 27 | −12 | (RR)-8 | 0.17 | (CH$_3$)$_2$CH | CO$_2$CH$_3$ | 0.92 | 3 |
| 28 | −16 | (RR)-8 | 0.20 | (CH$_3$)$_2$CH | CO$_2$CH$_3$ | 1.2 | 3 |
| 29 | −1 | (RR)-8 | 0.18 | C$_6$H$_5$CH$_2$ | CO$_2$CH$_3$ | 0.94 | 6 |
| 30 | −1 | (RR)-8 | 0.18 | CH$_3$ | CO$_2$CH$_3$ | 0.94 | 6 |
| 31 | 0 | (SS)-12 | 0.16 | C$_6$H$_5$ | CH$_3$ | 0.93 | 6 |
| 32 | 0 | (SS)-12 | 0.17 | C$_6$H$_5$ | CH$_3$ | 0.92 | 6 |
| 33 | −10 | (SS)-12 | 0.20 | C$_6$H$_5$ | CO$_2$CH$_3$ | 1.2 | 3 |
| 34 | −17 | (SS)-12 | 0.20 | C$_6$H$_5$ | CO$_2$CH$_3$ | 1.2 | 3 |
| 35 | −10 | (SSR)-15 | 0.06 | C$_6$H$_5$ | CO$_2$CH$_3$ | 2.70 | 45 |
| 36 | 0 | (SR)-48c' | 0.83 | C$_6$H$_5$ | CO$_2$CH$_3$ | 0.50 | 3 |
| 37 | +25 | (SS)-48c' | 0.20 | C$_6$H$_5$ | CO$_2$CH$_3$ | 1.20 | 3 |

TABLE V-continued

| | | | | | | | | |
|---|---|---|---|---|---|---|---|---|
| 38 | −17 | (SS)-48c' | 0.20 | $C_6H_5$ | | $CO_2CH_3$ | 1.20 | 3 |
| 39 | +26 | (RR)-48d' | 0.23 | $C_6H_5$ | | $CO_2CH_3$ | 1.20 | 3 |

| Run No. | T C° | Salt Type | Inorganic Salt Concn. (M) | pH | Method of anal. | (G)(H) | Complex Dominant config. | EDC ($K_A/K_B$) | Applicable model |
|---|---|---|---|---|---|---|---|---|---|
| 1 | +25 | $NaPF_6$ | 0.94 | — | A | 0.7 | (SS)-(R) | 1.5 | Steric |
| 2 | 0 | $NaPF_6$ | 0.94 | — | A | 0.9 | (SS)-(R) | 1.8 | Steric |
| 3 | +26 | $NaPF_6$ | 0.95 | — | A | 0.3 | (RR)-(R) | 2.0 | Steric |
| 4 | −1 | $NaPF_6$ | 0.94 | — | A | 0.9 | (RR)-(R) | 2.9 | Steric |
| 5 | −5 | $NaPF_6$ | 1.22 | — | A | 0.9 | (RR)-(R) | 3.0 | Steric |
| 6 | −15 | $NaPF_6$ | 2.13 | — | A | 0.9 | (RR)-(R) | 3.2 | Steric |
| 7 | −15 | $LiPF_6$ | 2.13 | <4 | A | 0.9 | (RR)-(R) | 3.2 | Steric |
| 8 | +26 | $LiPF_6$ | 4.0 | 4 | A | 0.8 | (RR)-(R) | 2.5 | Steric |
| 9 | +15 | $LiPF_6$ | 4.0 | 4 | A | 0.9 | (RR)-(R) | 2.5 | Steric |
| 10 | +2 | $LiPF_6$ | 4.0 | 4 | A | 0.9 | (RR)-(R) | 2.8 | Steric |
| 11 | −5 | $LiPF_6$ | 4.0 | 4 | A | 0.8 | (RR)-(R) | 3.0 | Steric |
| 12 | −10 | $LiPF_6$ | 4.0 | 4 | A | 0.9 | (RR)-(R) | 2.8 | Steric |
| 13 | −14 | $LiPF_6$ | 4.0 | 4 | A | 0.9 | (RR)-(R) | 3.1 | Steric |
| 14 | −18 | $LiPF_6$ | 4.0 | 4 | A | 1.0 | (RR)-(R) | 3.1 | Steric |
| 15 | −5 | $NaPF_6$ | 1.9 | — | B | 0.0 | — | — | — |
| 16 | −6 | $LiPF_6$ | 3.7 | <4 | B | 0.5 | (RR)-(R) | 3.4 | Steric |
| 17 | −15 | $LiPF_6$ | 5 | <4 | B | 1.0 | (RR)-(R) | 4.2 | Steric |
| 18 | −15 | $LiPF_6$ | 5 | 6 | B | 1.0 | (RR)-(R) | 6 | Steric |
| 19 | −23 | $LiPF_6$ | 5 | <4 | B· | 1.0 | (RR)-(R) | 4.2 | Steric |
| 20 | −1 | $NaPF_6$ | 0.95 | — | B | 0.0 | — | — | — |
| 21 | −26 | $LiPF_6$ | 4.0 | 4 | B | 0.0 | — | — | — |
| 22 | +1 | $LiPF_6$ | 4.0 | 4 | B | 0.55 | — | — | — |
| 23 | +1 | $LiPF_6$ | 4.0 | 4 | B | 0.63 | — | — | — |
| 24 | −10 | $LiPF_6$ | 4.0 | 4 | A | 0.68 | (RR)-(S) | 1.35 | Polar |
| 25 | −10 | $LiPF_6$ | 4.0 | 4 | A | 0.58 | (RR)-(S) | 1.49 | Polar |
| 26 | −10 | $LiPF_6$ | 4.0 | <4 | A | 0.66 | (RR)-(S) | 1.45 | Polar |
| 27 | −12 | $LiPF_6$ | 4.0 | <4 | A | 0.38 | (RR)-(S) | 1.34 | Polar |
| 28 | −16 | $LiPF_6$ | 4.0 | 4 | A | 0.87 | (RR)-(S) | 1.16 | Polar |
| 29 | −1 | $NaPF_6$ | 0.94 | — | A | 0.7 | (RR)-(S) | 1.8 | Polar |
| 30 | −1 | $NaPF_6$ | 0.94 | — | A | 0.0 | — | — | — |
| 31 | 0 | $NaPF_6$ | 0.93 | — | A | 1.0 | — | 1.0 | — |
| 32 | 0 | $KPF_6$ | 1.0 | — | A | 0.6 | — | 1.0 | — |
| 33 | −10 | $LiPF_6$ | 4.0 | 4 | A | 0.9 | (SS)-(R) | 2.2 | Steric |
| 34 | −17 | $LiPF_6$ | 4.0 | 4 | A | 0.9 | (SS)-(R) | 2.2 | Steric |
| 35 | −10 | $LiPF_6$ | 2.4 | <4 | B | 0.0 | — | — | — |
| 36 | 0 | $LiPF_6$ | 1.3 | 4 | A | 1.0 | (SR)-(R) | 1.2 | Steric |
| 37 | +25 | $LiPF_6$ | 4.0 | 4 | A | 1.0 | (SS)-(S) | 5.2 | Steric |
| 38 | −17 | $LiPF_6$ | 4.0 | 4 | A | 1.0 | (SS)-(S) | 10 | Steric |
| 39 | +26 | $LiPF_6$ | 4.0 | 4 | A | 1.0 | (RR)-(R) | 1.6 | Steric |

Method A is illustrated as applied to (RR(-8 and (R)(S)-phenyglycine methyl ester hydrochloride salt in run 13. A solution (0.20 M) of 3.1 g. of (RR)-1 (4,35 mmole) in 22 ml. of $CDCl_3$ was used to extract 2.62 g. (13 mmoles or 3 equivalents) of (R)(S)-phenylglycine methyl ester hydrochloride salt dissolved in 10.8 ml. of $D_2O$ (1.2 M in ester) containing 6.5 g. (42.8 mmole) of $LiPF_6$ (4.0 M solution) which had been brought to pH = 4.0 with 5 M LiOD in $D_2O$. The two solutions were shaken vigorously five times for 1 minute per time spread over 1 hour in a separatory funnel held at −14° by immersion in a constant temperature bath. The distribution equilibrium was reached instantaneously, but temperature equilibration took longer. The organic layer was drained rapidly into 40 ml. of dichloromethane, and the resulting solution was extracted with three successive 30 ml. portions of water. The combined water extracts were mixed with 100 ml. of dichloromethane, and enough concentrated ammonium hydroxide was added to give the aqueous layer a pH of 10. The layers were shaken, the organic layer was dried with magnesium sulfate, and evaporated at room temperature under vacuum to give the amino ester, weight, 0.65 g. (30%), $[\alpha]_{546}^{25}$ −68° (c 2.0, $CH_2Cl_2$). Thus (RR)-8-preferentially extracted (R)-ester, to give 37% optically pure material. From the original chloroform layer, (RR)-8 of unchanged optical rotation was isolated (98%).

The aqueous layer from the initial partitioning was diluted with 40 ml. of water, and extracted with three successive 30 ml. portions of dichloromethane. The aqueous layer was made basic with concentrated ammonium hydroxide. The amino ester was extracted with dichloromethane and isolated as before, wt 1.35 g. (63%), $[\alpha]_{546}^{25}$ +33° (c 2.0, $CH_2Cl_2$). Thus the material stored in the aqueous phase was 18% optically pure (S)-ester-salt. Thus the two phases gave 93% total recovery of amine. The EDC was calculated to be 3.1.

Comparable amounts were isolated in runs 3–14, 33 and 34. In runs 1, 2, 31 and 32, 60–75% of the amine salt used was isolated as amine. In runs 20–29, the amounts of ester isolated ranged from 74 to 87. In runs 33–36, the amounts ranged from 54 to 88%. In general, the larger the scale of the run made, and the less volatile the amine, the higher the recovery.

Method B is illustrated as applied in run 18 to (RR)-8 and (S)(R)-p-hydroxyphenylglycine methyl ester hydrochloride. The solutions was prepared as in Method A and equilibrated at −15°. A portion of the organic phase was pipetted out, and the pmr spectrum (100 MHz) was determined at 25°. The diastereomeric complexes differed as follows.

| | δ (ppm) and multiplicity (in parenthesis) of diastereomers | |
|---|---|---|
| | (RR)-(R)-Complex (major) | (RR)-(S)-Complex (minor) |
| $CO_2CH_3$ | 3.50 (s) | 3.48 (s) |
| N<br>\|<br>$ArCHCO_2$ | 4.39 (s) | 4.84 (s) |

-continued

| | δ (ppm) and multiplicity (in parenthesis) of diastereomers | |
|---|---|---|
| | (RR)-(R)-Complex (major) | (RR)-(S)-Complex (minor) |
| H H<br>O—⟨○⟩—C<br>H H | 6.40 (ABq) | 6.80 (ABq) |

Three integrations of the 4.39 and 4.84 singlet signals gave ratios of 16/3, 17/3 and 16/4, or an average of ](RR)—(R)]/[(RR)—(S)] = 5. Integration of all the signals of the aromatic protons vs. the guest's methine proton vs. all the aliphatic protons indicated roughly that the complex was 1:1.

| | Integrations of proton's signals | | |
|---|---|---|---|
| | All ArH | ArCHCO$_2$ | All aliphatic H's |
| Calcd for 1:1 complex | 228 | 8.15 | 155 |
| Observed | 228 | 7 | 155 |

From these values, the concentrations of the (S)- and (R)-ester salts in the chloroform and water layers (by difference) at equilibrium at −15° were calculated, and from these concentrations, the enantiomer distribution constant was calculated (EDC = 6).

Methods A and B are illustrated further in run 38 as applied to (SS)-48c' as host, and (S)(R)-phenylglycine methyl ester hydrochloride as guest compound. The solutions were prepared from 165 mg. of (SS)-48c' in 1.1 ml. of CDCl$_3$ (0.20 M), and 135 mg. of ester salt in 0.53 ml. of D$_2$O (1.25 M) that was 4 M in LiPF$_6$ at pH = 4.0. The equilibration and separation of layers was carried out at −17°. The pmr spectrum of the CDCl$_3$ layer at 25° showed widely different signals for the two diastereomers as follows.

| | δ (ppm) and multiplicity (in parenthesis) of diastereomers | |
|---|---|---|
| | (SS)-(S)-Complex (major) | (SS)-(R)-Complex (minor) |
| CO$_2$CH$_3$ | 3.68 (s) | 3.58 (s) |
| N<br>\|<br>ArCHCO$_2$ | 4.38 (s) | 4.92 (s) |
| H<br>⟨○⟩—C<br>H | 6.15 (d) | further downfield than 6.8, mixed with other ArH's |

Integrations of the 4.38 and 4.92 singlets gave [(SS)—(S)]/[(SS)]—(R)] = 6.0. Integration of the signals of all the aromatic protons vs. those of the cycle's ArCH$_3$ groups vs. those of all the aliphatic protons minus those of the ArCH$_3$ groups indicated that [G]/[H] = 1.0. From these values by difference, [G]$_R$/[G]$_S$ in the water phase was calculated to be 2.1. These values provide EDC = 12.6 which was based only on initial concentrations, and pmr measurements.

The organic layer of the original equilibrium mixture was diluted with 5 ml. of dichloromethane and extracted with three successive 5 ml. portions of H$_2$O. The combined water extracts were combined with 20 ml. of dichloromethane, brought to pH = 10 with concentrated ammonium hydroxide while being shaken. The layers were separated, the organic layer was dried with magnesium sulfate, evaporated and dried under vacuum at 25° to give 17.2 mg. of amino-ester, $[\alpha]_{546}^{25}$ +130° (c 1.7, CH$_2$Cl$_2$). This material was 70% optically pure (S)-enantiomer, as shown by its rotation.

The original aqueous phase was diluted with 5 ml. of H$_2$O, extracted with three successive 5 ml. portions of dichloromethane, and made basic with concentrated ammonium hydroxide. The amino ester was isolated by extraction with dichloromethane (see above) to give 55 mg. of material, $[\alpha]_{546}^{25}$ −51°, (c 2.7, CH$_2$Cl$_2$), which was 27% optically pure in the (R)-enantiomer.

The value of the enantiomer distribution constants obtained from the pmr data was EDC = 12.6, and from the product isolation date was EDC = 10.

The results of applications of these methods to various cycles and amine salts are found in Table V. The same results were obtained within experimental error when deuterated solvents were used as when protonated solvents were employed.

The pmr spectra of the diastereomeric complexes prepared from optically pure host and guest compounds provided direct experimental evidence for the structures of the complexes in some cases. Particularly informative were those prepared from (R)-phenylglycine methyl ester hexafluorophosphate, (R)-109a', and (RR)-8 to give complex (RR)-(R)-113, and from (R)-109a' and (SS)-8 to give (SS)-(R)-113. Both were prepared by extraction at −3° of a 1.25 M ester hydrochloride salt (6 equivalents) solution in D$_2$O, 1.25 M in NaPF$_6$ with an 0.16 M solution of cycle in CDCl$_3$. A control experiment showed the ester hydrochloride salt to be non-extractable into the chloroform solution. The CDCl$_3$ solution of each diastereomer gave [G]/[H] = 0.8. A pmr spectrum of (RR)-8 alone in CDCl$_3$ was also taken. The interesting chemical shifts (δ) in ppm downfield from TMS are recorded.

| | Chemical shifts of complexes (δ) | | |
|---|---|---|---|
| | (RR)-8 | (RR)-(R)-113 | (SS)-(R)-113 |
| —CO$_2$CH$_3$ | — | 3.60 | 3.52 |
| —N—<br>\|<br>Ar—CH—CO$_2$— | — | 4.59 | 4.97 |
| H<br>⟨○⟩—C—<br>\|<br>H | — | 6.56 | 6.9–7.4 |
| ArOCH$_2$CH$_2$O | 3.09 | ~2.9(broad) | 3.22 |
| ArOCH$_2$ | 3.74 | 3.98; 3.50 | 3.98; 3.54 |

Chemical shifts of complexes (δ)

| (RR)-8 | (RR)-(R)-113 | (SS)-(R)-113 |
|---|---|---|

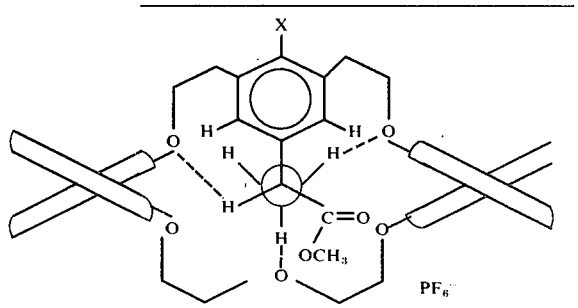

(RR)-(R)-113, X = H
(RR)-(R)-114, X = OH

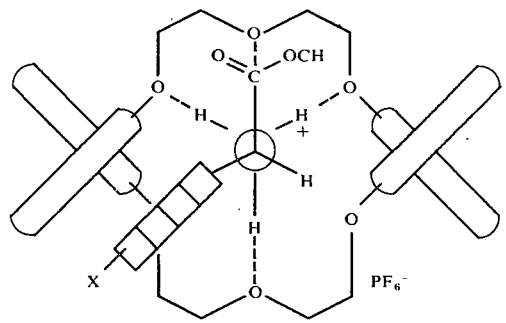

(SS)-(R)-113, X = H
(SS)-(R)-114, X = OH

---

The steric requirements of molecular models (CPK) of the two complexes and the pmr spectra combine to support the two structures formulated for the diastereomeric complexes. (1) The carbomethoxy groups can occupy similar environments in the models of the two complexes, but the models suggest the methyl in (SS)-(R)-113 is closer to an ether oxygen than in (RR)-(R)-113, and therefore shielded and move upfield, as is observed. (2) The methine proton in molecular models of (RR)-(R)-113 is predicted [J. Chem. Phys., 29, 1012 (1958)] by its distance (X = 2.16A, Y = 2.496A) from the center of the naphthalene ring current to be shielded and moved upfield by about 0.2 ppm relative to the methine proton in structure (SS)-(R)-113. The observed upfield shift is 0.38 ppm. (3) The ortho-phenyl protons in structure (RR)-(R)-113 should be shielded according to models, and moved upfield by the naphthalene ring current, but not in (RR)-(S)-113, as is observed. (4) The ArOCH$_2$C$\underline{\text{H}}_2$O protons of the host should be deshielded and moved downfield due to loss of electron density to hydrogen bonding in either complex. Those of (SS)-(R)-113 should be additionally deshielded by the oxygen-carbonyl interaction, which molecular models indicate is geometrically excellent. However, the ArOCH$_2$C$\underline{\text{H}}_2$O protons in models lie directly under the shielding ring current of the phenyl group in (RR)-(R)-113, which should move these protons upfield relative to the diastereomeric complex. In compatibility with these predictions based on models, the signals of (RR)-(R)-113 are upfield of those of (RR)-8, which are upfield of those of (SS)-(R)-113. (5) Molecular models of (RR)-8 suggest the two ArOC$\underline{\text{H}}_2$ protons are equilibrating between structures in which H$_a$ is shielded by the naphthalene ring current and H$_b$ deshielded in one, and the opposite is true in the other. In uncomplexed (RR)-8, the two protons should be averaged. However in the two complexes,

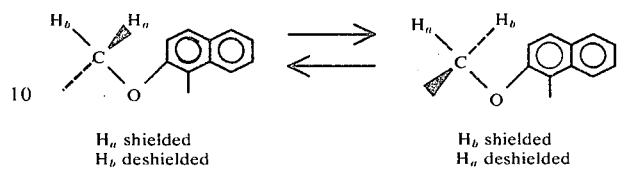

H$_a$ shielded  H$_b$ shielded
H$_b$ deshielded  H$_a$ deshielded models indicate the two protons are held rigidly in place, and the signal due to one should be moved upfield by an amount equal to that by which the other should be moved downfield relative to the averaged signal of (RR)-8. Such splitting is exactly what is observed.

A similar analysis of the pmr spectrum of the complex between (RR)-8 and (S)-α-phenylethylammonium hexaflorophosphate provided similar evidence for a structure resembling (RR)-(R)-113. The pmr spectrum of the complex between (RR)-8 and (R)-α-phenylethylammonium hexafluorophosphate was too complicated to interpret.

Detailed correlation between spectra and structural expectation based on molecular models indicates that two general structures between ester-ammonium salts and dilocular systems are possible. The first is based on the binding of the three hydrogen bonds (three point binding), and the best steric accommodation possible between host and quest. This is the steric model. The second is based on the binding of the three hydrogen bonds and that of carbonyl carbon to ether oxygen, and the best steric accommodation. This four-point binding model is the polar model. Since each model predicts the opposite stability order for the diastereomeric complexes, the observed result can be interpreted in terms of either model (Table V).

In cases where esters are involved, the two models compete, and the outcome is impossible to predict without further calibration. However, trends are visible in Table V. With α-phenylethylammonium salt (no ester group), phenylglycine ester-salt, p-hydroxyphenylglycine ester salt and 8, the steric model predicts the correct diastereomeric stability order. With valine ester salt and phenylalanine ester salt, the polar model dominates. When the steric model dominates, the effective size of the largest group attached to the asymmetric center of the host is larger than when the polar model dominates. Both molecular models and A values ["Topics in Stereochemistry", Interscience Publishers, New York, 1967, Vol. 1, p. 199] indicate the following order of increasing effective size of groups in the vicinity of their point of attachment: H (1.00) < CO$_2$CH$_3$ (1.27) < CH$_3$ (1.70) < CH$_2$C$_6$H$_5$ (2.0) < CH(CH$_3$)$_2$ (2.15) < C$_6$H$_5$ (3). In the less crowded complexes, the polar model dominates. In the more crowded complexes, the steric model dominates.

A striking example of the quantitative aspect of the above generalization involves runs 14 and 38 of Table V. These runs were made under comparable conditions, and both involved phenylglycine ester salt. In run 14, the host was the relatively unhindered (RR)-8, and the steric model dominated to give EDC = 3.1. In run 38, the host was (SS)-48c', which contains two extra methyl groups that extend the chiral barrier, and reduce the size of one of the cavities on each face of the host. In the derived complexes, the steric model dominated to give EDC = 10.

Runs 13 and 18 were made under roughly comparable conditions with (RR)-8 as host. Run 13 involved phenylglycine ester salt, and gave EDC = 3.1. Run 18 involved p-hydroxyphenylglycine ester salt, and gave EDC = 6. Both esters must have the same steric requirements for complexation. Thus steric-model complexes (RR)-(R)-113 and (RR)-(R)-114 are probably of comparable stability. Polar complex (RR)-(S)-113 (enantiomeric to (SS)-(R)-113 which is formulated) must be relatively more stable than polar complex (RR)-(S)-114(enantiomeric to (SS)-(R)-114 which is formulated). In molecular models of these polar complexes, one naphthalene of the host lies against the phenyl of the guest, and in a plane parallel to the plane of the phenyl of the guest. The alkoxynaphthalene is a pi-base. Introduction of the hydroxyl group into the phenyl of the guest increases its pi-basicity. The pi-pi repulsion between the alkoxynaphthalene and the p-hydroxyphenyl group should be greater than that between the alkoxynaphthalene and phenyl. Thus EDC for the p-hydroxyphenylglycine ester salt should be greater than EDC for phenylglycine ester salt, as is observed.

The acidity of the guest and basicity of the host must be high enough to induce complexation, since the main binding forces involve hydrogen bonding ["The Hydrogen Bond", W. H. Freedman, San Francisco, Calif., 1960]. The pKa's of the ammonium groups of the esters of the amino acids are about 2 pKa units lower than those of the amino acids [Aust. J. Chem., 19, 1197 (1966)]. The ammonium group's pKa of the amino acids are: phenylglycine, 8.91; phenylalanine, 9.13; valine, 9.62; alanine, 9.69. Runs 4, 29, 20 and 30 differ only in which ester-salts were used. The ester-salt of phenylglycine gave [G]/[H] = 0.9, that of phenylalanine gave [G]/[H] = 0.7, while those of the valine and alanine gave no detectable complexation. Thus the more acidic the guest, the more complex is formed.

The more basic the oxygens of the host compound, the more complex formed. The inductive effect of the methyl groups attached to the 3-naphthyl positions of (SS)-48c' should make the aryl oxygens of that cycle more basic than that of parent cycle (RR)-8. However, the methyl groups should sterically inhibit complexation somewhat. Runs 14 and 38 were carried out under the same conditions with phenylglycine ester salt as guest. For the more basic but hindered cycle, [G]/[H] = 1.0 (run 38) and for the less basic, [G]/[H] = 1.0 (run 14). Apparently the steric and electronic effects of the methyls of (SS)-48c' cancel one another. Cycle (SSR)-15 contains only the less basic aryl oxygens, and could not be induced to complex detectably with the most acidic guest under the most forcing of conditions (run 35).

Lower temperatures favored higher complexation, and higher chiral recognition, but only when the steric model applied. Runs 21, 22, 25 and 28 involved the ester-salt of valine and (RR)-8, and identical conditions except for temperature. As the temperature decreased in the order, +26°, +1°, −10° and −16°, [G]/[H] followed the order, 0, 0.55, 0.58 and 0.87 and EDC values the order -, -, 1.49 and 1.16 (polar model). Runs 8–14 involved the ester-salt of phenylglycine and (RR)-8, and identical conditions except for temperature. As the temperature decreased in the order +26°, +15°, +2°, −5°, −10°, −14°, −18°, the EDC values followed the order 2.5, 2.5, 2.8, 3.0, 2.8, 3.1, 3.1 (steric model).

Although as acidic as the ester salt of phenylglycine, p-hydroxyphenylglycine ester salt contains the very hydrophilic phenolic hydroxyl, which makes it harder for the chloroform solution of (RR)-8 to extract and complex the compound. Runs 15 and 16 involved the latter salt, and differed most importantly in that NaPF$_6$ was used in run 15, and [G]/[H] = 0, whereas when LiPF$_6$ was used in run 16, [G]/[H] = 0.5. Apparently Na$^+$ competes with the ammonium ion for complexation of (RR)-8 but Li$^+$ does not. The same effect is visible in runs 20 and 22 involving (RR)-8 and valine ester-salt. When NaPF$_6$ was used, [G]/[H] = 0, whereas LiPF$_6$ gave [G]/[H] = 0.55. Run 30 involved the relatively unacidic alanine ester salt and NaPF$_6$, and [G]/[H] = 0. Runs 31 and 32 that involved (SS)-12 and α-phenylethylammonium salt employed NaPF$_6$ ([G]/[H] = 1.0) and KPF$_6$ ([G]/[H] = 0.6). These and other results indicate that when the salts were distributed between water and chloroform, these dilocular systems complexed K$^+$ > Na$^+$ > Li$^+$. The pmr spectra of the (RR)-8 in the chloroform solutions obtained from those runs involving NaPF$_6$ (in which no ammonium salt was extracted) indicate some complexation, undoubtedly by the Na$^+$ ion.

Runs 31–34 involved the less symmetrical dilocular system, (SS)-12, as host molecule. In runs 31 and 32, α-phenylethylammonium salt was employed. Although complexation occurred, EDC = 1. In runs 33 and 34, phenylglycine ester salt was used, and EDC = 2.2.

This result correlates with the steric model, (SS)-(R)-115. The lack of chiral recognition when α-phenylethylammonium salt was employed suggests that due to the distribution of the two more basic oxygens on one side of the host, a less structured complex bound at only two points was formed with this less acidic ammonium salt. With the more acidic phenylglycine ester salt, the more structured steric model with three-point binding was formed with chiral recognition.

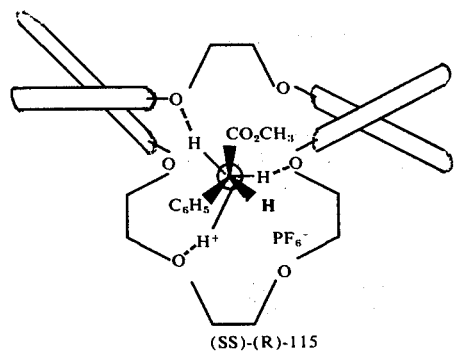

(SS)-(R)-115

Run 36 involved the unusual compound, (SR)-48c', as host, phenylglycine ester salt as guest, and gave EDC = 1.2. Compound (SR)-48c' would have a plane of symmetry but for the presence of the methyl groups. Structure (SR)-(R)-116 provides a steric model to explain the direction of chiral recognition.

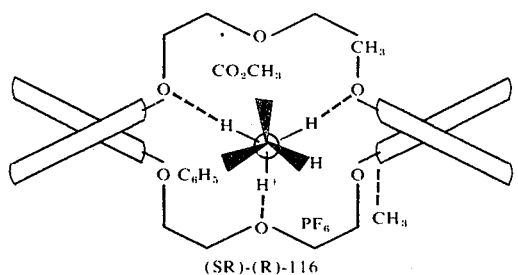

(SR)-(R)-116

Run 39 employed the dihydroxy compound (RR)-48d' as host, and phenylglycine ester salt as guest to give [G]/[H] = 1.0 and EDC = 1.6. Although a steric model explains this result, the chiral recognition is less than that observed for the dimethyl analogue, (SS)-48c', which gave EDC = 10. Although the hydroxymethylene groups undoubtedly extend the steric barrier (as do the methyl groups), their oxygen atoms offer hydrogen bonding opportunities possibly competitive with the ether oxygens of the macrocycle. A series of complexes are probably formed, with chiral recognition operating in opposite directions. The net observed value for EDC is therefore low.

These results make clear that properly designed chiral host multiheteromacrocycles can provide high chiral recognition in complexation of appropriate guest molecules.

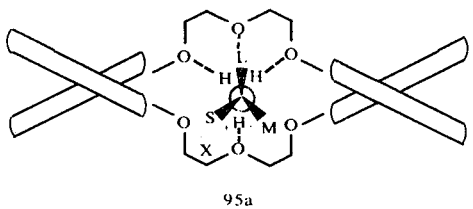

95a

Steric model of favored diastereomeric complex between (RR)-8 and generalized chiral alkylammonium salt of configuration

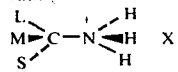

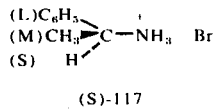

(S)-117

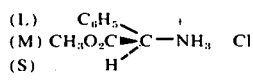

(R)-118

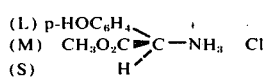

(R)-109b'

Procedure 2

One-plate partial separations of enantiomers by chiral recognition in liquid-liquid partitioning experiments were described in Procedure 1. Procedure 2 describes total separations of enantiomers by multiplate liquid-liquid countercurrent extraction. Liquid-liquid chromatography was used with water-NaPF$_6$ or water-LiPF$_6$ solutions supported on celite or silica as the stationary phase, and chloroform as the mobile phase. The mobile phase contained the optically pure host compound, and the enantiomers of racemic, primary amine hexafluorophosphate salts were continuously distributed between the phases. The enantiomer that complexed and was preferentially lipophilized by the host molecule was eluted first, followed by the other enantiomer. For convenience, the racemic amine hydrochloride or hydrobromide was put on the top of the column. By ion exchange at the top of the column with the large excess of hexafluorophosphate ion present in the water phase, the alkylammonium halide became the alkylammonium hexafluorophosphate salt, which appeared in complex form in the column eluate. The appearance of this complexed salt in the column eluate was monitored by conductivity of the chloroform solution. The concentrations of salt in the eluate were shown to be proportional to the relative conductivity of the eluate. Plots of the relative conductivity of the eluate vs. the ml. of eluate characterized the success of the separation. The complexed salt in the eluate was washed into water, isolated and characterized in representative cases. Various solid supports for the aqueous phase, and column conditions were characterized.

The procedure is illustrated with (RR)-8 as host, and 117, 118 and 109b' as amine salts introduced at the top of the column. The sign of rotation of the enantiomer first washed from the column indicated its configuration. For the three amine salts, the configuration of the faster moving enantiomer is indicated by the steric model for the complex 95a.

The proportional relationship between relative conductivity in micro-mho ($\mu$mho) and relative concentration in molarity (M) of complexed $\alpha$-phenylethylammonium hexafluorophosphate is shown in FIG. 1. An 8.25 × 10$^{-3}$ M solution of this salt in a 0.0375 M solution of (RR)-8 in chloroform (fraction 10 of column 1) was diluted with a chloroform solution of (RR)-8 (0.0375 M). The amine salt concentration varied from 8.25 × 10$^{-3}$ to 7.72 × 10$^{-4}$ M.

These columns had the characteristics of liquid-liquid chromatograph columns, whose behavior is governed by equations (5)–(11) [B. L. Karger in "Modern Practice of Liquid Chromatography", J. J. Kirkland, ed., Wiley, New York, 1971, pp. 8–14]. The terms in these equations are defined as follows: $V_M$ is the total volume of the mobile phase on the column; $V_S$ is the volume of the stationary liquid phase, in these columns the volume of the water, not that of the salt plus water; $V_{RA}$ is the retention volume of the better complexed and faster moving component A, measured from the top of the column to the conductance maximum of component A; $V_{RB}$ is the retention volume of the slower moving component B, measured from the top of the column to the conductance maximum of component B; $K_A = [G_A]_N/[G_A]_p$, or the ratio at equilibrium of the concentrations of guest component A in the non-polar phase (chloroform) to the concentration of guest component A in the polar phase (water); $K_B = [G_B]_N/[G_B]_p$, or the ratio at equilibrium of the concentrations of guest component B in the non-polar phase (chloroform) to that in the polar phase (water).

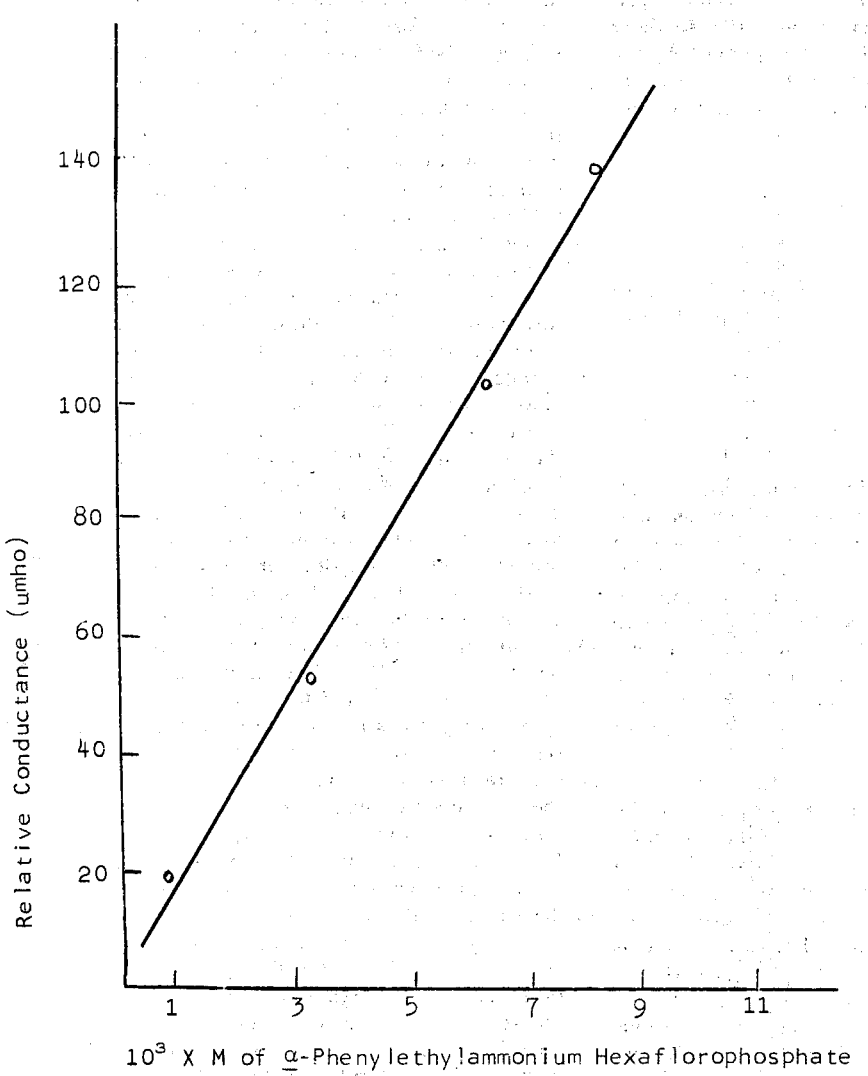

Figure 1. Linear relationship between conductance and moles of complex.

The capacity factor of the stationary phase (water) for component A ($k_A$), and the capacity factor of the stationary phase (water) for component B ($k_B$) are defined in equations (5). Combinations of equations (5) with the fundamental retention volume equations of chromatography (6) gives equations (7). In equations (7), the capacity factors are represented in terms of the retention volumes of components A and B relative to the volume of the mobile phase on the column.

The measure of the degree of separation of two components B and A, is given by the separation factor, $\alpha$. The separation factor is the ratio of the capacity factor of the slower moving component B to the capacity factor of the faster moving component A.

Combination of equations (8) and (5) produces equation (9), which relates the separation factor to the ratio of distribution constants of components A and B between the two phases. If components A and B are enantiomers, then $\alpha$ should be equal to the enantiomer distribution constant (EDC) defined in Procedure 1, as is indicated in equation (9).

$$k_A = \frac{V_s}{K_A V_M} \qquad k_B = \frac{V_s}{K_B V_M} \qquad (5)$$

$$V_{RA} = V_M + \frac{V_s}{K_A} \qquad V_{RB} = V_M + \frac{V_s}{K_B} \qquad (6)$$

$$k_A = \frac{V_{RA} - V_M}{V_M} \qquad k_B = \frac{V_{RB} - V_M}{V_M} \qquad (7)$$

$$\alpha = \frac{k_B}{k_A} \qquad (8)$$

$$\alpha = \frac{K_A}{K_B} = EDC \qquad (9)$$

The efficiency of a column, or the number of theoretical plates (N) is defined by equations (10). In these equations, $w_A$ is the band width of component A, and $w_B$ is the band width of component B measured in terms of the volume at the base line of a relative conductivity vs. eluant volume plot.

$$N = 16 \frac{V_{RA}^2}{w_A^2} \quad \text{or} \quad N = 16 \frac{V_{RB}^2}{w_B^2} \quad (10)$$

Equation 11 defines resolution, $R_s$. This term provides a measure of the useful degree of separation of components A and B $$R_s = 2 \frac{V_{RB} - V_{RA}}{w_B + w_A} \quad (11)$$

Besides these chromatographic parameters, the values of other terms are important in characterizing columns used for optical resolution by chiral recognition in molecular complexation. In a column which provides complete resolution, the integrated areas (units of $\mu$mho × ml.) under bands A and B in plots of relative conductance vs. volume of eluate should equal one another, since the enantiomers are originally present in the starting racemate in equal amounts. Thus the observed ratio, (Area A)/(Area B), provides a measure of column and detector behavior.

The amount of host compound needed to resolve a given amount of guest is important. The ratio, $(M_H/M_G)_{A-B}$ provides a measure. This ratio is the moles of host, $M_H$, to the moles of guest, $M_G$, involved in that part of a column's plot that spans the place where the first eluate containing guest appears to where the last eluate containing guest disappears. The ratios of moles of host to moles of guest involved in eluting just component A and just B are referred to as $(M_H/M_G)_A$ and $(M_H/M_G)_B$, respectively. The ratios of concentrations of host to guest at the maxima of the peaks are useful. In an ideal column, the host would be fully complexed at these points. The observed ratios are referred to as $([H]/[G])_{A-max}$ and $([H]/[G])_{B-max}$. The values of [H] were constant and known for each column. The values of [G]'s were estimated from the total moles of each enantiomeric guest put on the column, the total conductance-volume integral of each band, and the integral taken for a small volume taken at the peak maximum of each band.

Table VI reports the conditions employed for eight columns, and the characteristics of these columns in terms of the values of the above parameters. Column 1 involved racemic α-phenylethylammonium bromide (117) which was resolved with a chloroform solution of (RR)-8. The stationary phase was prepared by rolling (8 hours) 90 g. of Celite (Johns Manville Purified, dried to constant weight at 180° and 50μ) with 39.0 ml. of chloroform-saturated distilled water containing 6.52 g. of $NaPF_6$ (0.94 M). This not quite moist material was dry packed in small portions onto a 57 by 2.5 (I.D.) cm. jacketed chromatographic column. The stationary phase was 29% water-5% salt-66% Celite by weight. A solution of 0.75 ml. of chloroform-saturated distilled water containing 0.200 g. of racemic 117 and 0.175 g. of $NaPF_6$ was mixed with 1.6 g. of Celite. This material was packed at the top of the column (0.75 cm band). The column was cooled with circulating ice water to 0.5°. The column was developed by gravity flow with a 0.0375 M solution of (RR)-8 in chloroform saturated with water at 0°. The volume of the column's mobile phase $(V_M)$ was 164 ml., as shown by the amount of solution added before eluate appeared. Fractions (20 ml.) of the column eluate were collected, the flow rate being 0.3 ml/min. The relative conductivity of each fraction was measured with a dip cell with a constant of about 0.19 $cm^{-1}$, and an Industrial Instruments Inc. conductivity null bridge instrument. FIG. 2 provides a plot of ml. of eluate vs. relative conductivity of eluate for column 1. Fractions 8–12 (120 ml.) were combined, washed with three 40 ml. portions of water containing one drop of concentrated hydrochloric acid per 100 ml. of water. The amine salt in this aqueous solution was converted to its tosylamide derivative to give 117 mg. (42%) of non-optically fractionated material, $[\alpha]_{546}^{25}$ −102° (C 1.5, $CH_2Cl_2$). Fractions 19–28 (120 ml.) were combined, and similarly converted to the tosylamide derivative to give 84 mg. (30%) of non-optically fractionated material, $[\alpha]_{546}^{25}$ +101° (c 1.5, $CH_2Cl_2$). Optically pure (−)-(S)-α-phenylethylamine, $[\alpha]_D^{25}$ −40.8° (neat) when converted to its tosylamide derivative on the same scale by the same method gave a 90% yield of non-optically fractionated material, $[\alpha]_{546}^{25}$ −102° (C 1.5, $CH_2Cl_2$). A much larger sample prepared and recrystallized four times from dichloromethane-ether gave m.p. 99°–100°, $[\alpha]_{546}^{25}$ −108° (C 0.9, $CH_2Cl_2$), and $[\alpha]_D^{25}$ −79.7° (C 20, $C_6H_6$), comparable to literature values [J. Chem. Soc., 2145 (1954)]. Thus a minimum of 84% of the (S)-117 put on the column was eluted as optically pure salt in the first peak of column 1, and a minimum of 60% of the (R)-117 was eluted as optically pure salt in the second peak of column 1. The amine salt in fraction 16, which occurred immediately after the conductivity minimum in FIG. 2, was converted to its tosylamide derivative (4.9 mg.), and had a rotation of $[\alpha]_{546}^{25}$ +14° (C 0.5, $CH_2Cl_2$). Thus the material eluted at this cross-over point was only 14% optically pure in (R)-salt. An estimate of the relative peak areas (planimeter) of FIG. 2 gave (Area A)/(Area B) = 0.94. The column gave a separation factor of $\alpha = 1.76$, N = 24 theoretical plates, a resolution of $R_s = 0.6$, a ratio of moles of host to those of guest used of $(M_H/M_G)_{A-B} = 16$, and at the maximum of peak A, [H]/[G] = 4.5. Table VI summarizes these and other values.

TABLE VI

| | | | | | | | | | |
|---|---|---|---|---|---|---|---|---|---|
| CHARACTERISTICS OF LIQUID-LIQUID CHROMATOGRAPH COLUMNS | | | | | | | | | |
| | Dimensions(cm) | | | Salt | | % (w/w/w) | | | |
| Col. No. | Height | I.D. | Support | Kind | Concn(M) | Support | Salt | $H_2O$ | Host Concn.(M) |
| 1 | 57 | 2.5 | Celite | $NaPF_6$ | 0.94 | 66 | 5 | 29 | 0.0375 |
| 2 | 60 | 0.76 | Celite | $NaPF_6$ | 0.94 | 66 | 5 | 29 | 0.0375 |
| 3 | 60 | 0.76 | Silica 12 | $LiPF_6$ | 1.0 | 76 | 4 | 22 | 0.0375 |
| 4 | 60 | 0.76 | Silica 56 | $NaPF_6$ | 0.94 | 34 | 9 | 57 | 0.0375 |
| 5 | 60 | 0.76 | Silica 56 | $NaPF_6$ | 2.4 | 40 | 19 | 41 | 0.0375 |

TABLE VI-continued

| | | | | | | | | | |
|---|---|---|---|---|---|---|---|---|---|
| 6 | 60 | 0.76 | Silica 56 | NaPF$_6$ | 2.4 | 40 | 19 | 41 | 0.0375 |
| 7 | 60 | 0.76 | Silica 56 | NaPF$_6$ | 2.4 | 40 | 19 | 41 | 0.0375 |
| 8 | 60 | 0.76 | Silica 56 | LiPF$_6$ | 4.0 | 41 | 26 | 33 | 0.0750 |

| | Guest (RR'CHN̈H$_3$P̈F$_6$) | | | | | | |
|---|---|---|---|---|---|---|---|
| Col. No. | Structure | | Amount | | Temp °C | Flow rate (ml/min) | Press. drop (psi) |
| | R | R' | mg. | mmol | | | |
| 1 | C$_6$H$_5$ | CH$_3$ | 200 | 0.992 | 0.5 | 0.30 | gravity |
| 2 | C$_6$H$_5$ | CH$_3$ | 25 | 0.124 | 25 | 0.38 | 25 |
| 3 | C$_6$H$_5$ | CH$_3$ | 25 | 0.124 | 25 | 1.0 | <1 |
| 4 | C$_6$H$_5$ | CH$_3$ | 25 | 0.124 | 25 | 0.15 | 30 |
| 5 | C$_6$H$_5$ | CH$_3$ | 75 | 0.371 | −21 | 0.50 | 95 |
| 6 | C$_6$H$_5$ | CO$_2$CH$_3$ | 250 | 1.24 | −13 | 0.50 | 80 |
| 7 | C$_6$H$_5$ | CO$_2$CH$_3$ | 100 | 0.496 | −13 | 0.50 | 80 |
| 8 | p-HOC$_6$H$_4$ | CO$_2$CH$_3$ | 108 | 0.496 | −15 | 0.52 | 22 |

| Col. No. | Volumes (ml) | | | | | | Eluate | | Integr. μmho×ml (Area A) (Area B) | Capacity factors | |
|---|---|---|---|---|---|---|---|---|---|---|---|
| | $V_M$ | $V_s$ | $V_{RA}$ | $V_{RB}$ | $w_A$ | $w_B$ | Total | Used* | | ($k_A$) | ($k_B$) |
| 1 | 164 | 39 | 350 | 490 | 150 | 275 | 725 | 425 | 0.94 | 1.13 | 1.99 |
| 2 | 18.8 | 4.9 | 98 | 147 | 97 | 180 | 360 | 277 | — | 4.2 | 6.82 |
| 3 | 10.7 | 6.42 | 130 | 186 | — | — | — | — | — | 11.0 | 16.2 |
| 4 | 9.2 | 16.7 | 286 | 432 | 168 | 334 | 700 | 512 | — | 30.1 | 45.8 |
| 5 | 11.5 | 10.8 | 26.5 | 40 | 30 | 35 | 65 | 50 | — | 1.3 | 2.48 |
| 6 | 11.5 | 10.8 | 58 | 135 | — | — | 163 | 132 | — | 4.0 | 10.7 |
| 7 | 11.5 | 10.8 | 51.5 | 111 | 50 | 64 | 160 | 120 | 1.08 | 3.5 | 8.7 |
| 8 | 12.2 | 9.8 | 70 | 221 | 52 | 132 | 325 | 270 | .83 | 4.8 | 17.1 |

| Col. No. | Separat. fact. (α) | Theo. EDC ($K_A/K_B$) | pl. (N) | Resol. $R_s$ | $M_H/M_G$ | | | ([H]/[G])$_{max}$ | |
|---|---|---|---|---|---|---|---|---|---|
| | | | | | A-B | A | B | A | B |
| 1 | 1.76 | 1.78 | 24 | 0.6 | 16 | 11 | 21 | 4.5 | 8 |
| 2 | 1.62 | 1.48 | 7 | 0.35 | 110 | — | — | — | — |
| 3 | 1.47 | 1.48 | <5 | — | — | — | — | — | — |
| 4 | 1.52 | 1.48 | 19 | 0.6 | 155 | 101 | 202 | 65 | 136 |
| 5 | 1.9 | — | 18 | 0.75 | 6.5 | 6 | 7 | 3 | 3 |
| 6 | 2.65 | 2.48 | 18 | — | 4.0 | — | — | 1 | 2.2 |
| 7 | 2.48 | 2.48 | 18 | >1.25 | 9.1 | 7.6 | 9.7 | 2.1 | 3.3 |
| 8 | 3.6 | 4.2 | 18 | 1.57 | 40 | 19 | 48 | 8.6 | 25 |

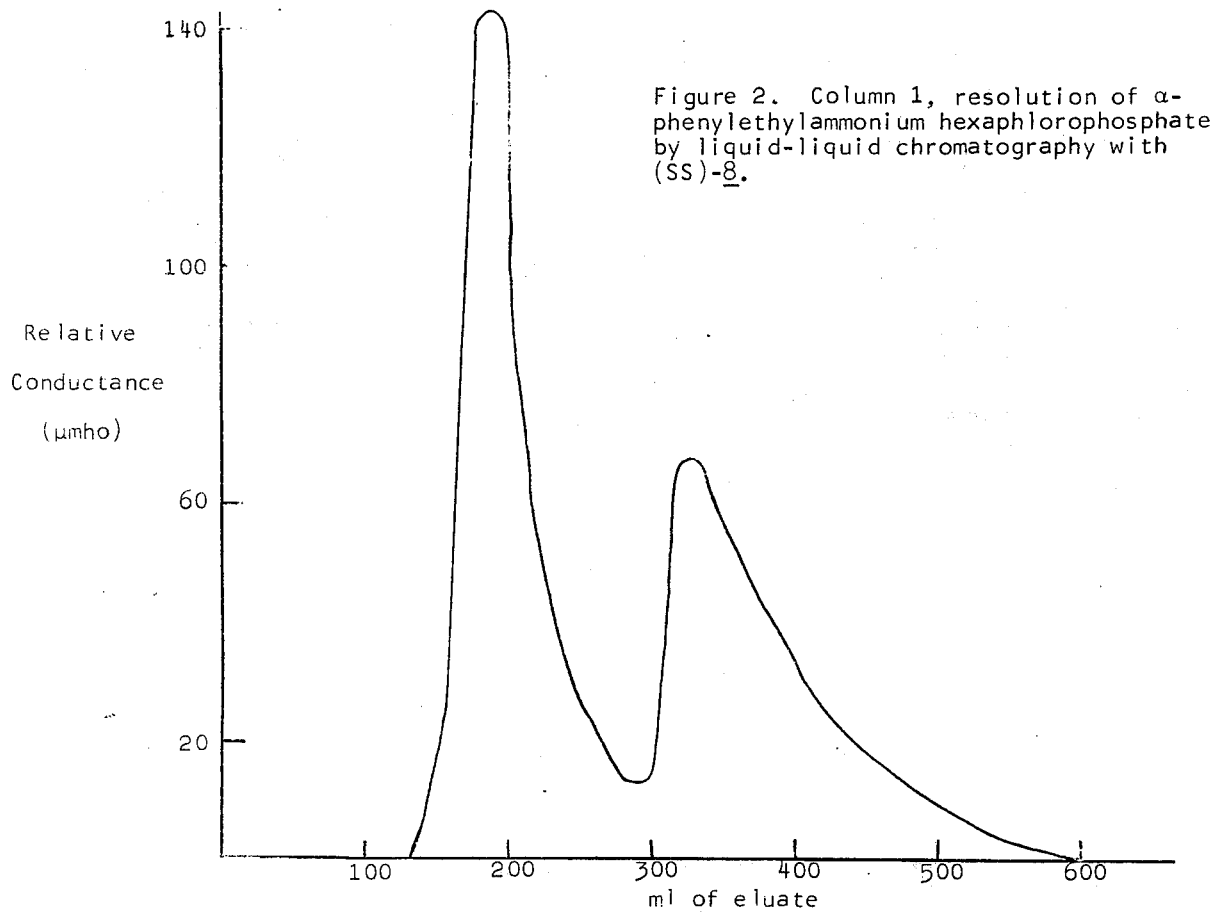

Figure 2. Column 1, resolution of α-phenylethylammonium hexaphlorophosphate by liquid-liquid chromatography with (SS)-8.

For the remaining columns, a conductivity cell was constructed through which all the eluate passed. The cell was composed of two brass plates held apart with a teflon gasket, and had a 0.1 ml. capacity. The cell constant was ~0.017 cm$^{-1}$. The conductance was continuously monitored by a Philips PR 9501 direct reading conductivity bridge attached to a strip chart recorder.

Columns 2, 3, and 4 were run to test the characteristics of Johns Manville Celite, Davidson Silica Grade 12 (pore volume 0.45 cc/g.; pore diameter 22A; surface area 800 m$^2$/g.; mesh size 28–200) and Davidson Silica Grade 56 (pore volume 1.2 cc/g.; pore diameter 168A; surface area 285 m$^2$/g.; mesh size 100–325) as supports for the aqueous phase. Each support was dried at 180° at 50$\mu$ to constant weight before treatment with a 0.94 M aqueous solution of NaPF$_6$ or LiPF$_6$. The Celite became pregressively wetter as more solution was added. The two Silicas appeared to stay dry and then suddenly became wet, Grade 12 at 25% (by weight), and Grade 56 at 57% (by weight) of solution added. The mixture of solution and support was shaken for 15 hours. The use of 6% water (by weight) on Celite, or of 44% water (by weight) on Silica 56 in trial columns failed. The guest never appeared in the eluate, and was absorbed by the support. At 57% water on Silica 56, a bleeding column resulted. Stainless steel columns, 0.75 I.D. by 56 cm were packed by adding small portions of solid and tamping after each addition. A filtered 0.0375 M solution of optically pure (RR)-8 in chloroform solution saturated with distilled water as circulated through the columns by a Milton-Roy Mini-pump, whose stroke length was varied between 6 and 20% to attain proper pressure drop and flow rate. Although tiny air bubbles were noted during all runs, they did not interfere with detection. The volume of the mobile phase was determined by measuring the volume of eluent pumped into the dry-packed column before effluent appeared. The columns were equilibrated with the chloroform solution of (RR)-8 at the temperature to be used in the chromatogram before guest was introduced. Racemic $\alpha$-phenylethylammonium hydrobromide (25 mg.) dissolved in 0.5 ml. of the chloroform solution of (RR)-8 was introduced onto the column through an SV 8031 Chromatronix Sample Injection valve block. Table VI reports the characteristics of the three columns. Columns 5–8 were run similarly to columns 2–4 with the following modifications. Silica 56 was used as the support. The temperatures were controlled by circulating cooled ethyleneglycol-water from a constant temperature bath through the insulated column jackets. The chloroform solution of host was saturated with water at the temperature to be used for the column. The salt to be resolved was introduced on the tops of these columns as it was in column 1, after the columns were equilibrated with host-chloroform solution at the temperature to be used.

Due to the greater hydrophilicity of the p-hydroxyphenylglycine ester-salt, a 4 M solution of LiPF$_6$ was used as the stationary phase. The LiPF$_6$ salted the guest out of the aqueous phase without its metal ion complexing the host. The solution was prepared by dissolving the salt in stirred water at 0°. The addition rate was controlled to maintain the temperature near 0°. After addition, the pH of the solution was raised to 4 by adding an appropriate amount of 5 M lithium hydroxide. Finally, the solution was cooled to the column temperature, filtered, and shaken with dried Silica 56 as before. A sample of the resulting material underwent no visible change on extended refrigeration at −15°, but a sample of 4 M LiPF$_6$ in water at −15° deposited a small amount of LiPF$_6$ after several days, but maintained its pH for several days. It ultimately became acidic by hydrolysis of the PF$_6^-$.

The characteristics of columns 5–8 are reported in Table VI. FIG. 3 is a plot for column 7, and FIG. 4 is a plot for column 8. In these last two columns, the conductance reached baseline between peaks A and B, indicating that complete optical resolution was accomplished. An additional check on the use of conductivity to locate the bands and empty fractions of column 8 made use of spot tests developed with ninhydrin spray reagent. The column effluent was collected in 25 ml. fractions. Fraction 6, collected between 125 and 150 ml. of column 8, gave a negative test for amino ester, whereas the adjacent fractions gave strong tests.

The same sample of (RR)-8 was used in columns 1–8, and columns 5–7 were run on the same support without unpacking the column. All of the columns were stainless steel except 1. At the end of a column, (RR)-8 was recovered as follows. The chloroform solution was washed with dilute hydrochloric acid, and then with water. The solution was dried with magnesium sulfate, filtered, and treated with a small amount of Norite and filtered through a 0.5 inch pad of alumina. Norite and filtered through a 0.5 inch pad of alumina. The colorless solution was evaporated under reduced pressure to give (RR)-8 as a white foam, which in some cases was crystallized from benzene-cyclohexane to give recovered, optically pure material, $[\alpha]_{578}^{25}$ +220°; (C 1, CH$_2$Cl$_2$). Recovery of host from a single column was nearly quantitative, particularly when deoxygenated solvents were used, and care was taken to make quantitative transfers.

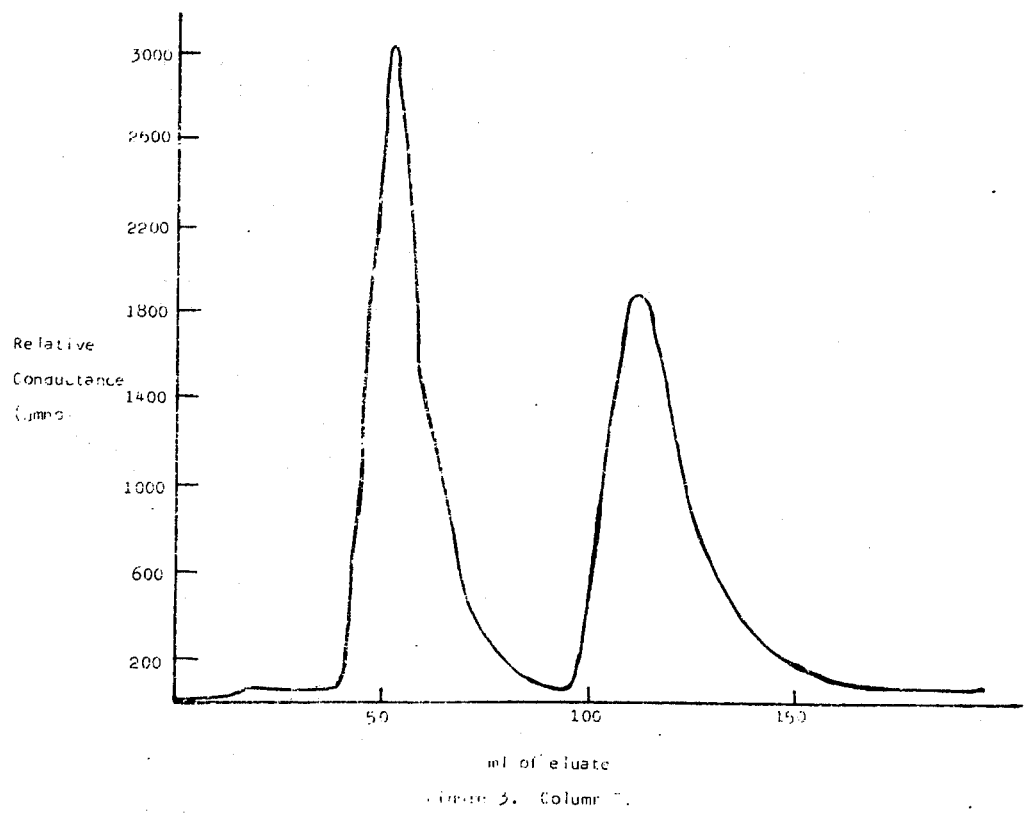
Figure 5. Column 5.
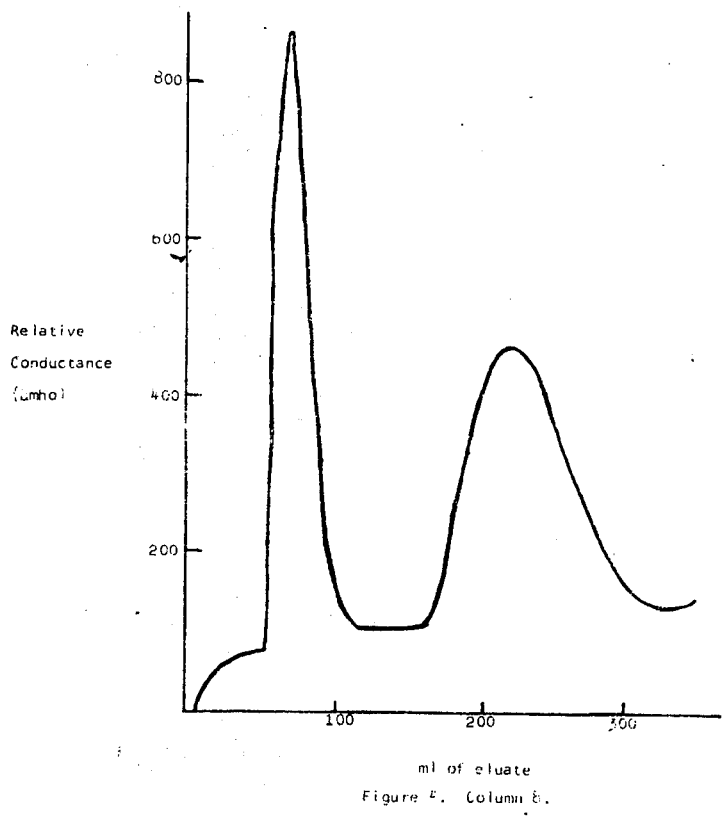
Figure 6. Column 6.

The values of the parameters for columns 1–8 that are listed in Table VI provide useful conclusions. Equation (8) indicates that if these columns are truly liquid-liquid chromatograms, then $\alpha \cong EDC$. The values of $\alpha$ were derived solely from the various volume and conductivity data derived from the columns, whereas the EDC values were determined by liquid-liquid distribution experiments (see Table V, Procedure 1). The values agree reasonably well for the seven columns for which comparisons are possible. Thus knowledge of either $\alpha$ or EDC allows the other to be estimated. Furthermore, the convenient conductivity means of detection of complex appears to be reliable. The fact that the values of (Area A)/(Area B) ~1 also supports the last conclusion, as did the use of ninhydrin as applied to the fractions from column 8.

Of the three kinds of supports used, Celite and Silica 56 both look useful. The number of theoretical plates, N, varied in columns 1 and 4–8 between 18 and 24, and was lowest (<5) when Silica 12 was used. Either $NaPF_6$ or $LiPF_6$ can be used for salting out and freezing-point lowering purposes, but $NaPF_6$ donates $Na^+$ to host molecules in competition with very hydrophilic or weakly acidic alkylammonium salts. The solid supports must be close to saturated with the salt water solution to avoid their acting as absorbents for the guest. The amount of salt in the water, and the amount of guest in the chloroform can be adjusted to allow an appropriate distribution of guest between phases. Only in column 6, which was probably overloaded, did the value of $([H]/[G])_{max}$ approach unity. The values of $M_H/M_G$ varied widely, from a high of 155 for column 4 to a low of 4 for column 6. The acid-base relationship between host and guest coupled with the hydrophilic-lipophilic balance of the guest seemed best matched with 8 and phenylglycine ester salt. Other more basic host molecules and higher host concentrations should reduce the value of $(M_H/M_G)_{A-B} = 40$ observed in column 8 that involved as guest the p-hydroxyphenylglycine ester salt. The large base-line separation of the two peaks in FIG. 4 indicate that host was wasted.

Although conductance-volume plots for columns 4, 5 and 8 gave nearly Gaussian band shapes, most of the bands showed evidence of tailing. The use of more uniform particle size supports would reduce channeling, tailing, and should increase the number of theoretical plates.

The lower temperatures provide the higher separation factors ($\alpha$), just as lower temperatures provide higher chiral recognition (EDC values). Host compounds whose structures provide high EDC values will provide the high separation factors.

EXAMPLE 13

The Effect of Host Structure on Chiral Recognition and Solubility Properties in Complexation of Amino Acids and Multiheteromacrocyles

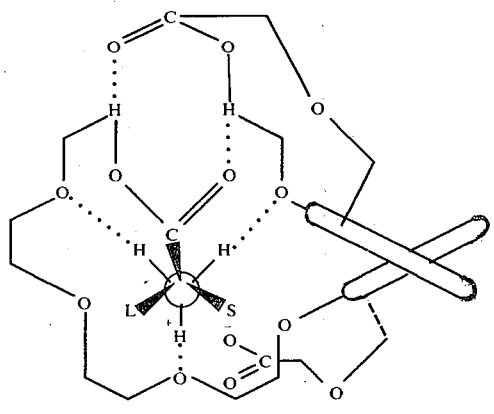

119

More stable complex between (R)-30 and generalized (R)-amino acid

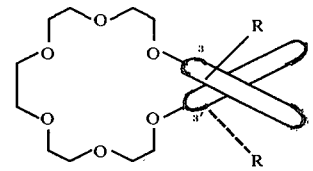

(R)-6, R=H
(R)-28, R=$CH_2OH$
(R)-30, R=$CH_2OCH_2CO_2H$
(R)-28b', R=$CH_2SCH_2CO_2H$
(R)-28c', R=$CH_2SCH_2CH_2CO_2H$
(R)-28d', R=$CH_2CH(CO_2H)_2$
(R)-28e', R=$CH_2CH_2CO_2H$

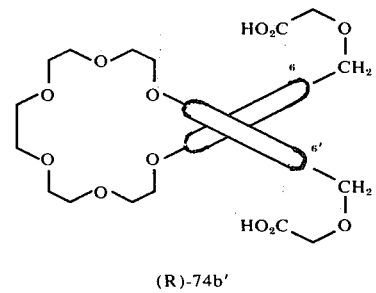

(R)-74b'

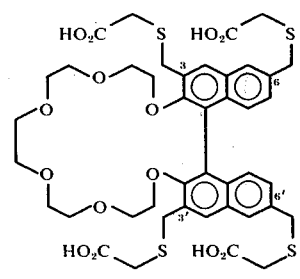

(S)(R)-6k'

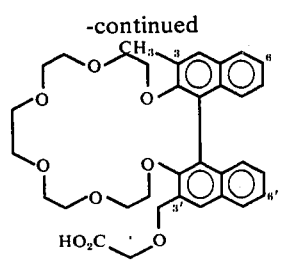

(S)(R)-28g'

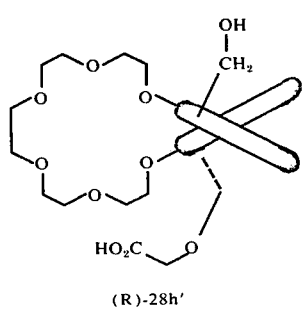

(R)-28h'

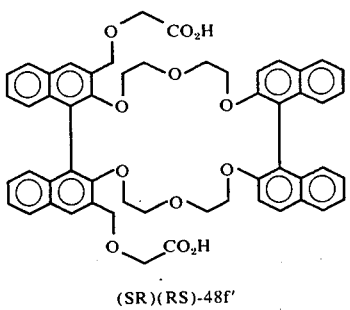

(SR)(RS)-48f'

Procedure 3

Two methods were used. In method 1, the question is answered of whether or not substantial complexation occurred between an amino acid as guest and a multiheteromacrocycle as host in solvents such as acetic, formic or trifluoroacetic acid. In method 2, the chiral recognition factor (CRF) was determined in the polar phase in distribution experiments of racemic host, optically pure guest, and complex between two liquid phases composed of water, chloroform, and acetic or formic acid.

In method A, deuterated solvents were employed, and pmr spectra was used as a criterion of complexation. Either valine or phenylglycine was guest, and monolocular multiheteromacrocycles were host compounds. Both host and guest individually were soluble enough in acetic, formic or trifluoroacetic acids to provide 100 MHz pmr spectra. The spectra of the two dissolved together in equivalent amounts were taken. If the pmr spectrum of the mixture was substantially different from that of the individual components superimposed on one another, complexation was presumed. Changes in the pmr signals in the complex of the ArOCH$_2$ and ArC$\underline{H}_2$ protons of the host, of the (CH$_3$)$_2$CH protons of valine, and of the ArCH protons of phenylglycine were particularly useful as criteria of complexation. Attempts then were made to distribute the components of the mixture of host, guest and complex between two phases composed of differing amounts of D$_2$O, CDCl$_3$ and AcOD or HCO$_2$H. The pmr spectra of each phase was used to locate the equilibrated host, guest and complex. Table VII indicates the host, guest, solvent and temperature used in those qualitative experiments that led to complexation.

Table VII

Complexation Between Equivalent Amounts of Multi-heteromacrocycles as Hosts and Amino Acids as Guests at ~0.20M Concentration in RCO$_2$D(H) at 25°

| Run No. | Host No. | Guest | RCO$_2$D |
|---|---|---|---|
| 1 | (S)(R)-6 | (S)-Valine | CD$_3$CO$_2$D |
| 2 | (S)(R)-30 | (R)-Phenylglycine | CD$_3$CO$_2$D |
| 3 | (S)(R)-28b' | (S)-Valine | CD$_3$CO$_2$D |
| 4 | (S)(R)-28b' | (S)-Valine | CF$_3$CO$_2$D |
| 5 | (S)(R)-28b' | (R)-Phenylglycine | CF$_3$CO$_2$D |
| 6 | (S)(R)-28b' | (R)-Phenylglycine | HCO$_2$H |
| 7 | (S)(R)-28c' | (R)-Phenylglycine | HCO$_2$H |
| 8 | (S)(R)-28d' | (S)-Valine | CD$_3$CO$_2$D |
| 9 | (S)(R)-6k' | (R)-Phenylglycine | HCO$_2$H |
| 10 | (SR)(RS)-48f' | (R)-Phenylglycine | HCO$_2$H |

In runs 1, 8 and 9 of Table VII, attempts were made to distribute host, guest and complex between two phases composed of differing amounts of RCO$_2$D(H), CDCl$_3$ and D$_2$O. In run 1, host (R)(S)-6 in either free or complexed form, could not be induced to leave the RCO$_2$D(H)—CDCl$_3$ layer and enter the RCO$_2$D(H)—D$_2$O layer in amounts measurable (5% of that present) by pmr. In runs 8 and 9, the two tetracarboxylic acids, (S)(R)-28d' and (S)(R)-6k', entered the RCO$_2$D(H)—D$_2$O layer, and measurable amounts (pmr, <5%) in either free or complexed form could not be induced to enter the RCO$_2$D—CDCl$_3$ layer. In the other runs of Table VII, hosts and host-guest complexes were distributed between the two layers in large enough amounts to apply method B.

In method B, equivalent amounts of racemic host and optical pure (R)-valine or (R)-phenylglycine were dissolved in either CD$_3$CO$_2$D OR HCO$_2$H to give approximately 0.1 M solutions. Two layers were produced by adding CDCl$_3$ and D$_2$O, and shaking the mixture at the desired temperature. The amounts of the two solvents added were adjusted to distribute 38–64% (as close to 50% as possible) of the host molecule in the aqueous phase at equilibrium. The two phases were separated at the temperature of their equilibration, and relative amounts of host and guest in each phase determined by pmr spectral integration experiments. Each phase was evaporated in vacuo to dryness, and the residue dissolved in 5 ml. chloroform. Each chloroform solution was washed with 5 ml. 0.5 M hydrochloric acid, with water, and evaporated to dryness in vacuo. Each host residue was dried as a foam at 30° and 50μ for 3 hrs. Rotations were taken in the same solvent and under the same conditions that were used with optically pure host compound. From the rotations, optical purities and configurations were determined. The absolute configurations and maximum rotations of the enantiomers of 28, 30, 28b', 28c', 28e' and 28h' were previously determined. In each run in which chiral recognition in complexation was observed, the signs of rotations of the host molecule recovered from the aqueous and organic layers were in the opposite direction. The magnitudes of the two rotations were consistent with the relative amounts of host distributed in each layer, and with each other. The amounts of host recovered amounted to 80–90% of the amounts initially used. Table VIII reports the conditions and results of the experiments.

TABLE VIII

Chiral Recognition Factors (CRF) in Partitioning an Equivalent of Racemic Host (H) and Optically Pure Amino Acid as Guest (G) and their Complexes Between Two Liquid Phases Composed from $RCO_2D(H)$, $CDCl_3$ and $D_2O$

| Run No. | Host Comp. No. | Amt. mmoles | Guest | Solvents used (ml) | | | |
|---|---|---|---|---|---|---|---|
| | | | | $CD_3CO_2D$ | $HCO_2H$ | $CDCl_3$ | $D_2O$ |
| 1 | (S)(R)-28 | 0.146 | (R)-Valine | 0.40 | — | 0.20 | 0.15 |
| 2 | (S)(R)-30 | 0.106 | (R)-Valine | 0.60 | — | 0.30 | 0.20 |
| 3 | (S)(R)-30 | 0.115 | (R)-Valine | 0.50 | — | 0.20 | 0.10 |
| 4 | (S)(R)-30 | 0.106 | (R)-Valine | — | 0.55 | 0.40 | 0.075 |
| 5 | (S)(R)-30 | 0.115 | (R)-Valine | — | 0.40 | 0.20 | 0.05 |
| 6 | (S)(R)-30 | 0.161 | (R)-Phenylglycine | 0.50 | — | 0.30 | 0.16 |
| 7 | (S)(R)-30 | 0.115 | (R)-Valine | 0.35 | — | 1.0$^a$ | 0.25 |
| 8 | (S)(R)-28b' | 0.148 | (R)-Valine | — | 0.40 | 0.30 | 0.14 |
| 9 | (S)(R)-28c' | 0.131 | (R)-Valine | 0.60 | — | 0.24 | 0.22 |
| 10 | (S)(R)-28e' | 0.114 | (R)-Valine | 0.60 | — | 0.20 | 0.28 |
| 11 | (S)(R)-74b' | 0.100 | (R)-Valine | 0.60 | — | 0.30 | 0.30 |
| 12 | (S)(R)-28g' | 0.121 | (R)-Valine | 0.60 | — | 0.24 | 0.21 |
| 13 | (S)(R)-28h' | 0.128 | (R)-Valine | 0.50 | — | 0.25 | 0.20 |

| Run No. | T °C | Concn. ratios at equilib. | | Host $D_2O$-layer at equilibrium | | |
|---|---|---|---|---|---|---|
| | | $D_2O$-layer [H]/[G] | $CDCl_3$-layer [G]/[H] | % | Config. | % Opt. purity | CRF |
| 1 | 30 | 0.38 | 0.38 | 38 | R | 6.5 | 1.14 |
| 2 | 30 | 0.50 | 0.05 | 50 | R | 27 | 1.7 |
| 3 | 1 | 0.50 | 0.05 | 45 | R | 8.5 | 1.18 |
| 4 | 30 | 0.50 | 0.10 | 50 | R | 16 | 1.38 |
| 5 | 0 | 0.45 | 0.05 | 52 | R | 27 | 1.7 |
| 6 | 30 | 0.50 | 0.50 | 36 | R | 4.7 | 1.09 |
| 7 | 30 | 0.50 | 0.05 | 50 | R | 8.3 | 1.25 |
| 8 | 30 | 0.50 | 0.30 | 38 | R | 12 | 1.27 |
| 9 | 30 | 0.55 | 0.31 | 64 | R | 4 | 1.08 |
| 10 | 30 | 0.59 | 0.10 | 59 | R | 4 | 1.08 |
| 11 | 30 | 0.39 | 0.10 | 39 | — | 0$^b$ | 1.0$^b$ |
| 12 | 30 | 0.50 | 0.26 | 42 | — | 0$^b$ | 1.0$^b$ |
| 13 | 30 | 0.50 | 0.20 | 50 | R | 7 | 1.15 |

$^a$Benzene was substituted for $CDCl_3$.
$^b$The rotation was within or close to experimental error of zero at several wave lengths.

The exact method is exemplified by run 13. A solution of 78 mg. (0.128 mmoles) of (S)(R)-28h' was dissolved in 0.50 ml. $CD_3CO_2D$, and 15 mg. (0.128 mmoles) of optically pure (R)-valine was added. To the resulting solution was added 0.25 ml. of $CDCl_3$ and 0.20 ml. of $D_2O$, the mixture was shaken for 1 minute at 30°, and the layers were separated at those temperature. The pmr spectra of each layer was taken (100 MHz). The relative amounts of valine and 28h' in the chloroform layer was estimated by the following integrations.

Pmr (100 MHz) relative integration values

| | $ArCH_2$ | $ArCO_2OCH_2$ | Rest of aliphatic H's of host | $CH(CH_3)_2$ | $CH(CH_3)_2$ |
|---|---|---|---|---|---|
| Calcd for [G]/[H] = 0.20 | 30 | 15 | 155 | 2 | 9 |
| Observed | 30 | 15 | 152 | 2 | 12 |

The relative amounts of valine and 28h' in the aqueous layer were estimated by the following integrations.

Pmr (100 MHz) relative integration values

| | ArH | Host aliphatic + CH—N | $CH(CH_3)_2$ | $CH(CH_3)_2$ |
|---|---|---|---|---|
| Calcd for [H]/[G] = 0.50 | 70 | 196 | 14 | 84 |
| Observed | 70 | 195 | 13 | 90 |

From the aqueous layer was isolated 31 mg. (50%) of recovered 28h', $[\alpha]_{546}^{25} = -5.0°$ (C 1, $CHCl_3$), which compares with $[\alpha]_{546}^{25} = -80.4°$ (C 1, $CHCl_3$) for optically pure (R) -28h'. From these values, the optical purity of the (R) -28h' extracted into the aqueous layer by the (R)-valine was calculated to be 6%, which indicates the mixture was 54% (R)-28h' and 46% (S)-28h'. Since the major complexation took place in the aqueous layer, the chiral recognition factor (CRF) was calculated. Values of the CRF were 54%/46% = 1.15.

From the original chloroform layer was isolated 31 mg. (50%) of 28h', $[\alpha]_{546}^{25} = +5.2°$ (C 1, $CHCl_3$). This material had an optical purity of 6%, and possessed the (S)-configuration. The total amount of starting host compound accounted for was 80%.

The CRF values of Table VIII provide only a limited measure of the chiral recognition potentialities of the amino acid-host relationships. Complexation and therefore chiral recognition occurred in both layers, and undoubtedly the (R)-(R)-configurational relationship was favored over the (R)-(S)-relationship in the chloroform as well as in the water layer. Thus some cancellation occurred, and the CRF values observed in the water layer are only a net effect. This cancellation was particularly large in run 6 with (R)-phenylglycine and (S)(R)-30 in $CD_3CO_2D$—$CDCl_3$—$D_2O$. In the water layer, [H]/[G] = 0.50, and in the chloroform layer, [G]/[H] = 0.50, 36% of the host was in the water layer, and a value of only 1.09 was observed for the CRF. In run 2 with (R)-valine and (S)(R)-30 in $CD_3CO_2D$—$CHCl_3$—$D_2O$, [H]/[G] = 0.50 in the water and [G]/[H] ⩽ 0.05 in the chloroform layer, and CRF = 1.7. Much cancellation occurred in run 6, but little in run 2. Unfortunately, EDC values can not be used for these runs since both host and guest were distributed in both layers. Possibly higher chiral recognition occurred in run 6 than run 2, but is not visible. However, qualitative conclusions about chiral recognition and its dependence on structure can be drawn from other comparisons.

In runs 2-5, 7, 10 and 11, [G]/[H] ⩽ 0.1 in the chloroform layer. Thus the CRF values in these runs should provide the most reliable correlation between the degree of chiral recognition and structure. Compounds 30 and 74b' both contain two $CH_2OCH_2CO_2H$ arms. In 30, they are positioned to bind the guest amino acid as in complex 119. Run 2 that involved 30 gave CRF = 1.7. In compound 74b', the arms occupy the remote 6,6'-positions, where one arm potentially could extend to and bind the carboxyl of the guest amino acid, but the other could not ion-pair the ammonium ion. Run 11 that involved 74b' gave no chiral recognition (CRF =1.0). The carboxyl groups in 74b' are in positions to hydrogen bond each other, which is not true in 30. The arms of 74b' appear to play no role in binding host to guest.

Comparisons in runs 2 and 10 are also instructive. Run 10 involved 28e' as host, whose two $CH_2CH_2CO_2H$ arms are in the 3,3'-positions and provide low chiral recognition (CRF = 1.08). Run 2 involved 30 as host, whose two $CH_2OCH_2CO_2H$ arms in the 3,3'-positions provided high chiral recognition (CRF =1.7). Molecular models (CPK) of complex 119 that involve 30 are less strained than those of a similar complex with $CH_2CH_2CO_2H$ arms. In the latter, energy rich gauche $CH_2$—$CH_2$ conformations are involved that are absent in the former, and the $CH_2CH_2CH_2H$ chain is not long enough to allow the carboxyl group to orient itself for full hydrogen bonding with the carboxyl group of the guest amino acid.

Comparisons of run 2 with 3, and of 4 with 5 indicate that temperature was an important variable. Interestingly, the higher temperature in acetic acid as cosolvent gave the higher CRF (run 2 vs. run 3), but the lower temperature in formic acid as cosolvent gave the higher CRF (runs 4 and 5). The CRF of 1.25 in run 7 indicates the benzene can be substituted for chloroform without loss of chiral recognition.

In run 12, some cancellation of visible chiral recognition was present since [G]/[H] = 0.26 in the chloroform layer as compared to [H]/[G] = 0.50 in the water layer. However, CRF ~1.0, which is low enough to make comparisons with run 2 valid. Run 2 involved 30, with two $CH_2OCH_2CO_2H$ arms in the 3,3'-positions. Run 12 involved 30, with two $CH_2OCH_2CO_2H$ arms in the 3,3'-positions. Run 12 involved 28q' with a $CH_3$ group in the 3-position and a $CH_2OCH_2CO_2H$ arm in the 3'-position. Thus substitution of a $CH_3$ for a $CH_2OCH_2CO_2H$ group on one side only of the macroring destroys the capacity for chiral recognition. This fact suggests that the ion-pairing between the $NH_3^+$ of the guest and the $CO_2^-$ of the host is more stabilizing for the complex than is the carboxyl-to-carboxyl hydrogen bonding

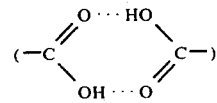

between host and guest. The favored complex of 28q' must involve the amino acid bound to the face of the macrocycle close to the $CH_3$ group. The $CH_3$ group can not bind the carboxyl of the guest, and thus does not enforce any conformational relationship between the chiral barrier of the host and the asymmetric center of the guest. The carboxyl group of 28q' in the complex on the face opposite the guest ion-pairs the $NH_3^+$, but does not provide chiral recognition.

Runs 8, 9 and 13 gave [H]/[G] in the aqueous layer of 0.5 to 0.55, and [G]/[H] in the chloroform layer of 0.2 to 0.31, and CRF values of 1.08 to 1.27. Complexation between host and guest was so strong that amino acid pulled the host into the aqueous layer, and the host pulled the amino acid into the chloroform layer. As a result, much of the chiral recognition, which must have been substantial, is invisible because of cancellation. Molecular models (CPK) of the complexes involved indicate that the geometric requirements are fulfilled for ionpairing on one face and hydrogen-bonding out from the opposite face of the host.

Runs 1 and 13 provide a valuable comparison. Each run gave CRF ~1.15. Run 1 ave [H]/[G] = 0.38 in the aqueous and [G]/[H] = 0.38 in the cloroform layer, and 38% of the total host was in the aqueous layer. Thus only a fraction of the total chiral recognition can be visible in the CRF. Run 13 gave [H]/[G] = 0.50 in the aqueous and [G]/[H] = 0.20 in the cloroform layer, and 50% of the host was in the aqueous layer. Again, only a fraction of the total chiral recognition is visible in the CRF. Compounds 28 (run 1) and 28h' (run 13) both have one $CH_2OH$ arm in the 3-position, but 28 has a second $CH_2OH$ arm in the 3'-position and 28h' has a $CH_2OCH_2CO_2H$ arm in the 3'-position. These facts indicate that provided the macroring is capable of complexing the $NH_3^+$ group, the presence or absence of a counterion for the $NH_3^+$ group in the host is not a condition for chiral recognition. What is surprising is that 28 is such a good complexing agent. Possibly the $CH_2OH$ group not involved with the carboxyl group of the guest helps locate the counterion ($OAc^-$) close to the $NH_3^+$ group by hydrogen bonding it. The less polar the medium, the more important this ion pairing is to complexation. Molecular models (CPK) of such a complex indicate that structure 120 is geometrically excellent.

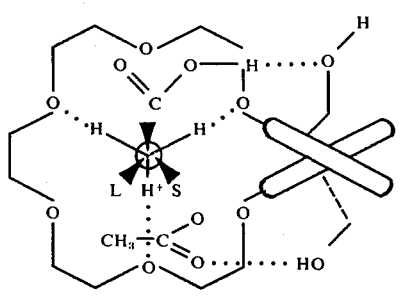

120

-continued

More stable complex between (R)-28 and generalized amino acid

EXAMPLE 14

Resolution by Liquid-Solid Chromatography of Amine Salts by Chiral Recognition in Molecular Complexation

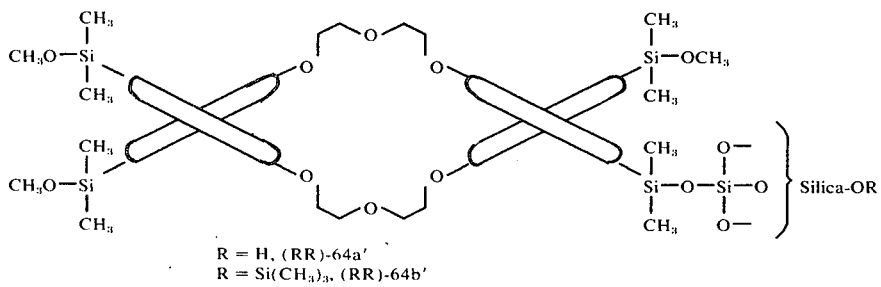

R = H, (RR)-64a'
R = Si(CH₃)₃, (RR)-64b'

Multiheteromacrocycles, (RR)-64a' and (RR)-64b' have been used to exemplifiy the use of chiral recognition in molecular complexation at a liquid-solid interface to resolve primary amine salts.

Procedure 1

In this procedure, (RR)-64a' (before it was treated with trimethylsilyl chloride, see Example 7, Procedure 7) was used as the solid phase in solid-liquid chromatography to resolve α-phenylethylammonium hexafluorophosphate (121). In each case, the solid phase complexed one enantiomer and slowed its passage down the chromatograph column more than the other. Chloroform or dichloromethane containing 18-crown-6 (122) [Tetrahedron Lett. 1793 (1972)] served as a carrier for the salts in the liquid phase. The column eluate was passed through the same conductance cell used in Example 12, Procedure 2, and the appearance of salt in the eluate was followed on a strip recorder. Plots of the relative conductance against the volume of column eluate provided the column's characteristics. The parameters that characterize the column's effectiveness in resolving racemates are defined and interrelated by equations (5)–(11) developed in Example 12, Procedure 2.

The same column, jacketed for maintenance of temperature, was used for runs 1–5. It was of stainless steel, 0.75 I.D. by 56 cm length, and contained 13.0 g. of (R)-64a' (0.57 mmole of cycle, at 0.044 mmole/g.). The column was packed by adding in small portions (R)-64a', (whose SiOH groups had not been capped) and tamping the material after each addition. The volume of the mobile phase on the column, $V_M$, was 26.0 ml. In each run, the column was preequilibrated with the mobile phase by passing several column volumes of the mobile phase through the column held at the desired temperature by circulating ethylene glycol-water from a constant temperature bath through the column's jacket. A constant flow rate was maintained by use of a Milton-Roy Minipump, and the % stroke length varied between 5 and 20% to attain a proper pressure drop and flow rate. Tiny air bubbles noted during the runs did not interfere with the detection. The detection cell constant was about 0.017 cm⁻¹. Essentially no conductivity for the column eluant was observed when either chloroform or dichloromethane alone was used as the mobile phase and salt 121 as employed. Dissolution of 122 in the mobile phase as a carrier not only moved the salt down the column faster, but also allowed salt in the eluate to be detected. The rate at which the salt passed through the column was controlled by the concentration of the carrier (122). Relative conductivities at peaks and base lines varied by factors of 14 to $10^2$, depending on salt and carrier concentrations. Pure, dried solvent was used, and the racemic salt was pumped into the top of the column dissolved in a minimum volumn of the carrier phase through a loop-valve device interposed between the pump and the column. Between runs, the column was washed with several column volumes of methanol, then with chloroform or dichloromethane, then with carrier solution.

Table IX reports the conditions for the various runs made with the column, and the results in terms of capacity factors, ($k_A$ and $k_B$), separation factors ($\alpha$), and the number of theoretical plates (N). The subscripts A and B refer to the enantiomers of the guest. The guest racemate used, the molar ratio of host to guest (H/G), the solvent, the concentration of carrier and the column temperature are the main experimental parameters.

In run 1, the column was deliberately overloaded with racemic α-phenylethylammonium hexafluorophosphate (121). Thus H/G = 3.4. Although the presence of two components was visible in a plot of relative conductance vs. column eluate, the first peak appeared as a shoulder on the second larger peak, and the capacity factors could not be measured. The fraction of column eluate under the shoulder (faster moving component A) was washed with four 100 ml. portions of water, the water layer was washed with four 50 ml. portions of chloroform to remove the carrier. The water layer was made basic with sodium hydroxide to pH 11 and extracted with chloroform. The chloroform was dried and evaporated to give (R)-α-phenylethylamine (R)-109, [α]₅₈₉²⁵ +30° (c 0.04, CDCl₃), of correct pmr spectrum. The fraction of the eluate under the latter part of the slower moving component B was similarly treated to give (S)-α-phenylethylamine ((S)-109), [α]₅₈₉²⁵ −40° (c 0.01, CDCl₃), of correct pmr spectrum. This experiment demonstrated that partial optical resolution had occurred, that the faster moving A component (less firmly bound to the column) possessed the (R)-configuration, and that the B component (more firmly bound to the column and slower moving) possessed the (S)-configuration. This result indicates that the dilocular system 8, functionalized at the 6-positions and bound to a solid support, shows the same kind of chiral recognition that was observed by 8 for 109 in liquid-liquid extraction (see Example 11, Procedure 1, formula 110). Structure 125 provides an explanation in molecular terms for this result.

TABLE IX

Liquid-Solid Chromatographic Optical Resolution of Racemic Primary Amine Salts Carried by 18-Crown-6 (122) in the Liquid Phase ($V_M$ = 26ml) with (RR)-64a' or (RR)-64b' as the Solid Phase Host at 0.44 mmole of Cycle per Gram.

| Run No. | Solid phase | Guest Salt Comp. No. | Guest Salt Wt. (mg) | Solid Phase Wt (g) | Solid Phase Mmole | Molar ratio H G | Mobil Phase Solvent | Mobil Phase Carrier Concn. (M) | T °C | Flow rate (ml/min) | Press. drop (psi) | Capacity factors ($k_A$) | Capacity factors (kg) | Seper. fact. α (kg/$k_A$) | Theor. plates (N) |
|---|---|---|---|---|---|---|---|---|---|---|---|---|---|---|---|
| 1 | (RR)-64a' | 121 | 45 | 13 | 0.57 | 3.4 | $CHCl_3$ | $1.0 \times 10^{-2}$ | 25 | 1.0 | 180 | — | — | — | — |
| 2 | (RR)-64a' | 121 | 8 | 13 | 0.57 | 19 | $CHCl_3$ | $5.5 \times 10^{-3}$ | 25 | 1.0 | 180 | 3.27 | 3.88 | 1.19 | 12±1 |
| 3 | (RR)-64a' | 121 | 1 | 13 | 0.57 | 150 | $CHCl_3$ | $5.5 \times 10^{-3}$ | 25 | 1.0 | 180 | 3.23 | 4.20 | 1.30 | 16±5 |
| 4 | (RR)-64a' | 121 | 8 | 13 | 0.57 | 19 | $CHCl_3$ | $5 \times 10^{-7}$ | 25 | 1.0 | 180 | 7.85 | 8.85 | 1.13 | 21±5 |
| 5 | (RR)-64a' | 121 | 2.8 | 13 | 0.57 | 54 | $CHCl_3$ | $1 \times 10^{-5}$ | −12 | 0.4 | 180 | 2.1 | 20.5 | 9.9 | 80±60 |
| 6 | (RR)-64b' | 121 | 8 | 14 | 0.62 | 21 | $CH_2Cl_2$ | $4.4 \times 10^{-5}$ | 25 | 1.0 | 900 | 3.64 | 5.35 | 1.47 | 36±10 |
| 7 | (RR)-64b' | 121 | 1.65 | 14 | 0.62 | 100 | $CHCl_3$ | $2.0 \times 10^{-4}$ | 25 | 0.63 | 975 | 2.88 | 4.81 | 1.67 | 30±10 |
| 8 | (RR)-64b' | 118 | 6.2 | 14 | 0.62 | 20 | $CH_2Cl_2$ | $4.4 \times 10^{-5}$ | 25 | 1.0 | 900 | 1.38 | 1.66 | 1.20 | 16±5 |
| 9 | (RR)-64b' | 123 | 12 | 14 | 0.62 | 8.6 | $CH_2Cl_2$ | $4.4 \times 10^{-5}$ | 25 | ·1.0 | 900 | 0.19 | 2.65 | 14 | 12±5 |
| 10 | (RR)-64b' | 124 | 11.4 | 14 | 0.62 | 11.7 | $CH_2Cl_2$ | $4.4 \times 10^{-5}$ | 25 | 1.0 | 900 | 0.29 | 2.94 | 10 | 25±5 |
| 11 | (RR)-64b' | 124 | 5.9 | 14 | 0.62 | 23 | $CHCl_3$ | $5.0 \times 10^{-3}$ | 25 | 0.6 | 975 | 4.37 | 19.39 | 4.44 | 45±5 |
| 12 | (RR)-64b' | (S)-124 | 10.6 | 14 | 0.62 | 13 | $CHCl_3$ | $5.0 \times 10^{-3}$ | 25 | 0.6 | 975 | — | 21.2 | — | — |

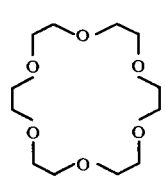

122

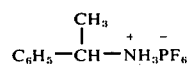

121

118

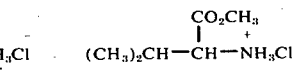

123

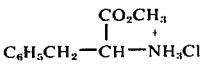

124

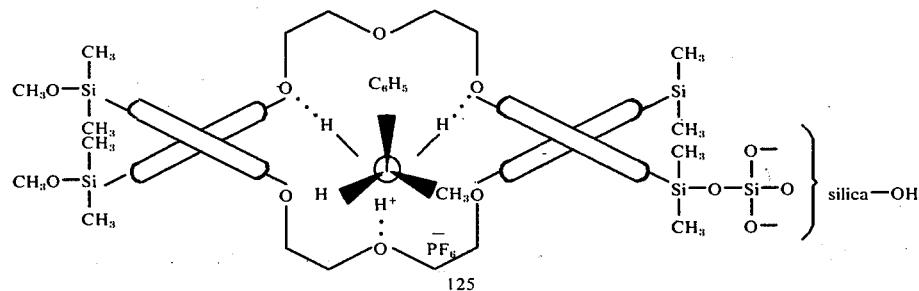

125
Favored diastereomeric complex between (RR)-64a' and hexafluorophosphate salt of (S)-α-phenylethylamine (109)

In runs 2–4 made at 25° with the same salt, the plots of relative conductance vs. volume of eluate exhibited two well defined maxima with separation factors that ranged from 1.13 to 1.30. These separation factors are lower than those observed in liquid-liquid extraction at the same temperature (see runs 2–4 of Table VI, Example 12, Procedure 2). However, in run 5 carried out at −12°, the separation factor rose dramatically to 9.9 as did the number of theoretical plates. A less pronounced increase in the value of the separation factor with a decrease in temperature was also observed in the liquid-liquid system (Table VI, runs 1 and 2).

Procedure 2

An undesirable feature of the column used in Procedure 1 was that considerable tailing was evident in the plots of relative conductance vs. volume of the column eluate. The column appeared to bind the salt both by complexation that involved the multiheteromacrocycle, and also by the SiOH sites. Thse sites were available to the small guest molecules, but were too confined to have been reached by the large host molecule during its attachment to the silica. The fact that SiOH sites remained on the support after treatment with just the host-Si($CH_3$)$_2$Cl was demonstrated by the fact that much ($CH_3$)$_3$SiCl reacted subsequently with the support. Accordingly, a second 14 g. column was prepared from (RR)-64b' that had been treated with ($CH_3$)$_3$SiCl (Example 7, Procedure 7). This material also contained about 0.044 mmole of host sites per gram. Table IX gives the conditions and results of runs 6–12 that were made with this column. The general techniques of these runs were the same as those of Procedure 1.

In runs 6 and 7, α-phenylethylammonium hexaflorophosphate (121) was used. Run 6 involved dichloromethane as solvent and an H/G ratio of 21, and gave a separation factor (α) of 1.47. Run 7 involved chloroform as solvent, and H/G ratio of 100, and gave α = 1.67. These factors are not far from those of the liquid-liquid column that involved the same temperature, the same non-polar phase, the same salt as guest compound, the same shaped host but in a liquid phase rather than attached to a surface [see run 4 of Table VI, Example 12, Procedure 2, where $\alpha = 1.48$]. This comparison indicates that the column of run 7 which involved optical resolution by liquid-solid chromatography shows chiral recognition properties similar to those of liquid-liquid chromatography, which in turn were similar to those observed in simple liquid-liquid enantiomer distribution experiments [Example 12, Procedure 1]. With the $\alpha$-phenylethylammonium hexaflorophosphate, the EDC value obtained in liquid-liquid enantiomer distribution experiments was the same as the $\alpha$ value of the liquid-liquid chromatograph column, and close to the $\alpha$ value for liquid-solid chromatography column. FIG. 1 is a plot of the relative conductance vs. volume of the column eluate from run 7.

Run 11 is an example of total resolution of an amino acid ester salt by liquid-solid chromatography. FIG. 2 is a plot for run 11, in which racemic phenylalanine methyl ester hydrochloride (124) was resolved with good base-line separation between the peaks for the two enantiomers. The separation factor was $\alpha = 4.44$, the solvent was chloroform, and the peaks were reasonable Gaussian. Run 10 involved the same salt with dichloromethane, $\alpha = 10$, and base-line separation was also evident. However, the peaks were much less Gaussian, and tailing was evident. Chloroform gives less tailing than dichloromethane.

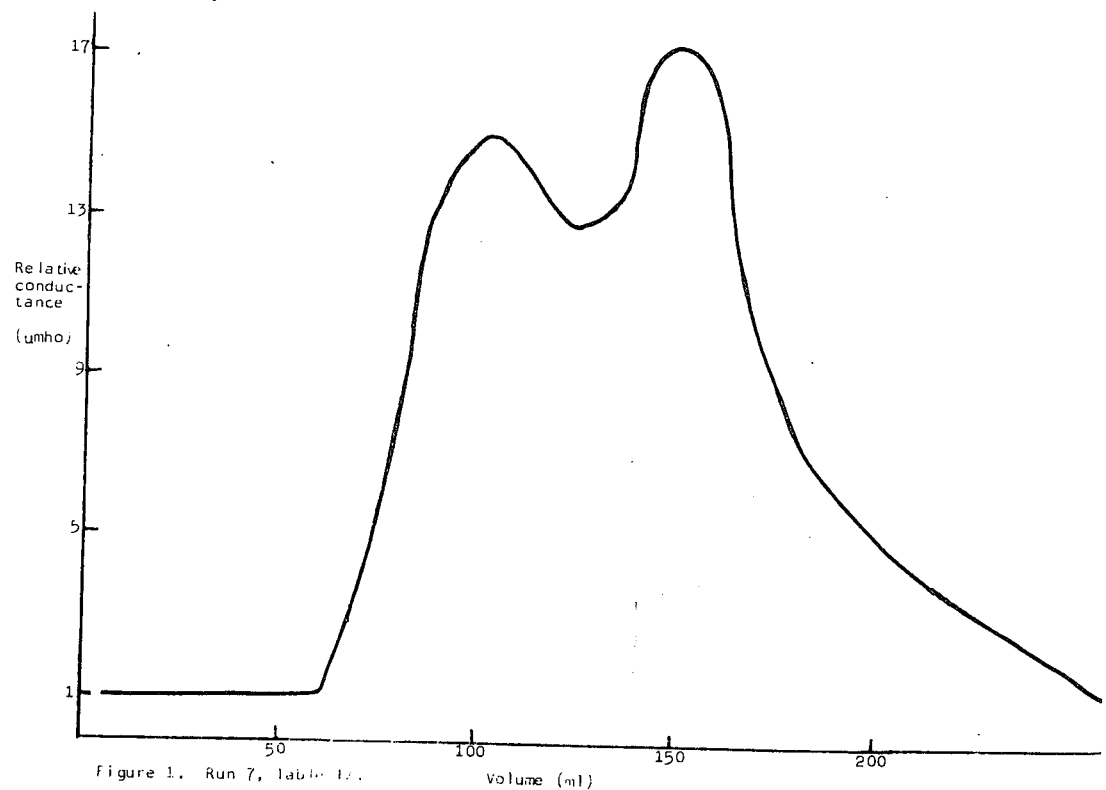

Figure 1. Run 7, Table IX.

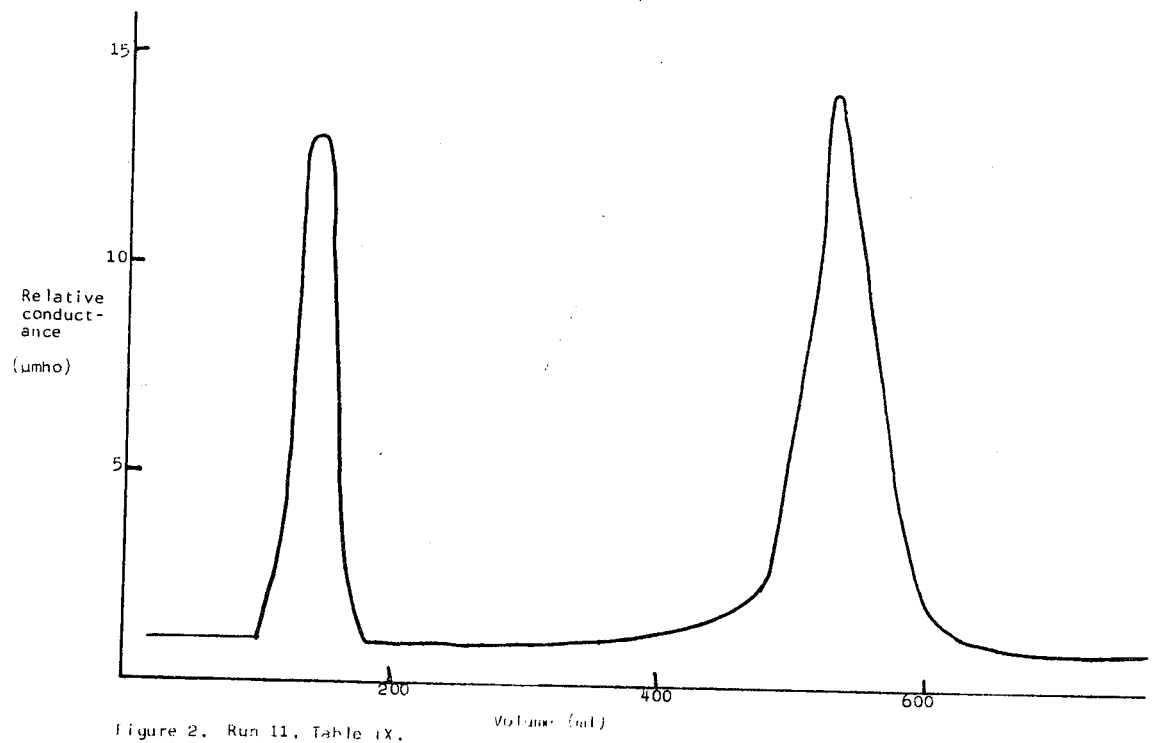

Figure 2. Run 11, Table IX.

Run 12 involved optically pure (S)-124 as salt, and was made under conditions essentially identical to those of run 11 that involved (S)(R)-124. The (S)-124 put on the column in run 12 gave $V_R = 576$ ml. as its retention volumne. This value compares with $V_{RA} = 140$ ml. and $V_{RB} = 530$ ml. for the two components of run 11. The $V_R = 576$ ml. and $V_{RB} = 530$ ml. values are within experimental error of one another, but $V_R = 576$ ml. is far from $V_{RA} = 140$ ml. Thus the B component of run 11 must have had the (S)-configuration. This result correlates with the polar model, 125, and is in accordance with the results of run 29, Table V (Example 12, Procedure 1). In run 29 of Table V, (RR)-8bound the (S)-enantiomer of phenylalanine methyl ester hexaflorophosphate more strongly in chloroform at $-1°$ than the (R)-enantiomer, and EDC = 1.8. In run 11 of Table IX, the hydrochloride was used, the temperature was 25°, and $\alpha = 4.44$. In this case, more chiral recognition was observed in the solid-liquid than in the liquid-liquid system although the differences in counterion and temperature could be responsible.

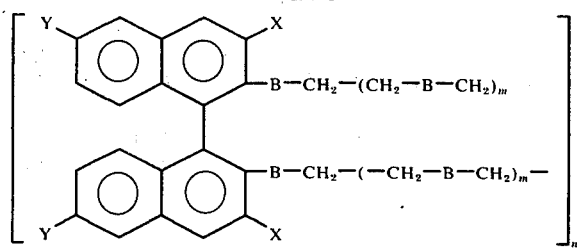

wherein $n$ is 1 to 3; each $m$ taken separately = 0 to 5, the sum being at least 1;

B is —O—;

X is $(CH_2)vR$, where $v = 1$ to 3 and R = H, $CH_3$, $CO_2H$, OH or $OCH_3$, or X is $CH_2OH$: $CH_2Cl$; $CH_2OCH_2CO_2H$; $CH_2OCH_2CO_2CH_3$; $CH_2SCH_2CO_2H$; $CH_2CH_2CO_2H$; $CH_2SCH_2CH_2CO_2H$;

Y is H, Br, $CO_2H$, $CH_2OH$, $CH_2Cl$, $CH_2OCH_2CO_2H$, $CH_2SCH_2CO_2H$, $CH_2CO_2CH_3(CH_2)_{16}C(CH_3)_2$ or $CH_3(CH_2)_{17}CHCH_3$.

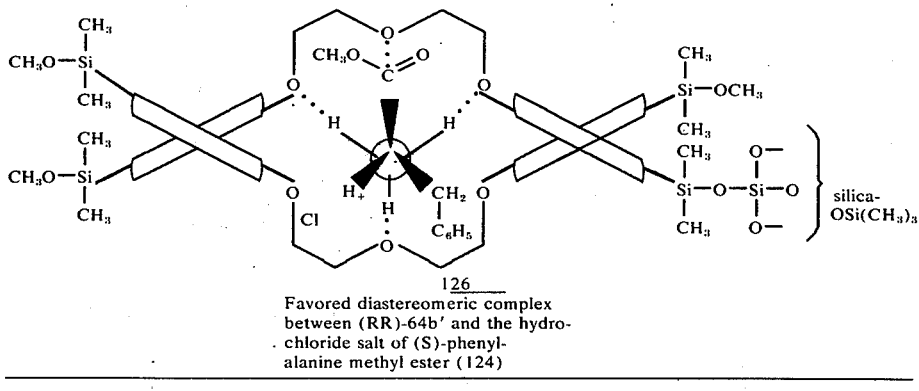

126

Favored diastereomeric complex between (RR)-64b' and the hydrochloride salt of (S)-phenylalanine methyl ester (124)

The results indicate that covalent binding of compounds such as optically active 8 and its derivatives to solid supports (such as silica) provide a molecular basis for constructing a resolving machine for amino acids and their derivatives. Because the different amino acids (their enantiomers and derivatives) all have different retention volumes (or times), columns such as this can be used to quantitatively and qualitatively identify the components in mixtures of amino acids and their derivatives

I claim:

1. A compound according to the formula:

2. According to claim 1 a compound of the formula:

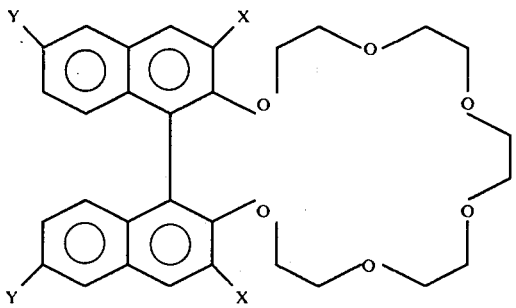

wherein

X is $(CH_2)vR$, where $v = 1$ to 3 and R = H, $CO_2H$, OH, or $OCH_3$, or X is $CH_2OCH_2CO_2H$ or $CH_2OCH_2CO_2CH_3$;

Y is H, Br, $CO_2H$, $CH_2OH$, $CH_2CO_2H$, or $CH_2Cl$.

3. According to claim 1 a compound of the formula:

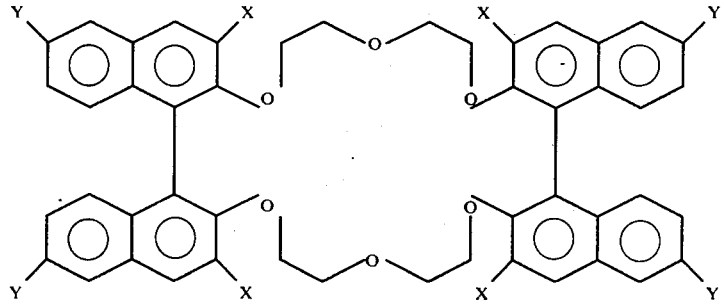

wherein

X is $(CH_2)vR$, where $v = 1$ to 3 and $R = H, CO_2H, OH$ or $OCH_3$; or X is $CH_2OCH_2CO_2H$ or $CH_2OCH_2CO_2CH_3$;

Y is $H, Br, CO_2H, CH_2OH, CH_2CO_2H$ or $CH_2Cl$.

4. According to claim 1, a compound of the formula:

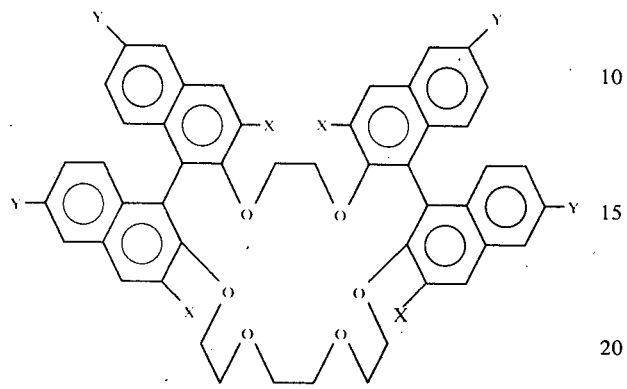

wherein

X is $(CH_2)vR$, where $v = 1$ to 3 and $R = H, CO_2H, OH$ or $OCH_3$, or X is $CH_2OCH_2CO_2H$ or $CH_2OCH_2CO_2CH_3$;

Y is $H, Br, CO_2H, CH_2OH, CH_2CO_2H$, or $CH_2Cl$.

5. A compound of the formula:

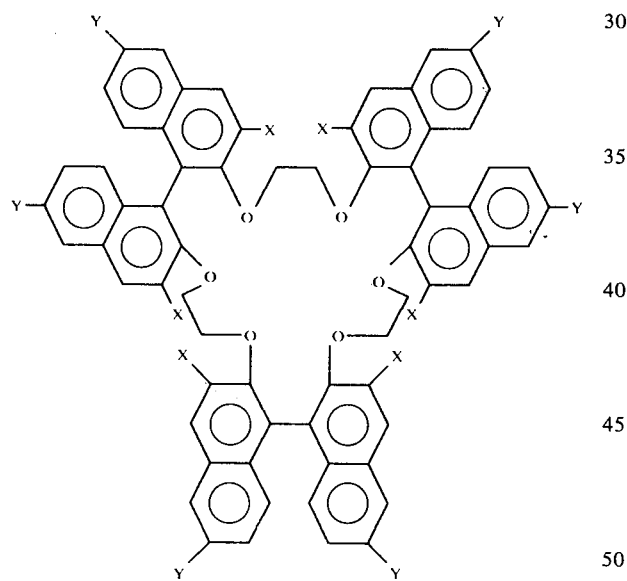

wherein

X is $(CH_2)vR$, where $v = 1$ to 3 and $R = H, CO_2H, OH$ or $OCH_3$, or X is $CH_2OCH_2CO_2H$ or $CH_2OCH_2CO_2CH_3$;

Y is $H, Br, CO_2H, CH_2OH, CH_2CO_2H$, or $CH_2Cl$.

6. According to claim 1, a compound of the formula:

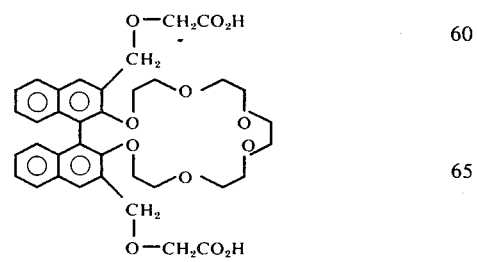

7. According to claim 1, a compound of the formula:

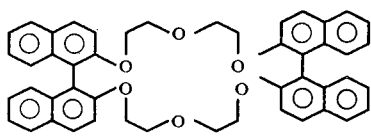

8. According to claim 1, a compound of the formula:

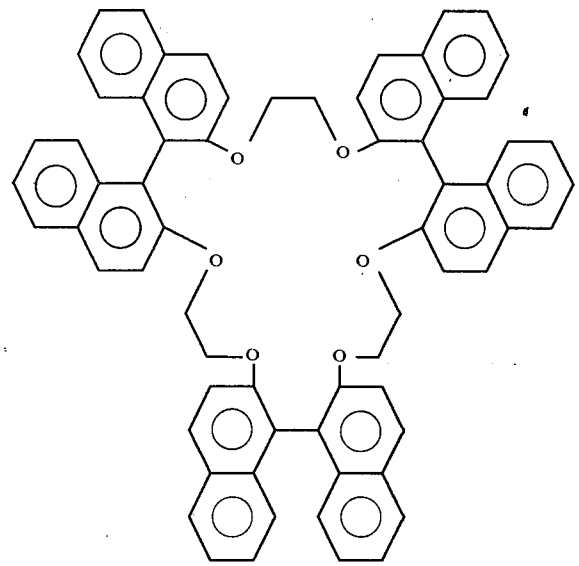

9. According to claim 1, a compound of the formula:

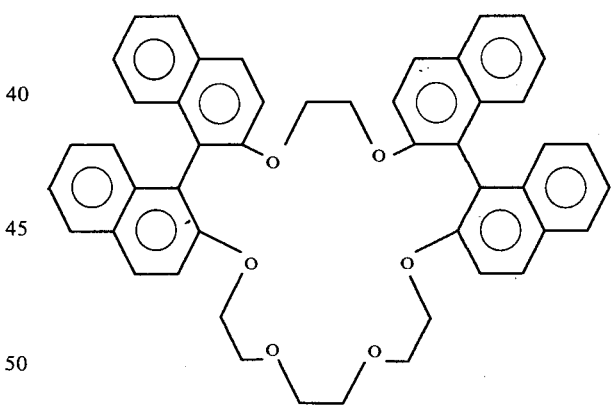

10. According to claim 1, a compound of the formula:

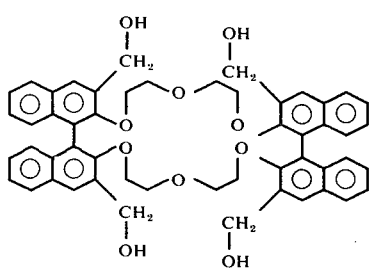

11. According to claim 1, a compound of the formula:

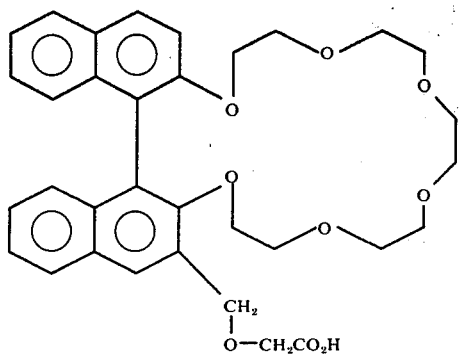

12. According to claim 1, a compound of the formula:

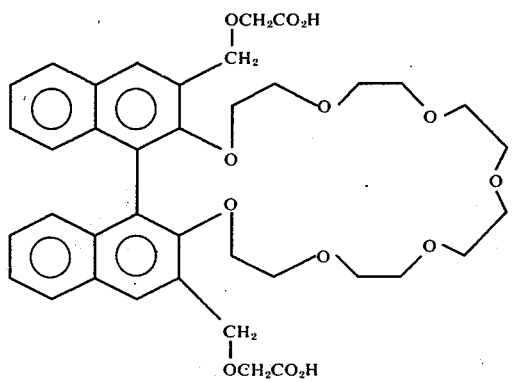

13. According to claim 1, a compound of the formula:

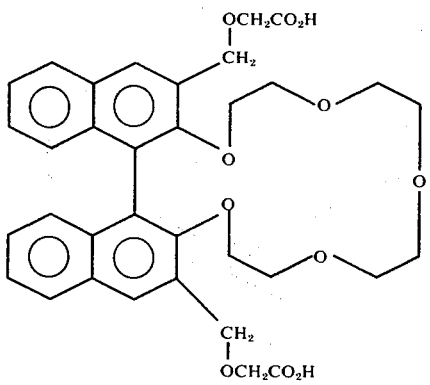

14. According to claim 1, a compound of the formula

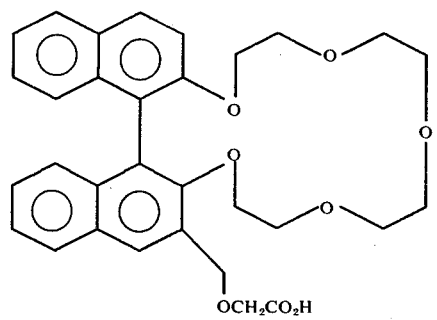

15. According to claim 1, a compound of the formula

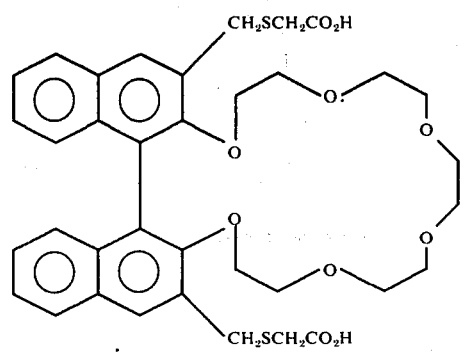

16. According to claim 1, a compound of the formula

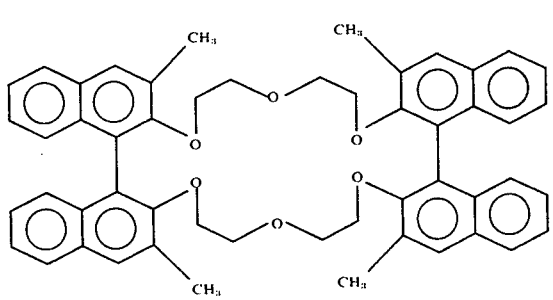

17. According to claim 1, a compound of the formula

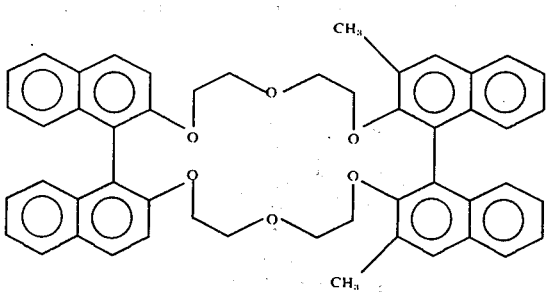

18. According to claim 1, a compound of the formula

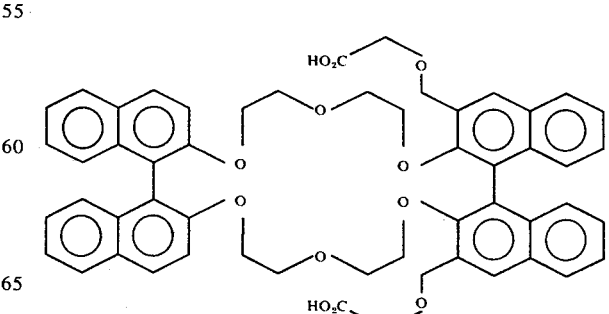

19. According to claim 1, a compound of the formula

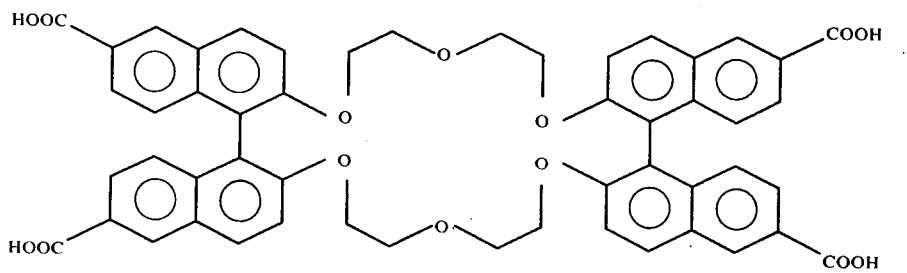
20. A compound of the formula
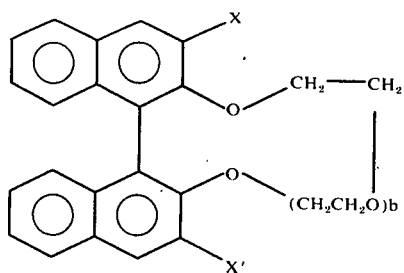
where b is 3 to 5 and X and X' are both —CH₂OCH₂CO₂H.
21. A compound of the formula
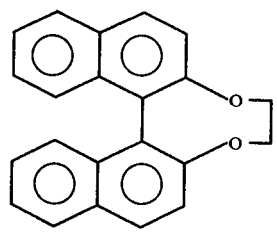
22. A compound of the formula
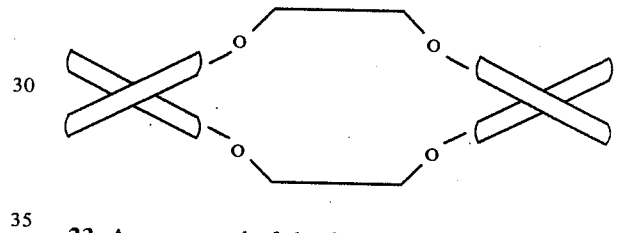
23. A compound of the formula:
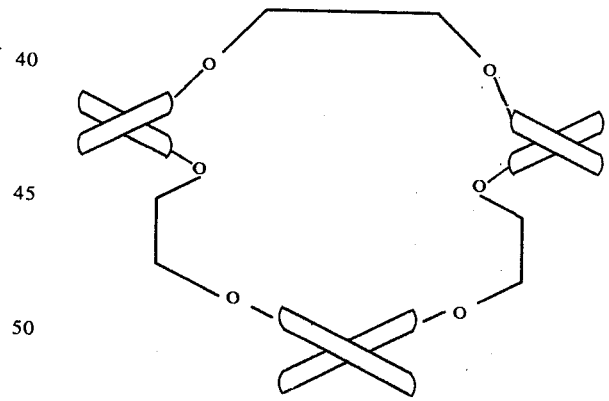
* * * * *